(12) United States Patent
Belema et al.

(10) Patent No.: US 6,933,294 B2
(45) Date of Patent: Aug. 23, 2005

(54) THIOPHENE-BASED TRICYCLIC COMPOUNDS AND PHARMACEUTICAL COMPOSITIONS COMPRISING SAME

(75) Inventors: Makonen Belema, New Haven, CT (US); Amy Bunker, Ann Arbor, MI (US); Van Nguyen, Middletown, CT (US); Francis Beaulieu, Laprairie (CA); Carl Ouellet, Boucherville (CA); Anne Marinier, Kirkland (CA); Stephan Roy, St-Lambert (CA); Xuejie Yang, Wallingford, CT (US); Yuping Qiu, Glastonbury, CT (US); Yunhui Zhang, Glastonbury, CT (US); Alain Martel, Delson (CA); Christopher Zusi, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 34 days.

(21) Appl. No.: 10/400,387

(22) Filed: Mar. 27, 2003

(65) Prior Publication Data

US 2004/0058930 A1 Mar. 25, 2004

Related U.S. Application Data

(60) Provisional application No. 60/369,698, filed on Apr. 3, 2002.

(51) Int. Cl.$^7$ .................. C07D 495/14; A61K 31/4985; A61P 19/02; A61P 11/06; A61P 17/06
(52) U.S. Cl. .................... 514/228.5; 544/346; 544/295; 544/60; 544/115; 514/233.2; 514/250
(58) Field of Search ............................... 544/346, 295, 544/60, 115; 514/228.5, 233.2, 250

(56) References Cited

U.S. PATENT DOCUMENTS

| 5,182,386 A | 1/1993 | Albaugh et al. |
|---|---|---|
| 5,306,819 A | 4/1994 | Albaugh et al. |
| 5,726,175 A * | 3/1998 | Aloup et al. ................. 514/250 |

FOREIGN PATENT DOCUMENTS

| EP | 573860 | 8/1993 |
|---|---|---|
| WO | WO 94/05665 | 3/1994 |

OTHER PUBLICATIONS

Goldstein et al., "Favorable Effects of Sulfasalazine on Small Bowel Crohn's Disease: A Long–Term Study", *The American Journal of Gastroenterology*, vol. 82, No. 9, 1987, pp. 848–853.

Weber et al., "Suppression of NF–kB Activity by Sulfasalazine is Mediated by Direct Inhibition of IkB Kinases α and β", *Gastroenterology*, vol. 119, No. 5, pp. 1209–1218.

*Asulfidine EN–tabs® sulfasalazine delayed release tablets, USP*; Prescribing Information, Pharmacia & Upjohn, Revised Oct. 2000.

R. Bureau, et al., "Conformational Analysis and 3D QSAR Study on Novel Partial Agonists of 5–$HT_3$ Receptors", *Quant. Struct.–Act. Relat*, vol. 15, pp. 373–381, 1996.

Sylvain Rault et al., "Pyrrolo[1,2-α]thieno[3,2,e]pyrazines", *J. Heterocycl. Chem.*, vol. 18, pp. 739–742, 1981.

P. Delagrange et al., "Effects of S–21007, a potent 5–$HT_3$ partial agonist, in mouse anxiety", *Zhongguo Yaoli Xuebao*, vol. 20, pp. 805–812, 1999.

H. Prunier et al., "Synthesis and Biological Evaluation of New Pyrrolothienopyrazine Derivatives as Potential 5–$HT_4$ Ligands", *Pharm. Sci.*, vol. 3, pp. 311–314, 1997.

J. Rouden et al., "Palladium mediated cross–coupling reaction of heteroaryl–imidoyl chloride and primary amines–preparation of a new ligand of serotoninergic receptors", *Tetrahedron Letters*, vol. 40, pp. 8109–8112, 1999.

P. Delagrange et al., "Interaction of S 21007 with 5–$HT_3$ receptors. In vitro and in vivo characterization", *European Journal of Pharmacology*, vol. 316, pp. 195–203, 1996.

I. Baglin et al., "First Tricyclic Oximino Derivatives as 5–$HT_3$ Ligands", *Bioorganic & Medicinal Chemistry Letters*, vol. 11, pp. 453–457, 2001.

H. Prunier et al., "Novel and Selective Partial Agonists of 5–$HT_3$ Receptors. 2. Synthesis and Biological Evaluation of Piperazinopyridopyrrolopyrazines, Piperazinopyrroloquinoxalines, and Piperazinopyridopyrroloquinoxalines", *J. Med. Chem.*, vol. 40, pp. 1808–1819, 1997.

S. Rault et al., "Novel Selective and Partial Agonists of 5–$HT_3$ Receptors. Part 1. Synthesis and Biological Evaluation of Piperazinopyrrolothienopyrazines", *J. Med. Chem.*, vol. 39, pp. 2068–2080, 1996.

R. Bureau et al., "Association of Two 3D QSAR Analyses. Application to the Study of Partial Agonist Serotonin–3 Ligands", *J. Chem. Inf. Comput. Sci.* vol. 41, pp. 815–823, 2001.

* cited by examiner

*Primary Examiner*—Mark L. Berch
(74) *Attorney, Agent, or Firm*—Mark K. VanAtten

(57) ABSTRACT

Compounds having the formula (I),

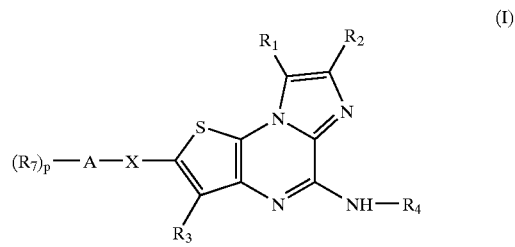

and pharmaceutically-acceptable salts, hydrates and prodrugs thereof, are useful as anti-inflammatory agents, in which $R_1$, $R_2$, and $R_3$ are hydrogen, halogen, alkyl, or perfluoroalkyl; $R_4$ is an optionally substituted alkyl or cycloalkyl group; X is a linker; A is an aryl, heteroaryl, heterocycle, cycloalkyl, or is absent; and $R_7$ is a substituent on A as defined in the specification.

19 Claims, No Drawings

THIOPHENE-BASED TRICYCLIC COMPOUNDS AND PHARMACEUTICAL COMPOSITIONS COMPRISING SAME

This application claims priority to U.S. Provisional Application Ser. No. 60/369,698 filed Apr. 3, 2002 the entirety of which is incorporated herein by reference.

FIELD OF THE INVENTION

The present invention relates to thiophene-based tricyclic compounds, to methods of using the compounds in treating inflammatory and immune diseases, and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. Certain neurodegenerative diseases such as Alzheimer's disease, Parkinson's disease, and Creutzfeldt-Jacob disease also are reportedly associated with enhanced TNF-α levels. See, e.g., Arvin et al., "The Role of Inflammation and Cytokines in Brain Injury," Neuroscience and Biobehavioral Reviews, Vol. 20, No. 3 (1996), at pp. 445–452.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs). These drugs are useful in treating a variety of diseases. See Dinarello, "Role of Pro- and Anti-Inflammatory Cytokines During Inflammation: Experimental and Clinical Findings, Review, Vol. 0393-974X (1997), at pp. 91–103.

Recently, attention has focussed on the role of Nuclear factor κB (NF-κB) in the activation pathway that leads to production of TNF-α and other inflammatory cytokines and gene types. Besides TNF-α, NF-κB is involved in the regulation of a variety of genes involved in immune function and inflammation, including IL-2, IL-6, IL-8, IL-2Rα, GM-GSF, intercellular adhesion molecule (ICAM-1), and vascular cellular adhesion molecule-1 (VCAM-1). Thus, inhibition of NF-κB and/or its activation pathway provides a means for treating various diseases including autoimmune diseases, Alzheimer's disease, atherosclerosis, oncogenesis, and so forth. See, e.g., Baldwin, "The NF-κB and IκB Proteins: New Discoveries and Insights," Annual Rev. Immunol., Vol. 14 (1996), at pp. 649–81; see also Christman et al., "Impact of Basic Research on Tomorrow's Medicine, The Role of Nuclear Factor-κB in Pulmonary Diseases," Chest, Vol. 117 (2000), at pp. 1482–87.

Potential inhibitors of the NF-κB and/or the NF-κB pathway have been identified as including Interleukin-10, glucocorticoids, salicylates, nitric oxide, and other immunosuppressants. IκB is a cytoplasmic protein that controls NF-κB activity by retaining NF-κB in the cytoplasm. IκB is phosphorylated by the Iib kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Glucocorticoids reportedly inhibit NF-κB activity by two mechanisms, i.e., upregulating IκB protein levels and inhibiting NF-κB subunits. Nitric oxide also reportedly inhibits NF-κB through upregulation of IκB. However, these mechanisms of interaction are complex; for example, production of nitric oxide in lymphocytes reportedly enhances NF-κB activity.

As may be appreciated, those in the field of pharmaceutical research continue to seek to develop new compounds and compositions having increased effectiveness, bioavailability, and solubility, having fewer side effects, and/or providing the consumer with a choice of options. Particularly in the area of immune response, many individuals respond differently depending upon the type of treatment and chemical agent used. Mechanisms of action continue to be studied to aid in understanding the immune response and in developing compounds effective for treating inflammatory and immune-related disorders.

The present invention provides thiophene-based tricyclic compounds useful as inhibitors of IKK. Pyrrolothioenopyrazines having binding affinity for 5-HT$_3$ receptors are disclosed in Rault et al., J. Med. Chem, Vol. 39 (1996), at pp. 2068–80, and European patent application No. 573,360 (Dec. 8, 1993). A broad genus of compounds including certain aromatic-substituted tricyclic thiophenes is disclosed in WO 94/05665 to Neurogen Corp. for use as GABA brain receptor ligands. Polycyclic thiophene compounds are also disclosed in GB Pat. Applic. 2,344,818 to Pharmacia and Upjohn (6/21/00), WO 00/35428 to Boehringer Ingelheim (6/22/00), EP Pat. Applic. 1,104,764 to Hokuriku Seiyaku Co. (Jun. 6, 2001), and Cardoso et al., Bioorg. Med. Chem. Lett., Vol. 12 (2002), at pp. 9–12. AstraZeneca (WO 01/58890, Aug. 16, 2001) reported that certain monocyclic, amide-substituted thiophene compounds may be useful as IKK inhibitors.

SUMMARY OF THE INVENTION

The invention is directed to compounds of formula (I), useful in treating inflammatory or immune conditions:

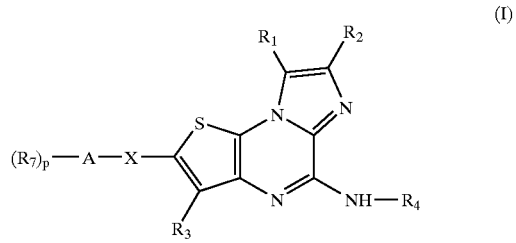

(I)

enantiomers, diastereomers, pharmaceutically-acceptable salts, and solvates thereof, in which:

$R_1$, $R_2$, and $R_3$ are independently selected from hydrogen, halogen, alkyl, and perfluoroalkyl;

$R_4$ is —$(CR_5R_6)_m$-Z or -(cycloalkyl)-Z;

$R_5$, $R_{5a}$, $R_6$ and $R_{6a}$ at each occurrence are independently selected from hydrogen, alkyl, substituted alkyl, amino, alkylamino, substituted alkylamino, hydroxy, alkoxy, substituted alkoxy, cycloalkyl, heterocycle, aryl, and heteroaryl;

$R_7$ at each occurrence is selected independently of each other $R_7$ from alkyl, substituted alkyl, alkenyl, substituted alkenyl, halogen, cyano, —$(CR_{5a}R_{6a})_q$—$OR_{8a}$, —$(CR_{5a}R_{6a})_q$—$SR_{8a}$, —$(CR_{5a}R_{6a})_q$—$SO_2R_{10}$, —$(CR_{5a}R_{6a})_q$—$NR_8R_9$, —$(CR_{5a}R_{6a})_q$—$NR_8SO_2$, —$(CR_{5a}R_{6a})_q$—$NR_8SO_2R_{10}$, —$(CR_{5a}R_{6a})_q$—$SO_2NR_8R_9$, —$(CR_{5a}R_{6a})_q$—$NR_{8a}C(=O)R_{9a}$, —$(CR_{5a}R_{6a})_q$—$NR_{8a}CO_2R_{9a}$, —$(CR_{5a}R_{6a})_q$—$C(=O)R_{8a}$, —$(CR_{5a}R_{6a})_q$—$CO_2R_{8a}$, —$(CR_{5a}R_{6a})_q$—$OC(=O)R_{8a}$, —$(CR_{5a}R_{6a})_q$—$C(=O)NR_8R_9$, —$(CR_{5a}R_{6a})_q$—$CO_2NR_8R_9$, —$(CR_{5a}R_{6a})_q$—$OC(=O)NR_8R_9$, —$(CR_{5a}R_{6a})_q$—$C(=O)NR_{8a}$—$NR_8R_9$, —$(CR_{5a}R_{6a})_q$—$C(=O)NR_{8a}SO_2R_{10}$, —$(CR_{5a}R_{6a})_q$—$NR_{8a}C(=O)NR_8R_9$, —$(CR_{5a}R_{6a})_q$—$NR_{8a}SO_2NR_8R_9$, —$(CR_{5a}R_{6a})_q$—$NR_{8a}C(=O)$—$C(=O)$—$NR_8R_9$, —$(CR_{5a}R_{6a})_q$—$NR_{8a}C(=O)$—$CO_2R_{9a}$, —$(CR_{5a}R_{6a})_q$—$N(SO_2R_{10})(SO_2R_{10a})$, —$(CR_{5a}R_{6a})_q$—$OSO_2NR_8R_9$, cycloalkyl, (cycloalkyl)alkyl, heterocycle, (heterocyclo)alkyl, aryl, (aryl)alkyl, heteroaryl, and (heteroaryl)alkyl, or when A is heterocycle or cycloalkyl, one of $R_7$ may be keto (=O), and when A is a bond, then $R_7$ may be hydrogen;

X is a bond, O, S, —$NR_{11}$—, —$(CH_2)_n$—, —CH=CH—, or —C≡C—;

A is a bond, aryl, heteroaryl, heterocycle, or cycloalkyl;

Z is selected from hydrogen, methyl, $OR_{14}$, —$C(=O)OR_{14}$, —$NR_{12}C(=O)R_{13}$, —$NHC(=NR_{14a})R_{15a}$, —$NR_{12}CO_2R_{13}$, —$NR_{12}SO_2R_{13}$, —$C(=O)NR_{14}R_{15}$, —$NR_{14}R_{15}$ and —$NR_{12}$—$C(=O)NR_{14}R_{15}$;

$R_8$ $R_{8a}$, $R_9$ and $R_{9a}$ are independently selected from hydrogen, alkyl, substituted alkyl, alkenyl, substituted alkenyl, cycloalkyl, (cycloalkyl)alkyl, heterocycle, (heterocylco)alkyl, aryl, (aryl)alkyl, heteroaryl, and (heteroaryl)alkyl;

or $R_8$ and $R_9$ together with the nitrogen atom to which they are bonded may combine to form a heterocyclo ring;

$R_{10}$ and $R_{10a}$ are independently alkyl, substituted alkyl, cycloalkyl, heterocycle, aryl, or heteroaryl;

$R_{11}$ is hydrogen, alkyl, aminoalkyl, or hydroxyalkyl;

$R_{12}$ is hydrogen or lower alkyl;

$R_{13}$ is hydrogen, alkyl, substituted alkyl, cycloalkyl, heterocyclo, aryl or heteroaryl;

$R_{14}$ $R_{14a}$, $R_{15}$ and $R_{5a}$ are independently selected from hydrogen, alkyl, substituted alkyl, cycloalkyl, (cycloalkyl)alkyl, heterocycle, (heterocylo)alkyl, aryl, (aryl)alkyl, heteroaryl, and (heteroaryl)alkyl;

or $R_{14}$ and $R_{15}$ together with the nitrogen atom to which they are bonded may combine to form a heterocyclo ring;

m and q are independently 0, 1, 2, 3, 4, 5 or 6;

n is 1 or 2; and p is 0, 1, 2, 3 or 4, except when A is a bond, then p is 1.

The invention also relates to pharmaceutical compositions containing at least one compound of formula (I) and a pharmaceutically-acceptable carrier or diluent, for use in treating inflammatory and immune diseases. Also included within the invention are methods of treating such diseases comprising administering to a mammal in need of such treatment an effective amount of at least one compound of formula (I).

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. When the subscript "0" is used, as in $C_0$, this refers to a bond. Thus, the term $C_{0-2}$hydroxyalkyl refers to hydroxy, hydroxymethyl, and hydroxyethyl.

The term "substituted alkyl" refers to an alkyl group as defined above having one, two, or three substituents selected from the group consisting of halogen, trifluoromethyl, alkenyl, alkynyl, nitro, cyano, keto (=O), haloalkoxy, —OR, —SR, —NRR', —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRC(=O)—NRR', —NRCO$_2$R', =N—OH, =N—O-alkyl, aryl, heteroaryl, heterocyclo and cycloalkyl, wherein R and R' are selected from hydrogen, alkyl, alkenyl, amino, alkylamino, substituted alkylamino, cycloalkyl, (cycloalkyl)alkyl, heterocycle, (heterocylco)alkyl, aryl, (aryl)alkyl, heteroaryl, (heteroaryl)alkyl, (alkoxy)alkyl, (CO$_2$H)alkyl, (NC(=O)R)alkyl, (hydroxy)alkyl, (amino)alkyl, (alkylamino)alkyl, or R and R' together may form a heterocyclo or heteroaryl ring, and R" is alkyl, alkenyl, benzyl, phenylethyl, cycloalkyl, heterocyclo, aryl, and/or heteroaryl. When an alkyl is substituted with an aryl, heteroaryl, heterocyclo or cycloalkyl, those groups are as recited below and thus optionally may be substituted as recited below. Each of R, R', and R" in turn may have zero to three substituents (preferably 0–2 substituents), selected from halogen, alkyl, haloalkyl, alkenyl, nitro, cyano, —OH, —O(alkyl), haloalkoxy, hydroxyalkoxy, aminoalkoxy, phenyl, benzyl, phenylethyl, phenyloxy, benzyloxy, —SH, —S(alkyl), —S(phenyl), —NH$_2$, —NH(alkyl), —N(alkyl)$_2$, —NH(cycloalkyl), —NHSO$_2$(alkyl), —SO$_2$(alkyl), —SO$_2$NH$_2$, —SO$_2$NH (alkyl), —SO$_2$N(alkyl)$_2$, —CO$_2$H, —CO$_2$(alkyl), —C(=O)H, —C(=O)alkyl, —C(=O)NH$_2$, —C(=O)NH(alkyl), —C(=O)N(alkyl)$_2$, —OC(=O)alkyl, —OC(=O)NH$_2$, —OC(=O)NH(alkyl), —OC(=O)N(alkyl )$_2$, —NHC(=O)alkyl, —NHCO$_2$(alkyl), $C_{3-7}$cycloalkyl, $C_{5-6}$heteroaryl, and $C_{4-7}$heterocyclo.

When the term alkyl is used as a suffix with a second named group, as in arylalkyl or cycloalkylalkyl, this refers to a substituted alkyl in which at least one of the substituents is the second named group. For example, the term arylalkyl includes benzyl and any other straight or branched chain alkyl having at least one aryl group attached at any point of the alkyl chain. Other substituents may be attached to the alkyl chain or the second named group. Such substituents may be selected as appropriate from the groups recited above in the definition of substituted alkyl and/or from those recited herein for the second named group.

The term "alkenyl" refers to straight or branched chain hydrocarbon groups having 2 to 12 carbon atoms and at least one double bond. Alkenyl groups of 2 to 6 carbon atoms and having one double bond are most preferred. Alkenyl groups may be optionally substituted as described in the definition of "substituted alkyl".

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene, these groups are substituted with one to three substitutents as defined above for alkyl groups. A substituted alkylene, alkenylene, or alkynylene may have a ringed substituent attached in a spiro fashion as in

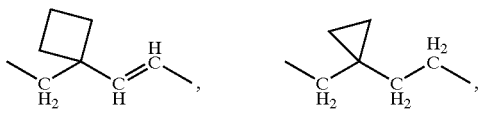

and so forth.

The term "alkoxy" refers to the group —OR, wherein R is alkyl or alkenyl. The term "alkylthio" refers to the group —SR, wherein R is alkyl or alkenyl. The term "alkylamino" refers to the group —NR'R", wherein each of R' and R" is selected from hydrogen, alkyl, alkenyl, cycloalkyl, aryl, heteroaryl, or heterocyclo, as defined herein, provided that both R' and R" are not hydrogen. The term "amino" refers to —NH$_2$. A substituted alkoxy, alkythio, or alkylamino may have zero to three substituents as defined above for substituted alkyl.

When a subscript is used with an alkoxy, alkylthio or alkylamino, the subscript refers to the number of carbon atoms that the group may contain in addition to heteroatoms. Thus, for example, monovalent C$_{1-2}$alkylamino includes the groups —NH—CH$_3$, —NH—CH$_2$—CH$_3$, and —N(CH$_3$)$_2$. A lower alkylamino comprises an alkylamino having one to four carbon atoms.

The alkoxy, alkylthio, or alkylamino groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—C$_{1-12}$alkyl, whereas a bivalent alkoxy includes groups such as —O—C$_{1-12}$alkylene-, etc.

The term "acyl" refers to a carbonyl {—C(=O)—} linked to an organic group i.e.,

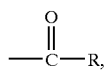

wherein R may be selected from alkyl, substituted alkyl, alkenyl, substituted alkenyl, aryl, heterocyclo, cycloalkyl, and heteroaryl, as defined herein.

The term "alkoxycarbonyl" refers to a carboxy or ester group {—CO$_2$—} linked to an organic radical, i.e.,

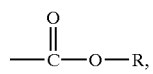

wherein R is as defined for acyl. "Carboxy" refers to the group CO$_2$H, and "carboxyalkyl" refers to —R—CO$_2$H, wherein R is alkylene or substituted alkylene.

The term "carbamyl" refers to a functional group in which a nitrogen atom is directly bonded to a carbonyl, i.e., as in —NRC(=O)R' or —C(=O)NRR', wherein R and R' can be hydrogen, alkyl, substituted alkyl, alkenyl, substituted alkenyl, alkoxy, cycloalkyl, aryl, heterocyclo, or heteroaryl.

The term "heteroatoms" shall include oxygen, sulfur and nitrogen.

The term "haloalkyl" means an alkyl having one or more halo substituents and thus includes, for example, trifluoromethyl.

The term "perfluoroalkyl" means an alkyl group having from one to five fluoro atoms, such as pentafluoroethyl. The term "perfluoromethyl" means a methyl group substituted by one, two, or three fluoro atoms, i.e., CH$_2$F, CHF$_2$ and CF$_3$.

The term "haloalkoxy" means an alkoxy group having one or more halo substituents. For example, "haloalkoxy" includes —OCF$_3$.

The term "sulfonyl" refers to a sulphoxide group (i.e., —S(O)$_{1-3}$) linked to an organic radical R", wherein R" is alkyl, substituted alkyl, alkenyl, substituted alkenyl, cycloalkyl, heterocyclo, heteroaryl, or aryl. Sulfonic acid is —SO$_3$H.

The term "sulfonamide" or "sulfonamido" refers to the group —S(O)$_2$NRR', wherein R and R' are selected from hydrogen, alkyl, substituted alkyl, alkenyl, substituted alkenyl, cycloalkyl, heterocyclo, heteroaryl or aryl. Preferably when one of R and R' is optionally substituted cycloalkyl, heterocyclo, heteroaryl or aryl (as defined below), the other of R and R' is hydrogen or alkyl.

The term "cycloalkyl" refers to fully saturated and partially unsaturated substituted or unsubstituted hydrocarbon rings of 3 to 20, preferably 3 to 7 carbon atoms. Cycloalkyl ring systems include monocyclic, bicyclic and tricyclic rings. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

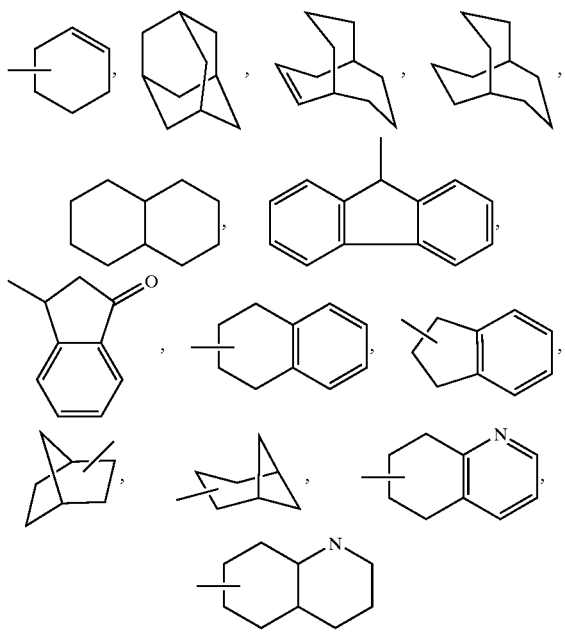

and the like.

When substituted, the cycloalkyl will contain one to three (preferably one to two) groups selected from alkyl, halogen, perfluoroalkyl, alkenyl, alkynyl, nitro, cyano, keto (=O), haloalkoxy, —OR, —SR, —NRR', —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', =N—OH, =N—O-alkyl, phenyl, 3 to 6 membered heteroaryl or heterocyclo, and/or $C_{3-7}$cycloalkyl, wherein R and R' are independently selected from hydrogen, alkyl, alkenyl, phenyl, benzyl, phenylethyl, $C_{3-7}$cycloalkyl, and 3 to 6 membered heterocyclo or heteroaryl, and R" is alkyl, alkenyl, phenyl, benzyl, phenylethyl, $C_{3-7}$cycloalkyl, and/or 3 to 6 membered heterocyclo or heteroaryl. The term "cycloalkyl" also includes such rings having a phenyl ring fused thereto or having a carbon-carbon bridge of 3 to 4 carbon atoms. Additionally, when a cycloalkyl is substituted with a further ring, i.e., phenyl, benzyl, etc., such ring in turn may be substituted with one to two $C_{0-4}$alkyl optionally substituted with (or linked to) one to two of halogen, $CF_3$, $OCF_3$, alkenyl, nitro, cyano, keto (=O), hydroxy, alkoxy, SH, S(alkyl), $NH_2$, NH(alkyl), N(alkyl)$_2$, $CO_2H$, $CO_2$(alkyl), C(=O)H, and/or C(=O)alkyl.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

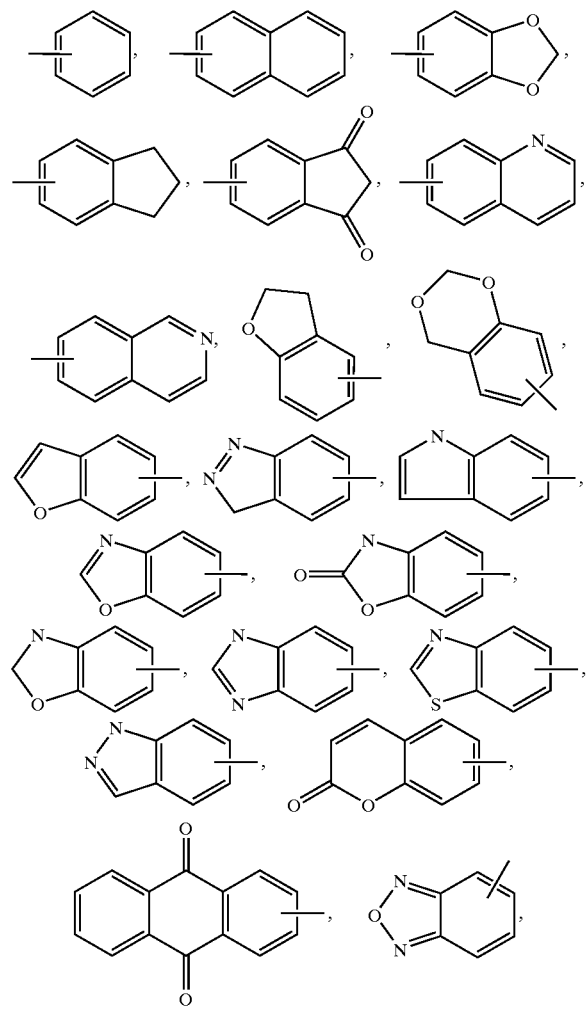

and the like. Preferred aryl groups include phenyl and naphthyl, with phenyl being generally more preferred.

The term "aryl" includes such rings having zero to three substituents (preferably 0–2 substituents). When substituted, the aryl ring will contain one to three groups independently selected from alkyl, halogen, perfluoroalkyl, alkenyl, alkynyl, nitro, cyano, haloalkoxy, —OR, —SR, —NRR', —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', phenyl, 3 to 6 membered heteroaryl or heterocyclo, and $C_{3-7}$cycloalkyl, wherein R and R' are independently selected from hydrogen, alkyl, alkenyl, phenyl, benzyl, phenylethyl, $C_{3-7}$cycloalkyl, or 3 to 6 membered heterocyclo and heteroaryl, and R" is alkyl, alkenyl, phenyl, benzyl, phenylethyl, $C_{3-7}$cycloalkyl, and/or 3 to 6 membered heterocyclo or heteroaryl. Additionally, two substituents attached to an aryl, particularly a phenyl group, may join to form a further ring including a spiro ring or a fused ring, e.g., spiro-cyclopentyl or fused cyclohexenyl, or fused heteroaryl or heterocyclo. When an aryl is substituted with a further ring, such ring in turn may be substituted with one to two $C_{0-4}$alkyl optionally substituted with (or linked to) one to two of halogen, $CF_3$, $OCF_3$, alkenyl, nitro, cyano, keto (=O), hydroxy, alkoxy, SH, S(alkyl), $NH_2$, NH(alkyl), N(alkyl)$_2$, $CO_2H$, $CO_2$(alkyl), C(=O)H, and/or C(=O)alkyl.

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms, provided that the total number of heteroatoms in each ring is four or less, and further provided that the ring contains at least one carbon atom and no two adjacent heteroatoms are simultaneously selected from —O— and —S—. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to three substituents independently selected from alkyl, halogen, perfluoroalkyl, alkenyl, alkynyl, nitro, cyano, haloalkoxy, =O, =NR, —OR, —SR, —NRR', —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', aryl, (aryl)alkyl, heteroaryl, (heteroaryl)alkyl, heterocyclo, (heterocyclo)alkyl, cycloalkyl and/or (cycloalkyl)alkyl, wherein R and R' are independently selected from hydrogen, alkyl, alkenyl, phenyl, benzyl, phenylethyl, $C_{3-7}$cycloalkyl, and 3 to 6 membered heterocyclo or heteroaryl, and R" is alkyl, alkenyl, phenyl, benzyl, phenylethyl, $C_{3-7}$cycloalkyl, or 3 to 6 membered heterocyclo or heteroaryl. The term "heterocyclo" also includes such rings having a phenyl ring fused thereto or having a carbon-carbon bridge of 3 to 4 carbon atoms. Additionally, when a heterocyclo is substituted with a further ring, such ring in turn may be substituted with one to two $C_{0-4}$alkyl optionally substituted with (or linked to) one to two of halogen, $CF_3$, $OCF_3$, alkenyl, nitro, cyano, keto (=O), hydroxy, alkoxy, SH, S(alkyl), $NH_2$, NH(alkyl), N(alkyl)$_2$, $CO_2H$, $CO_2$(alkyl), C(=O)H, and/or C(=O)alkyl.

Exemplary monocyclic groups include oxiranyl, aziridinyl, pyrrolidinyl, midazolinyl, imidazolidinyl, pyrazolidinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, tetrahydropyranyl, morpholinyl, thiamorpholinyl, and the like. Exemplary bicyclic heterocyclo groups include quinuclidinyl.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms, provided that the total number of heteroatoms in each ring is four or less, each ring has at least one carbon atom, and no two adjacent heteroatoms are simultaneously selected from —O— and —S—. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring, but the other fused ring or rings may be aromatic or non-aromatic. The heteroaryl group may be attached at any available nitrogen or carbon atom of any ring. The heteroaryl ring system may contain zero to three substituents (preferably 0–2 substituents), selected from $C_{0-6}$alkyl optionally substituted with (or linked to) one to two of halogen, perfluoroalkyl, alkenyl, alkynyl, nitro, cyano, haloalkoxy, keto (=O), —OR, —SR, —NRR', —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', phenyl, 3 to 6 membered heteroaryl or heterocyclo, and/or $C_{3-7}$cycloalkyl, wherein R and R' are independently selected from hydrogen, alkyl, alkenyl, phenyl, benzyl, phenylethyl, $C_{3-7}$cycloalkyl, and 3 to 6 membered heterocyclo or heteroaryl, and R" is alkyl, alkenyl, phenyl, benzyl, phenylethyl, $C_{3-7}$cycloalkyl, and/or 3 to 6 membered heterocyclo or heteroaryl. Additionally, when a heteroaryl is substituted with a further ring, such ring in turn may be substituted with one to two $C_{0-4}$alkyl optionally substituted with (or linked to) one to two of halogen, CF$_3$, OCF$_3$, alkenyl, nitro, cyano, keto (=O), OH, O(alkyl), phenyloxy, benzyloxy, SH, S(alkyl), NH$_2$, NH(alkyl), N(alkyl)$_2$, CO$_2$H, CO$_2$(alkyl), C(=O)H, and/or C(=O)alkyl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, indazolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups, as appropriate.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydroabietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309–396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard,atpp. 113–191 (1991);

c) H. Bundgaard, *Advanced Drug Delivery Reviews*, Vol. 8, p. 1–38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of salvation are generally known in the art.

Methods of Preparation

The inventive compounds may be prepared by methods such as those illustrated in the following Schemes I to VII. Starting materials are commercially available or can be readily prepared by one of ordinary skill in the art, and/or modifications can be made to the methods of Schemes I to VII by one skilled in the art, using known methods. For all of the schemes and compounds, the groups $R_1$, $R_2$, $R_4$, $R_6$ and $R_7$ are as described herein for a compound of formula I, unless otherwise indicated, and appropriate starting materials may be selected by one skilled in the field having the desired groups. Solvents, temperatures, pressures, and other reaction conditions may readily be selected as appropriate by one of ordinary skill in the art. For example, in these schemes chlorinating agents may include phosphorous oxychloride, catalytic agents may include metals such as Pd, and solvents may be selected from 1,2-dichlorobenzene, methylene chloride, DMF, alcohols, ethers, THF, dioxane, acetonitrile, water, mixtures of ethers and water, and the like.

"Cross-coupling" or coupling reactions as used in the schemes and examples may include all cross-coupling methods known by those skilled in the art. Such methods include Stille-type coupling (reacting a vinyl or aromatic triflate, bromide or iodide with a tin), Suzuki-type coupling (reacting a zinc, magnesium or boronate derivative catalyzed by palladium(O), palladium(II), nickel(O) or nickel (II)), Heck coupling, and Sonogashira coupling. Copper iodide, lithium chloride, zinc chloride, triphenylarsine, tris (2-furyl)phosphine or tris(2,4,6-trimethoxyphenyl)-phosphine advantageously may also be added. When a boronic acid derivative is used, the reaction may proceed in the presence of an inorganic base such as sodium carbonate or potassium phosphate or carbonate. The cross-coupling reactions are performed in an inert organic solvent.

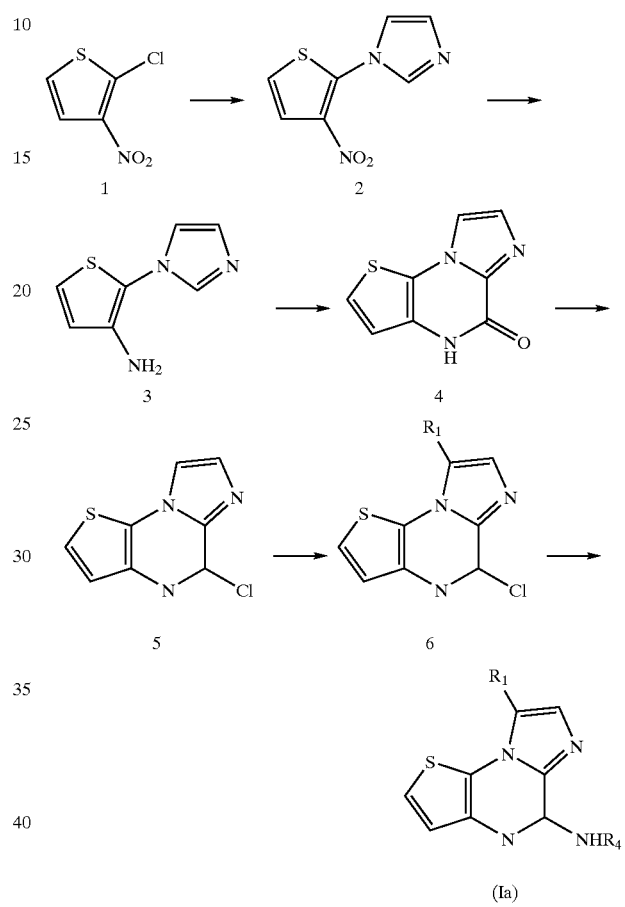

Compounds 5 can be prepared from 2-chloro-3-nitro-thiophene I by a route established in the literature for making imidazo[1,2-a]quinoxalines. (See *J. Med. Chem.*, Vol. 34 (1991) at p. 2671). For example, 2-chloro-3-nitro-thiophene 1 can be converted to 2 upon treatment with imidazole in DMF; compounds 2 can be hydrogenated in a solvent such as MeOH to provide 3; compounds 3 can be cyclized to 4 upon treatment in o-dichlorobenzene with 1,1'carbonyldiimidazole; and compounds 4 can be converted to 5 upon treatment with N,N-diethylaniline and POCl$_3$.

Compounds 6 wherein $R_1$ is bromo or chloro can be prepared from compounds 5 by halogenation with N-chlorosuccinimide or N-bromosuccinimide in a solvent such as THF. Compounds of formula (Ia) can be prepared from compounds 6 by aminolysis with an appropriate alkylamine (NH$_2$R$_4$) in a solvent such as THF.

Scheme II

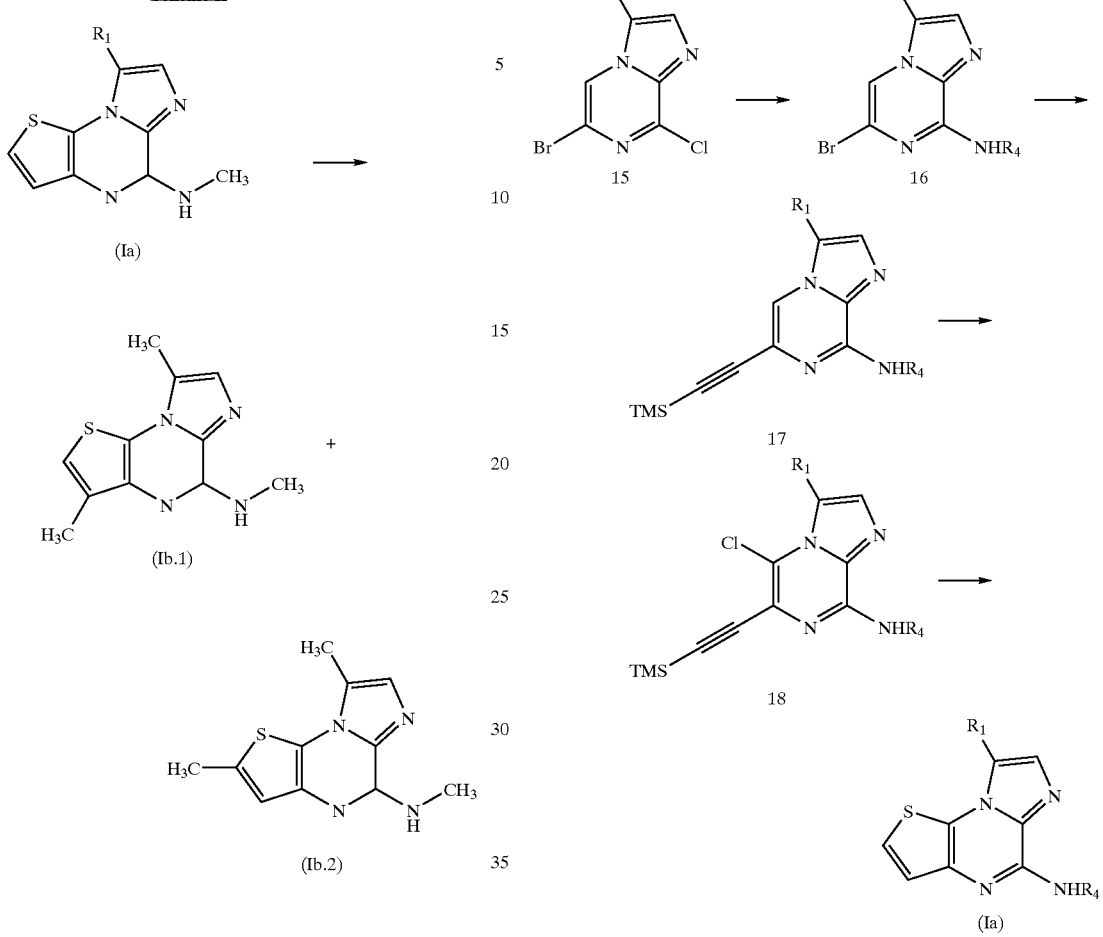

Compounds (Ia) (wherein $R_1$ is $CH_3$) can serve as a starting point for further functionalization of the thienoimidazopyrazine core structure. For example, compounds (Ib.1) and (Ib.2) can be prepared from (Ia) (wherein $R_1$ is $CH_3$) via lithiation followed by iodomethane quenching.

Scheme III

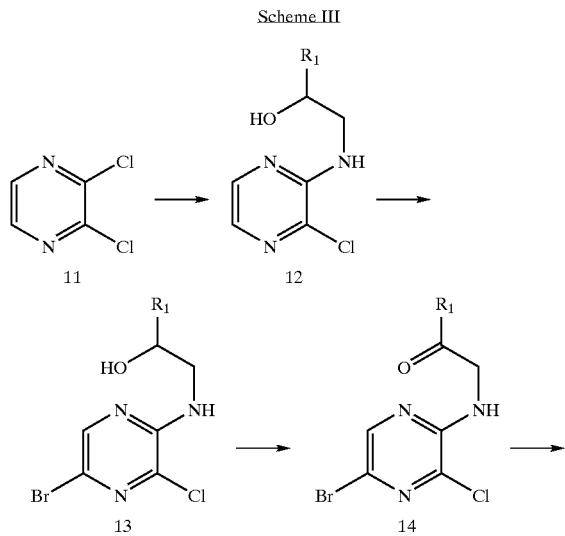

Scheme III shows an alternative route to Scheme I for making compounds of formula (Ia). Compounds of formula (Ia) can be prepared by cyclization of chloro compounds 18, e.g., upon treatment with $Na_2S.9H_2O$ in a solvent such as DMF. Chloro compounds 18 can be prepared from compounds 17 by chlorination with N-chlorosuccinimide in THF. Alkynes 17 can be prepared by performing Sonogashira coupling with (trimethylsilyl)acetylene of compounds 16, which in turn can be prepared from compounds 15 by selective aminolysis at the chlorine atom.

Imidazopyrazines 15 can be readily synthesized from dichloropyrazine II by a minor modification of a literature procedure. (See *J. Med. Chem.* Vol. 26 (1983), at pp. 357–36.) For example, dichloropyrazine 11 upon treatment with 1-amino-2-propanol affords compounds 12; compounds 12 can be brominated with NBS to form compounds 13; compounds 13 can be converted to 14 upon treatment with DMSO/oxalyl chloride, followed by addition of TEA; and compounds 14 can be cyclized to imidazopyrazines 15 when treated with trifluoroacetic anhydride/trifluoroacetic acid.

Scheme IV

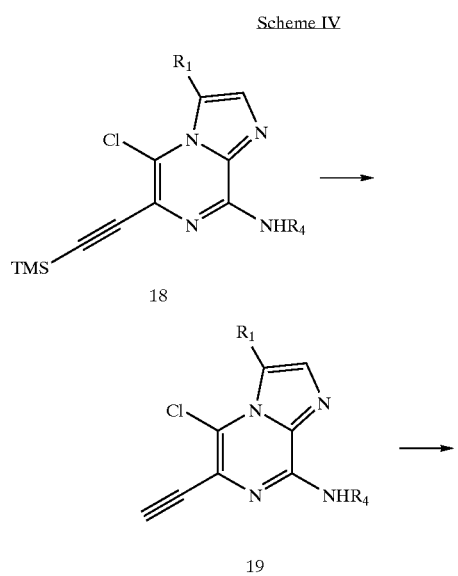

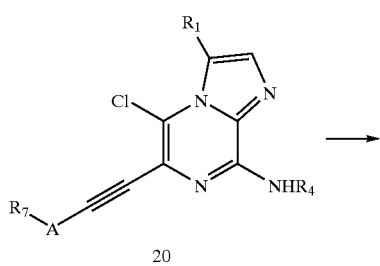

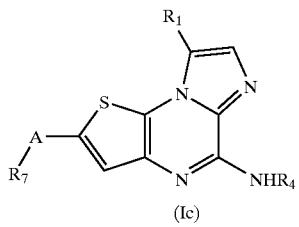

Substituted thienoimidazopyrazines (Ic) can be prepared from compounds 18 (Scheme III), via desilation to afford alkynes 19. Coupling 19 with various aryl or heteroaryl halides provides substituted chloroalkynes 20 which can be cyclized to compounds of formula (Ic) by treatment with $Na_2S \cdot 9H_2O$ in a solvent such as DMF. (See *J. Chem. Research*, (1985) at p. 1682).

Scheme V

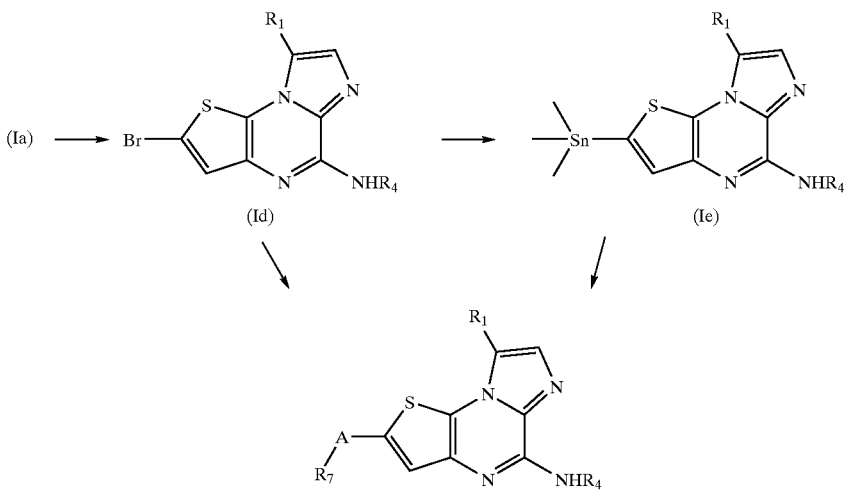

Alternatively, various substituted thienoimidazopyrazines (Ic) can be prepared from compounds (Ia) upon bromination of (Ia) with NBS in chloroform to form compounds (Id). Compounds (Id) can be coupled with various aryl or heteroaryl stannanes and boronic acids to directly form compounds (Ic). Alternatively, bromides (Id) can be first stannylated to compounds (Ie) and then compounds (Ie) may be coupled with various aryl or heteroaryl halides or triflates under Stille conditions to form compounds of formula (Ic). If the molecule contains protected functional groups, then appropriate protocols are employed to remove the protection groups. For example, when $NHR_4$ comprises a Boc-protected amine, removal of the Boc group may be effected using $TFA/CH_2Cl_2$.

Scheme VI

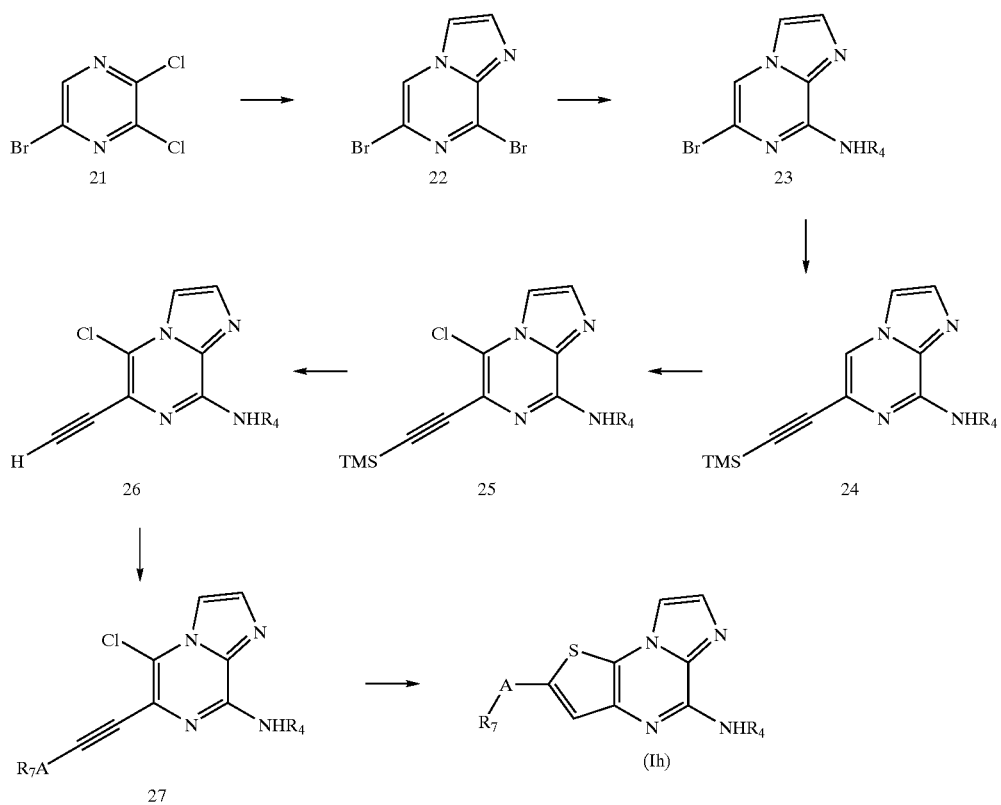

Scheme VI shows methods similar to those in Schemes III and IV for making compounds of Formula (I) where $R_1=H$, by starting from dibromide 22. Dibromide 22 was obtained from the condensation of chloroacetaldehyde and aminopyrazine 21 by employing a procedure described in *Biorganic & Medicinal Chemistry*, Vol. 7, (1999), at p. 1059.

Scheme VII

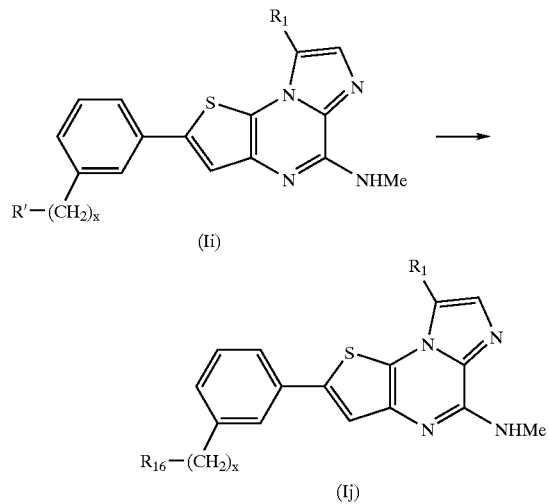

Compounds of formula (Ia) through (Ih) prepared as described in Schemes I through VI can be further elaborated into multiple final products applying techniques known in the field. As a non-limiting illustration, compounds of formula (Ii) containing R' can be further elaborated to form compounds of formula (Ij). For example, where R' is Br, compounds of (Ii) can be converted into compounds of (Ij) where $R_{16}$ is $NR_{17}R_{18}$ by aminolysis. Alternatively, where R' is COOR", synthesis of (Ij) where $R_{16}$ is $CONHR_{17}$ can likewise be achieved via aminolysis. Compounds (Ii) can be prepared as described above in Schemes IV and V.

Preferred Compounds

Preferred compounds are compounds of formula (I),

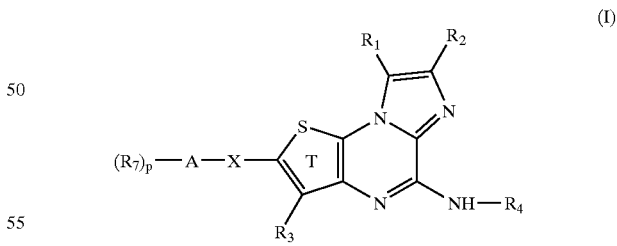

and pharmaceutically-acceptable salt, hydrate or prodrug thereof, in which:
$R_1$ is methyl;
$R_2$ is hydrogen;
$R_3$ is hydrogen or lower alkyl;
$R_4$ is $-(CR_5R_6)_m$-Z;
$R_5$ and $R_6$ at each occurrence are independently selected from hydrogen, alkyl, substituted alkyl, amino, alkylamino, substituted alkylamino, hydroxy, alkoxy, or substituted alkoxy;

R$_7$ at each occurrence is selected independently of each other R$_7$ from alkyl, substituted alkyl, alkenyl, substituted alkenyl, halogen, cyano, —(CR$_{5a}$R$_{6a}$)$_q$—OR$_{8a}$, —(CR$_{5a}$R$_{6a}$)$_q$—NR$_8$R$_9$, —(CR$_{5a}$R$_{6a}$)$_q$—NR$_{8a}$SO$_2$(C$_{1-4}$alkyl), —(CR$_{5a}$R$_{6a}$)$_q$—SO$_2$NR$_8$R$_9$, —(CR$_{5a}$R$_{6a}$)$_q$—NR$_{8a}$C(=O)R$_{9a}$, —(CR$_{5a}$R$_{6a}$)$_q$—NR$_{8a}$CO$_2$R$_{9a}$, —(CR$_{5a}$R$_{6a}$)$_q$—C(=O)R$_{8a}$, —(CR$_{5a}$R$_{6a}$)$_q$—CO$_2$R$_{8a}$, —(CR$_{5a}$R$_{6a}$)$_q$—C(=O)NR$_8$R$_9$, —(CR$_{5a}$R$_{6a}$)$_q$—OC(=O)NR$_8$R$_9$, five or six membered optionally substituted heterocycle or heteroaryl, or (heterocylo)alkyl, or when A is an unsaturated heterocycle, one of R$_7$ may be keto (=O), or when A is absent, R$_7$ may be hydrogen;

X is a bond, —CH=CH—, or —C≡C—;

A is a bond, phenyl, five or six membered heteroaryl;

Z is selected from hydrogen, methyl, hydroxy, —NHC(=O)R$_{13}$, —NHCO$_2$R$_{13}$, and —NR$_{14}$R$_{15}$;

R$_8$ and R$_9$ are independently selected from hydrogen, alkyl, substituted alkyl, cycloalkyl, heterocycle, aryl and heteroaryl;

R$_{12}$ is hydrogen or lower alkyl;

R$_{13}$ is alkyl, substituted alkyl, cycloalkyl, heterocyclo, aryl or heteroaryl;

R$_{14}$ and R$_{15}$ are independently selected from hydrogen, alkyl, substituted alkyl, cycloalkyl, heterocycle, aryl and heteroaryl;

M and q are independently 0, 1, 2, 3, or 4; and p is 0, 1, 2, or 3, except when A is absent, then p is 1.

More preferred are compounds of formula (I), as immediately defined above, wherein: R$_4$ is —(CH$_2$)$_m$-Z;

Z is hydrogen, methyl, hydroxy, —NH$_2$, —NH(C$_{1-4}$alkyl), —NHCO$_2$(C$_{1-4}$alkyl), or —N(C$_{1-4}$alkyl)$_2$; and A is attached to X and thienyl ring T at any available carbon or nitrogen atom of A and is selected from phenyl, pyridyl, pyrimidinyl, pyrazinyl, pyridazinyl, imidazolyl, pyrazolyl, thienyl, thiazolyl, furyl, pyrrolyl, pyranyl, dihydropyridyl, and

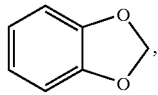

wherein A has 0 to 3 substituents selected from R$_7$.

Those skilled in the field will recognize that R$_7$ groups when present as a substituent on ring "A" may be selected from those groups recited above as well as possible equivalents known in the field. However, preferably R$_7$ substituents are selected from the groups consisting of:

a) hydrogen, cyano, trifluoromethyl, halogen, hydroxy, —(CR$_{5a}$R$_{6a}$)$_q$—O(C$_{1-4}$alkyl), —(CR$_{5a}$R$_{6a}$)$_q$—NH$_2$, —(CR$_{5a}$R$_{6a}$)$_q$—NH(C$_{1-4}$alkyl), —(CR$_{5a}$R$_{6a}$)$_q$—NH(C$_{1-4}$aminoalkyl), —(CR$_{5a}$R$_{6a}$)$_q$—NH(C$_{1-4}$hydroxyalkyl), —(CR$_{5a}$R$_{6a}$)$_q$—N(C$_{1-4}$alkyl)$_2$, , —(CR$_{5a}$R$_{6a}$)$_q$—NH(CH$_2$)$_r$(alkylamino), —(CR$_{5a}$R$_{6a}$)$_q$—NH(CH$_2$)$_r$(pyrrolidinyl), —(CR$_{5a}$R$_{6a}$)$_q$—NHC(=O)H, —(CR$_{5a}$R$_{6a}$)$_q$—NHC(=O)C$_{1-4}$alkyl, —(CR$_{5a}$R$_{6a}$)$_q$—C(=O)C$_{1-4}$alkyl, —(CR$_{5a}$R$_{6a}$)$_q$—C(=O)(CH$_2$)$_r$(Morpholinyl), —(CR$_{5a}$R$_{6a}$)$_q$—C(=O)(CH$_2$)$_r$(imidazolyl), —(CR$_{5a}$R$_{6a}$)$_q$—C(=O)(CH$_2$)$_r$(alkylamino), —(CR$_{5a}$R$_{6a}$)$_q$—C(=O)NH$_2$, —(CR$_{5a}$R$_{6a}$)$_q$—CO$_2$H, —(CR$_{5a}$R$_{6a}$)$_q$—CO$_2$(C$_{1-4}$alkyl), —(CR$_{5a}$R$_{6a}$)$_q$—OC(=O)NH$_2$, —(CR$_{5a}$R$_{6a}$)$_q$—OC(=O)NH(C$_{1-4}$alkyl), and —(CR$_{5a}$R$_{6a}$)$_q$—OC(=O)N(C$_{1-4}$alkyl)$_2$;

b) heterocyles or heteroaryls including morpholinyl, piperazinyl, pyrrolidinyl,

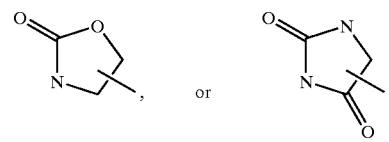

in turn optionally substituted with one to three C$_{1-4}$alkyl, hydroxyalkyl, amino, alkylamino, and/or keto; and c) C$_{1-6}$alkyl optionally substituted with one to two of hydroxy, cyano, halogen, —NH$_2$, —NH(C$_{1-4}$alkyl), —NH(C$_{1-4}$aminoalkyl), —NH(C$_{1-4}$hydroxyalkyl), —N(C$_{1-4}$alkyl)$_2$, , —NH(C=O)H, —NH(C=O)C$_{1-4}$alkyl, —NHSO$_2$(C$_{1-4}$alkyl), —C(=O)NH$_2$, —C(=O)(morpholinyl), —CO$_2$H, —CO$_2$(C$_{1-4}$alkyl), heterocycle, and/or heteroaryl said heterocycle or heteroaryl in turn optionally substituted with one to three C$_{1-4}$alkyl, hydroxyalkyl, amino, alkylamino, C(=O)H, C(=O)C$_{1-4}$alkyl, and/or keto.

Most preferred compounds include those having the formula:

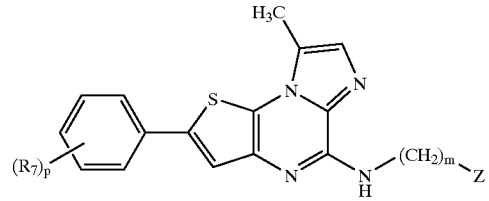

and pharmaceutically-acceptable salts, hydrates, or prodrugs thereof, in which:

Z is hydrogen, methyl, hydroxy, —NH$_2$, —NH(C$_{1-4}$alkyl), —NHCO$_2$(C$_{1-4}$alkyl) or —N(C$_{1-4}$alkyl)$_2$;

R$_7$ is C$_{1-6}$alkyl optionally substituted with one to two of hydroxy, cyano, halogen, —NH$_2$, —NH(C$_{1-4}$alkyl), —NH(C$_{1-4}$aminoalkyl), —NH(C$_{1-4}$hydroxyalkyl), —N(C$_{1-4}$alkyl)$_2$, , —NH(C=O)H, —NH(C=O)C$_{1-4}$alkyl, —NHSO$_2$(C$_{1-4}$alkyl), —C(=O)NH$_2$, —C(=O)(morpholinyl), —CO$_2$H, —CO$_2$(C$_{1-4}$alkyl), and/or a heterocycle or heteroaryl selected from morpholinyl, pyrazolyl, imidazolyl, piperazinyl, and pyrrolidinyl, said heterocycle or heteroaryl in turn optionally substituted with one to three C$_{1-4}$alkyl, hydroxyC$_{1-4}$alkyl, amino, C$_{1-4}$alkylamino, C(=O)H, C(=O)C$_{1-4}$alkyl, and/or keto;

m is 1, 2, 3 or 4;

q is 0 1, 2, 3 or 4 and p is 1 or 2.

Most preferred compounds include compounds having the formula:

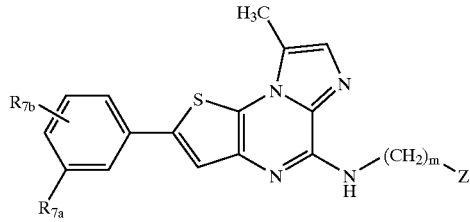

wherein

R$_{7a}$ is a) —(CR$_{5a}$R$_{6a}$)$_q$—NR$_8$R$_9$, and

R$_{5a}$ and R$_{6a}$ at each occurrence are selected from hydrogen, methyl, hydroxy, amino or alkylamino;

$R_8$ is hydrogen or alkyl;
$R_9$ is alkyl substituted with —C(=O)NH$_2$ or —C(=O)NH(alkyl);
q is 0, 1 or 2 (especially 1 or 2)

b) —(CR$_{5a}$R$_{6a}$)$_q$—CO$_2$R$_{8a}$
$R_{5a}$ and $R_{6a}$ at each occurrence are selected from hydrogen, methyl, hydroxy, amino or alkylamino;
$R_{8a}$ is alkyl;
q is 0, 1 or 2 (especially 1 or 2)

c) —(CR$_{5a}$R$_{6a}$)$_q$—C(=O)NR$_8$R$_9$
$R_{5a}$ and $R_{6a}$ at each occurrence are selected from hydrogen, methyl, hydroxy, amino or alkylamino;
$R_8$ is hydrogen;
$R_9$ is alkyl;
q is 0, 1 or 2 (especially 1 or 2)

d) heterocyclo or (heterocyclo)alkyl especially where heterocyclo is

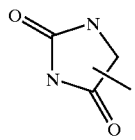

$R_{7b}$ is absent or halo (especially fluorine).

Utility

The compounds and compositions of this invention are useful in treating conditions that are characterized by the activity of IKK, release of NF-κB, and/or enhanced levels of TNF-α. The term "treating" or "treatment" denotes prevention, partial alleviation, or cure of the disease or disorder or its symptoms or consequences. Inhibition or suppression of IKK, NF-κB and/or TNF-α may occur locally, for example, within certain tissues of the subject, or more extensively throughout the subject being treated for such a disease. Inhibition or suppression of IKK, NF-κB and/or TNF-α may occur by one or more mechanisms, e.g., by inhibiting or suppressing any step of the pathway(s). The term "NF-α-associated condition" refers to diseases that are characterized by release of NF-κB from the cytoplasm (e.g., upon phosphorylation of IκB). The term "TNF-α-associated condition" is a condition characterized by enhanced levels of TNF-α. In the instant specification, the term "NF-κB-associated condition" will include a TNF-α-associated condition but is not limited thereto as NF-κB is involved in the activity and upregulation of other pro-inflammatory proteins and genes. The term "inflammatory or immune disease" is used herein to encompass IKK-associated conditions, NF-κB-associated conditions, and TNF-α-associated conditions, e.g., any condition, disease, or disorder that is associated with activity of IKK, NF-κB and/or enhanced levels of TNF-α.

The inventive compounds and compositions are useful for treating a variety of diseases including, but not limited to, treatment of transplant rejections (e.g., kidney, liver, heart, lung, pancreas, bone marrow, cornea, small bowel, skin allografts, skin homografts and heterografts, etc.); rheumatoid arthritis, psoriatic arthritis, multiple sclerosis, inflammatory bowel disease (such as Crohn's disease and ulcerative colitis); antiviral and autoimmune diseases including herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, and autoimmune polyglandular disease (also known as autoimmune polyglandular syndrome); Alzheimer's, Parkinson's, and Creutzfeldt-Jacob diseases; septic shock; hematopoiesis; inflammatory diseases such as osteoarthritis, acute pancreatitis, and chronic pancreatitis; inflammatory disorders of the central nervous system, including HIV encephalitis, cerebral malaria, and meningitis, atherosclerosis, and ataxia telangiectasis; respiratory allergies including asthma, hayfever, and allergic rhinitis; fungal infections such as mycosis fungoides; and psoriasis, glomerulonephritis, serum sickness, lupus (systematic lupus erythematosis), urticaria, scleraclerma, contact dermatitis, dermatomyositis, alopecia, atopic eczemas, and ichthyosis. The term "inflammatory or immune disease" as used herein includes all of the above-referenced diseases and disorders.

The inventive compounds are also effective in treating oncological diseases, in treating cancer and tumors, such as solid tumors, lymphomas and leukemia, and in particular, breast cancer, prostate cancer, and Hodgkin's lymphoma.

The present invention thus provides methods for treating such conditions, comprising administering to a subject in need thereof an effective amount of at least one compound of formula I or a salt thereof. Other therapeutic agents such as those described below may be employed in combination with compounds of formula I. In the methods of the present invention, such other therapeutic agent(s) may be administered prior to, simultaneously with, or following administration of the inventive compound(s).

The present invention also provides pharmaceutical compositions capable of treating IKK, NF-κB and/or TNF-α associated conditions, as described above. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like, subject to IKK, NF-κB and/or TNF-α associated conditions.

The inventive compounds and compositions may be employed alone or in combination with each other and/or other suitable therapeutic agents useful in treating IKK, NF-κB and/or TNF-α associated conditions. Exemplary of such other therapeutic agents include corticosteroids, rolipram, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof; and other cancer drugs and treatments, including radiation treatments and daunorubicin.

The above other therapeutic agents, when employed in combination with the compounds of the present invention, may be used, for example, in those amounts indicated in the Physicians' Desk Reference (PDR) or as otherwise determined by one of ordinary skill in the art.

The inventive compounds have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells ($1.4 \times 10^6$/mL, $2.5 \times 10^5$ cells/well) in 180 μL RPMI-1640 was added 10 μL of the test compound in 10% DMSO. Typically, test compound concentrations of 0.1–100 μM were used in the assay. After one hour at 37° C., 10 μL of 1000 ng/mL lipopolysaccharide (LPS from *Salmonella typhosa*, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFα secretion model. Likewise, assays known in the field are applied to establish the activity of the compounds as inhibitors of IKK, IkB, and/or the NF-κB pathway.

Abbreviations

For ease of reference, the following abbreviations are employed herein, including in the methods of preparation hereinbefore and in the Examples that follow:

Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DMF=dimethyl formamide
DMSO=dimethyl sulfoxide TEA=triethylamine
TFA=trifluoroacetic acid
THF=tetrahydrofuran
KOH=potassium hydroxide
$K_2CO_3$=potassium carbonate
$POCl_3$=phosphorous oxychloride
KOtBu=potassium t-butoxide
HOBt=1-hydroxybenzotriazole hydrate
NaH=sodium hydride
NaOH=sodium hydroxide
$Na_2S_2O_3$=sodium thiosulfate
Pd=palladium
min.=minute(s)
L=liter
mL=milliliter
μL=microliter
g=gram(s)
mg=milligram(s)
mol=moles
mmol=millimole(s)
meq=milliequivalent
RT=room temperature
ret. t.=HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point The following Examples illustrate embodiments of the invention and are not intended to limit the scope of the claims. In the following Examples, anhydrous reactions were performed under an atmosphere of nitrogen or argon using either commercially available dry solvents or freshly distilled solvents. Column chromatography was performed using EM Science silica gel 60 with the designated solvent system as eluant. HPLC purification was conducted using a Shimadzu LC8A with YMC S5 ODS or xTerra MS $C_{18}$ columns. HPLC purity determinations were done using either an HP 1090 DR5 with a diode array detector and a Waters Nova-Pak $C_{18}$ column, or a Shimadzu LC-10AS with a SPD-10AV UV-V detector and Waters xTerra $C_{18}$ column. Melting points were determined in an open capillary tube with a Thomas-Hoover melting point apparatus.

$^1$H-NMR spectra were recorded in DMSO (δ=2.50 ppm) using a 500 MHZ instrument (unless otherwise stated) and chemical shifts are expressed in parts per million (ppm or δ) with the solvent in use as an internal standard. Coupling constants are given in Hertz, and multiplets are designated as follows: singlet (s), doublet (d), triplet (t), quartet (q), multiplet (m), broad (br), and apparent (app).

Low resolution mass spectra were determined with a Finnigan Matt TSQ-7000 or SSQ-700, or with a Shimadzu LC-10AS coupled with Waters Micromass ZQ. HRMS were determined with a Finnigan Matt 900.

Examples for Preparation of Intermediate Halide-Coupling Components ($R_7$-A-Br and $R_7$-A-I)

Preparation 1

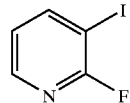

(P1)

2-Fluoro-3-iodopyridine (P1) was prepared from 2-fluoropyridine according to the procedure in *Heterocycles*, Vol. 35 (#1) (1993), at p. 151.

Preparation 2

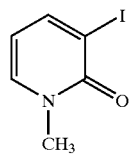

(P2)

A mixture of 2-fluoro-3-iodopyridine (1.035 g, 4.6415 mmol) and iodomethane (3.0 mL, 48.190 mmol) in a pressure tube was heated at 70° C. for 20.5 h. The reaction mixture was allowed to cool to rt, and the white suspension was filtered and washed with EtOAc and exposed to vacuum to afford the N-methyl pyridinium salt (284.1 mg). This salt was treated with NaOH solution (3.0 mL, 1.0 M/$H_2O$) and stirred at rt for 30 min. and at 70° C. for 30 min. The reaction mixture was cooled to rt, diluted with brine and extracted with EtOAc. The organic layer was dried ($MgSO_4$), filtered, and evaporated in vacuo. A silica gel mesh of the crude material was prepared and submitted to flash chromatography (EtOAc) to afford pyridone P2 as a yellow oil (165 mg, 15.1%). $^1$H NMR: 8.08 (dd, J=7.3, 1.8, 1H), 7.77 (dd, J=6.6, 2.1, 1H), 6.03 (app t, J=6.9, 1H), 3.48 (s, 3H). (ESI) m/z $(M+H)^+$=236.08.

Preparation 3

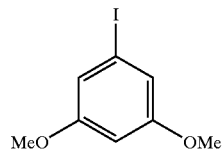

(P3)

Water (15.0 mL), concentrated HCl (10 mL, ~37%) and 3,5-dimethoxyaniline (4.3725 g, 28.5775 mmol) were mixed sequentially and the heterogeneous mixture was stirred for 50 min. The mixture was then cooled to 0° C. and treated with an aqueous solution of $NaNO_2$ (2.6164 g/11 mL, 37.91 mmol) over 7 min. After the reaction mixture was stirred for 15 min, it was slowly added to a beaker containing a cooled (0° C.) aqueous (10.0 mL) solution of KI (10.01 g, 60.30 mmol) over 10 min. The cooling bath was removed 13 min. later and the reaction rmixture was allowed to thaw to rt over 1 hr. It was then heated to 95° C. for about 30 min, and during this heating the side of the beaker was washed with water (10 mL). The mixture was allowed to cool to rt and extracted with ether. The organic phase was washed with water, a solution of NaOH/$Na_2SO_3$ (5 g of $Na_2SO_3$ dissolved in 50 mL of 1.0 M NaOH/$H_2O$) and brine. It was dried (MgSO$_4$), filtered and evaporated in vacuo. A silica gel mesh of the crude material was prepared and submitted to flash chromatography (5% EtOAc/hexanes) to afford iodide P3 as a white solid (3.979 g, 52.6%). $^1$H NMR (CDCl$_3$, δ=7.26 ppm; 500 MHZ): 6.86 (d, J=2.4, 2H), 6.40 (t, J=2.3, 1H), 3.76 (s, 6H).

Preparation 4

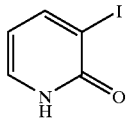
(P4)

NaOH (8.0 mL, 1.0 N/H$_2$O) was added to a THF (10.0 mL) solution of the fluoropyridine P1 (1.6281 g, 7.30 mmol), and the biphasic mixture was stirred at 80° C. for 91.5 h; during this time most of the THF evaporated. The reaction mixture was cooled to rt and the remaining solvent was removed in vacuo. A silica gel mesh of the crude material was prepared and submitted to flash chromatography (0–20% EtOAc/hexanes) to afford pyridone P4 as an off-white solid (504.4 mg, 31.3%). $^1$H NMR: 11.94 (br s, 1H), 8.10 (dd, J=7.0, 1.8, 1H), 7.45 (dd, J=6.5, 1.9, 1H), 5.99 (app t, J=6.8, 1H). (ESI) m/z (M+H)$^+$=221.97.

Preparation 5

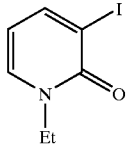
(P5)

Potassium tert-butoxide (1.3 mL, 1.0 M/THF) and ethyliodide (300 uL, 3.751 mmol) were added to a THF (3.0 mL) solution of pyridone P4 (256.7 mg, 1.1619 mmol). The resulting clear solution was stirred at rt for 21.5 h. The reaction mixture was diluted with sat'd NH$_4$Cl solution and extracted with EtOAc (2×). The organic layer was washed with brine, dried (MgSO$_4$), filtered and evaporated in vacuo. A silica gel mesh of the crude material was prepared and submitted to flash chromatography (60% EtOAc/hexanes) to afford pyridone P5 as a yellow oil (268.4 mg, 92.8%). $^1$H NMR: 8.08 (dd, J=7.0, 1.9, 1H), 7.78 (dd, J=6.8, 1.9, 1H), 6.05 (app t, J=6.9, 1H), 3.95 (q, J=7.1, 2H), 1.21 (t, J=7.0, 3H). (ESI) m/z (M+H)$^+$=249.94.

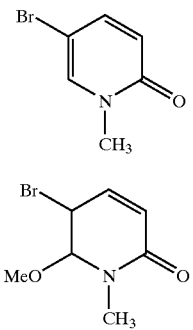
(P6)

(P6a)

N-Bromosuccinimide (1.7976 g, 16.472 mmol) was added to a MeOH (15.0 mL) solution of commercially-available N-methyl-2-pyridone (1.02 g, 9.347 mmol). The reaction flask was covered with aluminum foil and stirred at rt for 18 h. The solvent was removed in vacuo, and a silica gel mesh of the crude material was prepared and submitted to flash chromatography (30–70% EtOAc/hexanes) to retrieve the major component P6a as a colorless oil (965.4 mg). A fraction was also retrieved that contained bromide P6 and its C$_3$-Br regioisomer in ~4.1/5.3 mole ratio (647.4 mg, colorless oil). $^1$H NMR of P6a: 6.78 (ddd, J=9.5, 5.7, 1.7, 1H), 5.93 (d, J=9.4, 1H), 5.10 (dd, J=5.5, 1.6, 1H), 4.97 (app t, J=1.5, 1H), 3.37 (s, 3H), 3.01 (s, 3H). (ESI) m/z (M+H)$^+$=220.07/222.07.

NaN(TMS)$_2$ (3.0 mL, 1.0 M/THF) was added dropwise to a THF (10.0 mL) solution of bromide P6a (960 mg, 4.3624 mmol) over 1 hr. Each drop caused the appearance of a brown suspension that disappeared slowly. The reaction mixture was stirred for an additional 30 min. and quenched with sat'd NH$_4$Cl solution (0.5 mL). The organic layer was separated and evaporated in vacuo. A silica gel mesh of the crude material was prepared and submitted to flash chromatography (EtOAc) to afford bromide P6 as a faint yellow solid (651 mg, a two step combined yield of 37%). $^1$H NMR: 8.03 (d, J=2.8, 1H), 7.52 (dd, J=9.6, 2.9, 1H), 6.34 (d, J=9.4, 1H), 3.40 (s, 3H). (ESI) m/z (M+H)$^+$=188.02/190.02.

Preparation 7

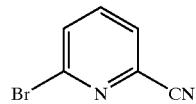
(P7)

DMF (10 mL) was added into a mixture of commercially-available 2,6-dibromopyridine (1.0470 g, 4.4194 mmol) and CuCN (402 mg, 4.4886 mmol). The reaction mixture was refluxed for 23 h. It was then cooled to rt, diluted with EtOAc and the suspension was filtered. The volatile component of the filtrate was removed in vacuo. A silica gel mesh of the crude material was prepared and submitted to flash chromatography (10–15% EtOAc/hexanes) to afford bromopyridine P7 as a white solid (126.5 mg, 15.6%). $^1$H NMR (CDCl$_3$, δ=7.26 ppm; 500 MHZ): 7.74 (dd, J=7.7, 1.9, 1H), 7.71 (app t, J=7.3, 1H), 7.68 (dd, J=7.0, 2.1, 1H). (ESI) m/z (M+H)$^+$=183.04/185.04.

Preparations 8 and 9

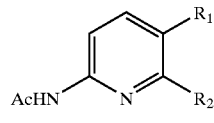

P8: R$_1$ = Br, R$_2$ = H
P9: R$_1$ = H, R$_2$ = Br

Triethylamine (0.650 mL, 4.6635 mmol) and acetic anhydride (1.30 mL, 13.7780 mmol) were added into a THF (6.0 mL) solution of the appropriately-substituted aminopyridine (507.9 mg, 2.94 mmol). The reaction mixture was stirred at 65° C. for 20 h, cooled to rt, and the volatile component removed in vacuo. A silica gel mesh of the crude material was prepared and submitted to flash chromatography (10–15% EtOAc/hexanes) to afford the acylated pyridine compounds P8 and P9 as white solids. For P8: 94.4% yield. $^1$H NMR: 10.64 (br s, 1H), 8.41 (dd, J=2.5, 0.6, 1H), 8.06 (d, J=8.9, 1H), 7.98 (dd, J=8.9, 2.5, 1H), 2.09 (s, 3H). For P9: 89.6% yield. $^1$H NMR: 10.79 (br s, 1H), 8.08 (app d, J=8.0, 1H), 7.71 (app t, J=8.0, 1H), 7.31 (app d, J=7.9, 1H), 2.08 (s, 3H). (ESI) m/z (M+H)+=215.01/217.01.

Preparation 10

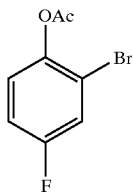
(P10)

A THF (5.0 mL) solution of 2-bromo-4-fluorophenol (200 mg, 1.05 mmol) was treated with TEA (300 uL, 2.152 mmol), acetic anhydride (200 uL, 2.1 mmol) and a catalytic amount of DMAP. The reaction mixture was stirred overnight at rt, diluted with EtOAc, and washed with 1 N HCl, sat'd aqueous NaHCO$_3$ solution and brine. It was then dried (MgSO$_4$), filtered and evaporated in vacuo. Acylated phenol P10 was retrieved as a colorless oil (215.6 mg, 82%).

Preparations 11 and 12

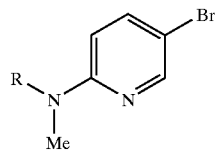

P11: R = H
P12: R = Me

NaN(TMS)$_2$ (4.50 mL, 1.0 M/THF) was added to a THF (5.0 mL) solution of 2-amino-5-bromopyridine (0.5007 g, 2.8939 mmol) and stirred at rt for 10 min. Iodomethane (400 uL, 6.4252 mmol) was added dropwise to the above solution over a few minutes. The reaction mixture was stirred at rt for 5.5 h, diluted with EtOAc, and washed with water and brine. The organic layer was dried (MgSO$_4$), filtered, and evaporated in vacuo. A silica gel mesh of the crude material was prepared and submitted to flash chromatography (20% EtOAc/hexanes) to afford pyridine P11 (light-pink solid, 127.8 mg, 23.6%) and pyridine P12 (light yellow solid, 297 mg, 51.0%). $^1$H NMR of P11: 8.03 (d, J=2.4, 1H), 7.50 (dd, J=8.9, 2.5, 1H), 6.72 (br m, 1H), 6.43 (dd, J=8.9, 0.7, 1H), 2.73 (d, J=4.9, 3H). $^1$H NMR of P12: 8.12 (dd, J 2.5, 0.6, 1H), 7.63 (dd, J=9.2, 2.8 m, 1H), 6.61 (dd, J=9.2, 0.6, 1H), 2.99 (s, 6H).

Preparation 13

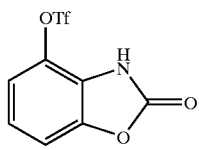
(P13)

Step A:

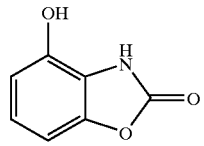
(P13A)

Phenol P13A was prepared from 2-nitroresorcinol according to EP 701907-A1.

Step B:

DMAP (672.6 mg, 5.51 mmol) and trifluoromethanesulfonic anhydride (780 uL, 1.15 mmol) were added into a cooled (0° C.) CH$_2$Cl$_2$ (5.0 mL) solution of phenol P13A (585 mg, 3.87 mmol). The reaction mixture was stirred for 30 min, the bath was removed, and stirring continued for an additional 30 min. The reaction mixture was poured into 1 N HCl and extracted with CH$_2$Cl$_2$. The organic layer was washed with brine, dried (MgSO$_4$), filtered and evaporated in vacuo. A silica gel mesh was prepared from the crude material and submitted to flash chromatography (50–100% CH$_2$Cl$_2$/hexanes–>20–50% EtOAc/CH$_2$Cl$_2$) to afford triflate P13 as a light brown solid (640 mg, 58.1%). $^1$H NMR (MeOH-d4, δ=3.30 ppm; 300 MHZ): 7.35–7.28 (m, 1H), 7.25–7.20 (m, 2H). (ESI) m/z (M+H)+=284.21.

Preparation 14

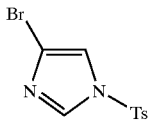
(P14)

Compound P14 was prepared upon tosylation of 4-Bromoimidazole according to the literature procedure described in *J. Org. Chem.*, Vol. 60 (1995), at pp. 2378–2383. $^1$H NMR: 8.40 (d, J=1.5, 1H), 8.05 (d, J=1.5, 1H), 8.01 (m, 2H), 7.54 (d, J=7.9, 2H), 2.42 (s, 3H). (ESI) m/z (M+H)+=300.97/302.97.

Preparation 15

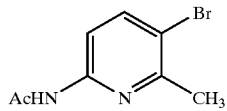
(P15)

Pyridine P15 was prepared from 6-amino-3-bromo-2-methylpyridine according to the procedure described above for making compounds P8 and P9.

Preparation 16

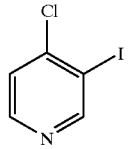
(P16)

Butyllithium (33.0 mL, 1.6 M/hexanes) was added to a cooled (−78° C.) THF (35 mL) solution of diisopropylamine (7.5 mL, 53.51 mmol) and stirred for 45 min. 4-chloropyridine (HCl salt, 3.8763 g, 25.84 mmol) was added in batches over 7 min. and the turbid yellow reaction mixture was stirred vigorously for 2 h. THF (15.0 mL) solution of 12 (6.7560 g, 26.6194 mmol) was added dropwise over 13 min. while shaking manually. After completing the 12 addition, the reaction mixture assumed a pasty texture and a spatula was used to mix it under a nitrogen atmosphere. The cooling bath was removed 70 min. later, and the reaction mixture was allowed to thaw over the next hour. It was quenched with 10% $Na_2S_2O_3$ (50 mL), and extracted with EtOAc (50 mL, 2×). The organic layer was washed with brine, dried ($MgSO_4$), filtered and evaporated in vacuo. A silica gel mesh of the crude material was prepared and submitted to flash chromatography (5–7% EtOAc/hexanes) to afford iodide P16 as a white solid (2.772 g, 44.8%). $^1$H NMR: 8.98 (s, 1H), 8.50 (d, J=5.2, 1H), 7.71 (d, J=5.2, 1H). (ESI) m/z (M+H)$^+$=239.89.

Preparation 17

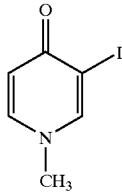

(P17)

A mixture of 4-chloro-3-iodopyridine (P16) (492.9 mg, 2.0586 mmol) and iodomethane (5.0 mL, 80.31 mmol) was heated at 70° C. in a pressure tube for 50 h. The reaction mixture was cooled to rt and the precipitate was filtered, washed with EtOAc and dried in vacuo. The N-methyl pyridinium salt was obtained as an off-white solid (786.9 mg). NaOH solution (5 mL, 1M/$H_2O$) was added to this salt and the resulting heterogeneous mixture was heated at 70° C. for about 2 h. The reaction mixture was cooled to rt and the volatile component removed in vacuo. A silica gel mesh of the crude material was prepared and submitted to flash chromatography (0–20% MeOH/EtOAc) to afford pyridone P17 as a yellow foam (473.5 mg, 97.7%). $^1$H NMR: 8.29 (d, J=2.1, 1H), 7.68 (dd, J=7.5, 2.3, 1H), 6.12 (d, J=7.4, 1H), 3.64 (s, 3H). (ESI) m/z (M+H)$^+$=235.95.

Preparation 18

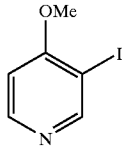

(P18)

A fresh sodium methoxide solution was prepared from sodium (222 mg, 9.6564 mmol) and MeOH (10 mL). 4-Chloro-3-iodopyridine (P16) (1.2071 g, 5.023 mmol) was added in one batch and the reaction mixture was stirred at 75° C. for 6 h. The solvent was removed in vacuo and a silica gel mesh was prepared from the crude material and submitted to flash chromatography (50% EtOAc/hexanes) to afford methoxypyridine P18 as a white crystalline solid (1.0166 g, 85.8%). $^1$H NMR: 8.69 (s, 1H), 8.39 (d, J=5.5, 1H), 7.09 (d, J=5.5, 1H), 3.91 (s, 3H). (ESI) m/z (M+H)$^+$=235.96.

Preparation 19

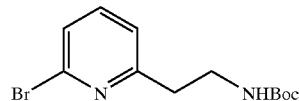

(P19)

$BH_3 \cdot Me_2S$ (2.60 mL of 2.0 M/THF) was added to a THF (3.0 mL) solution of (6-Bromo-pyridin-2-yl)acetonitrile (prepared according to Synlett, Vol. 10 [2000], at p. 1488) (505.6 mg, 2.5661 mmol). The mixture was stirred at rt for 20 min. and heated to 70° C. for 4.5 h. It was cooled to rt, quenched with MeOH, and the volatile component was removed in vacuo to afford a crude product. $Boc_2O$ (644.5 mg, 2.95 mmol) and DMAP (9.9 mg, 0.08 mmol) were added to a THF (7.0 mL) suspension of the above crude product and the heterogeneous mixture was vigorously stirred at rt for 75 min. The solvent was removed in vacuo, and a silica gel mesh of the crude material was prepared and submitted to flash chromatography (20–30% EtOAc/hexanes) to afford pyridine P19 as a faint yellow oil (225.9 mg, a combined yield of 29.2%). $^1$H NMR: 7.66 (app t, J=7.6, 1H), 7.47 (d, J=7.9, 1H), 7.29 (d, J=7.6, 1H), 6.89 (br t, J=5.4, 1H), 3.24 (app q, J=6.7, 2H), 2.81 (t, J=7.2, 2H), 1.36 (s, 9H). (ESI) m/z (M+H)$^+$=301.1/303.1.

Preparation 20

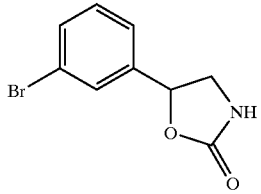

(P20)

1,1'-Carbonyldiimidazole (700.2 mg, 4.3182 mmol) was added to a THF (10 mL) semi-suspension of 2-amino-1-(3-bromo-phenyl)-ethanol (prepared according to J. Med. Chem., Vol. 14 [1971], at p. 266) (834 mg, 3.8597 mmol). The reaction mixture was stirred at rt for 15.5 h and at 70° C. for 13.5 h. The reaction mixture was cooled to rt and the volatile component removed in vacuo. A silica gel mesh of the crude material was prepared and submitted to flash chromatography (60–70% EtOAc/hexanes) to afford oxazolidinone P20 along with a minor impurity as a white solid (563.7 mg). $^1$H NMR ($CDCl_3$, δ=7.26 ppm; 500 MHZ): 7.54 (m, 1H), 7.51 (m, 1H), 7.32–7.27 (m, 2H), 5.60 (app t, J=8.0, 1H). 5.23 (br s, 1H), 4.00 (app t, J=8.6, 1H), 3.51 (app t, J=8.0, 1H). (ESI) m/z (M+H)$^+$=242.08/244.08.

Preparation 21

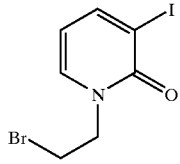

(P21)

$K_2CO_3$ (221 mg, 1.599 mmol) and bromoethanol (250 uL, 3.527 mmol) were added into an acetone (4.0 mL) solution of compound P4 (244 mg, 1.1 mmol). The reaction mixture was heated at 65° C. for 8 h and allowed to cool to rt. Silica gel was added to the reaction mixture and solvent removed in vacuo. The resulting mesh was submitted to flash chromatography (EtOAc) to afford alcohol P21 as a viscous oil (219.4 mg, 75.0%). ¹H NMR: 8.08 (dd, J=7.4, 1.9, 1H), 7.66 (dd, J=6.7, 1.9, 1H), 6.02 (app t, J=6.9, 1H), 4.88 (br, s, 1H), 3.98 (t, J=5.4, 2H), 3.61 (m, 2H). (ESI) m/z (M+H)⁺= 265.98.

Preparation 22

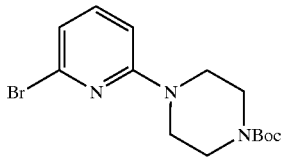

(P22)

Acetonitrile (10.0 mL) was added into a mixture of 2,6-dibromopyridine (1.0236 g, 4.3201 mmol), N-Boc piperazine (1.5548 g, 8.3475 mmol) and K₂CO₃ (1.0666 g, 7.7172 mmol). The reaction mixture was refluxed for ~64 h and allowed to cool to rt. It was diluted with EtOAc, filtered, and the filtrate was concentrated in vacuo. A silica gel mesh of the crude material was prepared and submitted to flash chromatography (10% EtOAc/hexanes) to afford bromide P22 as a white solid (1.2496 g, 84.5%). ¹H NMR: 7.45 (dd, J=8.3, 7.7, 1H), 6.81 (overlapping doublets, 2H), 3.47 (m, 4H), 3.41 (m, 4H), 1.42 (s, 9H). (ESI) m/z (M+H)⁺=342.14/344.14.

The synthesis of analogous amine-addition products was conducted under neat conditions where the dibromide was heated with an excess amount of amine (e.g. tert-butyl N-(2-aminoethyl)carbamate or ethanolamine) at 110° C. until completion of the reaction. The reaction mixture was then cooled to rt and submitted to standard flash chromatography to afford the mono-adducts in >85% yield.

Preparation 23

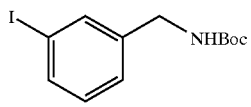

(P23)

TEA (520 uL, 3.71 mmol), di-tert-butyldicarbonate (0.81 g, 3.71 mmol) and DMAP (0.45 g, 3.71 mmol) were sequentially added to a THF (20 nL) solution of 3-iodobenzylamine hydrochloride (1.00 g, 3.71 mmol), and the reaction mixture was heated at 50° C. for 15 h. After it was allowed to cool to rt, the volatile component was removed in vacuo, and the residue dissolved in EtOAc and washed with water and brine. The organic layer was dried (MgSO₄), filtered, and evaporated in vacuo to afford a mixture of iodide P23 and DMAP (1.3:1.0 mole ratio) as a white semi-solid (1.60 g). The mixture was used for coupling without further purification.

Preparation 24

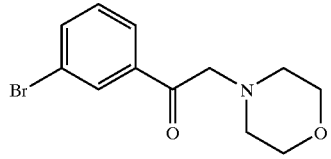

(P24)

K₂CO₃ (246.3 mg, 1.7821 mmol) and morpholine (400 uL, 4.5868 mmol) were added into a THF (5.0 mL) solution of 2,3'-dibromoacetophenone (512.4 mg, 1.84 mmol) and stirred at rt. A heavy suspension formed immediately after the morpholine was added and the reaction mixture was stirred overnight. Silica gel was added into the mixture and the solvent was removed in vacuo. The resulting silica gel mesh was submitted to flash chromatography (40% EtOAc/hexanes) to isolate bromide P24 as a colorless crystal (468.5 mg, 89.4%). ¹H NMR (CDCl₃, δ=7.26 ppm; 500 MHZ): 8.14 (app t, J=1.7, 1H), 7.94 (m, 1H), 7.71 (m, 1H), 7.35 (app t, J=8.0, 1H), 3.77 (m, 6H), 2.60 (m, 4H). (ESI) m/z (M+H)⁺=284.16/286.16.

Preparation 25

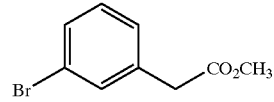

(P25)

TMSCHN₂ (10.0 mL of 2.0 M/hexanes) was added dropwise over 35 min. to a toluene/MeOH (20/8 mL) solution of 3-bromophenylacetic acid (2.01 gms, 9.34 mmol). The reaction mixture was stirred for 45 min. and quenched with acetic acid. The volatile component was removed in vacuo to afford ester P25 as a yellow oil (2.08 g, 97.2%). ¹H NMR (CDCl₃, δ=7.26 ppm; 500 MHZ): 7.44 (m, 1H), 7.41 (app dt, J 7.0, 2.0, 1H), 7.23–7.18 (m, 2H), 3.71 (s, 3H), 3.60 (s, 2H). (ESI) m/z (M+H)⁺=229.0/231.0.

Preparation 26

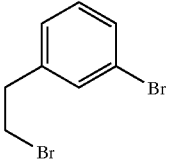

(P26)

Ph₃P—Br₂ (4.90 g, 11.608 mmol) was added in batches over a few min. to a CH₃CN (30.0 mL) solution of 3-bromophenylethanol (2.0055 g, 9.9741 mmol), and the reaction mixture was stirred at rt for 19.25 h. The volatile component was removed in vacuo, and the residue was diluted with hexanes/ether (1:1, 50 mL), shaken briefly, and filtered. The filtered solid was washed with hexanes/ether (1:1, 50 mL). The combined filtrate was rotovaped to afford a colorless oil. ¹H NMR analysis of the oil indicated that the desired dibromide P26 contained a Ph₃PO impurity in a ~30:1 mole ratio (1.7585 g, ~64%). ¹H NMR (CDCl₃, δ=7.26 ppm; 500 MHZ): 7.40 (m, 1H), 7.37 (m, 1H), 7.20 (app t, J=7.8, 1H), 7.15 (m, 1H), 3.55 (t, J=7.5, 2H), 3.14 (t, J=7.5, 2H).

Preparation 27

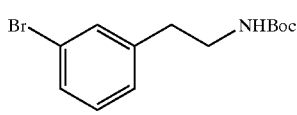
(P27)

Step A:

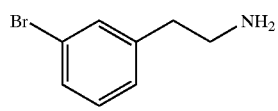
(P27A)

Carbamate P27 was prepared from 3-bromophenylacetonitrile, according to the procedure described for the synthesis of Preparation 19, in a combined yield of 65.7%. $^1$H NMR: 7.39–7.38 (m, 2H), 7.25 (m, 1H), 7.20 (app d, J=7.6, 1H), 6.87 (br m, 1H), 3.14 (app q, J=6.3, 2H), 2.69 (t, J=7.2, 2H), 1.35 (s, 9H). (ESI) m/z (M+Na)$^+$= 322.06/324.06.

Step B:

If required, the amine intermediate P27A could be isolated by preparing a silica gel mesh from the crude material obtained from the reduction step of Preparation 19 and submitting it to flash chromatography (EtOAc; 20% MeOH/CHCl$_3$). $^1$H NMR: 7.42 (m, 1H), 7.39–7.37 (m, 1H), 7.24 (app t, J=7.7, 1H), 7.22–7.20 (m, 1H), 2.76 (t, J=7.2, 2H), 2.63 (t, J=7.2, 2H), 1.75 (br s, 2H). (ESI) m/z (M+H)$^+$= 200.09/202.09.

Preparation 28

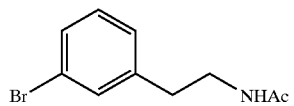
(P28)

TEA (400 uL, 2.8698 mmol) and acetic anhydride (230 uL, 2.4377 mmol) were added into a THF (5.0 mL) solution of amine P27A (311.6 mg, 1.5574 mmol), and the reaction mixture was stirred at rt for 15.5 h. The volatile component was removed in vacuo, and a silica gel mesh of the crude material was prepared and submitted to flash chromatography (50–60% EtOAc/hexanes) to afford bromide P28 as an off-white solid (285.3 mg, 75.7%). $^1$H NMR: 7.90 (m, 1H), 7.42 (m, 1H), 7.40 (m, 1H), 7.26 (app t, J=7.8, 1H), 7.21 (m, 1H), 3.25 (m, 2H), 2.70 (t, J=7.4, 2H), 1.77 (s, 3H). (ESI) m/z (M+H)$^+$=242.11/244.11.

Preparation 29

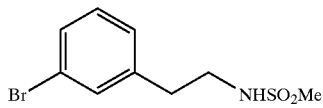
(P29)

Methanesulfonyl chloride (140 uL, 1.8088 mmol) was added dropwise over 1 min. to a cooled (0° C.) CH$_2$Cl$_2$ (5.0 mL) solution of amine P27A (297.7 mg, 1.49 mmol). The reaction mixture was stirred for 15 h while the bath was allowed to thaw. The solvent was removed in vacuo, and a silca gel mesh of the residue was prepared and submitted to flash chromatography (30–40% EtOAc/hexanes) to afford sulfonamide P29 as a colorless viscous oil (317.8 mg, 76.8%). $^1$H NMR: 7.48 (m, 1H), 7.42 (m, 1H), 7.29–7.25 (m, 2H), 7.08 (t, J=5.8, 1H), 3.18 (m, 2H), 2.84 (s, 3H), 2.76 (t, J=7.4, 2H). (ESI) m/z (M+H)$^+$=278.08/280.08.

Preparation 30

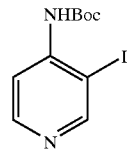
(P30)

Step A:

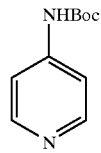
(P30A)

NaH (1.34 g of 60%, 33.50 mmol) was added in portions over 10 min. to a THF (60 mL) solution of 4-aminopyridine (3.07 g, 32.62 mmol), and the reaction mixture was stirred for 1 hr. Di-tert-butyldicarbonate (7.32 g, 33.54 mmol) followed by additional THF (30 mL) were added and the mixture was stirred overnight. It was then diluted with water and extracted with EtOAc. The organic layer was washed with brine, dried (MgSO$_4$), filtered, and evaporated in vacuo. The resulting solid was recrystallized from EtOAc/hexanes to afford carbamate P30A as a light pink crystalline solid (5.97 g, 94.2%). $^1$H NMR (CDCl$_3$, δ=7.26 ppm; 300 MHZ): 8.43 (d, J=6.3, 2H), 7.31 (d, J=6.4, 2H), 6.93 (br s, 1H), 1.52 (s, 9H). (ESI) m/z (M+H)$^+$=195.0.

Step B:

Butyllithium (8.10 mL of 1.6 M/hexanes, 12.96 mmol) was added dropwise to a cooled (−78° C.) THF (15.0 mL) solution of carbamate P30A (1.00 g, 5.149 mmol) and TMEDA (1.96 mL, 13.00 mmol). 15 min. later, the −78° C. bath was replaced with a −10° C. bath, and the reaction was stirred for 2 h. The yellow suspension was cooled back to −78° C. and treated dropwise with a THF (13.0 mL) solution of I2 (3.30 g, 13 mmol). The reaction mixture was stirred at −78° C. for 2 h, and the cooling bath was removed and the reaction quenched with a THF/H$_2$O solution. The mixture was extracted with ether; the organic layer was washed with an aqueous sodium bisulfite solution and brine, dried (MgSO$_4$), filtered and evaporated in vacuo. A silica gel mesh of the crude material was prepared and submitted to flash chromatography (5% MeOH/EtOAc) to afford iodide P30 as a yellow oil (1.27 g, 77.1%). $^1$H NMR (CDCl$_3$, δ=7.26 ppm; 300 MHZ): 8.75 (s, 1H), 8.34 (d, J=5.6, 1H), 8.10 (d, J=5.6, 1H), 7.04 (br s, 1H), 1.54 (s, 9H). (ESI) m/z (M+H)$^+$=320.9.

Preparation 31

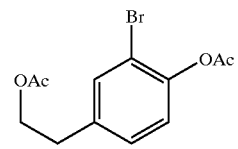

Preparation 31 was prepared from 2(3′-bromo-4′-hydroxyphenyl)ethanol by protection of both alcohol groups as described above for Preparation 10.

Preparation 32

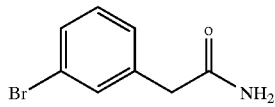
(P32)

Anhydrous ammonia was bubbled through a MeOH (50.0 mL) solution of Preparation 25 (2.34 g, 10.21 mmol) in a Parr-bomb for 10 min. The apparatus was capped and heated at 100° C. for 28 h. After it was allowed to cool to room temperature, the volatile component was removed in vacuo, and a silica gel mesh was prepared from the residue and submitted to flash chromatography (EtOAc) to afford amide P32 as an off-white fluffy solid (1.887 g, 86.3%). $^1$H NMR (500 MHZ): 7.50 (br s, 1H), 7.47 (s, 1H), 7.42 (m, 1H), 7.28–7.25 (m, 2H), 6.92 (br s, 1H), 3.38 (s, 2H). (ESI) m/z (M+H)$^+$=213.99/215.99.

Preparation 33–34

Ester 33 and amide 34, shown in the table below, were prepared from 3-(3-bromophenyl) propionic acid according to the procedure described for the synthesis of ester 25 and amide 32, respectively.

| Pre. # | | (M + H)$^+$ | Other Data ($^1$H NMR) |
|---|---|---|---|
| P33 | 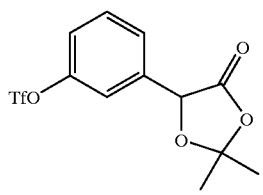 | | (CDCl$_3$, 500 MHZ): 7.35–7.33 (m, 2H), 7.17–7.12 (m, 2H), 3.68 (s, 3H), 2.92 (t, J=7.77, 2H), 2.62 (t, J=7.77, 2H). |
| P34 | 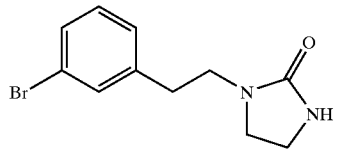 | 227.94/229.94 | (500 MHZ): 7.42 (s, 1H), 7.37 (m, 1H), 7.28 (br s, 1H), 7.25–7.21 (m, 2H), 6.77 (br s, 1H), 2.79 (t, J= 7.5, 2H), 2.35 (t, J=7.5, 2H). |

Preparation 35

(P35)

Step A:

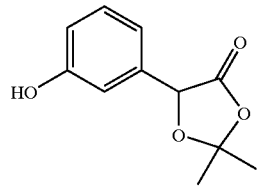
(P35A)

Benzene (10 mL) and 2,2-dimethoxypropane (900 uL, 7.319 mmol) were added into a flask containing hydroxy-(3-hydroxy-phenyl)-acetic acid (1.073 g, 6.38 mmol). The flask was equiped with a Dean-Stark apparatus, and the heterogeneous reaction mixture was refluxed for 2.75 h and allowed to cool to room temperature. Silica gel was added and the volatile component was removed in vacuo and the resulting silica gel mesh was submitted to flash chromatography (20–30% EtOAc/hexanes) to afford phenol P35A as a viscous faint yellow oil (1.196 g, 90%). $^1$H NMR (CDCl$_3$, 500 MHZ): 7.29–7.26 (m, 1H), 7.04 (m, 1H), 6.94 (m, 1H), 6.83 (m, 1H), 5.34 (s, 1H), 4.99 (br s, 1H), 1.72 (s, 3H), 1.67 (s, 3H).

Step B:

2-[N,N-Bis(trifluoromethylsulfonyl)amino]pyridine (1.3298 g, 3.7120 mmol) was added in one batch to an ice-water cooled CH$_2$Cl$_2$ (10.0 mL) solution of Et$_3$N (700 uL, 5.0222 mmol) and alcohol P35A (693.8 mg, 3.3322 mmol) and stirred for 45 min. The cooling bath was removed and the reaction mixture was stirred for an additional 80 min. Silica gel was added and the volatile component was removed in vacuo, and the resultant silica gel mesh was submitted to flash chromatography (15% EtOAc/hexanes) to afford triflate P35 as an oil (1.0407 g, 92%). $^1$H NMR (CDCl$_3$, 500 MHZ): 7.57 (d, J=7.2, 1H), 7.51 (app t, J=8.0, 1H), 7.45 (br s, 1H), 7.29 (dd, J=2.3, 1H), 5.43 (s, 1H), 1.72 (s, 3H), 1.70 (s, 3H).

Preparation 36

(P36)

Step A:

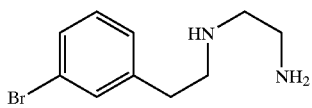
(P36A)

Preparation 26 (1.0149 g, 3.845 mmol) was added to ethylenediamine (51.0 mL) and the resulting solution was heated at 70 °C. for 4.75 h. All the volatile component was removed in vacuo, and the crude oil was triturated with EtOAc, filtered and the filterate was rotervaped. The crude material was submitted to Prep-HPLC to afford a TFA (2×) salt of dimaine P36A as a yellow oil. The salt was free-based according to the procedure described in Examples 159–173 (297 mg). (ESI) m/z (M+H)$^+$=243.01/245.01.

Step B:

Carbonyl diimidazole (218.4 mg, 1.3469 mmol) was added in one batch to a THF (7.0 mL) solution of the above diamine, and stirred for 23 h. The volatile component was removed in vacuo and the residue was loaded onto an SCX column (pre-equilibrated with MeOH) and eluted with MeOH. The solvent was removed in vacuo to afford urea P36 along with imidazole impurity in a 6.5 to 1.0 mole ratio ($^1$H NMR), respectively. The solid weighed 322.7 mg. $^1$H NMR: 7.46 (br s, 1H), 7.39 (m, 1H), 7.27–7.24 (m, 2H), 6.26 (s, 1H), 3.31–3.26 (m, 4H), 3.18 (m, 2H), 2.74 (t, J=7.3, 2H). (ESI) m/z (M+H)$^+$=268.99/270.99.

Preparation 37

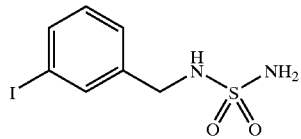
(P37)

Sulfamide (2.08 g, 21.65 mmol) was added in one batch to a dioxane (20.0 mL) solution of 3-iodobenzylamine (1.060 g, 4.548 mmol), and the reaction mixture was heated at 90° C. until the benzylamine was totally consumed (>20 h). The volatile component was removed, and a silica gel mesh was prepared from the residue and submitted to flash chromatography (40–50% EtOAc/hexanes) to afford sulfamide P37 as a white solid (1.05 g, 74.0%). $^1$H NMR: 7.74 (s, 1H), 7.61 (d, J=8.0, 1H), 7.36 (d, J=7.5, 1H), 7.15–7.10 (m, 2H), 6.65 (s, 2H), 4.04 (d, J=6.5, 2H). (ESI) m/z (M+Na)$^+$=334.90.

Preparation 38

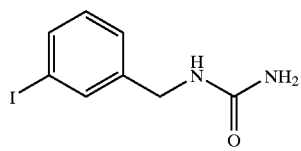
(P38)

Acetic acid (1.30 mL, 22.71 mmol) was added into a mixture of 3-iodobenzylamine (1.00 g, 4.30 mmol) and potassium cyanate (1.707 g, 21.04 mmol), and the reaction mixture was stirred for 75 min. All the volatile component was removed in vacuo, and a silica gel mesh was prepared from the residue and submitted to flash chromatography (0–10% MeOH/EtOAc) to afford urea P38 as a white fluffy solid (1.139 g, 96%). $^1$H NMR: 7.61 (s, 1H), 7.58 (d, J=8.0, 1H), 7.26 (d, J=8.0, 1H), 7.12 (t, J=7.8, 1H), 6.45 (br t, J=5.8, 1H), 5.55 (s, 2H), 4.13 (d, J=6.0, 2H). (ESI) m/z (M+H)$^+$=276.97.

Preparation 39

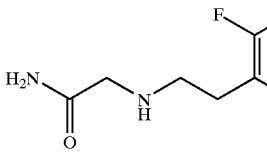
(P39)

Step A:

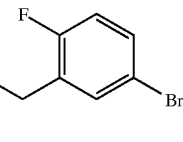
(P39A)

Bromide P39A was prepared from 5-Bromo-2-fluorotoluene according to PCT U.S. 00 11643.

Step B:

(P39B)

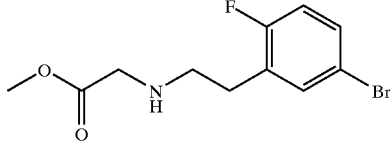

BH$_3$·SMe$_2$ (8.0 mL, 16.0 mmol) was added to a THF (20.0 mL) solution of bromide P39A (2.26 g, 10.56 mmol). The reaction mixture was refluxed for 10 h, allowed to cool to room temperature, treated with MeOH (15.0 mL) and concentrated HCl (3.0 mL) and stirred overnight. It was heated at 75° C. for 37 min, allowed to cool to room temperature and concentrated in vacuo. The residue was diluted with 1N HCl and washed with ether. The aqueous phase was carefully neutralized with solid NaOH, and extracted with CH$_2$Cl$_2$ (2×). The combined organic phase was washed with brine, dried (MgSO$_4$), filtered and evaporated in vacuo to afford amine P39B as a colorless oil (1.682 g). $^1$H NMR: 7.51 (dd, J 6.5,2.5, 1H), 4.42 (ddd, J=8.8, 4.5, 2.8, 1H), 7.13 (app t, J=9.3, 1H), 2.75 (app t, J=7.0, 2H), 7.3 (app t, J=7.3, 2H), 1.71 (br s, 2H). (ESI) m/z (M+H)$^+$= 218.11/220.11.

Step C:

(P39C)

Methyl bromoacetate (440 uL, 4.648 mmol) was added dropwise over 1 min to a THF (17.0 mL) solution of amine P39B (1.00 g, 4.586 mmol) and Et$_3$N (2.0 mL, 14.349 mmol), and the reaction mixture was stirred for 15.25 h. About 3 ml of MeOH was added and the volatile component was removed in vacuo. The residue was partitioned between EtOAc and water, and the aqueous layer was extracted with EtOAc. The combined organic phase was washed with brine, dried (MgSO$_4$), filtered and evaporated in vacuo. A silica gel mesh of the crude material was submitted to flash chromatography (50–80% EtOAc/hexanes) to afford ester P39C as a colorless oil (975 mg, 73%). $^1$H NMR: 7.55 (dd, J=6.7, 2.7, 1H), 7.42 (ddd, J=8.8, 4.5, 2.7, 1H), 7.13 (app t, J=9.4, 1H), 3.61 (s, 3H), 3.35 (s, 2H), 2.75–2.70 (m, 4H), 2.20 (br s, 1H). (ESI) m/z (M+H)$^+$=290.10/292.10.

Step D:

Anhydrous ammonia was bubbled through a MeOH (30 mL) solution of ester P39C, in a Parr-bomb, for 10 min. The apparatus was capped and heated at 61° C. for 20 h. The volatile component was removed in vacuo, a silica gel mesh was prepared from the residue and submitted to flash chromatography (5–10% MeOH/EtOAc) to afford amide P39 as an off-white solid (826.8 mg, 89.6%). $^1$H NMR: 7.54 (dd, J=6.7, 2.7, 1H), 7.43 (m, 1H), 7.18 (br s, 1H), 7.14 (app t, J=9.2, 1H), 7.02 (br s, 1H), 3.05 (s, 2H), 2.74–2.69 (m, 4H). (ESI) m/z (M+H)$^+$=275.04/277.04.

Preparation 40

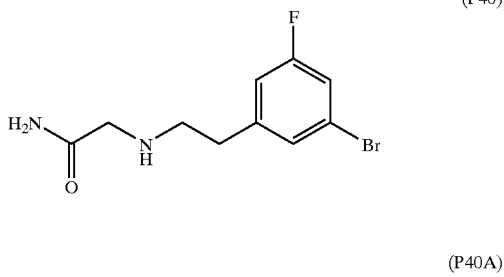

(P40)

Step A:

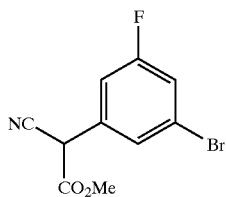

(P40A)

Ester P40 was prepared from Bromo-3,5-difluorobenzene according to Synthesis, 1997, p.1411.

Step B:

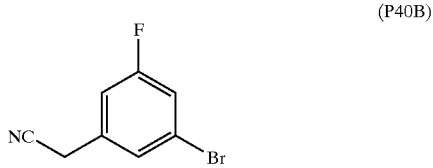

(P40B)

DMSO (64.0 mL) and water (700 uL) were added into a mixture of NaCl (387.8 mg, 6.4676 mmol) ester P40A (5.45 g, 19.05 mmol), and the reaction mixture was heated at 160° C. for 4 h—a vigorous evolution of gas was observed. After it was allowed to cool to room temperature, it was diluted with water (100 mL) and extracted with ether (100 mL, 3×) with a gentle shaking to prevent emulsification. HCl (1.0 mL of 1N) was added to the aqueous phase and additional ether extraction was conducted (100 mL, 2×). The combined organic phase was washed with brine, dried (MgSO$_4$), filtered and evaporated in vacuo. A silica gel mesh was prepared and submitted to flash chromatography (7.5% EtOAc/hexanes) to afford nitrile P40B as a faint yellow oil (3.69 g, 86.1%). $^1$H NMR: 7.56 (dt, J=8.5, 2.1, 1H), 7.46 (br s, 1H), 7.28 (app d, J=9.5, 1H), 4.10 (s, 2H). (ESI) m/z (M–H)$^-$=211.84/213.84.

Step C:

Nitrile P40B was elaborated to amide P40 through a three step procedure described in the synthesis amide P39. $^1$H NMR: 7.35 (dt, J=7.4, 2.0, 1H), 7.31 (app br s, 1H), 7.17 (br s, 1H), 7.14 (m, 1H), 7.01 (br s, 1H). 3.04 (s, 2H), 2.71 (s, 4H), 2.30 (br s, 1H). (ESI) m/z (M+H)$^+$=275.10/277.10.

Preparation 41

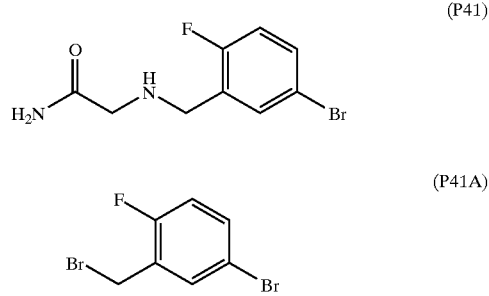

(P41)

Step A:

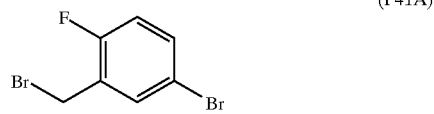

(P41A)

Dibromide P41A was prepared from 5-Bromo-2-fluorotoluene according to PCT U.S. 00 11643.

Step B:

Dibromide P41A (1.048 g, 3.910 mmol), HCl salt of H$_2$NCH$_2$CONH$_2$ (1.632 g, 14.76 mmol), K$_2$CO$_3$ (2.736 g, 19.80 mmol) and DMF (30 mL) were sequentially added into a flask and the mixture was heated at 60° C. 3.75 h, and allowed to cool to room temperature. All the volatile component was removed in vacuo, and the residue was partitioned between 50% saturated NaCl and EtOAc. The aqueous phase was extracted with EtOAc, and the combined organic phase was washed with brine, dried (MgSO4), filtered and evaporated in vacuo. A silica gel mesh was prepared and submitted to flash chromatography (0–5% MeOH/EtOAc) to afford amide P41 as a white solid (614.4 mg, 60.2%). $^1$H NMR: 7.68 (dd, J=6.6, 2.6, 1H), 7.48 (ddd, J=8.7, 4.7, 2.7, 1H), 7.30 (br s, 1H), 7.16 (dd, J=9.8, 8.6, 1H), 7.05 (br s, 1H), 3.7 (s, 2H), 3.05 (s, 2H), 2.79 (br s, 1H). (ESI) m/z (M+H)$^+$=261.08/263.08.

Preparation 42–48

Amides 42–48 were prepared from 3-iodobenzyl bromide according to the procedure described for amide P41. The use of 1,2,4-triazole afforded the regioisomeric iodides 47 and 48.

| Pre. # | | (M + H)⁺ | Other Data (¹H NMR) |
|---|---|---|---|
| P42 | | 305.10 | 7.76 (br s, 1H), 7.62 (d, J=7.5, 1H), 7.39 (d, J=7.3, 1H), 7.29 (br s, 1H), 7.13 (app t, J=7.8, 1H), 7.10 (br s, 1H), 3.51 (s, 2H), 2.89 (s, 2H), 2.15 (s, 3H). |
| P43 | | 290.96 | 7.73 (br s, 1H), 7.60 (app d, J=7.9, 1H), 7.34 (app d, J=7.6, 1H), 7.29 (br s, 1H), 7.12 (app t, J=7.6, 1H), 7.04 (s, 1H), 3.64 (s, 2H), 3.01 (s, 2H). |
| P44 | | 345.00 | 7.68 (br s, 1H), 7.63 (app d, J=7.9, 1H), 7.33 (app d, J=7.9, 1H), 7.14 (app t, J=7.8, 1H), 3.45 (s, 2H), 3.44–3.40 (m, 4H), 2.34 (app t, J=5.0, 2H), 2.28 (app t, J=5.0, 2H), 1.97 (s, 3H). |
| P45 | | 317.01 | 7.75 (br s, 1H), 7.69 (br s, 1H), 7.64 (app d, J=7.9, 1H), 7.34 (7.6, 1H), 7.15 (app t, J=7.8, 1H), 3.50 (s, 2H), 3.16–3.13 (m, 2H), 2.89 (s, 2H), 2.54–2.52 (m, 2H). |
| P46 | | | 7.74 (br s, 1H), 7.61 (app d, J=7.9, 1H), 7.39 (app d, J=7.6, 1H), 7.25 (br s, 1H), 7.12 (app t, J=7.8, 1H), 7.04 (br s, 1H), 3.80 (d, J=13.4, 1H), 3.32 (signal overlapped with that of water, 1H), 2.94–2.91 (m, 1H), 2.86–2.82 (m, 1H), 2.22–2.17 (m, 1H), 2.08–2.00 (m, 1H), 1.74–1.69 (m, 3H). |
| P47 | | 285.93 | 8.62 (s, 2H), 7.71–7.69 (m, 2H), 7.32 (app d, J=7.9, 1H), 7.18 (app t, J=7.8, 1H), 5.25 (s, 2H). |
| P48 | | 285.99 | 8.67 (s, 1H), 8.00 (s, 1H), 7.69–7.67 (m, 2H), 7.29 (app d, J=7.6, 1H), 7.17 (app t, J=7.8, 1H), 5.39 (s, 2H). |

Preparation 49

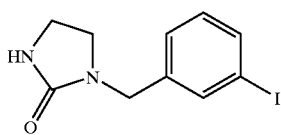

(P49)

Sodium hydride (60%, 2.74 g, 68.5 mmol) was added to a DMF (100 mL) solution of 2-imidazolidone (5.82 g, 19.6 mmol), and stirred at ambient temperature for 1.5 h. 3-Iodobenzyl bromide (2.01 g, 6.77 mmol) was added and stirring continued for 4 h. It was quenched with methanol and the volatile component was removed in vacuo, the residue was partitioned between water and ethyl acetate. Two additional EtOAc extraction of the aqueous layer was conducted. The combined organic phase was dried (MgSO₄), filtered and evaporated in vacuo. A silica gel mesh of the residue was submitted to flash chromatography (EtOAc) to afford urea P49 as a white solid (793.7 mg, 38.7% yield). ¹H NMR: 7.63 (app d, J=7.6, 1H), 7.61 (br s, 1H), 7.26 (app d, J=7.9, 1H), 7.16 (app t, J=7.6, 1H), 6.46 (br s, 1H), 4.19 (s, 2H), 3.25–3.18 (m, 4H). (ESI) m/z (M+H)⁺=302.93.

Preparation 50

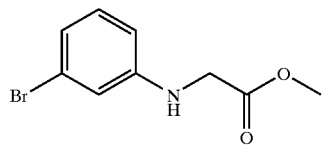

(P50)

Potassium carbonate (1.93 g, 13.9 mmol) was added to a DMF (50 mL) solution of 3-bromoaniline (2.00 g, 11.6 mmol) and methyl bromoacetate (2.15 g, 14.1 mmol), and the reaction mixture was heated at 60° C. for 23 h. It was cooled to room temperature and the volatile component was removed in vacuo. Water was added to the residue and the product extracted with ethyl acetate. The organic layer was washed with brine, dried (MgSO₄), filtered and evaporated in vacuo to afford ester P50 as a white solid (2.8 g; >95% yield). The crude was used with out further purification. ¹H NMR: 7.01 (app t, J=8.1, 1H), 6.73 (t, J=2.0, 1H), 6.71–6.70 (m, 1H), 6.54 (dd, J=8.4, 1.7, 1H), 6.31 (t, J=6.3, 1H), 3.93 (d, J=6.4, 2H), 3.65 (s, 3H). (ESI) m/z (M+H)⁺=245.97/243.97.

Preparation 51

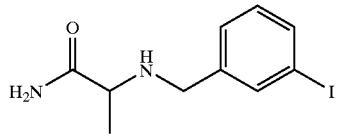

(P51)

Step A:

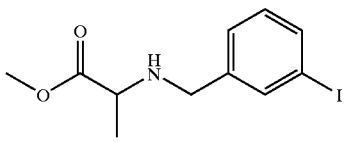

(P51A)

Ester P51A was prepared from 3-iodobenzyl bromide according to the procedure described for amide P41. ¹H NMR: 7.69 (s, 1H), 7.58 (app d, J=7.6, 1H), 7.31 (app d, J=7.3, 1H), 7.11 (app t, J=7.6, 1H), 3.69 (d, J=13.7, 1H), 3.62 (s, 3H), 3.55 (d, J=14.1, 1H), 3.26 (m, 1H), 2.58 (br s, 1H), 1.20 (d, J=7.0, 3H). (ESI) m/z (M+H)⁺=320.08.

Step B:

Aminolysis of ester P51A was conducted according to the procedure described for the synthesis of amide P39. ¹H NMR (400 MHZ): 7.72 (s, 1H), 7.59 (app d, J=7.6, 1H), 7.35–7.33 (m, 2H), 7.12 (app t, J=7.8, 1H), 6.98 (br s, 1H), 3.65 (d, J=14.0, 1H), 3.50 (d, J=14.0, 1H), 2.99 (q, J=6.8, 1H), 1.13 (d, J=7.2, 3H). (ESI) m/z (M+H)⁺=305.06.

Preparation 52

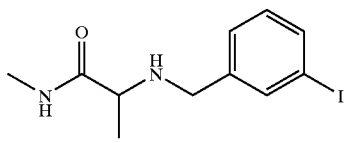

(P52)

MeNH₂ (20 mL of 40% wt/H₂O) was added into a MeOH (10 mL) solution of ester P51A (1.0091 g, 3.162 mmol) in a Parr-bomb, and the reaction mixture was heated at 60° C. for 22.25 h. After it was allowed to cool to room temperature, all the volatile component was removed in vacuo. A silica gel mesh was prepared from the residue and submitted to flash chromatography (0–2% MeOH/EtOAc) to afford amide P52 as a viscous oil (728 mg, 72.4%). ¹H NMR: (400 MHZ): 7.78 (m, 1H), 7.73 (s, 1H), 7.59 (d, J=8.0, 1H), 7.34 (d, J=7.6, 1H), 7.11 (app t, J=7.6, 1H), 3.62 (d, J=14.0, 1H), 3.49 (d, J=14.0, 1H), 3.00 (q, J=6.8, 1H), 2.60 (d, J=4.8, 3H), 1.12 (d, J=6.8, 3H). (ESI) m/z (M+H)⁺= 319.04.

Preparation 53

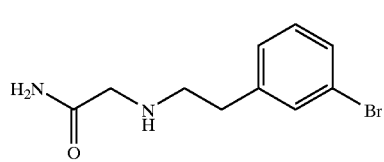

(P53)

Step A:

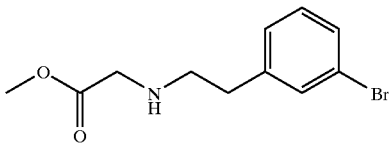

(P53A)

Ester P53A was prepared from amine P27A according to the procedure described for the synthesis of ester P39C. ¹H NMR: 7.44 (s, 1H), 7.38–7.36 (m, 1H), 7.25–7.21 (m, 2H), 3.61 (s, 3H), 3.34 (s, 2H), 2.76–2.67 (m, 4H), 1.98 (br s, 1H). (ESI) m/z (M+H)⁺=272.03/274.03.

Step B:

Conversion of ester P53A to amide P53 was conducted according to the procedure described for the synthesis of ester P39C. ¹H NMR: 7.43 (s, 1H), 7.38 (app td, J=6.5, 2.3, 1H), 7.26–7.23 (m, 2H), 7.17 (br s, 1H), 7.00 (br s, 1H), 3.04 (s, 2H), 2.69 (s, 4H), 2.07 (br s, 1H). (ESI) m/z (M+H)⁺= 257.15/259.15.

Preparation 54

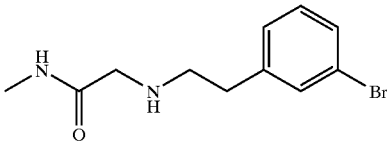

(P54)

Ester P53A was converted to amide P54 according to the procedure described for the synthesis of amide P52. ¹H NMR: 7.61 (br s, 1H), 7.43 (br s, 1H), 7.39 (app dt, J=7.3, 1.8, 1H), 7.26–7.22 (m, 2H), 3.07 (s, 2H), 2.69 (s, 4H), 2.57 (d, J=4.5, 3H). (ESI) m/z (M+H)⁺=271.09/273.09.

Preparation 55

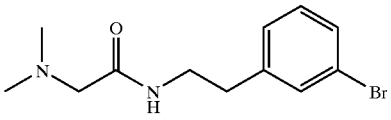

(P55)

The HCl salt of Me₂NCH₂COCl (1.02 g, 6.454 mmol) was added into a DMF (20.0 mL) solution of amine P27A (602 mg, 3.009 mmol) and Et₃N (3.0 mL, 21.52 mmol) and the heterogeneous mixture was sonicated for 1 min and vigorously stirred until the starting material is completely consumed. The volatile component was removed in vacuo and residue was partitioned between EtOAc and dilute NaHCO₃ solution. The aqueous layer was extracted with EtOAc, and the combined organic phase was washed with brine, dried (MgSO₄), filtered and evaporated in vacuo. The resulting viscous oil was directly submitted to flash chromatography (0–2% MeOH/EtOAc) to afford bromide P55 as light red oil (451.5 mg, 52.6%). ¹H NMR: 7.76 (br m, 1H), 7.41–7.38 (m, 2H), 7.26–7.22 (m, 2H), 3.35–3.29 (m, 2H), 2.80 (s, 2H), 2.75 (app t, J=7, 2H), 2.14 (s, 6H). (ESI) m/z (M+H)⁺=285.12 / 287.12.

Preparation 56

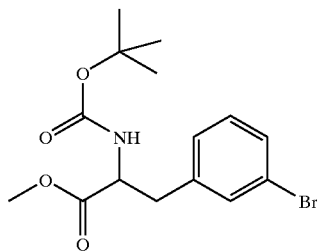

(P56)

N-Boc-3-bromophenylalanine was converted to ester P56 according to the procedure described for the synthesis of ester P25. $^1$H NMR: 7.45 (br s, 1H), 7.42–7.40 (m, 1H), 7.32 (d, J=8.3, 1H), 7.25 (m, 2H), 4.21–4.18 (m, 1H), 3.62 (s, 3H), 3.02 (dd, J=13.8, 4.6, 1H), 2.84 (dd, J=13.7, 10.4, 1H), 1.32 (s, 9H). (ESI) m/z (M+Na)⁺=379.97/381.97.

Preparation 57

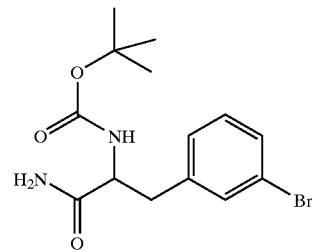

(P57)

Anhydrous ammonia was bubbled through a MeOH (10.0 mL) solution of ester P56 (305.2 mg, 0.852 mmol) for 30 min, and the reaction mixture was stirred at ambient temperature for 63 h. Removal of the volatile component in vacuo afforded amide P57 as an off-white solid (290 mg, >95%). The product was used without further purification. $^1$H NMR: 7.48 (br s, 1H), 7.39–7.38 (m, 2H), 7.28–7.22 (m, 2H), 7.03 (br s, 1H), 6.85 (d, J=8.9, 1H), 4.10–4.06 (m, 1H), 2.96 (dd, J=13.7, 4.0, 1H), 2.71 (dd, J=13.7, 10.7, 1H), 1.30 (s, 9H). (ESI) m/z (M+Na)⁺=364.98/366.98

Preparation 58

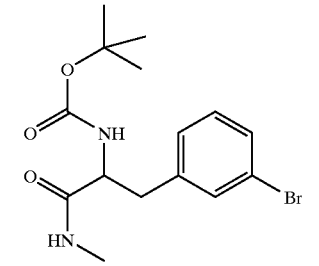

(P58)

Methylamine (15 mL of 40 wt % in water) was added to a MeOH (5.0 mL) solution of ester P58 (248.7 mg, 0.7225 mmol), and the reaction mixture was stirred at ambient temperature for 6 days. Removal of the volatile component in vacuo afforded amide P58 as an off-white solid (185 mg; it is not apparent why the yield is not quantitative). The product was used without further purification. $^1$H NMR:

7.86 (br m, 1H), 7.46 (app s, 1H), 7.38 (app d, J=6.4, 1H), 7.24–7.21 (m, 2H), 6.95 (d, J=8.5, 1H), 4.2 (m, 1H), 2.93 (dd, J=13.6, 4.2, 1H), 2.70 (m, 1H), 2.59 (d, J=4.2, 3H), 1.29 (s, 9H). (ESI) m/z (M+Na)⁺=381.04/379.04

Preparation 59

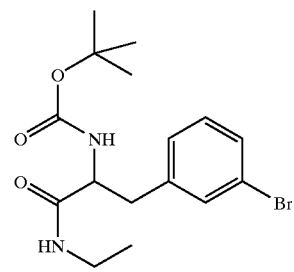

(P59)

Ethylamine (15.0 mL of 70 wt. % in water) was added to a methanol (5.0 mL) solution of ester P56 (252.1 mg, 0.7324 mmol), and the reaction mixture was stirred at 25° C. for 68 h. Removal of the volatile component in vacuo afforded amide P59 as an off-white solid (270 mg; this is 8.6 mg above the theoretical yield). The product was used without further purification. $^1$H NMR: 7.89 (app br t, J=5.2, 1H), 7.46 (br s, 1H), 7.38 (m, 1H), 7.26–7.21 (m, 2H), 6.90 (app d, J=8.8, 1H), 4.09–4.05 (m, 1H), 3.11–3.02 (m, 2H), 2.91 (dd, J=13.6, 4.5, 1H), 2.71 (dd, J=13.5, 10.4, 1H), 1.30 (s, 9H), 0.98 (t, J=7.2, 3H). (ESI) m/z (M−Boc+H)⁺=273.09/271.09

Preparation 60 and 61

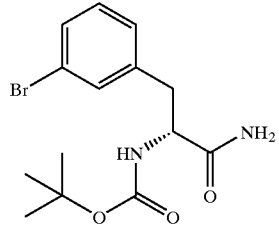

(P60)

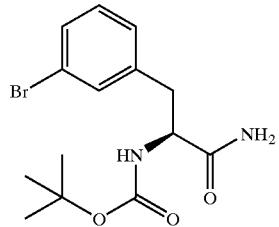

(P61)

Isobutyl chloroformate (87.4 mg, 0.640 mmol) was added to a cooled (−30 ° C.) CH₂Cl₂ (3.0 mL) solution of (R)-N-Boc-3-bromophenylalanine (202.0 mg, 0.5869 mmol) and N-methylmorpholine (64.8 mg, 0.641 mmol). After the reaction mixture was allowed to warm up to −20 ° C. over 30 min, ammonia was bubbled through it for 15 min. The cold bath was removed and the reaction mixture was stirred for an additional 1 hr. It was then partitioned between water and CH₂Cl₂, and the aqueous phase was extracted with CH₂Cl₂. The combined organic phase was dried (Na₂SO₄), filtered, and concentrated in vacuo to afford amide P60 as an off-white solid (200 mg, >95% yield). The product was used without further purification. $^1$H NMR: (see the data for P57). (ESI) m/z (M+Na)⁺=365.16/367.16.

The (S) enantiomer (P61) was synthesized by employing the same procedure. $^1$H NMR: (see the data for P57). (ESI) m/z (M+Na)$^+$=365.14/367.16

Preparation 62

(P62)

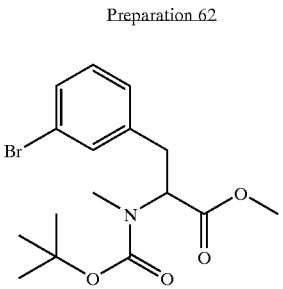

Sodium hydride (400 mg of 60%, 10 mmol) was added to a cooled, −10 °C., DMF (25 mL) solution of N-BOC-(3-bromophenyl)alanine (1.49 g, 4.32 mmol). After the mixture was stirred at −10° C. for 0.5 h, methyl iodide (1.6 g, 67 mmol) was added; the bath temperature was allowed to reach 0° C. and the reaction mixture was stored in a refrigerator (~6° C.) for 29 h. It was quenched with water (50 mL) at 0° C., and the product was extracted with ethyl acetate (100 mL, 3×). The combined organic phase was washed with water (50 mL, 3×), saturated aqueous sodium bicarbonate, brine (50 mL), and dried (MgSO$_4$), filtered and evaporated in vacuo. The resultant crude material was submitted to flash chromatography (0–25% EtOAc/hexanes) to afford ester P62 as an oil (1.5 g, 93% yield). $^1$H NMR: 7.47–7.39 (m, 2H), 7.27–7.21 (m, 2H), 4.85–4.71 (m, 1H), 3.69 and 3.67 (s, 3H), 3.18 (dd, J=14, 4.6, 1H), 3.07–2.97 (m, 1H), 2.60 and 2.57 (s, 3H), 1.32 and 1.25 (s, 9H). (ESI) m/z (M+Na)$^+$=394.05/396.05

Preparation 63

(P63)

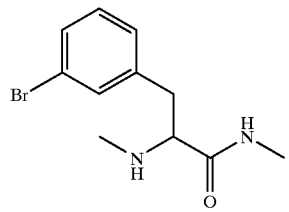

A TFA/CH$_2$Cl$_2$ (20%; 25 mL) solution of carbamate P62 (1.50 g, 4.0 mmol) was stirred at ambient temperature for 1 h. The volatile component was removed in vacuo and the residue was dissolved in MeOH and loaded onto an SCX column (preconditioned with MeOH). The column was first washed with MeOH and then with 2N NH$_3$/methanol to afford amine P63 as a viscous oil (1.10; >95%). $^1$H NMR (400): 7.40–7.38 (m, 2H), 7.25–7.18 (m, 2H), 3.58 (s, 3H), 3.35 (app t, J=7.1, 1H), 2.28 (app d, J=7.1, 2H), 2.20 (s, 3H), 2.09 (br s, 1H). (ESI) m/z (M+H)$^+$=272.06/274.06.

Preparation 64

(P64)

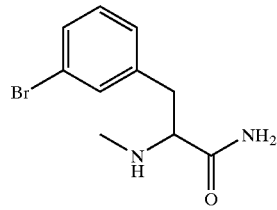

Anhydrous ammonia was bubbled through a MeOH (30 mL) solution of ester P63 (287.9 mg, 1.058 mmol) in a Parr-bomb for 10 min. The apparatus was capped and heated at 60° C. until the staring material was totally consumed (>2 days). The volatile component was removed in vacuo, and a silica gel mesh was prepared from the residue and submitted to flash chromatography (5% MeOH/CHCl$_3$) to afford amide P64 as a white solid (180 mg, 66.2%). $^1$H NMR: 7.42 (br s, 1H), 7.39–7.37 (m, 1H), 7.35 (br s, 1H), 7.24–7.21 (m, 2H), 7.03 (br s, 1H), 3.09 (m, 1H), 2.79 (dd, J=13.6, 6.0, 1H), 2.67 (dd, J=13.6, 8.4, 1H), 2.17 (s, 3H). (ESI) m/z (M+H)$^+$=257.10/259.10.

Preparation 65

(P65)

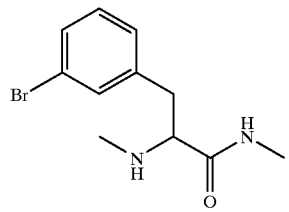

Methylamine (20 mL of 40 wt. % in water) was added into a MeOH (10.0 mL) solution of ester P63 (294.6 mg, 1.083 mml) in a Parr-bomb, the apparatus was capped and heated at 60° C. for 8.5 h. After it was cooled to room temperature, the volatile component was removed in vacuo. The residue was loaded onto an SAX column (preconditioned with MeOH) and eluted with 2.0 M NH$_3$/MeOH. A silica gel mesh of the resultant product was submitted to a flash chromatography (EtOAc) to afford amide P65 as colorless oil. (ESI) m/z (M+H)$^+$=271.16/273.16.

Preparation 66

(P66)

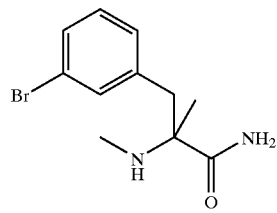

Step A:

-continued (P66A)

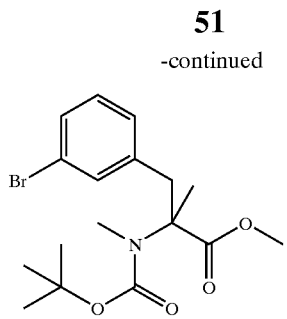

Sodium hydride (2.7 g of 60%, 67.5 mmol) was added in batches to a cooled, 0° C., DMF (75 mL) solution of N-BOC-(3-bromophenyl)alanine (2.5 g, 7.26 mmol) and methyl iodide (14.36 g, 36.47 mmol). The cooling bath was removed and the reaction mixture was stirred at ambient temperature for 61 h. It was then poured into water and the product was extracted with ethyl acetate (150 mL, 3×). The combined organic layer was washed with water (3×50 mL) and brine, dried (MgSO$_4$), filtered and evaporated in vacuo. A silica gel mesh of the crude material was submitted to flash chromatography (75% hexanes/ethyl acetate) to afford ester P66A as a colorless oil (1.9 g, 68%). $^1$H NMR: 7.47–7.45 (m, 1H), 7.30–7.26 (app t, J=7.8, 2H), 7.12 (app d, J=7.3, 1H), 3.36 (br s, 3H), 3.43 (br s, 1H), 2.89 (br s, 1H), 2.39 (br s, 3H), 1.40 (br s, 9H), 1.31 (br s, 3H). (ESI) m/z (M-Boc+H)$^+$=286.09/288.09.

Step B:

(P66B)

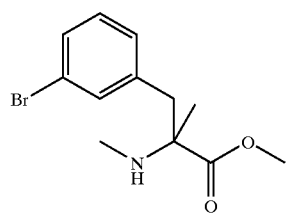

Carbmate P66A was deprotected and free-based according to the procedure described in the synthesis of ester P63. $^1$H NMR: 7.42–7.40 (m, 1H), 7.34 (m, 1H), 7.23 (app t, J=7.8, 1H), 7.14 (app d, J=7.6, 1H), 3.62 (s, 3H), 2.83 (s, 2H), 2.16 (s, 3H), 1.06 (s, 3H). (ESI) m/z (M+H)$^+$=286.09/288.09.

Step C:

Anhydrous ammonia was bubbled through a MeOH (30 mL) solution of ester P66B (287.9 mg, 1.06 mmol) in a Parr-bomb, and the apparatus was capped and heated at 100° C. for 6 days. The volatile component was removed in vacuo, and the residue was taken up in CHCl$_3$ and submitted to flash chromatography (100% CHCl$_3$→5% MeOH/CHCl$_3$) to afford amide P66 as a white solid (180 mg). $^1$H NMR: 7.39–7.36 (m, 2H), 7.23–7.16 (m, 3H), 7.02 (br s, 1H), 2.79 (s, 2H), 2.18 (s, 3H), 1.04 (s, 3H). (ESI) m/z (M+H)$^+$=271.16/273.16.

Preparation 67

(P67)

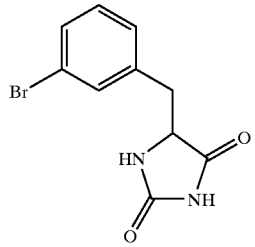

Water (5 mL) was added to a mixture of (3-bromophenyl)alanine hydrochloride (1.02 g, 3.64 mmol) and potassium cyanate (325.3 mg, 4.01 mmol), and the mixture was heated at 90° C. for 3.5 h. Additional potassium cyanate (650 mg, 8.0 mmol) was added and stirring continued at 90° C. for 0.5 h. The mixture was allowed to cool to room temperature, concentrated HCl (3 mL) was added and then it was heated at 90° C. for 0.5 h. After it cooled to room temperature, it was diluted with water and the suspension was filtered and washed with water, and allowed to air dry. Hydantoin P67 was obtained as a tan solid (800 mg, 82% yield). $^1$H NMR (400 MHZ): 10.49 (s, 1H), 7.93 (s, 1H), 7.44–7.40 (m, 2H), 7.26 (app t, J=7.7, 1H), 7.19 (m, 1H), 4.37–4.34 (m, 1H), 2.96 (dd, J=13.9, 4.9, 1H), 2.90 (dd, J=14.0, 5.4, 1H). (ESI) m/z (M+H)$^+$=269.08/271.08.

Preparation 68

(P68)

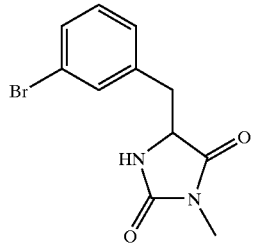

Hydantoin P67 was methylated according to the procedure described for the synthesis of ester P25. It was obtained as an off-white solid. $^1$H NMR: 8.23 (br s, 1H), 7.43 (app d, J=7.9, 1H), 7.39 (m, 1H), 7.25 (app t, J=7.8, 1H), 7.18 (app d, J=7.6, 1H), 4.38 (m, 1H), 2.99 (dd, J=14, 4.9, 1H), 2.90 (dd, J=14, 6.1, 1H), 2.69 (s 3H). (ESI) m/z (M+H)$^+$=283.08/285.08.

Preparation 69

(P69)

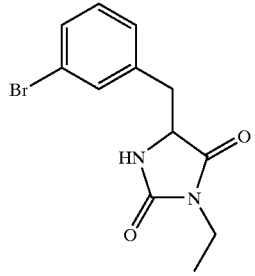

DMF (3.0 mL) followed by ethyl iodide (104.4 mg, 0.6694 mmol)were added to a mixture of hydantoin P67 (1.49.4 mg, 0.5552 mmol) and potassium carbonate (92.8 mg, 0.671 mmol). The reaction mixture was heated at 90° C. for 20 h, cooled to room temperature, and all the volatile component was removed in vacuo. The residue was diluted with water and extracted with ethyl acetate (3×50 mL). The combined organic phase was washed with water and brine, dried (MgSO$_4$), filtered and evaporated in vacuo to afford hydantoin P69 as an off-white solid (150 mg, 91% yield). The product was used without further purification. $^1$H NMR: 8.22 (br s, 1H), 7.42 (app d, J=8.3, 1H), 7.35 (m, 1H), 7.24 (app t, J=7.8, 1H), 7.17 (app d, J=7.7, 1H), 4.37 (t, J=4.6, 1H), 3.27–3.13 (m, 2H), 2.96 (d, J=4.9, 2H), 0.77 (t, J=6.9, 3H), (ESI) m/z (M+H)$^+$=297.06/299.06.

Preparation 70

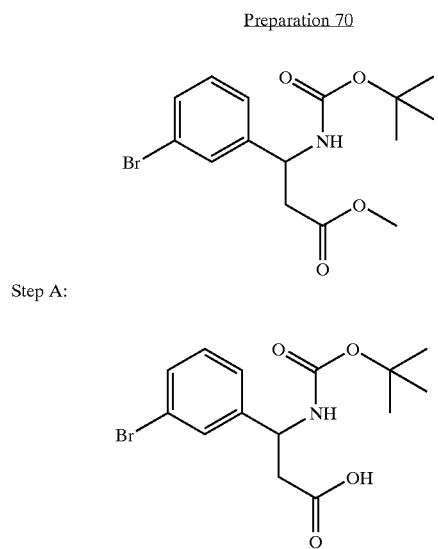

Step A:

A THF (5.0 mL) solution of Boc-anhydride (449.5 mg, 2.060 mmol) was added to a mixture of 3-amino-3-(3-bromophenyl)propanoic acid (503.4 mg, 2.062 mmol) and potassium carbonate (212.4 mg, 2.121 mmol) in water (5 mL). The reaction mixture was stirred at 25° C. for 24 h. Additional Boc-anhydride (500 mg, 2.291 mmol) was added and the reaction was stirred at 25° C. for another 18 h. Most of the THF was removed in vacuo and the residue was partitioned between ethyl acetate and water. The aqueous layer was neutralized with 1N HCl, and extracted with ethyl acetate (3×50 mL). The combined organic phase was washed with water (1×50 mL) and brine, dried (MgSO$_4$), filtered and evaporated in vacuo to afford carbamate P70A as an oil that solidified upon standing (618 mg, 87.1% yield). The product was used without further purification. $^1$H NMR: 12.26 (s, 1H), 7.49 (br m, 2H), 7.44–7.42 (m, 1H), 7.31–7.26 (m, 1H), 4.85 (m, 1H), 2.66 (dd, J=15.7, 8.4, 1H), 2.59 (dd, J=15.6, 6.7, 1H), 1.35 (s, 9H). (ESI) m/z (M+Na)$^+$=366.02/368.02.

Step B:

Ester P70 was prepared from acid P70A according to the procedure described for the synthesis of ester P25. The product was obtained as a colorless oil. $^1$H NMR: 7.53–7.51 (m, 2H), 7.44–7.43 (m, 1H), 7.32–7.27 (m, 2H), 4.89 (m, 1H), 3.56 (s, 3H), 2.75 (dd, J=15.7, 8.7, 1H), 2.69 (dd, J=15.9, 6.4, 1H), 1.35 (s, 9H). $^1$H NMR: (ESI) m/z (M+Na)$^+$=379.99/381.99.

Preparation 71

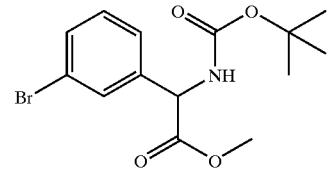

Step A:

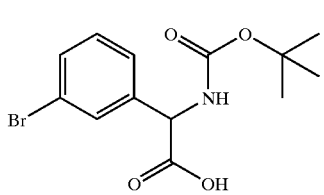

Acid P71A was prepared from 2-amino-2-(3-bromophenyl)acetic acid according to the procedure described for the synthesis of ester P70A. $^1$H NMR: 12.93 (br s, 1H), 7.70 (d, J=8.2, 1H), 7.62 (br s, 1H), 7.51 (d, J=7.9, 1H), 7.41 (d, J=7.6, 1H), 7.31 (app t, J=8, 1H), 5.15 (d, J=8.5, 1H), 1.39 (s, 9H). (ESI) m/z (M+Na)$^+$=353.98/351.98.

Step B:

Acid P71A was elaborated to ester P71 according to the procedure described for the synthesis of ester P70. $^1$H NMR: 7.89 (d, J=8.2, 1H), 7.62 (br s, 1H), 7.52 (d, J=8.0, 1H), 7.40 (d, J=7.7, 1H), 7.32 (app t, J=7.9, 1H), 5.27 (d, J=8.2, 1H), 3.62 (s, 3H), 1.39 (s, 9H). (ESI) m/z (M+Na)$^+$=365.95/367.95.

Preparation 72

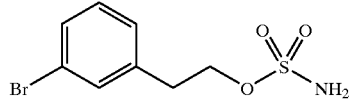

Sodium hydride (119.8 mg of 60%, 2.995 mmol) was added to a cooled, 0° C., DMF (12 mL) solution of 3-bromophenethyl alcohol (0.50 g, 2.5 mmol), and stirred for 45 min. Sulfamoyl chloride (431.5 mg, 3.735 mmol), was added and the mixture was allowed to warm up to room temperature over 15.25 h. The reaction was quenched with methanol, diluted with ethyl acetate (100 mL) and washed with water (3×25 mL), and brine. The organic layer was dried (MgSO$_4$), filtered and evaporated in vacuo to afford sulfamate P72 as a white solid (682 mg, >95%). The product was used without further purification. $^1$H NMR: 7.52 (br s, 1H), 7.48 (br s, 2H), 7.45–7.43 (m, 1H), 7.30–7.28 (m, 2H), 4.24 (t, J=6.7, 2H), 2.98 (t, J=6.8, 2H). (ESI) m/z (M+Na)$^+$= 301.91/303.91

Preparation 73

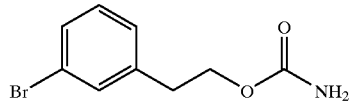

Potassium cyanate (1.68 g, 20.7 mmol) followed by TFA (2.28 g, 20.0 mmol) were added into a CH$_2$Cl$_2$ (25.0 mL) a solution of 3-bromophenethyl alcohol (1.01 g, 5.02 mmol), and the mixture was stirred at 25° C. for 31 h. Water (100 mL) was added and the organic layer was separated. The aqueous layer was extracted with ethyl acetate (100 mL, 3×). The combined organic phase was washed with brine, dried (MgSO$_4$) and filtered and evaporated in vacuo. The residue was recrystallized (hexanes/ethyl acetate) to afford carbamate P73 as an off-white solid (720 mg, 58.7% yield). $^1$H NMR: δ 7.47 (br s, 1H), 7.43–7.40 (m, 1H), 7.28–7.24 (m, 2H), 6.51 (br m, 2H), 4.11 (t, J=6.8, 2H), 2.85 (t, J=6.8, 2H).

Preparation 74

(P74)

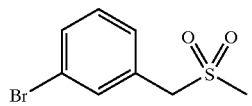

A mixture of 3-bromobenzyl bromide (3.01 g, 12.0 mmol) and methanesulphinic acid sodium salt (3.12 g, 30.6 mmol) in DMF/water (1:9 v/v, 180 mL) was heated at 45° C. for 19.75 h. It was cooled to room temperature and extracted with ethyl acetate (150 mL, 3×). The combined organic phase was washed with water (3×50 mL) and brine (100 mL), dried (MgSO$_4$), filtered and evaporated in vacuo to afford sulphone P74 as a white solid (3.00 g, >95%). The product was used without further purification. $^1$H NMR: 7.62–7.59 (m, 2H), 7.43–7.42 (m, 1H), 7.38 (app t, J=7.8, 1H), 4.52 (s, 2H), 2.92 (s, 3H).

Preparation 75

(P75)

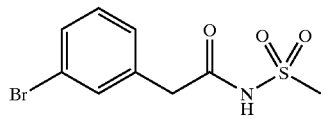

A CH$_2$Cl$_2$ (4.0 mL) solution of 1,3-dicyclohexylcarbodiimide (1.25 g, 6.06 mmol) was added over 1 min. to a cooled, 0° C., mixture of (3-bromophenyl)acetic acid (1.00 g, 4.66 mmol), 4-dimethylaminopyridine (740.0 mg, 6.057 mmol), and methansulfonamide (575.9 mg, 6.054 mmol) in dichloromethane (17 mL). The mixture was stirred for 20.5 h at ambient temperature and filtered, and the filtrate was rotovaped. The residue was submitted to flash chromatography (ethyl acetate; 5% MeOH/CH$_2$Cl$_2$) to afford a mixture of sulphonamide P75 and DMAP as a colorless gum (1.8 g; 1:1 mole ratio according to $^1$H NMR). The mixture was used for the coupling step with out further purification. $^1$H NMR: 7.45 (s, 1H), 7.41–7.39 (m, 1H), 7.26–7.23 (m, 2H), 3.42 (s, 2H), 2.92 (s, 3H). (ESI) m/z (M+H)$^+$=292.03/294.03.

Preparations 76–78

The following compounds were prepared according to the indicated literature procedures:

76) 4-Iodo-3-o-pyridyl N,N-diethylcarbamate: *Organic Letters*, Vo. 21 (2000) at p. 2291.

77) 2-Amino-3-iodopyridine: *J. Org. Chem.*, Vol. 53 (1988) at p. 2740; and 78) 2-Bromo-1-methyl-1H-imidazole: *Aust. J. Chem.*, Vol. 52 (1999) at p. 159.

Preparation 79

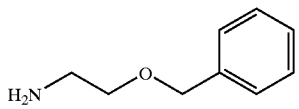

At room temperature, sodium hydride (3.33 g, 83.5 mmol) was added in small portion to THF (90 ml) solution of the ethanolamine (5.04 ml, 83.5 mmol), and the mixture was stirred under reflux for 30 mins. The reaction mixture was cooled to rt and benzyl chloride (7.7 ml, 67.1 mmol) was added. The mixture was stirred again under reflux for 15 h. Water (6 ml) was added to quench the reaction. The reaction mixture was cooled to rt and solvent was removed in vacuo. The residue was dissolved in dichloromethane and washed with water. The organic layer was washed with brine, dried (MgSO$_4$), filtered and evaporated in vacuo. The crude material was submitted to flash chromatography (ethyl acetate, methanol) to afford clear oil (7.57 g, 60%). $^1$H NMR (DMSO, 400 MHZ): 7.32 (m, 5H), 4.47 (s, 2H), 3.39 (t, J=5.8, 2H), 2.69 (t, J=5.8, 2H), 1.51 (br, 2H). (ESI) m/z (M+H)$^+$=152.2 1.

Step A:

Preparation 80

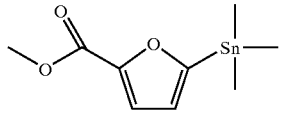

A toluene (10 ml) solution of hexamethylditin (2.924 g, 8.93 mmol) was treated with methyl 5-bromo-2-furoate (500 mg, 2.44 mmol) and triethylamine (0.68 mL, 4.88 mmol). After nitrogen was bubbled through the mixture for 5 min, Pd(Ph$_3$P)$_4$ (96.0 mg, 0.083 mmol) was added. The reaction mixture was heated with a 100° C. oil bath for 35 min. The dark reaction mixture was cooled to room temperature, filtered through a pad of Celite, washed with EtOAc, and the filtrate was evaporated in vacuo. The residue was triturated with ether, and the light brown solid was filtered and washed with copious ether and dried in vacuo (490 mg of the title compound was retrieved). m/z (M+H)$^+$=289.

EXAMPLE 1

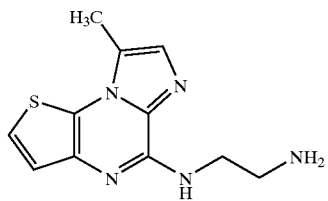

Step A:

-continued

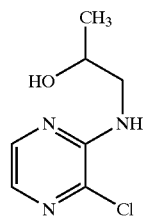

(1A)

1-Amino-2-propanol (25.0 ml, 0.3239 mol) was added to a 1,4-dioxane (81.0 mL) solution of 2,3-dichloropyrazine (19.7 g with 95% purity, 0.1256 mol). The reaction mixture was heated with an oil bath (pre-equilibrated at 110° C.) for 6.75 h. It was then removed from the oil bath and allowed to cool to rt. The two phases were separated, and the upper layer was exposed to vacuum to remove volatile components. The viscous residue was diluted with $CH_2Cl_2$ and rotovaped a few times to remove residual dioxane and provide the crude compound 1A.

Step B:

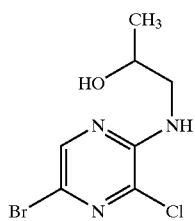

(1B)

N-Bromosuccinimide (26.09 g, 0.1466 mol) was slowly added to a $CHCl_3$ (170 mL) solution of crude 1A and the resulting reaction mixture was refluxed for 3.15 h, cooled to rt, washed with water (100 mL, 2×) and brine, and dried over $MgSO_4$. It was then filtered and evaporated in vacuo to afford bromide compound 1B as a dense yellow solid. $^1H$ NMR ($CDCl_3$, d=7.281 ppm; 500 MHz): 8.03 (s, 1H), 5.61 (br s, 1H), 4.08 (br m, 1H), 3.66 (ddd, J=13.9, 6.5, 3.2, 1H) 3.34 (ddd, J=13.9, 7.9, 5.2, 1H), 2.23 (br s, 1H), 1.29 (d, J=6.3, 3H). (ESI) m/z $(M+H)^+$=267.94.

Step C:

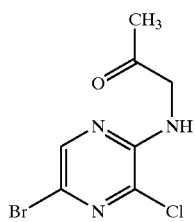

(1C)

DMSO (30 mL, 0.4228 mol) was added dropwise over 30 min. to a cooled (−78° C.) $CH_2Cl_2$ (250 mL) solution of oxalyl chloride (20.3 mL, 0.2327 mol). The reaction mixture was stirred for 70 min, and then a $CH_2Cl_2$ (275+25 mL) solution of the crude alcohol from step B was added to it over 70 min. and stirring continued at −78° C. Half an hour later, TEA (60.0 mL) was added over 10 min, and then half an hour later, the cold bath was removed and the reaction mixture was allowed to thaw to rt over the next hour. The reaction mixture was washed with water (3×) and brine, dried ($MgSO_4$), filtered, and evaporated in vacuo. A silica gel mesh of the crude material was prepared and submitted to flash chromatography ($CHCl_3$) to afford ketone 1C as a yellow solid (26.18 g, a three step combined yield of 78.8%). $^1H$ NMR ($CDCl_3$, δ=7.26 ppm; 500 MHz): 8.02 (s, 1H), 5.97 (br s, 1H), 4.29 (d, J=4.7, 2H), 2.28 (s, 3H). (ESI) m/z $(M+H)^+$=265.98.

Step D:

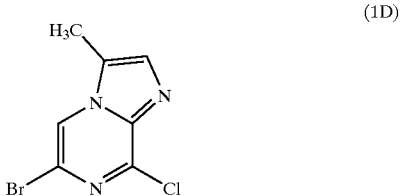

(1D)

Trifluoroacetic anhydride (40.0 ml, 0.2832 mole) was added dropwise over 30 min. to a stirred trifluoroacetic acid (65.0 ml) solution of ketone 1C from step C (26.18 g, 0.0990 mole). The reaction mixture was stirred for 2.25 h and the volatile component was removed in vacuo. The resulting crude oil was dissolved in $CHCl_3$ and washed with a sufficient amount of sat'd $NaHCO_3$ that the wash had a slightly basic pH. The organic phase was washed with brine, dried ($MgSO_4$), filtered, and evaporated in vacuo. A silica gel mesh of the crude material was prepared and submitted to flash chromatography (50% EtOAc/hexanes) to afford imidazopyrazine 1D as an off-white fluffy solid (22.60 g, 92.6%). $^1H$ NMR ($CDCl_3$, δ=7.26 ppm; 500 MHz): 8.00 (s, 1H), 7.65 (s, 1H), 2.53 (s, 3H). (ESI) m/z $(M+H)^+$=247.91.

Step E:

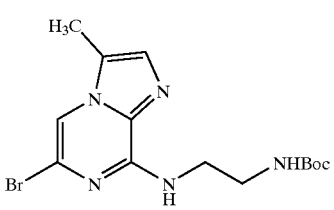

(1E)

Imidazopyrazine 1D (8.23 g, 33.3888 mmol) was added to a THF (60.0 mL) solution of tert-butyl N-(2-aminoethyl) carbamate (6.20 g, 38.6968 mmol) and TEA (9.0 mL, 64.5716 mmol). The reaction mixture was heated with an oil bath (65° C.) for 17 h, cooled to rt, and the precipitate filtered. Silica gel was added to the filtrate and evaporated in vacuo. The resulting silica gel mesh was submitted to flash chromatography (50–70% EtOAc/hexanes) to afford bromide 1E as an off-white solid (11.149 g, 90.2% yield). $^1H$ NMR ($CDCl_3$, δ=7.26 ppm; 500 MHz): 7.37 (s, 1H), 7.24 (s, 1H), 6.37 (br s, 1H), 5.13 (br s, 1H), 3.73 (app q, J=5.7, 2H), 3.44 (m, 2H), 2.4 (d, J=0.7, 3H), 1.43 (s, 9H). (ESI) m/z $(M+H)^+$=369.96/371.96.

Step F:

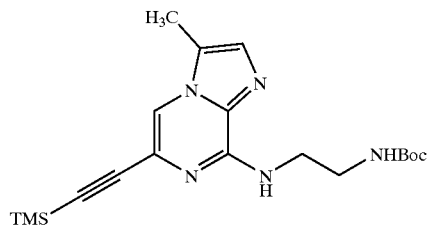
(1F)

A mixture of Pd(Ph₃P)₄ (2.9180 g, 2.525 mmol) and CuI (0.8034 g, 2.204 mmol) was added to a pressure tube containing a DMF (200 mL) solution of bromide 1E (22.67 g, 61.229 mmol), (trimethylsilyl)acetylene (20.0 mL, 0.1415 mol), and TEA (36.0 mL, 0.2582 mol). The reaction flask was flushed with nitrogen, capped, and heated at 64° C. for ~16 h. The reaction mixture was then allowed to cool to rt and the precipitate was filtered. The filtrate was exposed to vacuum to remove the DMF and other volatile components. A silica gel mesh was prepared from the residue and submitted to flash chromatography (50–60% EtOAc/hexanes) to afford alkyne 1F as a yellow foam (23.90 g). $^1$H NMR (CDCl₃, δ=7.26 ppm; 500 MHz):7.50 (s, 1H), 7.26 (s, 1H), 6.22 (app br s, 1H), 5.09 (app br s, 1H), 3.76 (app q, J=5.8, 2H), 3.45 (m, 2H), 2.41 (s, 3H), 1.42 (s, 9H), 0.28 (s, 9H). (ESI) m/z (M+H)⁺=388.1.

Step G:

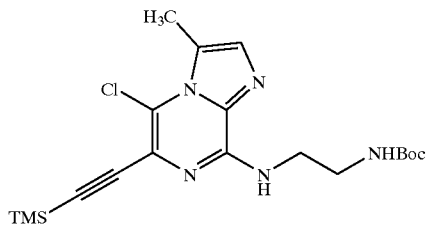
(1G)

N-Chlorosuccinimide (9.1477 g, 68.51 mmol) was added to a THF (200 mL) solution of alkyne 1F (23.90 g, 61.67 mmol), and the resulting reaction mixture was heated with an oil bath (~64° C.) for 6 h. The solvent was removed in vacuo, and the residue was dissolved in CH₂Cl₂ and washed with water (2×) and brine. The organic layer was dried (MgSO₄), filtered, and evaporated in vacuo. The crude material was submitted to flash chromatography (the sample was loaded onto column with the eluting solvent; 30–40% EtOAc/hexanes) to afford a clean chloride 1G and some impure fraction. The impure fraction was further purified as above to retrieve more pure material. Chloride 1G was obtained as a light yellow solid (20.07 g, a two step combined yield of 77.7%). $^1$H NMR: 7.61 (br t, J=5.7, 1H), 7.35 (d, J=0.7, 1H), 6.93 (br t, J=5.4, 1H), 3.45 (app q, J=5.9, 2H), 3.17 (app q, J=5.9, 2H), 2.69 (s, 3H), 1.36 (s, 9H), 0.25 (s, 9H). (ESI) m/z (M+H)⁺=422.24.

Step H:

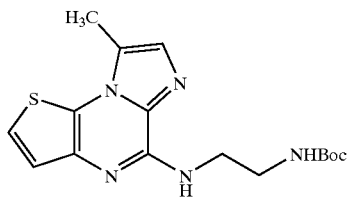
(1H)

DMF (54.0 mL) was added to a mixture of chloroalkyne 1G (3.1377 g, 7.4353 mmol) and Na₂S.9H₂O (5.48 g, 22.82 mmol; the solid was crushed with mortar and pestle; 99.99% pure). The resulting heterogeneous reaction mixture was heated for 65 min. with an oil bath pre-equilibrated at 100° C. The reaction mixture was allowed to cool to rt and the volatile component removed in vacuo. A silica gel mesh of the residue was prepared and submitted to flash chromatography (50% EtOAc/hexanes) to afford amine 1H as a light yellow solid (1.46 g, ~56%). $^1$H NMR: 7.52 (d, J=5.5, 1H), 7.36 (d, J=0.9, 1H), 7.33 (br t, J=5.7, 1H), 7.25 (d, J=5.5, 1H), 6.96 (br t, J=5.1, 1H), 3.53 (app q, J=6.1, 2H), 3.22 (app q, J=6.0, 2H), 2.69 (d, J=0.8, 3H), 1.36 (s, 9H). (ESI) m/z (M+H)⁺=348.05.

Step I:

EXAMPLE 1

The Boc-protected compound 1H was deprotected by treatment with 20% TFA/CH₂Cl₂ and stirring of the reaction mixture at rt for 0.5–1.0 hr. The volatile component was removed in vacuo, and the residue was treated with MeOH and rotervaped twice to remove most of the TFA. The resulting crude material was dissolved in either MeOH and/or DMF and purified on a PREP-HPLC to afford the TFA salt of Example 1. (ESI) m/z (M+H)⁺=248.27.

EXAMPLE 2

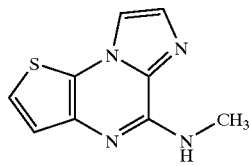

Step A:

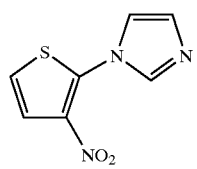
(2A)

DMF (40 mL) was added into a flask containing imidazole (2.891 g, 42.4647 mmol) and 1-chloro-2-nitrothiophene (2.9047 g, 17.7571 mmol), and the reaction mixture was heated at 90° C. for 13.5 h. It was allowed to cool to rt and filtered, and the solvent was removed in vacuo. The resulting crude material was partitioned between EtOAc and water. The organic layer was washed with brine, dried (MgSO₄), filtered, and evaporated in vacuo. A silica gel mesh of the residue was prepared and submitted to flash chromatography (75–90% EtOAc/hexanes) to afford the coupled material (2A) as a dull-yellow crystal (2.46 g, 71.0%). ¹H NMR (CDCl₃, δ=7.26 ppm; 500 MHz): 7.86 (s, 1H), 7.65 (d, J=6.2, 1H), 7.28 (d, J=6.3, 1H), 7.27 (1H, overlapped signal), 7.22 (m, 1H). (ESI) m/z (M+H)⁺= 196.03.

Step B:

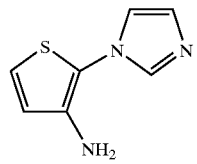
(2B)

MeOH (80 mL) was added into a hydrogenation apparatus that contained nitrothiophene 2A (2.32 g, 11.885 mmol), 10% Pd/C (930 mg), and hydrogenated at 40 PSI. The reaction was allowed to proceed for a total of 22.25 h, the catalyst was filtered, and the filtrate rotovaped. The resulting crude oil was submitted to flash chromatography (0–5% MeOH/EtOAc) to afford amine 2B as a dark-yellow oil that slowly crystallized to a waxy solid (1.72 g, 87.6%). ¹H NMR (CDCl₃, δ=7.26 ppm; 500 MHz): 7.65 (s, 1H), 7.20 (s, 1H), 7.09 (m, 1H), 7.07 (d, J=5.9, 1H), 6.61 (d, J=6.0, 1H). (ESI) m/z (M+H)⁺=166.21.

Step C:

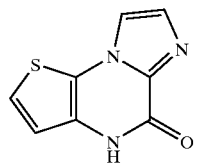
(2C)

o-Dichlorobenzene (30 mL) was added into a flask containing compound 2B (1.639 g, 9.9201 mmol) and 1,1'carbonyldiimidazole (1.961 g, 12.0937 mmol). The heterogeneous reaction mixture was heated at 140° C. for 5.75 h and then allowed to cool to rt. It was diluted with ether (150 mL), and the solid was filtered and washed with copious ether. The brown solid was transferred into a flask containing EtOAc (20 mL), stirred for 15 min, filtered, and washed with EtOAc (20 mL). The solid was then transferred into a flask containing water (10 mL), stirred for 10 min, filtered, and washed with copious water. The resulting solid was dried in vacuo to provide 1.35 g of cyclized material 2C. ¹H NMR: 12.06 (s, 1H), 8.16 (d, J=1.1, 1H), 7.56 (s, 1H), 7.51 (d, J=5.7, 1H), 6.97 (d, J=5.7, 1H) (ESI) m/z (M+H)⁺= 192.01.

Step D:

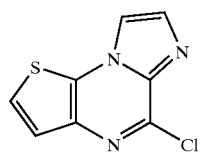
(2D)

N,N-Diethylaniline (2.0 mL, 12.57 mmol) and POCl₃ (20 mL) were added to the impure tricycle compound 2C (1.28 g), and the reaction mixture was refluxed for 6 h. After it was allowed to cool to rt, most of the volatile POCl₃ was removed in vacuo. The residue was partitioned between EtOAc and water. The aqueous layer was neutralized with solid Na₂CO₃, and an EtOAc extraction was done. The combined organic phase was washed with brine, dried (MgSO₄), filtered, and evaporated in vacuo. A silica gel mesh of the crude material was prepared and submitted to flash chromatography (40–50% EtOAc/hexanes) to afford chloride 2D as a white solid (0.8593 g, a two-step combined yield of 43.6%). ¹H NMR (CDCl₃, δ=7.26 ppm; 500 MHz): 7.93 (d, J=0.85, 1H), 7.86 (s, 1H), 7.51 (d, J=5.7, 1H), 7.37 (d, J=5.7, 1H).

Step E:

EXAMPLE 2

Excess methylamine (2.0 mL, 40% wt /H₂O) was added to a THF (3.0 mL) suspension of compound 2D (74.2 mg, 0.3539 mmol). The reaction mixture was stirred at rt for 13.75 h and at 60° C. for 1.75 h, and the volatile component was removed in vacuo. A silica gel mesh of the crude material was prepared and submitted to flash chromatography (40% EtOAc/hexanes) to afford Example 2 as a white fluffy solid (56 mg, 77.5%). ¹H NMR (CDCl₃, δ=7.26 ppm; 500 MHz): 7.60 (s, 1H), 7.58 (s, 1H), 7.32 (d, J=5.6, 1H), 7.16 (d, J=5.5, 1H), 6.09 (br s, 1H), 3.22 (d, J=5.1, 3H). (ESI) m/z (M+H)⁺=205.05.

EXAMPLE 3

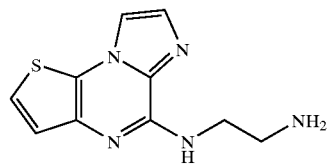

Excess ethylenediamine (5.0 mL) was added to chloride 2D (74 mg, 0.353 mmol), and the resulting reaction mixture was stirred at rt for 27 h. Most of the ethylenediamine was removed in vacuo, and the residue was partitioned between EtOAc and sat'd NaHCO₃ solution. The aqueous layer was saturated with NaCl, and additional EtOAc extractions were conducted until no more product was removed as determined by TLC. The combined organic layer was directly submitted to flash chromatography (MeOH) to afford a viscous oil that ultimately crystallized into a white solid (59.6 mg, 72%). ¹H NMR: 8.18 (s, 1H), 7.62 (s, 1H), 7.48 (d, J=5.7, 1H), 7.34 (br t, J=5.6, 1H), 7.24 (d, J=5.7, 1H), 3.48 (m, 2H), 2.80 (app t, J=6.5, 2H). (ESI) m/z (M+H)⁺= 234.02.

EXAMPLE 4

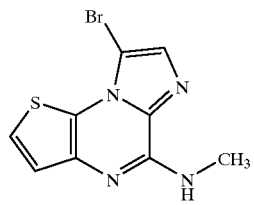

Step A:

(4A)

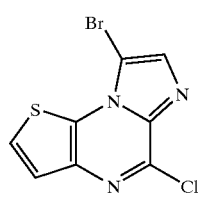

N-Bromosuccinimide (134.0 mg, 0.7529 mmol) was added in batches over a few minutes to a cooled (0° C.) THF (4.5 mL) solution of compound 2D (152.5 mg, 0.7274 mmol), and the reaction mixture was stirred for 2.25 h. Silica gel was added into the reaction mixture, and the solvent was removed in vacuo. The resulting silica gel mesh was submitted to flash chromatography (15–20% EtOAc/hexanes) to afford bromide 4A as a fluffy white solid (196.4 mg, 93.6%). $^1$H NMR (CDCl$_3$, δ=7.26 ppm; 500 MHz): 7.83 (s, 1H), 7.53 (d, J=5.7, 1H), 7.44 (d, J=5.7, 1H). (ESI) m/z (M+H)$^+$=287.83/289.83.

Step B:

EXAMPLE 4

Excess methylamine (2.0 mL, 40% wt /H$_2$O) was added to a THF (3.0 mL) suspension of chloride 4A (105 mg, 0.3639 mmol). The reaction mixture was stirred at rt for 16.25 h, and the volatile component was removed in vacuo. A silica gel mesh of the crude material was prepared and submitted to flash chromatography (40% EtOAc/hexanes) to afford Example 4 as a white fluffy solid (94.2 mg, 91.4%). $^1$H NMR: 7.71 (s, 1H), 7.59 (m, 1H), 7.56 (d, J=5.6, 1H), 7.29 (d, J=5.7, 1H), 2.97 (d, J=4.9, 3H). (ESI) m/z (M+H)$^+$= 282.90/284.90.

EXAMPLE 5

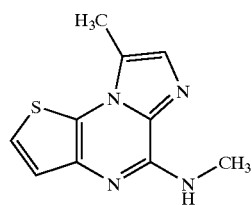

Step A:

(5A)

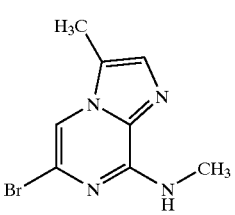

Methylamine (30.0 mL, 40% wt in water) was added to a THF (100 mL) solution of chloride 1D (21.65 g, 87.8331 mmol) in a pressure tube. A heavy suspension appeared in 10 min. The reaction mixture was stirred at rt for 5.5 h and then stored in a refrigerator for an additional 20 h. The precipitate was filtered, and the solid was washed with copious water and dried under vacuum to afford amine 5A as an off-white solid (17.6 g). The filtrate afforded a second crop when stored at rt for a few h (3.36 g off-white solid, a combined yield of >98%). $^1$H NMR: 7.85 (m, 1H), 7.78 (s, 1H), 7.27 (d, J=0.7, 1H), 2.91 (d, J=4.9, 3H), 2.38 (d, J=0.9, 3H). (ESI) m/z (M+H)$^+$=(241.11/243.11).

Step B:

(5B)

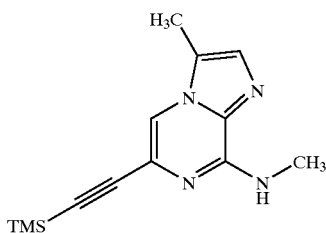

Bromide 5A (17.60 g, 73.00 mmol) was converted to alkyne 5B following the procedure of Example 1, Step F, except: (a) 30% less catalyst and co-catalyst were employed; and (b) the column was eluted with 40–60% EtOAc/hexanes. Amine 5B was retrieved as a yellow solid (17.88 g). $^1$H NMR 7.85 (s, 1H), 7.56 (m, 1H), 7.29 (d, J=0.6, 1H), 2.92 (d, J=4.9, 3H), 2.40 (s, 3H), 0.25 (s, 9H). (ESI) m/z (M+H)$^+$=259.42.

Step C:

(5C)

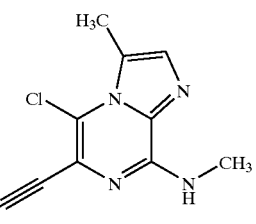

N-Chlorosuccinimide (10.4825 g, 78.50 mmol) was added to a THF (200 mL) solution of compound 5B (17.88 g, 69.20 mmol), and the resulting reaction mixture was heated with an oil bath (~60° C.) for 14 h. It was allowed to cool to rt, and the solvent was removed in vacuo. The residue was dissolved in CHCl$_3$ (350 mL), washed with water (150 mL, 3×) and brine, and the organic layer was evaporated in vacuo. A silica gel mesh was prepared from the crude material and submitted to flash chromatography (30% EtOAc/hexanes, until all the higher Rf impurities were eluted, then 50% EtOAc/hexanes) to afford chloride 5C as an off-white solid (16.52 g, a two-step combined yield of 77.3 %). $^1$H NMR: 7.66 (m, 1H), 7.33 (d, J=0.9, 1H), 2.89 (d, J=4.9, 3H), 2.69 (d, J=1.0, 3H), 0.26 (s, 9H). (ESI) m/z (M+H)$^+$=293.27.

Step D:

EXAMPLE 5

A stirred suspension of chloroalkyne 5C (17.68 g, 60.37 mmol) in DMF (310 mL, bubbled with argon) was treated with grounded sodium sulfide nonahydrate (43.5 g, 181.12 mmol, 99.99% purity) at rt. After 5 min, LC/MS analysis of the reaction mixture showed complete desilylation. The mixture was then heated at 80° C. for ~1 hr and the solvent evaporated in vacuo. The residue was dissolved in chloroform and washed with water. The aqueous phase was extracted with chloroform (3×) and the combined organic phase was dried (MgSO$_4$), filtered, and concentrated. The residue was submitted to flash chromatography (50–100% CH$_2$Cl$_2$/EtOAc) to afford Example 5 as a yellowish solid (8.35 g, 63.4%).

Alternate Process to Prepare Example 5

Alternatively to Steps A-D, Example 5 was prepared from Example 4 as follows: Tetramethyltin (2.4 mL, 17.326 mmol) was added into a DMF (19.0 mL) suspension of Example 4 (704 mg, 2.4863 mmol), PdCl$_2$(Ph$_3$P)$_2$ (185.1 mg, 0.2637 mmol) and KF (311 mg, 5.3528 mmol). After nitrogen was bubbled through the heterogeneous mixture for 30 seconds, it was heated at 90° C. for 13.75 h. It was allowed to cool to rt and the volatile component was removed in vacuo. A silica gel mesh of the crude material was prepared and submitted to flash chromatography (50% EtOAc/hexanes) to afford a mixture of Example 5 and Ph$_3$PO in a 10:1 molar ratio ($^1$H NMR) (351 mg). A portion of the impure product was purified further on a PREP-HPLC, and the resulting TFA salt of Example 5 was converted to the free base: the salt was dissolved in water; the aqueous medium was basified with NaHCO$_3$ solution and extracted with EtOAc; the organic layer was dried over MgSO$_4$ and the solvent was removed in vacuo. $^1$H NMR: 7.51 (d, J=5.5, 1H), 7.39 (m, 1H), 7.34 (d, J=0.9, 1H), 7.27 (d, J=5.6, 1H), 2.96 (d, J=4.8, 3H), 2.69 (d, J=0.8, 3H). (ESI) m/z (M+H)$^+$=218.98.

EXAMPLE 6

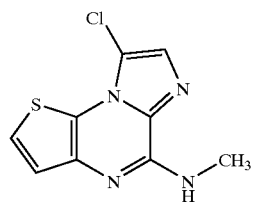

Step A:

(6A)

N-Chlorosuccinimide (103.4 mg, 0.7744 mmol) was added to a THF (4.0 mL) solution of compound 3D (150.9 mg, 0.7198 mmol), and the reaction mixture was stirred at rt for 16 h. Silica gel was added to the mixture, and the solvent was removed in vacuo. The resulting silica gel mesh was submitted to flash chromatography (20–30% EtOAc/hexanes) to afford dichloride 6A as a white fluffy solid (157.4 mg, 89.6%). $^1$H NMR (CDCl$_3$, δ=7.26 ppm; 500 MHz): 7.78 (s, 1H), 7.54 (d, J=5.5, 1H), 7.47 (d, J=5.8, 1H).

Step B:

EXAMPLE 6

THF (3.0 mL) and methylamine (3.0 ml of 2.0M/THF) were added into a pressure tube containing dichloride 6A (51.3 g, 0.2102 mmol), and the reaction mixture was heated at 70° C. for 3.25 h. It was transferred to a flask containing NaHCO$_3$ (29 mg) and a few drops of water, shaken briefly, and the volatile component was removed in vacuo. A silica gel mesh of the crude material was prepared and submitted to flash chromatography (25–30% EtOAc/hexanes) to afford Example 6 as a white solid (41.5 mg, 82.7%). $^1$H NMR: 7.71 (s, 1H), 7.63 (m, 1H), 7.59 (d, J=5.7, 1H), 7.30 (d, J=5.6, 1H), 2.98 (d, J=4.6, 3H). (ESI) m/z (M+H)$^+$=238.88.

EXAMPLE 7

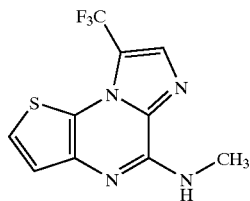

Step A:

(7A)

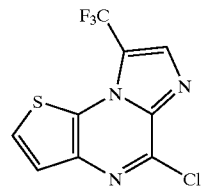

FO$_2$SCF$_2$CO$_2$Me (70 uL, 0.550 mmol) was added into a DMF (2.0 mL) suspension of compound 4A (156 mg, 0.5406 mmol) and CuI (13.1 mg, 0.0688 mmol). The reaction mixture was heated at 80° C. for 4.25 h, FO$_2$SCF$_2$CO$_2$Me (70 uL) was added, it was heated for 4 more h, additional FO$_2$SCF$_2$CO$_2$Me (100 uL) was added, and it was heated for a final 23 h. Heating was stopped and the volatile component was removed in vacuo. A silica gel mesh of the crude material was prepared and submitted to flash chromatography (15% EtOAc/hexanes) to afford compound 7A as a white solid (17 mg). $^1$H NMR (CDCl$_3$, δ=2.50 ppm; 500 MHz): 8.21 (s, 1H), 7.57 (d, J=5.8, 1H), 7.52 (d, J=5.8, 1H). (ESI) m/z (M+H)$^+$=277.91.

Step B:

EXAMPLE 7

Methylamine (0.5 mL of 2.0 M/THF) was added into a THF (1.0 mL) solution of chloride 7A prepared above, and the reaction mixture was stirred at rt for 15.5 h. It was partitioned between EtOAc and 50% sat'd NaHCO$_3$ solution. The organic layer was washed with brine, dried (MgSO$_4$), filtered, and evaporated in vacuo. A silica gel mesh of the crude material was prepared and submitted to flash chromatography (20% EtOAc/hexanes) to afford impure Example 7. It was purified on a PREP-HPLC, and the resulting TFA salt was converted to the free base as described in Example 5. Pure Example 7 was obtained as a white solid (9.8 mg, a combined yield of 6.7%). $^1$H NMR (CDCl$_3$, δ=7.26 ppm; 500 MHz): 7.89 (s, 1H), 7.33 (d, J=5.7, 1H), 7.29 (d, J=5.8, 1H), 6.09 (br s, 1H), 3.22 (d, J=5.1, 3H). (ESI) m/z (M+H)$^+$=272.97.

EXAMPLES 8a AND 8b

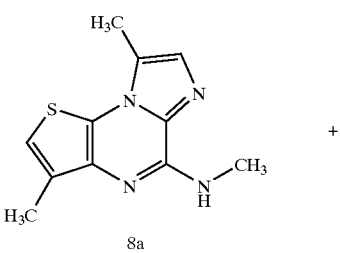

8a

-continued

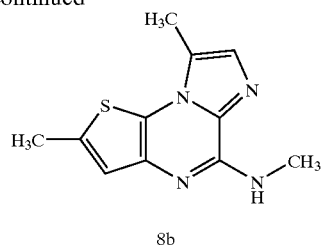

8b

Butyllithium (500 uL of 1.6 M/hexanes, 0.80 mmol) was added over 2 min. to a cooled (−78° C.) THF (3.0 mL) solution of Example 5 (81.0 mg, 0.3712 mmol), and the reaction mixture was stirred for 33 min. Iodomethane (50 uL, 0.8032 mmol) was added dropwise over 2 min, and stirring was continued at −78° C. for an additional 8.75 h. The reaction mixture was quenched with MeOH and partitioned between EtOAc and water. The organic layer was washed with brine, dried ($MgSO_4$), filtered, and evaporated in vacuo. A silica gel mesh of the crude material was prepared and submitted to flash chromatography (35–50% EtOAc/hexanes) to afford pure amine 8a and impure amine 8b. Amine 8b was purified on a PREP-HPLC, and the resulting TFA salt was converted to the free base as described for Example 5 to provide Examples 8a (18.1 mg, 21%), and 8b (17.2 mg, 20%). $^1$H NMR of 8a: 7.37 (br q, J=4.5, 1H), 7.34 (d, J=0.85, 1H), 7.17 (d, J=1.2, 1H), 3.00 (d, J=4.8, 3H), 2.68 (d, J=0.70, 3H), 2.34 (d, J=1.1, 3H). $^1$H NMR of 8b: 7.34 (m, 1H), 7.31 (d, J=0.85, 1H), 7.00 (d, J=1.3, 1H), 2.94 (d, J=4.8, 3H), 2.65 (d, J=0.7, 3H), 2.53 (d, J=1.1, 3H). For both samples, (ESI) m/z (M+H)$^+$=232.92.

EXAMPLE 9

Step A:

(9A)

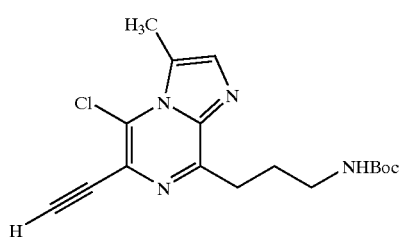

$K_2CO_3$ (615 mg, 4.4498 mmol) was added to a MeOH (140 mL) solution of compound 1G (9.178 g, 21.7488 mmol), and the mixture was stirred for 46 min. The volatile component was removed in vacuo and the resulting residue was diluted with $CH_2Cl_2$ and washed with brine. The organic layer was dried ($MgSO_4$), filtered, and evaporated in vacuo. Chloride 9A was obtained as a gray solid (7.51 g, 98.7%). $^1$H NMR: 7.64 (t, J=5.7, 1H), 7.36 (d, J=0.6, 1H), 6.93 (t, J=5.4, 1H), 4.45 (s, 1H), 3.44 (app q, J=6.1, 2H), 3.17 (app q, J=6.0, 2H), 2.70 (d, J=0.6, 3H), 1.36 (s, 9H). (ESI) m/z (M+H)$^+$=350.15.

Step B:

(9B)

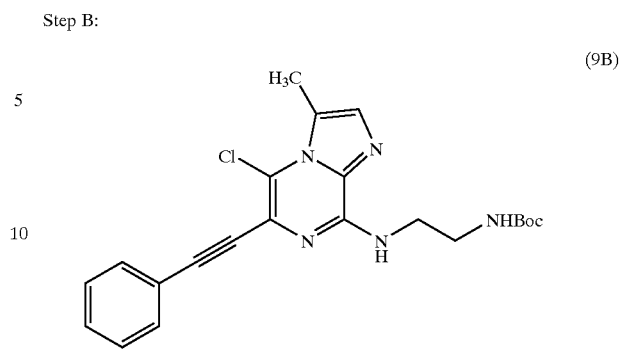

A mixture of $Pd(Ph_3P)_4$ (22.8 mg, 0.1973 mmol) and CuI (6.7 mg, 0.0352 mmol) was added to a DMF (2.0 mL) solution of alkyne 9A (70.8 mg, 0.2024 mmol), iodobenzene (196.8 mg, 0.9647 mmol), and TEA (150 uL, 1.076 mmol). The reaction mixture was stirred at rt for 15 h. The volatile components were removed in vacuo, and a silica gel mesh of the residue was prepared and submitted to flash chromatography (35% EtOAc/hexanes) to afford alkyne 9B as an off-white foam (71.6 mg, 83%). $^1$H NMR (CDCl$_3$, δ=7.26 ppm; 500 MHz): 7.62 (m, 2H), 7.37 (m, 3H), 7.22 (s, 1H), 6.25 (br s, 1H), 5.11 (br s, 1H), 3.75 (app q, J=5.7, 2H), 3.45 (m, 2H), 2.78 (s, 3H), 1.42 (s, 9H). (ESI) m/z (M+H)$^+$= 426.17.

Step C:

(9C)

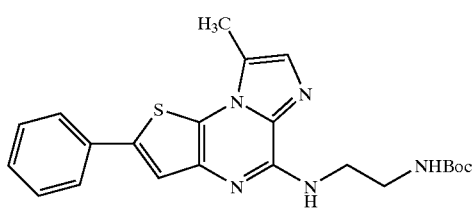

DMF (2.0 mL) was added to a mixture of chloride 9B (70.3 mg, 0.1651 mmol) and $Na_2S.9H_2O$ (239 mg, 0.995 mmol, 99.99%). The heterogeneous mixture was heated for 45 min. at 100° C. The volatile component was removed in vacuo, and the residue was partitioned between EtOAc and 50% sat'd NaCl solution. The organic layer was dried ($MgSO_4$), filtered, and evaporated in vacuo. A silica gel mesh was prepared from the crude material and submitted to flash chromatography (50–60% EtOAc/hexanes) to afford the cyclized Boc-protected product 9C as an orange foam (52 mg, 74% yield). $^1$H NMR (CDCl$_3$, δ=7.26 ppm; 500 MHz): 7.65 (m, 2H), 7.51 (s, 1H), 7.43 (m, 2H), 7.34 (m, 1H), 7.29 (s, 1H), 6.22 (br s, 1H), 5.39 (br s, 1H), 3.78 (app q, J=5.7, 2H), 3.48 (m, 2H), 2.77 (s, 3H), 1.44 (s, 9H).

$^{13}$C-NMR (CDCl$_3$, δ=77.0 ppm; 125.7 MHz): 156.2, 147.8, 140.1, 136.7, 133.8, 132.5, 130.1, 129.1, 128.1, 125.5, 123.9, 119.5, 119.4, 79.3, 41.1, 41.0, 28.4, 10.4. Anal. Calcd for $C_{22}H_{25}N_5O_2S$: C, 62.38; H, 5.94; N, 16.53. Found: C, 62.21; H, 5.89; N, 16.49. HRMS calcd for (M+H)$^+$ 424.1807, found 424.1815.

Step D:

EXAMPLE 9

Amine 9C (52 mg, 0.1228 mmol) was treated with 25% TFA/$CH_2Cl_2$ (4.0 mL), and the reaction mixture was stirred for 1.25 hr. The volatile component was removed in vacuo, and the residue was treated with 2 mL MeOH and 1.0 mL of 1.0 M NaOH/H$_2$O solution and rotovaped again. A silica gel mesh of the crude material was prepared and submitted to flash chromatography (short column; MeOH) to afford the deprotected Example 9 as an off-white solid (29.3 mg, 76%). (ESI) n/z (M+H)$^+$=324.15.

A portion of the compound obtained above (24 mg, 0.0743 mmol) was dissolved in 2-propanol (9.0 mL) with mild heating, and the solution was filtered to remove particles. HCl (75 uL of 1.00 M/H$_2$O, 0.075 mmol) was added to the filtrate and the volatile component was removed in vacuo to afford the HCl salt of amine 9 as an off-white solid. $^1$H NMR of HCl salt: 7.77 (d, J=7.3, 2H), ~7.77 (br s, 3H, overlapped with the doublet, RNH$_3^+$), 7.72 (s, 1H), 7.68 (app t, J=5.7, 1H), 7.47 (app t, J=7.7, 2H), 7.43 (s, 1H), 7.37 (app t, J=7.5, 1H), 3.74 (app q, J=5.8, 2H), 3.14 (app t, J=6.1, 2H), 2.75 (s, 3H). HRMS calcd for (M+H)$^+$ 324.1283, found 324.1287.

Alternatively, when clean compound 9C is submitted to the Boc deprotection protocol, removal of the volatile component affords a clean TFA salt. $^1$H NMR: 7.81 (br s, 3H), 7.77 (m, 2H), 7.71 (s, 1H), 7.69 (t, J=5.8, 1H), 7.47 (m, J=7.8, 2H), 7.43 (d, J=0.9, 1H), 7.37 (m, 1H), 3.75 (app q, J=5.9, 2H), 3.16 (m, 2H), 2.76 (d, J=1.0, 3H).

EXAMPLES 10–12

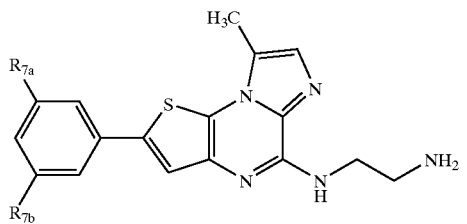

(Ik)

Compounds having the formula (Ik), above, wherein the R$_7$ substituents have the values listed in Table 1, were prepared following the procedure described in Example 9, except instead of iodobenzene in step B, appropriately-substituted iodobenzene compounds were used (e.g., P3 for Example 12). In Step D, MeOH may be used instead of 2-propanol for HCl salt formation. For Example 12, deprotection and purification was carried out as per Example 1, Step I.

TABLE 1

| EX. # | R$_{7a}$ | R$_{7b}$ | ESI (M + H)$^+$ |
|---|---|---|---|
| 10 | —CH$_3$ | H | 338.13 |
| 11 | —CH$_3$ | —CH$_3$ | 352.18 |
| 12 | —OCH$_3$ | —OCH$_3$ | 384.25 |

EXAMPLES 13–16

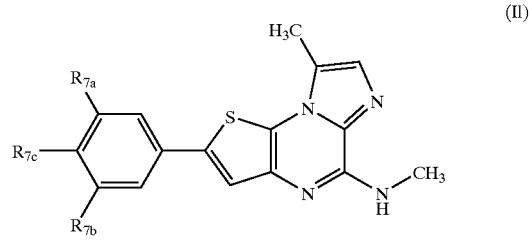

(Il)

Compounds having the formula (Il) wherein the R$_7$ substituents have the values listed in Table 2, were prepared following the procedure described hereinafter for Example 56, Step B, using appropriately-substituted iodobenzene compounds as the coupling components. For Examples 15 and 16, the crude material obtained from Step C was purified with a combination of flash chromatography and PREP HPLC, and the resultant TFA salt was converted to the free base as described for Example 5.

TABLE 2

| EX. # | R$_{7a}$ | R$_{7c}$ | R$_{7b}$ | (M + H)$^+$ |
|---|---|---|---|---|
| 13 | —CH$_3$ | H | H | 309.13 |
| 14 | H | —CH$_2$CH$_3$ | H | 323.12 |
| 15 | —CH$_3$ | H | —CH$_3$ | 323.13 |
| 16 | —CH$_3$ | —CH$_3$ | H | 323.12 |

EXAMPLES 17–27

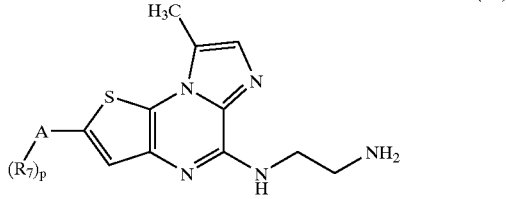

(Im)

Compounds having the formula (Im), wherein A-(R$_7$)$_p$ together have the values listed in Table 3, were prepared as described in Example 9, except in Step B, appropriately-substituted aryl or heteroaryl halides were used, and in Step C (cyclization), the aqueous work-up step was omitted.

TABLE 3

| Ex. # | A-(R$_7$)$_p$ | (M + H)$^+$ | $^1$H-NMR |
|---|---|---|---|
| 17 | Me—O—(3-phenyl) | 354.08 | |
| 18 | Me—O—(4-phenyl) | 354.10 | |

TABLE 3-continued

| Ex. # | A-(R₇)ₚ | (M + H)⁺ | ¹H-NMR |
|---|---|---|---|
| 19 | 3-pyridyl | 325.13 | |
| 20 | 4-methylphenyl | 338.05 | |
| 21 | 2-fluorophenyl | 342.06 | |
| 22 | 3-fluorophenyl | 342.06 | |
| 23 | 4-pyridyl | 325.06 | 8.70 (d, J=6.4, 2H), 8.17 (s, 1H), 7.96 (d, J=5.5, 2H), 7.81 (m, 4H), 7.47 (s, 1H), 3.75 (app q, J=5.9, 2H), 3.16 (m, 2H), 2.77 (s, 3H). |
| 24 | 2-methoxyphenyl | 354.05 | |
| 25 | 4-fluorophenyl | 341.99 | |
| 26 | 2-pyridyl | 325.02 | |
| 27 | 2-aminophenyl | 339.21 | |

EXAMPLES 28–55

(Im)

Compounds having the formula (Im), wherein A-(R₇)ₚ together have the values listed in Table 4, were prepared as described in Example 9, except in Step B (coupling), appropriately-substituted halides were used in place of iodobenzene and the reaction mixture was heated at about 60° C. until the chloroalkyne was completely consumed; in Step C (cyclization), the aqueous work-up step was omitted; and in Step D (deprotection), the deprotection procedure described in Example 1, Step I was used to produce the deprotected compounds as the TFA salt. For Example 55, P14 was used in Step B and then the tosyl group was removed during the cyclization step.

TABLE 4

| Ex. # | A-(R₇)ₚ | (M + H)⁺ | ¹H-NMR |
|---|---|---|---|
| 28 | 1H-pyrazol-4-yl | 314.19 | 8.06 (br s, 2H), 7.79 (br s, 3H), 7.63 (br t, J=5.7, 1H), 7.40 (d, J=0.9, 1H), 7.37 (s, 1H), 3.73 (app q, J=5.9, 2H), 3.14 (m 2H), 2.71 (d, J=0.9, 3H). |

TABLE 4-continued

| Ex. # | A-(R$_7$)$_p$ | (M + H)$^+$ | $^1$H-NMR |
|---|---|---|---|
| 29 | thiazol-2-yl | 331.13 | 7.87 (d, J=3.3, 1H), 7.84 (s, 1H), 7.82 (d, J=3.3, 1H), 7.79 (br t, J=5.7, 1H), 7.85–7.80 (broad signal, 3H), 7.45 (d, J=0.9, 1H), 3.74 (app q, J=5.8, 2H), 3.15 (m, 2H), 2.75 (s, 3H) |
| 30 | 1-methyl-imidazol-5-yl | 328.20 | 9.11 (s, 1H), 8.00 (s, 1H), 7.84 (br s, 3H), 7.81 (br t, J=5.8, 1H), 7.69 (s, 1H), 7.46 (s, 1H), 3.95 (s, 3H), 3.74 (app q, J=6.0, 2H), 3.15 (m, 2H), 2.72 (s, 3H). |
| 31 | 3-hydroxyphenyl | 340.19 | |
| 32 | 4-hydroxyphenyl | 340.20 | |
| 33 | 3-trifluoromethylphenyl | 392.15 | |
| 34 | 3-(dimethylamino)phenyl | 367.23 | |
| 35 | 2,3-dimethylphenyl | 352.21 | |
| 36 | 3,4-difluorophenyl | 360.15 | |
| 37 | 3-aminophenyl | 339.16 | 7.83 (br s, 3H), 7.71 (br t, J=5.7, 1H), 7.58 (s, 1H), 7.43 (d, J=1.0, 1H), 7.22 (app t, J=7.8, 1H), 7.14 (br d, J=7.3, 1H), 7.08 (s, 1H), 6.75 (br d, J=7.0, 1H), 3.74 (app q, J=5.9, 2H), 3.15 (m, 2H), 2.75 (s, 3H) |
| 38 | 4-aminophenyl | 339.19 | |

TABLE 4-continued
| Ex. # | A-(R$_7$)$_p$ | (M + H)$^+$ | $^1$H-NMR |
|---|---|---|---|
| 39 | 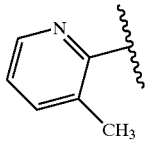 | 339.18 | |
| 40 | 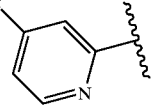 | 339.18 | |
| 41 | 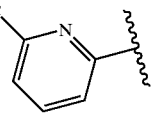 | 339.13 | |
| 42 | 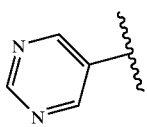 | 326.12 | 9.24 (s, 2H), 9.16 (s, 1H), 7.97 (s, 1H), 7.83 (br s, 3H), 7.78 (br t, J=5.8, 1H), 7.46 (d, J=0.8, 1H), 3.75 (app q, J =5.9, 2H), 3.16 (m, 2H), 2.76 (d, J=0.6, 3H) |
| 43 | 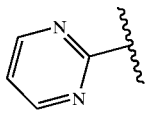 | 326.13 | |
| 44 | 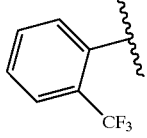 | 392.14 | |
| 45 | 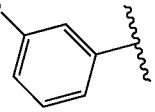 | 368.22 | 7.84 (br s, 3H), 7.74 (s, 1H), 7.69 (br t, J =5.6, 1H), 7.43 (d, J=0.9, 1H), 7.36 (app t, J=7.9, 1H), 7.31–7.28 (m, 2H), 6.93 (ddd, J=8.2, 2.3, 0.7, 1H), 4.12 (q, J=6.9, 2H), 3.74 (app q, J=5.9, 2H), 3.16 (m, 2H), 2.75 (d, J= 0.6, 3H), 1.36 (t, J=6.9, 3H) |
| 46 | 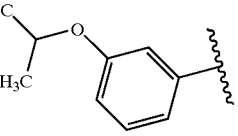 | 382.24 | |
| 47 | 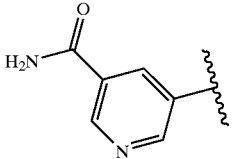 | 368.17 | |

TABLE 4-continued
| Ex. # | A-(R$_7$)$_p$ | (M + H)$^+$ | $^1$H-NMR |
|---|---|---|---|
| 48 | [2-amino-pyridin-5-yl] | 340.12 | 8.36 (d, J=2.1, 1H), 8.24 (d, J=8.6, 1H), 7.82 (br s, 3H), 7.72 (br t, J=5.7, 1H), 7.68 (s, 1H), 7.44 (d, J=0.9, 1H), 6.99 (d, J=9.2, 1H), 3.73 (app q, J=5.8, 2H), 3.15 (m, 2H), 2.73 (s, 3H). |
| 49 | [6-amino-pyridin-2-yl] | 340.18 | |
| 50 | [6-methoxy-pyridin-3-yl] | 355.20 | |
| 51 | [2-methoxy-pyridin-3-yl] | 355.13 | |
| 52 | [1-methyl-imidazol-4-yl] | 328.34 | |
| 53 | [2-amino-5-methyl-pyridin-3-yl] | 354.19 | |
| 54 | [1-methyl-2-oxo-1,2-dihydropyridin-5-yl] | 355.14 | |
| 55 | [imidazol-4-yl] | 314.13 | |
EXAMPLE 56
Step A:
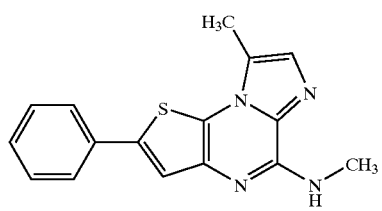
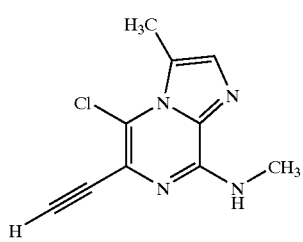
(56A)
-continued Trimethylsilyl compound 5C was desilylated according to the procedure in Example 9, step A to afford chloroalkyne 56A. $^1$H NMR: 7.69 (m, 1H), 7.34 (d, J=0.9, 1H), 4.44 (s, 1H), 2.89 (d, J=4.9, 3H), 2.69 (s, 3H). (ESI) m/z (M+H)$^+$=221.13.

Step B:

The coupling procedure of Example 9, Step B, was followed, except the reaction mixture was heated at 60° C. until the chloroalkyne was completely consumed. The resulting phenylalkynyl compound was then cyclized following Example 9, Step C, to afford Example 56A above as a free-base. (ESI) m/z (M+H)$^+$=295.12.

EXAMPLE 57

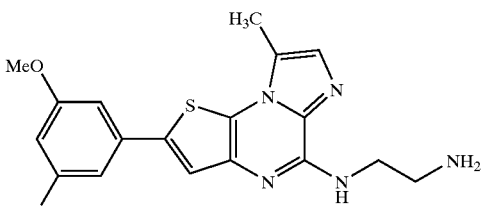

Step A:

(57A)

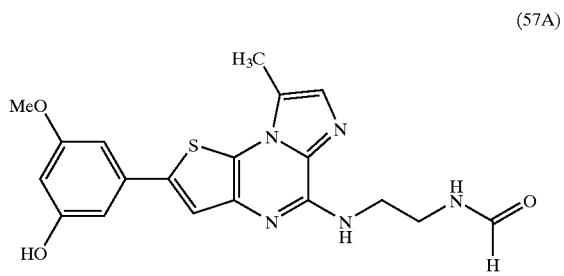

DMF (1.5 mL) was added into a mixture of the Boc-protected precursor of Example 12 (50.8 mg, 0.1050 mmol) and NaSMe (52.3 mg, 0.7461 mg). The reaction mixture was lowered into a 100° C. oil bath, and within minutes a heavy suspension was formed. The heterogeneous mixture was stirred at 100° C. for 16 h. LC/MS of the crude reaction mixture indicated the presence of amine 57A. To ensure removal of the Boc group and quench the NaSMe, DMF was removed in vacuo and the residue was treated with 20% TFA/CH$_2$Cl$_2$ (2.5 mL) for 30 min. The volatile component was removed in vacuo and the residue azeotroped with MEOH (2×). The crude material was dissolved in MeOH and submitted to PREP-HPLC purification to afford the TFA salt of amine 57A.

Step B:

EXAMPLE 57

The TFA salt of compound 57A was treated with hydrazine (2.0 mL), and stirred at 100° C. for 4.5 h. The hydrazine was removed in vacuo and the residue dissolved in MeOH/H$_2$O (2:1) and purified on PREP HPLC to afford the TFA salt of Example 57 as an off-white solid (10.7 mg). (ESI) m/z (M+H)$^+$=370.18.

EXAMPLE 58

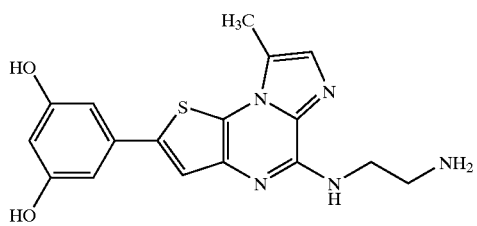

BBr$_3$ (1.5 mL of 1.0 M/CH$_2$Cl$_2$) was added dropwise over 3 min. to a cooled (−25° C.) CH$_2$Cl$_2$ (2.0 mL) solution of Boc-protected precursor of Example 12 (125 mg, 0.2585 mmol). A yellow suspension appeared after the first drop of BBr$_3$ was added. The heterogeneous reaction mixture was stirred for 5.5 h while allowing the bath to thaw to ~0° C. The bath was removed and the side of the reaction flask was washed with CH$_2$Cl$_2$ (3.0 mL). The reaction mixture was stirred for an additional 1 hr, then quenched with MeOH and the solvent removed in vacuo. The crude material was dissolved in water and purified on a PREP-HPLC to afford the TFA salt of Example 58 as an off-white solid (77 mg). (ESI) m/z (M+H)$^+$=356.17.

EXAMPLE 59

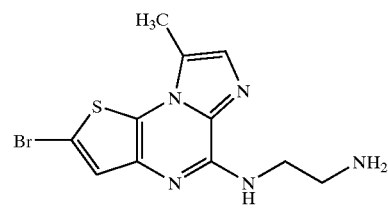

Step A:

(59A)

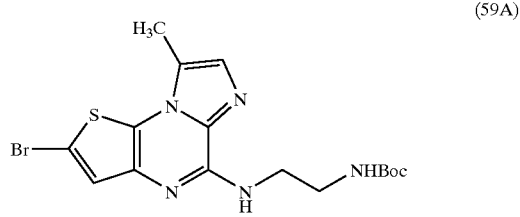

N-Bromosuccinimide (1.42 g, 7.9780 mmol) was added in batches over 5 min to a cooled (ice-water) THF (47.0 mL) suspension of amine from Example 1, Step H (2.59 g, 7.4545 mmol). The reaction mixture was stirred for 17 h while allowing the bath to thaw. After removing the solvent in vacuo, the resultant solid residue was dissolved in CHCl$_3$ (300 mL; pre-washed with NaHCO$_3$ solution) and washed with water (150 mL, 3×) and brine. It was dried (MgSO$_4$), filtered, and evaporated in vacuo. A silica gel mesh of the crude material was prepared and submitted to flash chromatography (50–70% EtOAc/hexanes) to afford bromide 59A as an off-white fluffy solid (2.7570 g, 86.8% yield). $^1$H NMR: 7.49 (br t, J=5.8, 1H), 7.46 (s, 1H), 7.36 (d, J=0.8, 1H), 6.96 (br t, J=5.4, 1H), 3.52 (app q, J=6.0, 2H), 3.21 (app q, J=5.9, 2H), 2.64 (s, 3H), 1.36 (s, 9H). (ESI) m/z (M+H)$^+$=425.90/427.90. HRMS calcd for (M+H)$^+$ 426.0599, found 426.0599.

Step B:

Compound 59A was deprotected following the procedure described in Example 1, Step I. The residue obtained after the removal of the volatile components was taken up in water and washed with EtOAc. The aqueous layer was evaporated to dryness. The resultant crude material was dissolved in MeOH and submitted to PREP-HPLC to afford the TFA salt of Example 59. $^1$H NMR: 7.81 (br s, 3H), 7.74 (br t, J=5.8, 1H), 7.46 (s, 1H), 7.41 (d, J=0.9, 1H), 3.71 (app q, J=6.0, 2H), 3.12 (m, 2H), 2.65 (d, J=0.6, 3H). (ESI) m/z (M+H)$^+$=327.7.

EXAMPLES 60–68

To prepare compounds having the formula (Im), above (as in Examples 28–55) wherein A-(R$_7$)$_p$ together have the values listed in Table 5, below, 1.0 mL each of MeOH, toluene, and sat'd NaHCO$_3$ solution were added into a pressure tube containing bromide 59A (99.9 mg, 0.2343 mmol), (R$_7$)$_p$A-B(OH)$_2$ (1.5–1.8 mol equiv.) and Pd(Ph$_3$P)$_4$ (10.2 mg, 0.0087 mmol). Nitrogen was bubbled through the biphasic reaction mixture for a few minutes, and it was heated at 80° C. for at least 9 h. When bromide 59A was totally consumed, the reaction mixture was cooled to rt and partitioned between brine and EtOAc. The organic layer was dried (MgSO$_4$), filtered and evaporated in vacuo. A silica gel mesh was prepared from the crude material and submitted to flash chromatography to afford compound of Examples 60–68 wherein the ethylamine side chain was Boc-protected. Deprotection following the procedure of Example 59, step B afforded Examples 60–68 as the TFA salt. At times, the crude material obtained after the work-up step of the deprotection procedure could be purified via trituration from MeOH.

TABLE 5

| Ex. # | A-(R$_7$)$_p$ | (M + H)$^+$ | Other Data ($^1$H NMR) |
|---|---|---|---|
| 60 | 3-hydroxymethylphenyl (HO-CH$_2$-C$_6$H$_4$-) | 354.0 | (TFA salt): 7.84 (br s, 3H), 7.71–7.66 (m, 4H), 7.44–7.41 (m, 2H), 7.31 (d, J=7.6, 1H), 4.57 (s, 2H), 3.75 (app q, J=5.8, 2H), 3.16 (m, 2H), 2.76 (d, J=0.6, 3H). |
| 61 | 3-cyanophenyl (NC-C$_6$H$_4$-) | 349.1 | (TFA salt): 8.28 (app t, J=1.6, 1H), 8.08 (ddd, J=8.1, 1.9, 1.2, 1H), 7.93 (br s, 3H), 7.90 (s, 1H), 7.80 (dd, J=7.9, 1.2, 1H), 7.73 (br t, J=5.7, 1H), 7.66 (app t, J=7.9, 1H), 7.44 (d, J=0.9, 1H), 3.75 (app q, J=5.9, 2H), 3.16 (m, 2H), 2.75 (d, J=0.9, 3H) |
| 62 | furan-2-yl | 314.0 | (TFA salt): 7.82 (br s, 3H), 7.78 (dd, J=1.8, 0.6, 1H), 7.71 (br t, J=5.7, 1H), 7.50 (s, 1H), 7.43 (d, J=0.9, 1H), 6.94 (d, J=3.3, 1H), 6.66 (dd, J=3.7, 1.9, 1H), 3.74 (app q, J=6.0, 2H), 3.14 (m, 2H), 2.73 (d, J=0.6, 3H). |
| 63 | benzo[1,3]dioxol-5-yl | 368.1 | (TFA salt): 7.85 (br s, 3H), 7.66 (br t, J=5.7, 1H), 7.59 (s, 1H), 7.41 (d, J=0.9, 1H), 7.40 (d, J=1.8, 1H), 7.21 (dd, J=8.1, 2.0, 1H), 7.00 (d, J=8.0, 1H), 6.09 (s, 2H), 3.74 (app q, J=5.9, 2H), 3.15 (m, 2H), 2.73 (d, J=1.0, 3H) |
| 64 | 4-cyanophenyl (NC-C$_6$H$_4$-) | 349.1 | |
| 65 | 4-hydroxymethylphenyl (HO-CH$_2$-C$_6$H$_4$-) | 354.0 | |
| 66 | 3-isopropyl-4-hydroxyphenyl ((CH$_3$)$_2$CH-C$_6$H$_3$(OH)-) | 382.1 | |

TABLE 5-continued

| Ex. # | A-(R$_7$)$_p$ | (M + H)$^+$ | Other Data ($^1$H NMR) |
|---|---|---|---|
| 67 | 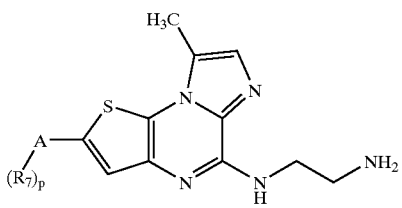 | | (TFA salt): 7.83 (br s, 3H), 7.66 (br t, J=5.8, 1H), 7.43 (d, J= 0.9, 1H), 7.27 (dd, J=8.1, 7.2, 1H), 7.19 (d, J=7.6, 2H), 7.09 (s, 1H), 3.75 (app q, J=5.9, 2H), 3.15 (m, 2H), 2.69 (s, 3H), 2.19 (s, 6H) |
| 68 | 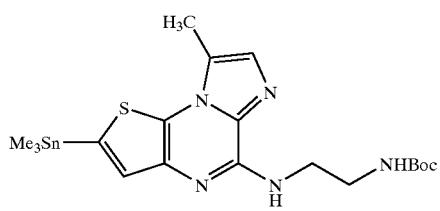 | 344.0 | |

EXAMPLES 69–87

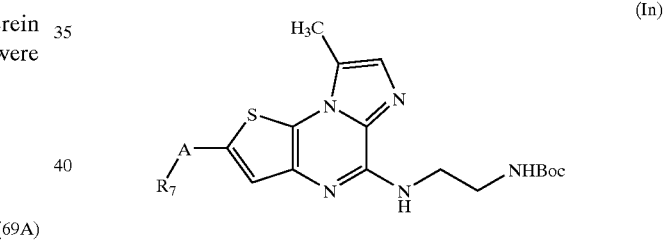

Compounds having the above formula (Im), wherein A-(R$_7$)$_p$ together have the values listed in Table 6, were prepared following Steps A and B below.

Step A:

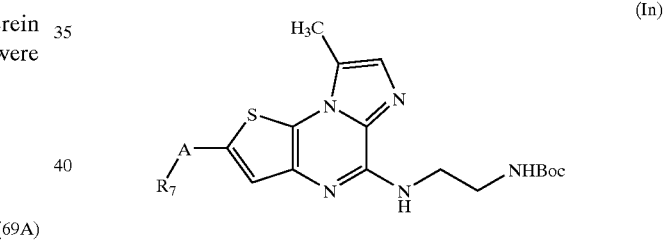

A toluene (40 mL) solution of hexamethylditin (8.40 g, 25.64 mmol) was treated with bromide 59A (3.00 g, 7.0 mmol) and TEA (1.96 mL, 14.06 mmol). After nitrogen was bubbled through the mixture for 5 min, Pd(Ph$_3$P)$_4$ (0.28 g, 0.24 mmol) was added. The reaction mixture was heated with a 100° C. oil bath for 35 min. The dark reaction mixture was cooled to rt, filtered through a pad of Celite, washed with EtOAc, and the filtrate was evaporated in vacuo. The resulting oil was triturated with 5% EtOAc/hexanes and the black precipitate removed by filtration. The filtrate was again evaporated to dryness, the residue treated with hexanes, heated to boiling and allowed to cool to rt. The side of the flask was scratched to induce crystallization and the solid allowed to stand at rt. The yellow/brown solid was collected by filtration, washed with hexanes, and allowed to air dry under vacuum to produce stannane 69A with traces of Ph$_3$PO and amine 1H as impurities (2.90 g, ~80% yield). $^1$H NMR: 7.33 (d, J=0.6, 1H), 7.31–7.29 (m, 2H), 6.99 (br t, J=5.2, 1H), 3.53 (app q, J=6.0, 2H), 3.22 (app q, J=5.9, 2H), 2.69 (s, 3H), 1.36 (s, 9H), 0.40 (s, 9H; 2 satellite peaks are observed with a J=57.3, 60.2). (ESI) m/z (M+H)$^+$= 511.88.

Step B:

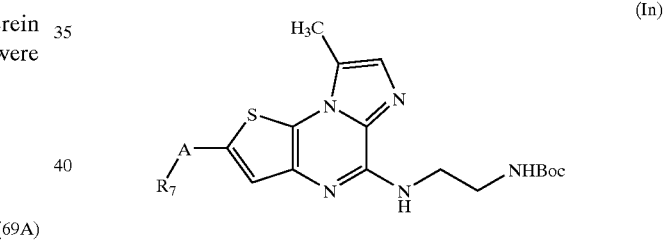

A mixture of PdCl$_2$(Ph$_3$P)$_2$ (10.9 mg, 0.0155 mmol) and CuI (4.0 mg, 0.0210 mmol) was added to a THF (2.0 mL) solution of stannane 69A (79.0 mg, ~0.1548 mmol) and appropriately-selected (R$_7$)$_p$A-Br or (R$_7$)$_p$A-I (2–3 mole equiv) (see, e.g., Preparations 1–78 or commercially available sources). (A catalyst "pre-mix" could be prepared from PdCl$_2$(Ph$_3$P)$_2$ and CuI for multiple use by mixing and grinding together according to the indicated relative amounts). Nitrogen was bubbled through the solution for a few minutes, and the reaction mixture was lowered into a 70° C. oil bath. After stannane 69A was completely consumed, a silica gel mesh was prepared from the reaction mixture and submitted to standard flash chromatography protocol to afford the aryl-tricycle compound of formula (In), above. Also, the Stille product was contaminated with amine 1H and Ph$_3$PO to various degrees. The impure product was deprotected as described in Example 1, Step I, to provide Examples 69–87 as the TFA salt.

TABLE 6

| Ex. # | A-(R₇)ₚ | (M + H)⁺ | Other Data (¹H NMR) |
|---|---|---|---|
| 69 | Me—O-pyridine | 355.19 | |
| 70 | phenol (OH) | 340.20 | (TFA salt): 10.55 (s, 1H), 7.82 (br s, 3H), 7.79 (dd, J=8.0, 1.6, 1H), 7.77 (s, 1H), 7.63 (br t, J=5.5, 1H), 7.41 (d, J=0.9, 1H), 7.18 (m, 1H), 6.99 (dd, J=8.0, 1.0, 1H), 6.91 (m, 1H), 3.75 (app q, J=5.8, 2H), 3.16 (m, 2H), 2.75 (s, 3H). |
| 71 | o-tolyl (CH₃) | 338.22 | |
| 72 | 3-hydroxypyridine | 341.03 | |
| 73 | pyridine-3-yl N,N-diethylcarbamate | 440.20 | |
| 74 | 2-(hydroxymethyl)phenyl | 354.0 | |
| 75 | 2-cyanophenyl (CN) | 349.0 | |
| 76 | 1-methyl-4-pyridone | 355.20 | |
| 77 | 1-methyl-2-pyridone | 355.18 | (TFA salt): 8.29 (dd, J=7.3, 1.8, 1H), 7.89 (s, 1H), 7.82 (dd, J=6.6, 1.7, 1H), ~7.82 (br s, 3H, overlapping signal), 7.61 (br t, J=5.6, 1H), 7.41 (d, J=0.9, 1H), 6.48 (app t, J=6.9, 1H), 3.74 (app q, J=5.9, 2H), 3.60 (s, 3H), 3.16 (m, 2H), 2.77 (d, J=0.6, 3H). |

TABLE 6-continued

| Ex. # | A-(R$_7$)$_p$ | (M + H)$^+$ | Other Data ($^1$H NMR) |
|---|---|---|---|
| 78 | 3-(N-ethyl-2-oxo-pyridin-3-yl) | 369.19 | |
| 79 | furan-3-yl | 313.9 | (TFA salt): 8.22 (app t, J=1.1, 1H), 7.81 (app t, J=1.7, 1H), 7.79 (br s, 3H), 7.65 (br t, J=5.7, 1H), 7.47 (s, 1H), 7.42 (d, J=0.9, 1H), 6.98 (dd, J=2.0, 0.8, 1H), 3.73 (app q, J=5.9, 2H), 3.14 (m, 2H), 2.72 (d, J=0.9, 3H) |
| 80 | 5-cyano-pyridin-3-yl | 350.18 | (TFA salt): 9.28 (d, J=2.4, 1H), 8.97 (d, J=1.8, 1H), 8.74 (app t, J=2.1, 1H), 8.00 (s, 1H), 7.82 (br s, 3H), 7.76 (br t, J=5.7, 1H), 7.46 (d, J=0.9, 1H), 3.75 (app q, J=5.9, 2H), 3.16 (m, 2H), 2.76 (d, J=0.6, 3H) |
| 81 | 6-cyano-pyridin-2-yl | 350.19 | |
| 82 | 3-(cyanomethyl)phenyl | 362.9 | (TFA salt): 7.81 (br s, 3H), 7.77 (br d, J=7.6, 1H), 7.74 (s, 1H), 7.72–7.70 (m, 2H), 7.51 (app t, J=7.8, 1H), 7.44 (d, J=0.9, 1H), 7.36 (br d, J=7.6, 1H), 4.12 (s, 2H), 3.75 (app q, J=5.9, 2H), 3.16 (m, 2H), 2.76 (s, 3H) |
| 83 | 2-fluoro-pyridin-3-yl | 343.17 | |
| 84 | 6-fluoro-pyridin-3-yl | 343.14 | |
| 85 | 6-acetamido-pyridin-3-yl | 382.16 | |
| 86 | 2-amino-pyridin-3-yl | 340.13 | |
| 87 | 6-(dimethylamino)-pyridin-3-yl | 368.12 | |

EXAMPLE 88

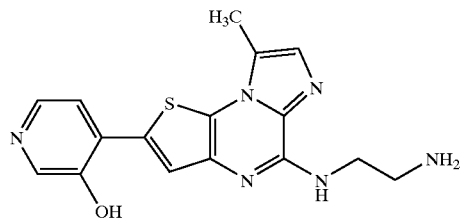

Example 88 may be prepared by adding MeOH (2.0 mL) and NaOH (1 mL of 1.0 M/H$_2$O) to the Boc-protected precursor of Example 73 (68 mg, 0.1260 mmol) and stirring the heterogeneous reaction mixture at 75° C. for 17 h. Since the deprotection was still not complete, MeOH (2.0 mL) and excess NaOH (244 mg, 6.10 mmol) were added and heating continued for an additional 3 h. The reaction mixture was neutralized with 1.0 N HCl, and the volatile component removed in vacuo. A silica gel mesh of the crude material was prepared and submitted to flash chromatography (0–100% MeOH/EtOAc) to afford the Boc-protected precursor of Example 88 (~30 mg, 54%). Deprotection was carried out as described in Example 1, Step I, to afford Example 88. (ESI) m/z (M+H)$^+$=341.11.

EXAMPLES 89–106

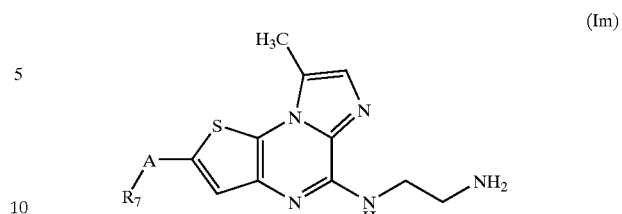

To prepare compounds having the formula (Im), above, wherein A-R$_7$ together have the values listed in Table 7, compound 69A (82.2 mg, ~0.1611 mmol), the coupling partner ((R$_7$)$_p$A-Br or (R$_7$)$_p$A-I, 2–3 mol equiv)(see, e.g., Preparations 1–78 or commercially available sources), PdCl$_2$(Ph$_3$P)$_2$ (0.0158 mmol), KF (19.4 mg, 0.3339 mmol) and DMF (2.0 mL) were sequentially added into a vial. Nitrogen was bubbled through the heterogeneous reaction mixture for about one minute, and it was lowered into a 90° C. oil bath and heated for at least 6 h. When the stannane 69A was completely consumed, the DMF was removed in vacuo, and a silica gel mesh was prepared from the resulting crude material and submitted to flash chromatography to afford the desired compound.

The Boc-protected amines were deprotected as set forth in Example 1, step I, to provide the TFA salt. The Boc-protected precursor of Example 100 was deprotected, however, following the procedure set forth above for Examples 60–68. Example 101 was made by reversing the stannane and halide groups on the coupling partners. For Examples 102–106, an acylated phenol (e.g., P10 or an analog thereof) was used as the coupling partner and the resulting product was deacylated using a known protocol (K$_2$CO$_3$/MeOH/water) and Boc-deprotected as in Example 59, step B, to achieve the desired compound.

TABLE 7

| Ex. | A-R$_7$ | (M + H)$^+$ | $^1$H NMR |
|---|---|---|---|
| 89 | 3-CH$_3$, 2-NH$_2$-pyridin-5-yl | 354.10 | |
| 90 | 2-NH$_2$-pyrimidin-5-yl | 341.10 | |
| 91 | pyrazin-2-yl | 326.11 | (MeOH, δ=3.31 ppm; TFA salt): 9.17 (d, J=1.5, 1H), 8.56 (dd, J= 2.4, 1.5, 1H), 8.45 (d, J=2.4, 1H), 8.03 (s, 1H), 7.45 (d, J=0.9, 1H), 3.92 (t, J=5.7, 2H), 3.33 (t, J=5.8, 2H), 2.84 (d, J=0.9, 3H). |
| 92 | 2-(NHCH$_3$)-pyridin-5-yl | 354.10 | |
| 93 | 3,4-(CH$_3$)$_2$, 2-NH$_2$-pyridin-5-yl | 368.20 | |

TABLE 7-continued
| Ex. | A-R7 | (M + H)+ | 1H NMR |
|---|---|---|---|
| 94 | 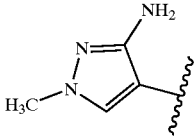 | 343.20 | |
| 95 | 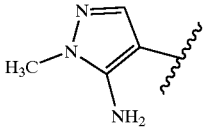 | 343.16 | |
| 96 | 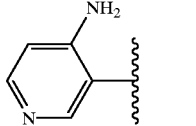 | 340.13 | |
| 97 | 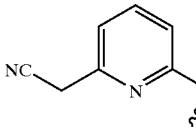 | 364.13 | |
| 98 | 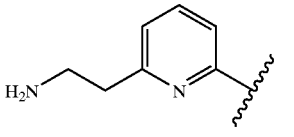 | 368.19 | |
| 99 | 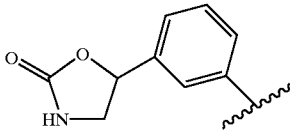 | 409.18 | |
| 100 | 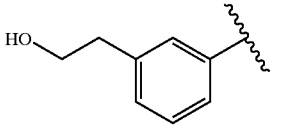 | 368.0 | (TFA salt): 7.83 (br s, 3H), 7.70–7.67 (m, 2H), 7.61–7.59 (m, 2H), 7.43 (d, J=0.6, 1H), 7.37 (m, 1H), 7.23 (d, J= 7.6, 1H), 3.75 (app q, J=5.8, 2H), 3.67 (t, J=6.9, 2H), 3.16 (m, 2H), 2.79 (t, J=6.9, 2H), 2.76 (s, 3H). |
| 101 | 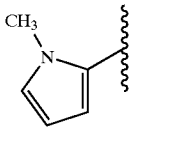 | 327.0 | (TFA salt): 7.84 (br s, 3H), 7.67 (br t, J=5.8, 1H), 7.42 (d, J=1.0, 1H), 7.29 (s, 1H), 6.96 (app t, J=2.2, 1H), 6.36 (dd, J=3.8, 1.7, 1H), 6.10 (dd, J=3.7, 2.8, 1H), 3.79 (s, 3H), 3.74 (app q, J=5.9, 2H), 3.15 (m, 2H), 2.71 (d, J=0.7, 3H). |
| 102 | 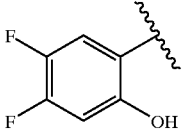 | 375.9 | |
| 103 | 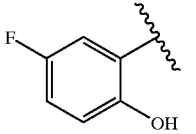 | 357.9 | |

TABLE 7-continued

| Ex. | A-R₇ | (M + H)⁺ | ¹H NMR |
|---|---|---|---|
| 104 | 4-F, 2-OH phenyl | 357.9 | |
| 105 | 3-OH, 4-F, 5-F phenyl | 375.9 | |
| 106 | 3-F, 5-F, 2-OH phenyl | 375.9 | |

EXAMPLES 107

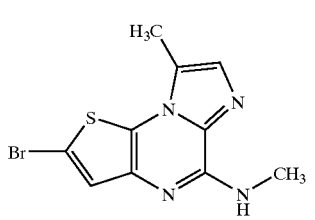

N-Bromosuccinimide (5.7055 g, 32.0552 mmol) was added in batches, over 5 min, to a cooled (0° C.) chloroform (250 mL) solution of Example 5 (6.00 g, 27.4876 mmol). The reaction mixture was stirred for 8 h at 0° C. and for an additional 16 h while allowing the bath to thaw to 10° C. The cooling bath was removed and 1 hr later the reaction mixture was washed with water (100 ml, 3×) and brine. It was dried (MgSO₄), filtered and evaporated in vacuo. A silica gel mesh of the crude material was prepared and submitted to flash chromatography using a short column (50–60% EtOAc/hexanes) to afford Example 107 as a fluffy gray solid (6.56 g, 80.3%). ¹H NMR: 7.54 (br m, 1H), 7.48 (s, 1H), 7.34 (s, 1H), 2.96 (d, J=4.8, 3H), 2.63 (s, 3H). (ESI) m/z (M+H)⁺ = 297.10/299.10

EXAMPLES 108–125

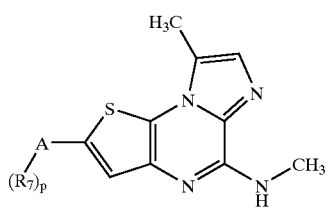

Compounds having the formula (Io) wherein A-(R₇)ₚ together have the values listed in Table 8, below, were prepared following Steps A and B below.

Step A:

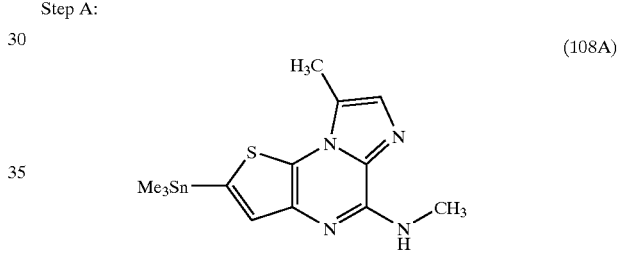

Stannylation of Example 107 (4.064 g, 13.6752 mmol) was set up according to the procedure described for compound 69A. The reaction mixture was quite heterogeneous initially but homogenized after heating. After 40 min of heating, the mixture was cooled to rt and filtered through a pad of celite, and the filtrate was rotovaped. The residue was triturated with ether (~100 mL), and the ash-colored solid was filtered and washed with copious ether and dried in vacuo (3.2929 g of 108A was retrieved). LC/MS and ¹H NMR analysis of the sample indicated that it contained minor impurities including Example 5; according to LC/MS, the ratio of stannane 108A to Example 5 was greater than 30. ¹H NMR: 7.32 (overlapped signals, 3H), 2.96 (d, J=4.9, 3H), 2.69 (d, J=0.9, 3H), 0.40 (s, 9H; 2 satellite peaks are observed with J=57.3, 59.9). (ESI) m/z (M+H)⁺=383.06.

Step B:

Compounds of Examples 108–125 were prepared from stananne 108A following the coupling procedure described above for Examples 89–106, using the desired coupling partner ((R₇)ₚA-Br or (R₇)ₚA-I) (see, e.g., Preparations 1–34 or commercially available compounds). The resultant product was purified with flash chromatography, recrystallization and/or PREP-HPLC and was obtained as a free base or TFA salt. For Examples 109, 118, and 115, the left amino side chain (e.g, attached to the pyridyl or phenyl rings) was deprotected under standard conditions (TFA/CH₂Cl₂). For Example 122, the compound was deacylated following the procedure described above for Examples 102–106.

TABLE 8
| Ex. # | A-(R7)p | (M + H)+ | Other Data (1H NMR) |
|---|---|---|---|
| 108 | 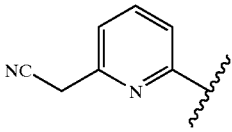 | 335.16 | |
| 109 | 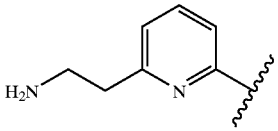 | 339.21 | |
| 110 | 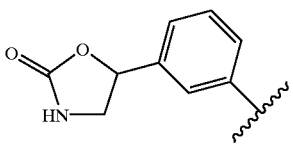 | 380.15 | (TFA salt): 7.80 (s, 1H), 7.79 (m, 1H), 7.76 (m, 2H), 7.53 (app t, J=7.8, 1H), 7.45 (s, 1H), 7.40 (d, J=7.7, 1H), 5.68 (app t, J=8.1, 1H), 3.93 (app t, J=8.7, 1H), 3.43 (app t, J=8.3, 1H), 3.03 (s, 3H), 2.75 (d, J=0.6, 3H). |
| 111 | 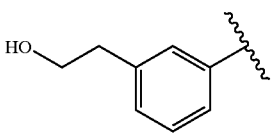 | 339.0 | (Free base): 7.73 (s, 1H), 7.60–7.59 (m, 2H), 7.46 (br q, J=4.8, 1H), 7.37–7.34 (m, 2H), 7.21 (app d, J=7.6, 1H), 4.68 (t, J=5.2, 1H), 3.67 (m, 2H), 2.99 (d, J=4.6, 3H), 2.79 (t, J=7.0, 2H), 2.73 (d, J=0.6, 3H). |
| 112 | 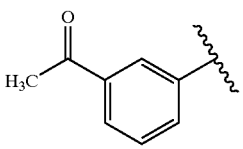 | 337.0 | |
| 113 | 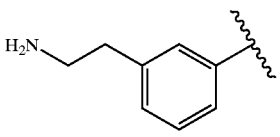 | 338.0 | |
| 114 | 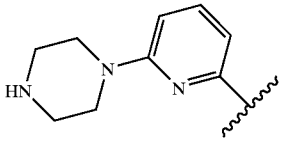 | 380.22 | |
| 115 | 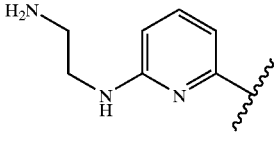 | 354.24 | |
| 116 | 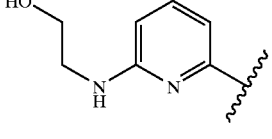 | 355.20 | (TFA salt): 7.84 (s, 1H), 7.46 (dd, J=8.1, 7.5, 1H), 7.45 (s, 1H), 7.16 (d, J=7.0, 1H), 6.47 (d, J=8.3, 1H), 3.61 (t, J=6.1; 2H), 3.39 (t, J=6.1, 2H), 3.03 (s, 3H), 2.75 (d, J=0.6, 3H). |
| 117 | 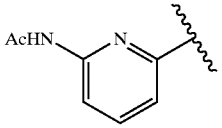 | 353.16 | |

TABLE 8-continued
| Ex. # | A-(R7)p | (M + H)+ | Other Data (1H NMR) |
|---|---|---|---|
| 118 |  | 324.0 | (TFA salt): 8.23 (br s, 3H), 7.86 (s, 1H), 7.83 (d, J=7.9, 1H), 7.80 (s, 1H), 7.67 (br s, 1H), 7.52 (app t, J=7.8, 1H), 7.43 (d, J=7.9, 1H), 7.41 (d, J=0.9, 1H), 4.12 (q, J=5.8, 2H), 3.00 (d, J=3.4, 3H), 2.74 (d, J=0.6, 3H). |
| 119 |  | 380.23 | (Free base): 7.95 (br t, J=5.4, 1H), 7.76 (s, 1H), 7.62 (br d, J=7.9, 1H), 7.58 (m, 1H), 7.45 (br q, J=4.4, 1H), 7.37 (app t, J=7.6, 1H), 7.36 (d, J=0.9, 1H), 7.19 (d, J=7.7, 1H), 2.99 (d, J=4.8, 3H), 2.77 (t, J=7.4, 2H), 2.73 (d, J=0.6, 3H), 1.80 (s, 3H). |
| 120 |  | 416.17 | (Free base): 7.78 (s, 1H), 7.65 (m, 1H), 7.63 (d m, J=7.7, 1H), 7.47 (q, J=4.7, 1H), 7.39 (app t, J=7.6, 1H), 7.36 (d, J=0.9, 1H), 7.24 (d, J=7.6, 1H), 7.13 (t, J=5.8, 1H), 3.25 (m, 2H), 2.99 (d, J=4.9, 3H), 2.85 (s, 3H), 2.84 (t, J=7.5, 2H), 2.74 (d, J=0.6, 3H). |
| 121 |  | 285.09 | (TFA salt): 7.78 (d, J=1.2, 1H), 7.53 (s, 1H), 7.43 (s, 1H), 6.96 (d, J=3.4, 1H), 6.66 (dd, J=3.4, 1.9, 1H), 3.02 (s, 3H), 2.71 (d, J=0.9, 3H). |
| 122 |  | 355.0 | |
| 123 |  | 422.24 | |
| 124 |  | 380.22 | |
| 125 |  | 367.16 | (Free base): 7.75 (s, 1H), 7.69 (m, 1H), 7.65 (m, 1H), 7.48 (m, 1H, NH), 7.41 (app t, J=7.8, 1H), 7.36 (d, J=0.9, 1H), 7.25 (m, 1H), 3.77 (s, 2H), 3.65 (s, 3H), 2.99 (d, J=4.5, 3H), 2.73 (d, J=0.7, 3H). |
| 126 |  | 353.15 | |

EXAMPLES 127–129

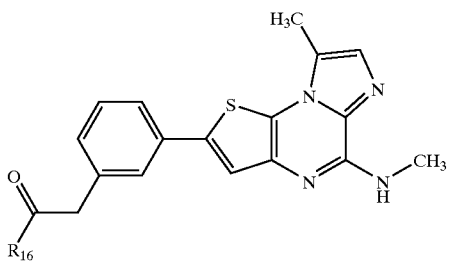

(Is)

Examples 127–129 having formula (Is) above, wherein $R_{16}$ is OH (Ex. 127), $NH_2$ (Ex. 128), and morpholinyl (Ex. 129), were each prepared from Example 125 as follows:

EXAMPLE 127

NaOH (200 uL of 1.0 $M/H_2O$) was added to a MeOH (2.0 mL) suspension of Example 125 (33 mg, 0.090 mmol) and the mixture was stirred at 70° C. for 2.5 h. The reaction mixture was diluted with MeOH and submitted to a PREP-HPLC to afford the TFA salt of Example 127 as a yellow solid (25 mg). (ESI) m/z $(M+H)^+=353.15$.

EXAMPLE 128

MeOH (5.0 mL) was added into a Parr bomb containing Example 125 (40.7 mg, 0.1111 mmol), and dry ammonia gas was bubbled through it for 5 min. The apparatus was capped and heated at 70° C. for 16.25 h. It was cooled to rt and the suspension filtered and washed MeOH. The solid was dissolved in DMF and submitted to a PREP-HPLC to afford the TFA salt of Example 128 as an off-white solid (17.5 mg). $^1H$ NMR: 7.72 (s, 1H), 7.67 (d, J=7.6, 1H), 7.63 (app br s, 1H), 7.53 (br s, 1H), 7.44 (br s, 1H), 7.40 (app t, J=7.6, 1H), 7.26 (d, J=7.6, 1H), 6.94 (br s, 1H), 3.45 (s, 2H), 3.03 (s, 3H), 2.75 (d, J=0.6, 3H). (ESI) m/z $(M+H)^+=352.15$.

EXAMPLE 129

A mixture of morpholine (2.0 mL) and Example 125 (43.1 mg, 0.1176 mmol) was heated at 120 ° C. for 46.5 h. The volatile component was removed in vacuo and the resulting crude material was passed through an SAX column (prewashed with MeOH; column eluted with MeOH) to remove an impurity (e.g., Example 127). The solvent was removed in vacuo, and a silica gel mesh was prepared from the residue and submitted to flash chromatography (0–5% MeOH/EtOAc) to afford Example 129 as a light yellow semi-solid (17.5 mg). (ESI) m/z $(M+H)^+=422.19$.

EXAMPLES 130–132

Examples 130–132 having formula (Is) above, were prepared from Example 125 and the respective amines according to the procedure described for Example 129, with a slight modification where in the reaction was heated at 110 ° C. until the ester was totally consumed. For Examples 130 and 132, the volatile component was removed in vacuo and the crude residue was purified on a Prep-HPLC. For Example 131, after the reaction mixture was allowed to cool to room temperature, the suspension was filtered and washed with copious EtOAc and MeOH.

TABLE 9

| Ex. # | $R_{16}$ in (Is) | $(M + H)^+$ | Other Data ($^1H$ NMR) |
|---|---|---|---|
| 130 | ![structure] | 423.34 | |
| 131 | ![structure] | 367.19 | |
| 132 | ![structure] | 396.32 | |

EXAMPLES 133

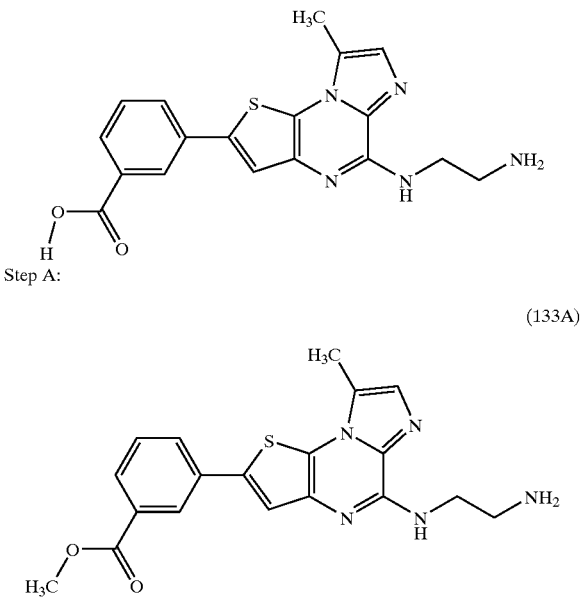

(133A)

The TFA salt of compound 133A was obtained following the same procedure described above for Examples 69–87.

Step B:

Compound 133A was treated with MeOH (2.0 mL) and NaOH (0.20 mL of 1.0 $M/H_2O$, 0.20 mmol), and heated with an oil bath (~65° C.) for 95 min. It was cooled to rt, diluted with MeOH and purified on a PREP-HPLC. The TFA salt of Example 130 was obtained as an off-white solid (~13 mg). (ESI) m/z $(M+H)^+=368.21$.

EXAMPLE 134

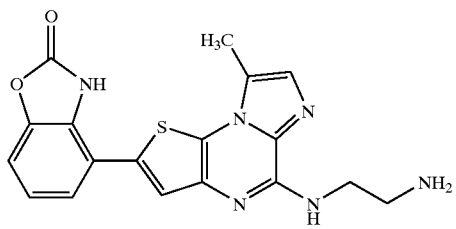

A dioxane (3.0 mL) solution of stannane 69A (100 mg, 0.196 mmol) and compound P13 (~3 mol equiv.) was degassed with nitrogen and treated with Pd(Ph$_3$P)$_4$ (7.0 mg, 0.0061 mmol) and LiCl (30 mg, 0.708 mmol). The reaction mixture was stirred at 100° C. for 16 h, cooled to rt, diluted with EtOAc, and evaporated onto silica gel. The resulting silica gel mesh was submitted to flash chromatography to afford the Boc-protected precursor to Example 134. The compound was deprotected as described for Examples 60–68. $^1$H NMR: 11.95 (s, 1H), 7.83 (br s, 3H), 7.72 (br t, J=5.7, 1H), 7.68 (s, 1H), 7.45 (d, J=0.9, 1H), 7.38 (dd, J=7.9, 0.6, 1H), 7.34 (dd, J=7.9, 0.6, 1H), 7.20 (app t, J=8.1, 1H), 3.75 (app q, J=5.8, 2H), 3.17 (app br s, 2H), 2.76 (s, 3H). (ESI) m/z (M+H)$^+$=381.0.

EXAMPLES 135–136

To prepare compounds having the formula (Im) above wherein A-R$_7$ are as in TABLE 10, toluene/acetone/water (1:1:0.5, 4.5 mL) and K$_2$CO3 were added to a mixture of bromide 59A (100 mg, 0.2346 mmol) and (A-R$_7$)B(OH)$_2$ (~2.0 mol. equiv). After nitrogen was bubbled through the biphasic mixture for a few minutes, the mixture was treated with PdCl$_2$(dppf)-CH$_2$Cl$_2$ complex (2 mg, 0.002 mmol) and heated at 70° C. until complete consumption of the bromide. The reaction mixture was cooled to rt, diluted with EtOAc and washed with water and brine. It was dried (MgSO$_4$), filtered, and evaporated in vacuo. A silica gel mesh was prepared from the crude material and submitted to a standard flash chromatography protocol to afford Boc-protected amines. The compounds were protected as described for Examples 60–68 to afford Examples 135 and 136 as the TFA salt.

TABLE 10

| Ex. # | A-R$_7$ | (M + H)$^+$ |
|---|---|---|
| 135 | ![pyrrole] | 313.0 |
| 136 | ![methylfuran] | 328.0 |

EXAMPLES 137

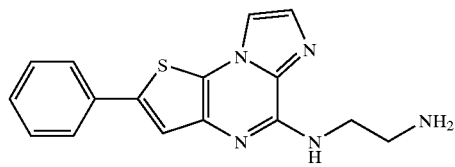

Step A:

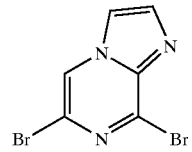

(137A)

Ethanol (10.0 mL) and chloroacetaldehyde (2.6953 g of 50% by weight solution in water, 17.17 mmol) were added into a pressure tube containing 2-amino-3,5-dibromopyrazine (2.015 gm, 7.97 mmol). The heterogeneous reaction mixture was stirred at 70° C. The reaction mixture assumed a homogenous appearance after heating began, and precipitation started to appear 3 h later. After a total of 22 h of heating, the reaction mixture was cooled to rt. The precipitate was filtered, washed with EtOH (~10 mL), and exposed to high vacuum to afford impure imidazopyrazine 137A as an ash-colored solid (1.699 g). $^1$H NMR: 9.03 (s, 1H), 8.24 (d, J=0.9, 1H), 7.91 (d, J=1.2, 1H). (ESI) m/z (M+H)$^+$=277.79.

Step B:

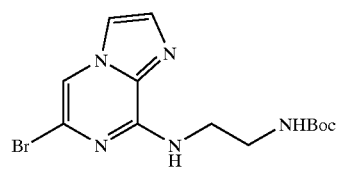

(137B)

The impure imidazopyrazine 137A was added to a THF (10.0 mL) solution of tert-butyl N-(2-aminoethyl)carbamate (1.1232 g, 7.0104 mmol). In less than a minute, the homogenous reaction mixture formed a solid. TEA (2.0 mL, 14.349 mmol) was added and the mixture was stirred at rt for 3.75 h and at 64 ° C. for 4.5 h. The side of the flask was washed with THF (8.0 mL), and it was heated for an additional 2 h. It was cooled to rt and the precipitate filtered and washed with EtOAc. A silica gel mesh was prepared from the filtrate and submitted to flash chromatography (40–50% EtOAc/hexanes) to afford bromide 137B as a faint yellow solid (1.495 g, a two step combined yield of 52.7%). $^1$H NMR (CDCl$_3$, δ=7.26 ppm; 300 MHz): 7.58 (s, 1H), 7.50 (d, J=1.1, 1H), 7.45 (d, J=1.5, 1H), 6.69 (br s, 1H), 5.14 (br s, 1H), 3.73 (m, 2H), 3.45 (m, 2H).1.43 (s, 9H). (ESI) m/z (M+H)$^+$=355.93/357.93.

Step C:

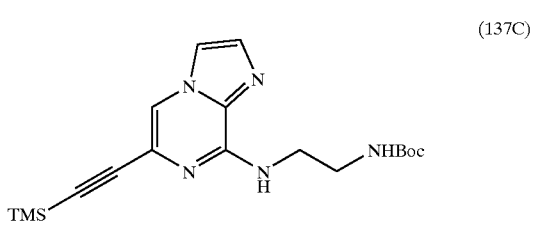
(137C)

The coupling of bromide 137B with (trimethylsilyl) acetylene was conducted according to Example 1, Step F to afford alkyne 137C as an off-white solid in 80.4% yield. $^1$H NMR: 8.11 (s, 1H), 7.81 (d, J=1.3, 1H), 760 (br t, J=5.2, 1H), 7.53 (d, J=1.2, 1H), 6.94 (br t, J=5.2, 1H), 3.48 (m, 2H), 3.19 (m, 2H), 1.37 (s, 9H), 0.24 (s, 9H). (ESI) m/z (M+H)$^+$=374.16.

Step D:

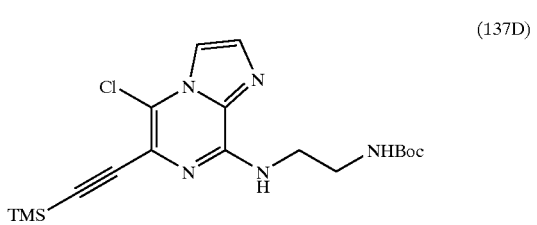
(137D)

The chlorination of compound 137C was conducted according to Example 1, Step G to afford chloride 137D as an off-white dense solid in 87.8% yield. $^1$H NMR (CDCl$_3$, δ=7.26 ppm; 500 MHz): 7.67 (s, 1H), 7.56 (s, 1H), 6.27 (app br s, 1H), 4.99 (app br s, 1H), 3.75 (m, 2H), 3.45 (m, 2H), 1.43 (s, 9H), 0.30 (s, 9H). (ESI) m/z (M+H)$^+$=408.09.

Step E:

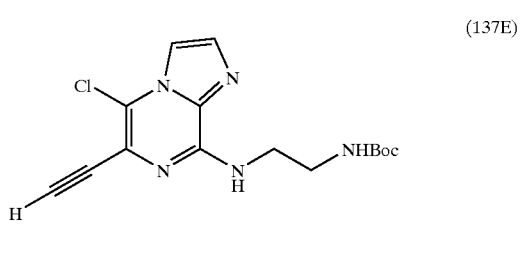
(137E)

Example 137D was desilylated as described in Example 9 to form chloroalkyne 137E as an off-white solid. $^1$H NMR: 8.00 (d, J=1.2, 1H), 7.82 (br t, J=5.7, 1H), 7.67 (d, J=1.2, 1H), 6.93 (br t, J=5.5, 1H), 4.51 (s, 1H), 3.47 (app q, J=6.1, 2H), 3.19 (app q, J=6.1, 2H), 1.36 (s, 9H).

Step F:

EXAMPLE 137

Chloroalkyne 137E was coupled with an iodobenzene and cyclized as described above for Examples 17–27. Deprotection followed by HCl salt formation likewise proceeded as described in Example 9, Step D, to afford Example 137 as an HCl salt. $^1$H-NMR of salt: 8.28 (d, J=0.9, 1H), 7.78–7.70 (m, 8H), 7.48 (m, 2H), 7.38 (m, 1H), 3.75 (app q, J=5.9, 2H), 3.14 (app t, J=6.1, 2H). (ESI) m/z (M+H)$^+$=310.31.

EXAMPLE 138

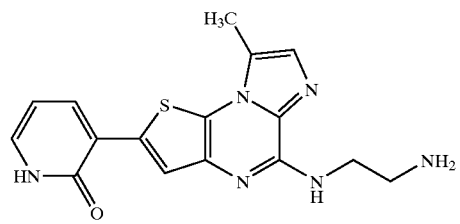

BBr$_3$ (1.5 mL, 1.0 M/CH$_2$Cl$_2$) was added to a cooled (0° C.) CH$_2$Cl$_2$ (2.0 mL) solution of the the Boc-protected precursor of Example 51 (methyl ether) (70 mg, 0.154 mmol) and stirred for 50 min. The bath was removed, and the heterogeneous reaction mixture was stirred for an additional 14 h and quenched with MeOH. The volatile component was removed in vacuo, and the residue was dissolved in a MeOH/H$_2$O mixture and purified on a PREP-HPLC to afford the TFA salt of Example 138 as light yellow solid (13.7 mg). (ESI) m/z (M+H)$^+$=341.12.

EXAMPLE 139

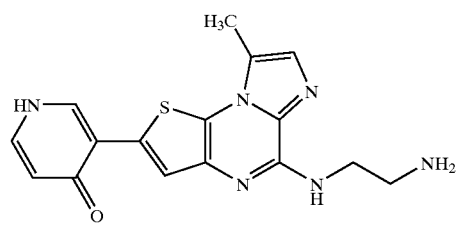

Example 139 was prepared following a similar procedure to that described above for Examples 28–55, starting from P18. In this case, 0-demethylation occurred during the cyclization step. (ESI) m/z (M+H)$^+$=341.12.

EXAMPLE 140

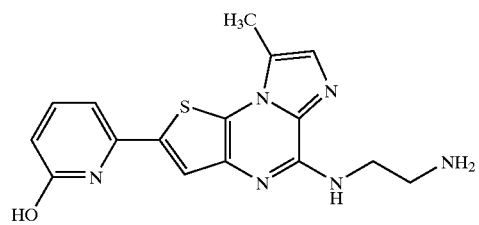

A mixture of MeOH (3.0 mL) and 48% HBr (1.0 mL) was added to the Boc-protected precursor to Example 69 (115 mg, 0.2530 mmol). The resulting heterogeneous mixture was stirred at rt for 40 min. Water (1.0 mL) was added and 20 min later it was lowered into a 70° C. oil bath and heated for 2.5 hr. LC/MS analysis indicated that the methyl ether was unaffected and only the Boc group was removed. The heterogeneous reaction mixture was cooled to rt and the suspension (an HBr salt of Example 69) was filtered and washed with MeOH and dried in vacuo (off-white solid, 116.8 mg).

Trimethylsilyl chloride (150 uL, 1.1819 mmol) was added to a CH$_3$CN (4.0 mL) suspension of the HBr salt of Example 69 and NaI (165.7 mg, 1.1435 mmol). The heterogeneous mixture was stirred at rt for 22 h. Additional NaI (142.1 mg, 0.9807 mmol) and trimethylsilyl chloride (150 uL, 1.1819 mmol) were added and the mixture was stirred at rt for 26 h and at 70° C. for 24 h. The reaction was quenched with MeOH (4.0 mL) and heated at 70° C. for 10 min. It was cooled to rt and the volatile component was removed in vacuo. The crude material was dissolved in DMF and purified on a PREP-HPLC to afford the TFA salt of Example 140 as a yellow solid (39 mg). (ESI) m/z (M+H)$^+$=341.12.

EXAMPLES 141–142

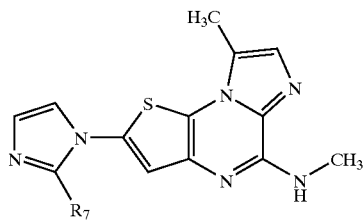

To prepare Example 141 wherein R$_7$ hydrogen, CuI (51.2 mg, 0.2689 mmol), imidazole (1.067 g, 15.69 mmol) and Example 107 (51.9 mg, 0.1746 mmol) were mixed in a vial and heated at 120° C. for 63 h. LC/MS analysis of the crude mixture indicated that it contained Example 141 and the debrominated product, i.e. Example 5, in a 3:2 ratio. The reaction mixture was cooled to rt, dissolved in MeOH and purified on a PREP-HPLC. The TFA salt of Example 141 was obtained as a yellow dense foam containing a minor amount of an unidentified impurity (26.9 mg). $^1$H NMR: 9.17 (s, 1H), 8.07 (s, 1H), 7.76 (overlapping signals, 2H), 7.66 (s, 1H), 7.42 (d, J=0.9, 1H), 2.99 (d, J=2.4, 3H), 2.70 (d, J=0.9, 3H). (ESI) m/z (M+H)$^+$=285.16.

Example 142 wherein R$_7$=methyl was prepared as a free base following the same procedure as for Example 141, starting with 2-methyl imidazole instead of imidazole. (ESI) m/z (M+H)$^+$=299.12.

EXAMPLE 143

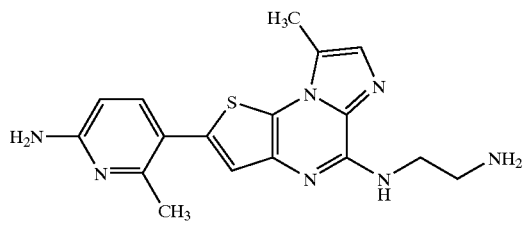

Step A:

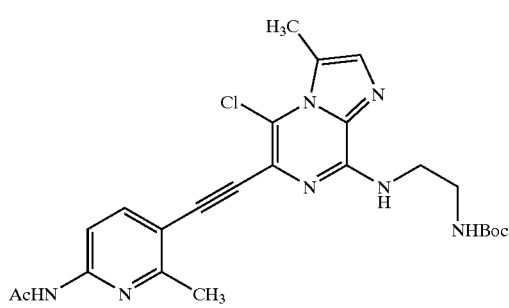

Aminopyridine P15 was coupled with Example 9A according to the procedure described for Examples 28–55 to produce 143A.

Step B:

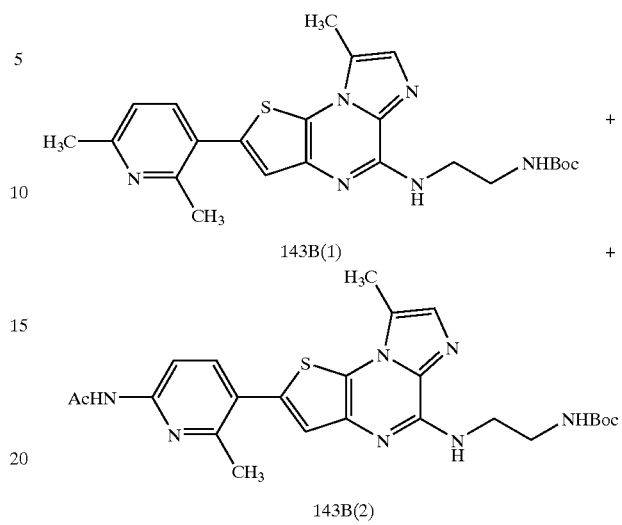

Compound 143A was cyclized according to the procedure described for Examples 28–58 to produce a mixture of 143B(1) and 143B(2) with a 1:5 HPLC ratio (20 mg).

Step C:

Hydrazine (2.0 mL) was added to the mixture from Step B and the reaction mixture was stirred at 100° C. for 2 h. After it was allowed to cool to rt, the hydrazine was removed in vacuo to afford crude compound 143B1. The Boc group of 143B1 was removed following Example 1, Step I, to afford Example 143 as the TFA salt. (ESI) m/z (M+H)$^+$=354.26.

EXAMPLES 144–146

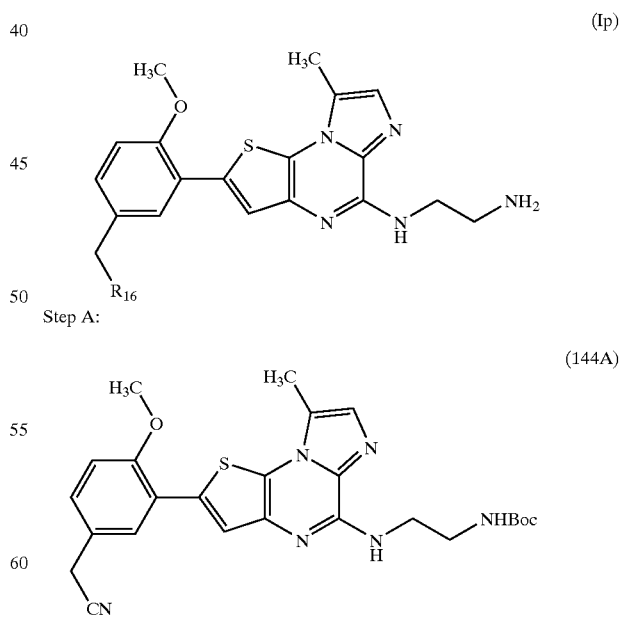

Compound 144A was prepared by coupling 3-bromo-4-methoxyphenylacetonitrile with compound 69A according to the process described for Examples 89–106.

Step B:

EXAMPLES 144–146

BBr$_3$ (380 uL of 1.0 M/CH$_2$Cl$_2$) was added to a cooled (−30 ° C.) CH$_2$Cl$_2$ (2.0 mL) solution of compound 144A (61.7 mg). The reaction mixture was stirred for 5 h by allowing the bath to thaw to 0° C. It was quenched with MeOH, solvent was removed in vacuo, and the residue was purified on a PREP-HPLC. Three compounds having the above formula (Ip), wherein R$_{16}$ has the values listed in Table 11, were isolated as TFA salts: Example 144 (18.7 mg), Example 145 (6.2 mg), and Example 146 (4.2 mg).

TABLE 11

| Ex. # | R$_{16}$ | (M + H)$^+$ |
|---|---|---|
| 144 | —CN | 393.0 |
| 145 | —C(=O)NH$_2$ | 411.0 |
| 146 | —CO$_2$Me | 426.0 |

EXAMPLE 147

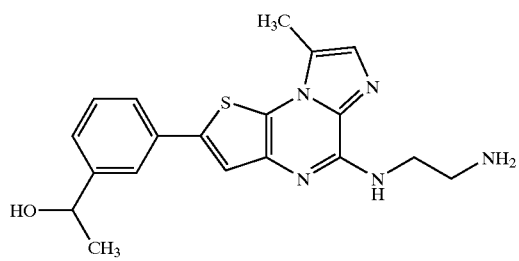

Step A:

(147A)

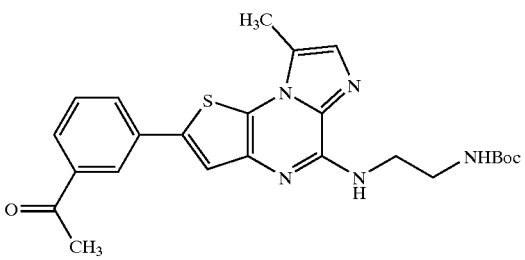

Compound 147A was prepared following the procedure of Examples 89–106 using 3-iodoacetophenone as the halide-coupling component.

Step B:

Compound 147A (51.1 mg, 0.11 mmol) was dissolved in EtOH (8.0 mL) and treated with NaBH$_4$ (7.0 mg, 0.185 mmol), and the reaction mixture was stirred at rt for 2 h. After the solvent was removed in vacuo, the residue was dissolved in EtOAc and washed with sat'd NH$_4$Cl and brine. The organic layer was dried (MgSO$_4$), filtered and evaporated in vacuo to afford Boc-protected precursor of Example 147 as a yellow solid (46 mg). The compound was deprotected following the procedure in Example 59 to afford the TFA salt of Example 147. $^1$H-NMR: 7.86 (br s, 3H), 7.69–7.64 (m, 3H), 7.43–7.39 (m, 3H), 7.33 (br d, J=7.3, 1H), 4.79 (q, J=6.3, 1H), 3.75 (app q, J=5.5, 2H), 3.16 (m, 2H), 2.76 (s, 3H), 1.38 (d, J=6.5, 3H). (ESI) m/z (M+H)$^+$= 368.1.

EXAMPLE 148

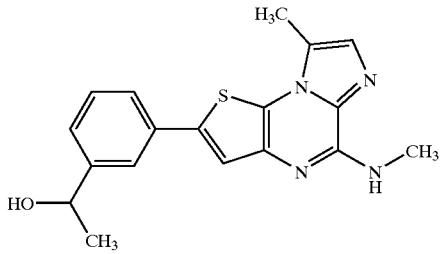

The same coupling and reduction procedures as described for Example 147 were applied to Example 108A to produce Example 148 as the free base. (ESI) m/z (M+H)$^+$=339.0.

EXAMPLE 149

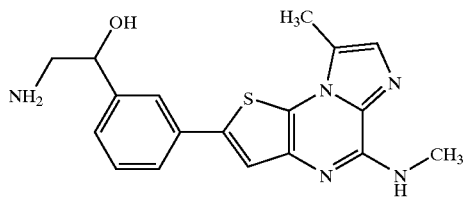

THF/H$_2$O (3.0 mL of 3:1 mixture) and LiOH (31.5 mg) were added to Example 110 (44 mg, 0.1451 mmol). The reaction mixture was heated at 70° C. for 7.5 h, additional LiOH (54 mg) was added, then 14.25 h later water (0.5 mL) was added, and 8.45 h after that THF (2.0 mL) was added. The reaction mixture was heated for an additional 53 h and allowed to cool to rt. It was diluted with MeOH, slightly acidified with TFA, and loaded onto a MeOH pre-washed SCX column. The column was washed with MeOH and the compound eluted with 2.0 M NH$_3$/MeOH. The volatile component was removed in vacuo and the residue dissolved in MeOH and purified on a PREP-HPLC to afford the TFA salt of Example 149 as an off-white foam. Recrystallizing from MeOH afforded an off-white solid (~5.5 mg). (ESI) m/z (M+H)$^+$=354.13.

EXAMPLE 150

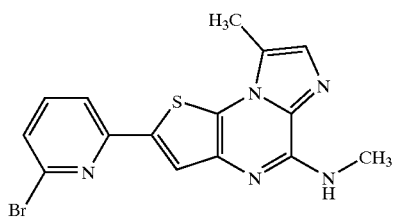

2,6-dibrompyridine was coupled with stannane 108A according to the procedure described for Examples 69–87 to afford Example 150 along with minor impurities.

EXAMPLES 151–154

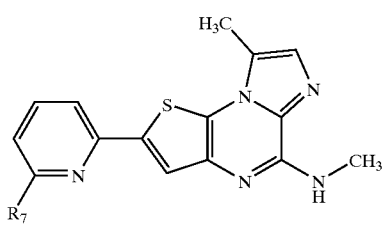
(Iq)

A mixture of Example 150 (25.3 mg, ~0.0676 mmol) and an appropriate R₇H amine (i.e., N,N-dimethylethylenediamine [504.6 mg, 5.718 mmol] for Example 151) was heated at 110° C. for 6.5 h and at 120° C. for 37 h. It was allowed to cool to rt, diluted with MeOH and purified on a PREP-HPLC to afford the TFA salt of pyridine of formula (Iq), above, wherein $R_7$ is as in Table 12, depending on the amine selected. The salt was free-based according to the procedure described for Example 5 to afford the desired pyridine as a yellow foam (e.g., 10.5 mg for Example 151).

TABLE 12

| Ex. # | $R_7$ | $(M + H)^+$ |
|---|---|---|
| 151 | —NH(CH₂)₂N(Me)₂ | 382.16 |
| 152 | (pyrrolidinyl-CH₂CH₂-NH-) | 408.20 |
| 153 | (morpholinyl-) | 381.19 |
| 154 | (HO-CH₂-pyrrolidinyl-) | 395.22 |

EXAMPLE 155

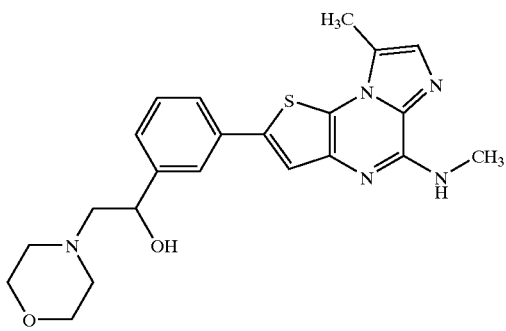

NaBH₄ (14.2 mg, 0.375 mmol) was added to a cooled (0° C.) MeOH (3.0 mL) suspension of Example 123 (42 mg, 0.100 mmol). The reaction mixture was stirred for 2.15 h at 0° C. and for 2 h at rt. NaBH₄ (14.3 mg, 0.3780 mmol) was added and stirring continued for 22.5 h. The reaction was quenched with acetone (1.0 mL) and the solvent removed in vacuo. A silica gel mesh of the crude material was prepared and submitted to flash chromatography (0–10% MeOH/EtOAc) to afford Example 155. The alcohol was further purified on a PREP-HPLC to afford the TFA salt of Example 155 as an off-white solid (35 mg). (ESI) m/z (M+H)⁺= 424.31.

EXAMPLES 156–157

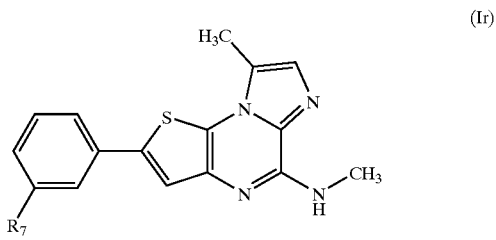
(Ir)

Compounds having the formula (Ir), wherein $R_7$ has the values listed in Table 13, were prepared following the same procedure as for Example 155, starting with the appropriate ketone prepared as described above for Examples 108–125 (e.g., Ex. 124 was used to make Example 157).

TABLE 13

| Ex. # | $R_7$ | $(M + H)^+$ | ¹H NMR |
|---|---|---|---|
| 156 | (imidazolyl-CH₂-CH(OH)-) | 405.24 | (TFA salt): 14.29(br s, 1H), 9.06(s, 1H), 7.78(s, 1H), 7.76 (m, 1H), 7.74(app t, J=1.7, 1H), 7.72(m, 1H), 7.68(app t, J=1.5, 1H), 7.48(app t, J=7.7, 1H), 7.41(d, J=0.9, 1H), 7.38 (d, J=7.7, 1H), 6.11(br s, 1H), 5.05(dd, J=8.4, 3.2, 1H), 4.51 (dd, J=13.8, 3.4, 1H), 4.35(dd, J=13.9, 8.4, 1H), 3.00(d, J=3.7, 3H), 2.75 (d, J=0.9, 3H). |
| 157 | (Me₂N-CH₂-CH(OH)-) | 382.22 | |

EXAMPLE 158

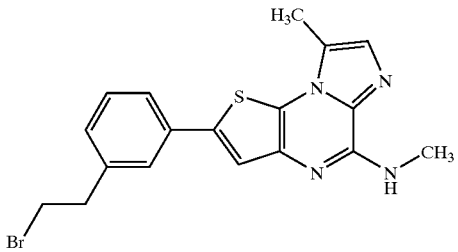

Stannane 108A (80.8 mg, 0.2120 mmol), dibromide P26 (132.8 mg, ~0.4869 mmol), PdCl₂(Ph₃P)₂ (13.0, 0.0185 mmol), KF (27.5 mg, 0.4733 mmol) and DMF (2.6 mL) were sequentially added into a vial. Nitrogen was bubbled through the heterogeneous mixture for about a minute; it was heated at 90° C. for 4.5 h and allowed to cool to rt. The solvent was removed in vacuo and a silica gel mesh was prepared and submitted to flash chromatography (50–60% EtOAc/hexanes) to afford impure Example 158 (33 mg).

EXAMPLES 159–173

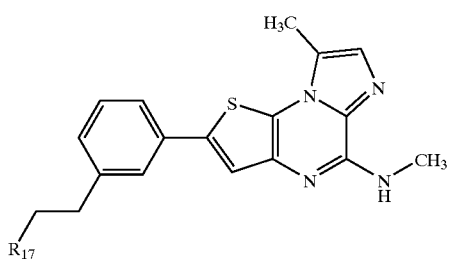
(It)

To prepare compounds having the formula (It), wherein $R_{17}$ has the values listed in Table 14, DMF (2.0 mL), an appropriate heterocycle or amine (i.e., morpholine for Example 159 [150 uL, 1.720 mmol]), and $K_2CO_3$ (13.1 mg, 0.0948 mmol) were added into a vial containing impure Example 158 (33 mg, <). The reaction mixture was stirred at 90° C. for 2.75 h, cooled to rt and the solvent removed in vacuo. The residue was dissolved in MeOH and submitted to a PREP-HPLC to afford the TFA salt of the desired compound. The TFA salt was converted to the free-base by the following route:

The material obtained from the PREP-HPLC was dissolved in MeOH and loaded onto an MEOH-prewashed SCX column. The column was washed with methanol and then the compound eluted from the column with 2.0 M $NH_3$/MeOH. The solvent was removed in vacuo to afford the free-base form of the desired compound.

For Examples 172 and 173, the respective starting materials which were available as HCl salts were free-based, by employing the above SCX methodology, before they were submitted to the alkylation step.

TABLE 14

| Ex. # | $R_{17}$ | $(M + H)^+$ | $^1H$ NMR |
|---|---|---|---|
| 159 | morpholine | 408.18 | |
| 160 | imidazole | 389.20 | |
| 161 | 4-methylpiperazine | 421.27 | |
| 162 | pyrrolidine | 392.24 | |
| 163 | piperazine | 407.25 | |
| 164 | 2,5-dimethylpiperazine | 435.31 | |
| 165 | 4-acetylpiperazine | 449.27 | |
| 166 | 3-oxopiperazine | 421.21 | (Free base): 7.76(s, 1H), 7.73(br s, 1H), 7.65(m, 1H), 7.59(m, 1H), 7.47(q, J=4.7, 1H), 7.37–7.34 (m, 2H), 7.23(d, J= 7.7, 1H), 3.16(m, 2H), 3.02 (s, 2H), 2.99(d, J=4.9, 3H), 2.82(m, 2H), 2.73(d, J=0.6, 3H), 2.67–2.64 (m, 4H). |
| 167 | —N(CH$_3$)$_2$ | 366.27 | |
| 168 | —NH(CH$_2$)$_2$OH | 382.23 | |
| 169 | 2-ethylimidazole | 417.16 | |
| 170 | 2-methylimidazoline | 405.13 | |
| 171 | 2-imino-3-methyl-imidazolidinone | 434.09 | |
| 172 | glycinamide | 395.18 | |
| 173 | N-methylglycinamide | 409.18 | |

EXAMPLE 174

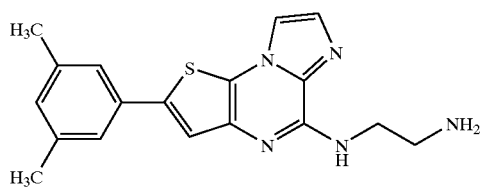

The HCl salt of Example 174 was prepared as described for Example 137, using 5-iodo-m-xylene instead of iodobenzene. $^1$H-NMR: 8.24 (d, J=0.9, 1H), 7.82 (br s, 3H), 7.77 (br t, J=5.7, 1H), 7.70 (d, J=1.2, 1H), 7.65 (s, 1H), 7.36 (s, 2H), 7.02 (s, 1H), 3.76 (app q, J=5.9, 2H), 3.15 (app t, J=6.1, 2H), 2.34 (s, 6H). (ESI) m/z (M+H)$^+$=338.21.

EXAMPLES 175–176

Me$_3$Al (350 ul of 2.0 M/hexanes) was added into a THF (2.0 mL) semi-solution of the respective piperazine (0.7151 mmol)and the resultant solution was stirred for 15 min. Example 125 (42.3 mg, 0.1154 mmol) was added in one batch and the heterogeneous mixture was heated at 70° C. for 14.25 h. It was allowed to cool to room temperature and quenched with MeOH. After the volatile component was removed in vacuo, the residue was treated with wet DMF, the precipitate filtered, and the filtrate was submitted to a Prep-HPLC. The resulting material was free-based according to the procedure described for Examples 155–164.

TABLE 15

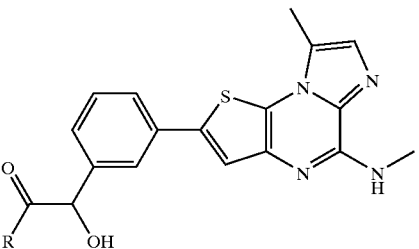

| Ex. # | R | (M + H)$^+$ | Other Data ($^1$H NMR) |
|---|---|---|---|
| 175 | HN⌐N– | 421.14 | |
| 176 | —N⌐N– | 435.23 | |

EXAMPLE 177

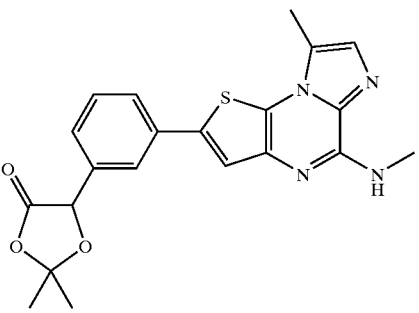

LiCl (30.8, 0.7266 mmol) and Pd(Ph$_3$P)$_4$ (9.1 mg, 0.0079 mmol) were sequentially added into a mixture of Stannane 108A, (80.6mg, 0.2115 mmol) and triflate P35 (149.6 mg, 0.4397 mmol) in dioxane (3.0 mL). The reaction mixture was flushed with N$_2$ and heated at 90° C. for 4.5 h. After it was allowed to cool to room temperature, the volatile component was removed in vacuo. A silica gel mesh was prepared and submitted to flash chromatography (60–75% EtOAc/hexanes) to afford Example 177 (86.5 mg) as an off-white solid, containing Example 5 and Ph$_3$PO impurities. The sample was recrystallized from EtOAc to afford pure Example 177 as a dull-yellow solid (32.1 mg). $^1$H NMR: 7.83 (m, 1H), 7.82 (s, 1H), 7.75 (m, 1H), 7.53 (app t, J=7.8, 1H), 7.51 (br s, 1H), 7.40 (app d, J=7.7, 1H), 7.37 (d, J=1.0, 1H). 5.84 (s, 1H), 2.99 (d, J=4.7, 3H), 2.74 (d, J=0.6, 3H), 1.76 (s, 3H), 1.69 (s, 3H). (ESI) m/z (M+H)$^+$=409.12.

EXAMPLES 178–182

Examples 178–182 having formula above, wherein R is OH (Ex. 178), NH$_2$ (Ex. 179), N-methylpypirizinyl (Ex. 180), morpholinyl (Ex. 181), OMe (Ex. 182) were each prepared from Example 177 as follows:

EXAMPLE 178

The mother liquor retrieved from the recrystalization of Example 177 was rotovaped, and the resulting crude material was treated with MeOH (4.0 mL) and NaOH (260 uL of 1.0 M/H$_2$O; 0.260 mmol) and heated at 70° C. for 5 h. After it was allowed to cool to room temperature, the volatile component was removed in vacuo and the crude material was purified with Prep-HPLC, followed by recrystallization (MeOH) to afford the free-base form of Example 178 as an off-white solid (6 mg). (ESI) m/z (M+H)$^+$=369.19.

EXAMPLE 179

Anhydrous NH$_3$ was bubbled through a mixture of MeOH (8.0 mL) and Example 177 (51.6 mg, 0.1264 mmol) in a Parr bomb for 7 min. The apparatus was capped and heated at 70° C. for 27 h. It was allowed to cool to room temperature, and the suspension was filtered and washed with MeOH to afford Example 179 as an off-white solid (27.6 mg). (ESI) m/z (M+H)$^+$=368.22.

EXAMPLE 180

A mixture of N-methyl piperazine (1.0 mL) and Example 177 (40.2 mg, 0.0985 mmol) was heated at 70° C. for 4.25 h. The volatile component was removed in vacuo, and the crude material was submitted to a Prep-HPLC to afford the TFA salt of Example 180. The salt was free-based according to the procedure described for Examples 159–173 to afford Example 180 as an off-white foam (24.7 mg). (ESI) m/z (M+H)$^+$=451.23.

EXAMPLE 181

A mixture of morpholine (1.0 mL) and Example 177 (43.7 mg, 0.1071 mmol) was heated at 70° C. for 2 h. The volatile component was removed in vacuo and the resulting crude material was submitted to a Prep-HPLC to afford Example 181 as a light yellow solid (15.8 mg). Interestingly the material obtained from the Prep-HPLC purification was in a free-base form as confirmed by F-19 NMR. (ESI) m/z (M+H)$^+$=438.10.

EXAMPLE 182

MeOH (5.0 mL) was added into a mixture of K$_2$CO$_3$ (9.3 mg, 0.0673 mmol) and Example 177 (47 mg, 0.1152 mmol), and the heterogeneous reaction mixture was vigorously stirred for 2 h. A silica gel mesh was prepared directly from the reaction mixture and submitted to flash chromatography (0–5% MeOH/EtOAc) to afford Example 182 as an off-white solid (13.0 mg). (ESI) m/z (M+H)$^+$=383.17.

EXAMPLES 183–190

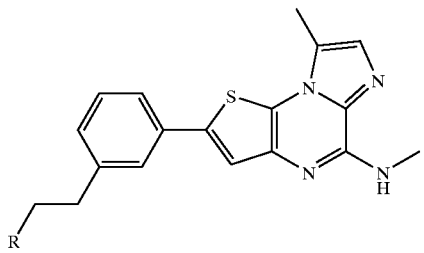

Examples 183–190 having formula above, wherein R is shown in Table 16, were prepared from the free-base form of Example 113 as follows:

EXAMPLE 183

Et$_3$N (40 uL, 0.287 mmol) and Me$_2$NSO$_2$Cl (30 uL, 0.2793 mmol) were added into a THF (2.0 mL) suspension of Example 113 (43.7 mg, 0.1296 mmol). The reaction mixture was stirred for 18 h, additional Me$_2$NSO$_2$Cl (50 uL, 0.466 mmol) was added and it was stirred for 24 h. MeOH (2.5 mL) was added and the mixture was heated to a reflux briefly and cooled to room temperature. The volatile component was removed in vacuo, and the residue was submitted to a Prep-HPLC purification to afford the TFA salt of Example 183 as a white solid (42.7 mg).

EXAMPLE 184

MeOH (2.0 mL) was added into a mixture of Example 113 (30.5 mg, 0.090 mmol) and potassium cyanate (118.7 mg, 1.4633 mmol). Two pipet drops of acetic acid were added and the reaction mixture was vigorously stirred for 1.75 h. It was then diluted with DMF, filtered and submitted to a Prep-HPLC to afford the TFA salt of Example 184 as an off-white solid (20.5 mg).

EXAMPLE 185

K$_2$CO$_3$ (10.1 mg, 0.073 mmol), DMF (2.0 mL) and bromoacetamide (15.4, 0.1116 mmol) were sequentially added into a flask containing Example 113 (31.0 mg, 0.0919 mmol), and the reaction mixture was heated at 60° C. for 3.75 h. A second batch of bromoacetamide (10.4 mg, 0.0754 mmol) was added and 5 h hours later a third batch of bromoacetamide (8.6 mg) was added, and the reaction mixture was heated for an additional 12 h. It was diluted with MeOH, filtered and submitted to Prep-HPLC to afford the TFA salt of Example 185 as an off-white solid (37.9 mg).

EXAMPLE 186

Et$_3$N (30 uL, 0.215 mmol) and 1-Methyl-1H-imidazole-4-sulfonyl chloride (20.9 mg, 0.1157 mmol) were added into a THF suspension of Example 113 (31.5 mg, 0.0934 mmol), and the reaction mixture was vigorously stirred for 5.75 h. Additional sulfonyl chloride (4.4 mg, 0.0244 mmol) was added and stirring continued for 65 min. The volatile component was removed in vacuo, and the residue was submitted to a Prep-HPLC to afford the TFA salt of Example 186 as an off-white solid (35.5 mg).

EXAMPLE 187

A mixture of Example 113 (30.4 mg, 0.0901 mmol) and H$_2$NSO$_2$NH$_2$ (38.5 mg, 0.4006 mmol) in dioxane (2.0 mL) was heated at 90° C. for about 19 h. The volatile component was removed in vacuo and the residue was submitted to Prep-HPLC to afford Example 187 as an off-white solid (23.4 mg).

EXAMPLE 188

Et$_3$N (30 uL, 0.215 mmol) was added to a THF (2.0 mL) semi-suspension of Example 113 (30.7 mg, 0.091 mmol), and the mixture was cooled (ice-water) and treated with MeSO$_2$CH$_2$SO$_2$Cl (24.5 mg, 0.127 mmol). The cold bath was removed 1 hr later and stirring was continued for 4.75 h. Additional sulfonyl chloride (54.9 mg, 0.285 mmol) was added and the reaction mixture was stirred for 25.5 h. MeOH was added and the reaction mixture was allowed to stand overnight. All the volatile component was removed in vacuo and the crude material was submitted to Prep-HPLC to afford the TFA salt of Example 188. The salt was free-based according to the procedure described for Examples 159–173 to retrieve an off-white solid (4.6 mg).

EXAMPLE 189

Methyl isocyanate (15 uL, 0.240 mmol) was added into a MeOH (2.0 mL) suspension of Example 113 (29.1 mg, 0.0863 mmol). There was a brief dissolution followed by the formation of heavy suspension. After stirring for 40 min, the suspension was filtered and washed with MeOH to afford Example 189 as an off-white solid (24.1 mg).

EXAMPLE 190

Isopropyl isocyanate (40 uL, 0.407 mmol) was added into a MeOH (3.0 mL) suspension of Example 113 (39.0 mg, 0.1156 mmol) and the reaction mixture was stirred for about 30 min. The precipitate was filtered and washed with MeOH. The solid was submitted to Prep-HPLC purification to afford the TFA salt of Example 190 as an off-white solid (32.7 mg).

TABLE 16

| Ex. # | R | (M + H)+ | Other Data (¹H NMR) |
|---|---|---|---|
| 183 | O=S(=O)(N(CH₃)₂)NH- | 445.08 | |
| 184 | H₂N-C(=O)-NH- | 381.14 | |
| 185 | O=C(NH₂)-CH₂-N(-CH₂-C(=O)NH₂)- | 452.13 | |
| 186 | (1-methylimidazol-4-yl)-S(=O)₂-NH- | 482.06 | |
| 187 | H₂N-S(=O)₂-NH- | 417.08 | |
| 188 | CH₃-S(=O)₂-CH₂-S(=O)₂-NH- | 494.02 | |
| 189 | CH₃-NH-C(=O)-NH- | 395.18 | |
| 190 | (iPr)NH-C(=O)-NH- | 423.1 | |

EXAMPLES 191–196

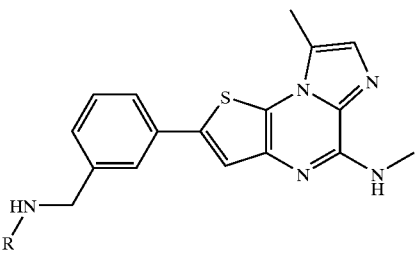

Examples 191–196 having formula above, wherein R is described in Table 17, were prepared from the free-base form of Example 118 as follows:

EXAMPLE 191–192

Examples 191 and 192 were prepared from Example 118 according the procedure described for the synthesis of 184 and 187, respectively.

EXAMPLE 193

Acetic anhydride (11.4 mg, 0.112 mmol) and triethylamine (14.4 mg, 0.142 mmol) were added into a mixture of Example 118 (25 mg, 0.077 mmol) and THF (25 mL). The mixture was stirred at 25° C. for 16 h. The volatile component was removed in vacuo and the residue was purified by prep-HPLC to afford the TFA salt of Example 193 as a yellow solid (24.4 mg).

EXAMPLE 194

Methanesulfonyl chloride (2 mL of 0.0458 M/THF; 0.0916 mmol) and triethylamine (6 mg, 0.06 mmol) were added to Example 118 (19.7 mg, 0.0609 mmol). The reaction mixture was stilTed at 25° C. for 53.5 h. All the volatile component was removed in vacuo, and the residue was purified by prep-HPLC to afford the TFA salt of Example 194 as a yellow solid (10.1 mg).

EXAMPLE 195–196

A mixture of Example 118 (25 mg, 0.077 mmol) and oxalamic acid ethyl ester (90.5 mg, 0.773 mmol) in methanol (10 mL) was refluxed for 17 h. All the volatile component was removed in vacuo, and the residue was purified by prep-HPLC to afford the TFA salt of Example 195 (16.4 mg, yellow solid) and the TFA salt of Example 196 (5.9 mg, yellow solid).

TABLE 17

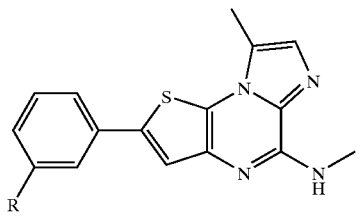

| Ex. # | R | (M + H)⁺ | Other Data (¹H NMR) |
|---|---|---|---|
| 191 | H₂N-C(O)- | 367.07 | (TFA salt): 7.71(s, 1H), 7.65 (d, J=7.9, 1H), 7.61(br s, 1H), 7.44(br s, 1H), 7.41(app t, J=7.8, 1H), 7.26(d, J=7.6, 1H), 6.51(br m, 1H), 4.24(br d, J=4.6, 2H), 3.03(br s, 3H), 2.74(s, 3H). |
| 192 | H₂N-S(O)₂- | 403.02 | (TFA salt): 7.77(s, 1H), 7.74 (br s, 1H), 7.67(d, J=7.9, 1H), 7.41(app t, J=7.8, 1H), 7.39(s, 1H), 7.33(d, J=7.6, 1H), 7.16 (br t, J=6.1, 1H), 6.71 (br s, 2H), 4.15(br d, J=5.5, 2H), 3.00(br d, J=3.6, 3H), 2.74(s, 3H) |
| 193 | CH₃-C(O)- | 366.08 | (TFA salt): 8.41(br t, J=5.7, 1H), 7.72(s, 1H), 7.66(d, J=8.0, 1H), 7.62(s, 1H), 7.44(s, 1H), 7.42(app t, J=7.7, 1H), 7.25 (d, J=7.6, 1H), 4.32(d, J=6.1, 2H), 3.03(br s, 3H), 2.74 (s, 3H), 1.90(s, 3H) |
| 194 | CH₃-S(O)₂- | 402.01 | |
| 195 | H₂N-C(O)-C(O)- | 395.07 | |
| 196 | CH₃O-C(O)-C(O)- | 410.04 | |

EXAMPLE 197

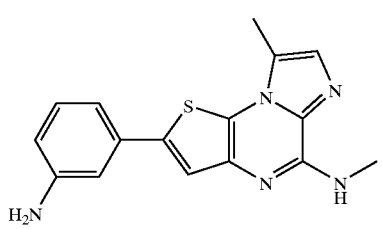

Example 197 was prepared from 3-Iodoaniline and stannane 108A according to the procedure described for the synthesis of Example 177. ¹H NMR: 7.54 (s, 1H), 7.43 (q, J=4.6, 1H), 7.35 (s, 1H), 7.09 (t, J=7.8, 1H), 6.93 (app d, J=7.6, 1H), 6.90 (app t, J=2.0, 1H), 6.55 (dd, J=8.0, 1.6, 1H), 5.26 (br s, 2H), 2.99 (d, J=4.9, 3H), 2.72 (br s, 3H). (ESI) m/z (M+H)⁺=310.11.

EXAMPLE 198–201

Examples 198–201 having formula above, wherein R is shown in Table 18, were prepared from the free-base form of Example 197 as follows:

EXAMPLE 198

Acetoxyacetyl chloride (2 mL of 0.07M/THF, 0.14 mmol) and triethylamine (26.2 mg, 0.259 mmol) were added to Example 197 (40.0 mg, 0.129 mmol). The reaction mixture was stirred at 25° C. for 14 h, filtered and washed with THF (1 mL). The filtrate was concentrated in vacuo, and a silica gel mesh of the residue was submitted to flash chromatography (EtOAc) to afford a light yellow solid (22.4 mg).

Potassium carbonate (18.6 mg, 0.135 mmol) was added to a mixture of the above solid (21.4 mg, 0.0523 mmol) and methanol/DMF (2.0/1.0 mL). The reaction mixture was stirred at 25° C. for 15.5 h. The volatile component was removed in vacuo and the residue was purified by prep-HPLC to afford the TFA salt of Example 198 as an off-white solid (16.4 mg).

EXAMPLE 199

Example 197 (30.6 mg, 0.0989 mmol) was added to ethyl isocyanate (2 mL of 0.07M/CH₂Cl₂, 0.14 mmol), and the reaction mixture was stirred at 25° C. for 7.5 h. Additional ethyl isocyanate (200 uL 0.07M/CH₂Cl₂, 0.014 mmol) was added and the reaction was stirred for 88.5 h. All the volatile component was removed in vacuo and the residue was purified by prep-HPLC to afford the TFA salt of Example 199 as a tan solid (30.1 mg).

EXAMPLES 200 and 201

Ethanesulfonyl chloride (2 mL of 0.07M/CH₂Cl₂, 0.14 mmol) and triethylamine (14.7 mg, 0.145 mmol) were added to Example 197 (31.5 mg, 0.102 mmol), and the mixture was stirred at 25° C. for 5 h. The volatile component was removed in vacuo and the residue was purified by prep-HPLC to afford the TFA salt of Example 200 (10.9 mg, yellow solid) and the TFA salt of Example 201 (11.5 mg, yellow solid).

TABLE 18

| Ex. # | R | (M + H)+ | Other Data (¹H NMR) |
|---|---|---|---|
| 198 | HO-CH2-C(=O)-NH- | 368.05 | |
| 199 | Et-NH-C(=O)-NH- | 381.07 | |
| 200 | Et-S(=O)2-NH- | 401.97 | |

TABLE 18-continued

| Ex. # | R | (M + H)+ | Other Data (¹H NMR) |
|---|---|---|---|
| 201 | (Et-S(=O)2)2-N- | 493.88 | |

EXAMPLES 202–241

Examples 202–241, having formula shown above, were prepared from stannane 108A following the coupling procedure described above for Example 177, using the desired coupling partners (see, e.g., Preparations 1–75 or commercially available sources). The resultant products were purified with flash chromatography, Prep-HPLC and/or recrystallization and were obtained as free-bases or TFA salts.

TABLE 19

| Ex. # | R | (M + H)+ | Other Data (¹H NMR) |
|---|---|---|---|
| 202 | 3-(H2N-S(=O)2)-C6H4- | 374.17 | |
| 203 | 3-(NC-CH2CH2)-C6H4- | 348.10 | (Free base): 7.78(s, 1H), 7.71(m, 1H), 7.66(m, 1H), 7.46(m, 1H), 7.41(app t, J=7.8, 1H), 7.36(d, J=0.6, 1H), 7.28(app d, J=7.6, 1H), 2.99(d, J=4.6, 3H), 2.97–2.88(m, 4H), 2.74(s, 3H). |
| 204 | 3-(2-oxoimidazolidin-1-yl-CH2CH2)-C6H4- | 407.13 | |

TABLE 19-continued
| Ex. # | R | (M + H)+ | Other Data (¹H NMR) |
|---|---|---|---|
| 205 | 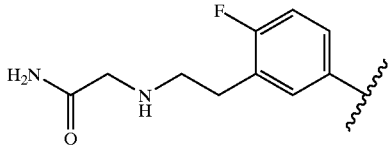 | 413.12 | |
| 206 | 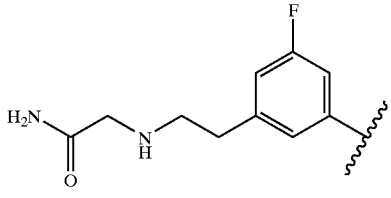 | 413.12 | |
| 207 | 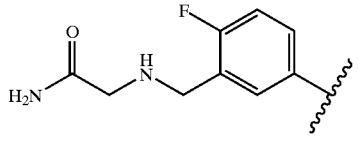 | 399.16 | |
| 208 | 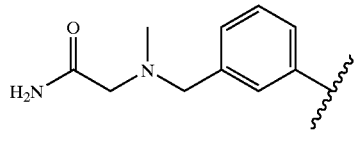 | 395.15 | |
| 209 | 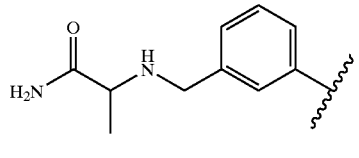 | 395.15 | |
| 210 | 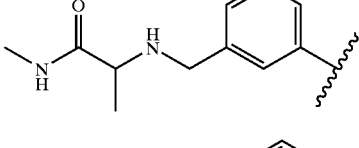 | 409.18 | |
| 211 | 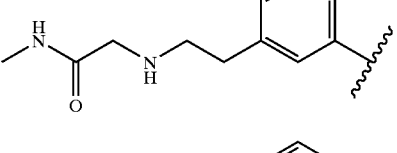 | 409.18 | (Free base): 7.76(s, 1H), 7.68(br s, 1H), 7.61–7.60(m, 2H), 7.47(m, 1H), 7.38–7.35(m, 2H), 7.20(d, J=7.7, 1H), 3.13(s, 2H), 2.99(d, J= 4.6, 3H), 2.78(br s, 4H), 2.73(s, 3H), 2.58(d, J=4.9, 3H). |
| 212 | 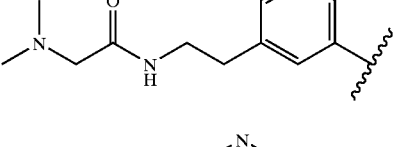 | 423.19 | |
| 213 | 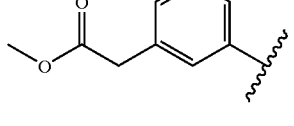 | 368.03 | (Free base): 8.94(d, J=2.3, 1H), 8.43(d, J=1.9, 1H), 8.04(s, 1H), 7.90(s, 1H), 7.52(m, 1H), 7.38(d, J=0.9, 1H), 3.84(s, 2H), 3.67(s, 3H), 2.99(d, J=4.8, 3H), 2.74(d, J= 0.5, 3H). |
| 214 | 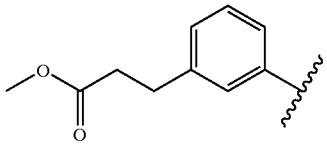 | 381.21 | (Free base): 7.76(s, 1H), 7.63(m, 1H), 7.60(m, 1H), 7.47(m, 1H), 7.38–7.34(m, 2H), 7.21(app d, J= 7.7, 1H), 3.60(s, 3H), 2.99(d, J= 4.9, 3H), 2.91(t, J=7.6, 2H), 2.73 (d, J=1.0, 3H), 2.72(d, J=7.6, 2H). |

TABLE 19-continued

| Ex. # | R | (M + H)+ | Other Data (1H NMR) |
|---|---|---|---|
| 215 | methyl (3-aminophenyl)glycinate substituent | 382.05 | |
| 216 | 1-(3-substituted-benzyl)imidazolidin-2-one | 393.12 | |
| 217 | 4-acetyl-1-(3-substituted-benzyl)piperazine | 435.12 | |
| 218 | 2-amino-N-(3-substituted-benzyl)acetamide | 381.08 | |
| 219 | 1-(3-substituted-benzyl)-1H-1,2,4-triazole | 376.10 | (Free base): 8.73(s, 1H), 8.01(s, 1H), 7.76(s, 1H), 7.74(d, J=7.9, 1H), 7.71(s, 1H), 7.48(q, J=4.8, 1H), 7.44(app t, J=7.7, 1H), 7.36 (s, 1H), 7.22(d, J=7.6, 1H), 5.48 (s, 2H), 2.99(d, J=4.9, 3H), 2.73 (s, 3H) |
| 220 | 4-(3-substituted-benzyl)-4H-1,2,4-triazole | 376.10 | |
| 221 | 4-(3-substituted-benzyl)piperazin-2-one | 407.06 | |
| 222 | 1-(3-substituted-benzyl)pyrrolidine-2-carboxamide | 421.10 | |
| 223 | methyl 2-amino-3-(3-substituted-phenyl)propanoate | 396.08 | |

TABLE 19-continued
| Ex. # | R | (M + H)+ | Other Data (¹H NMR) |
|---|---|---|---|
| 224 | 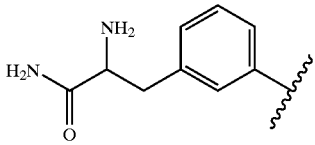 | 381.07 | |
| 225 | 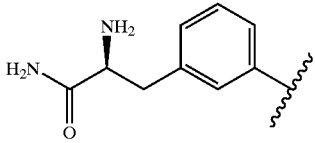 | 381.06 | |
| 226 | 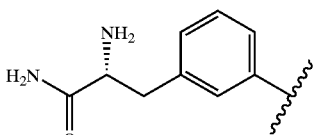 | 381.06 | |
| 227 | 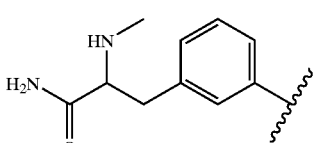 | 395.15 | |
| 228 | 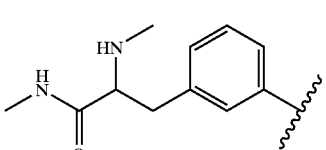 | 409.25 | |
| 229 | 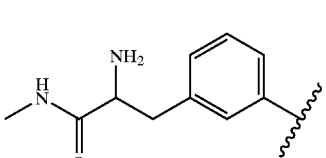 | 395.22 | (TFA salt): 8.38(br q, J=4.5, 1H), 8.19(br d, J=3.9, 3H), 7.77(s, 1H), 7.72(d, J=8.3, 1H), 7.60(br s, 1H), 7.43(app t, J=7.7, 1H), 7.40(s, 1H), 7.18(d, J=7.6, 1H), 3.98(br m, 1H), 3.11(dd, J=14, 6.1, 1H), 3.03–2.99(m, 4H), 2.74 (s, 3H), 2.66(d, J=4.6, 3H) |
| 230 | 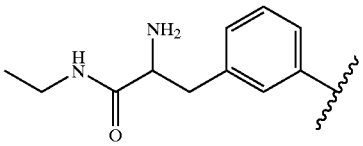 | 409.18 | |
| 231 | 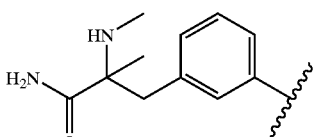 | 409.25 | |
| 232 | 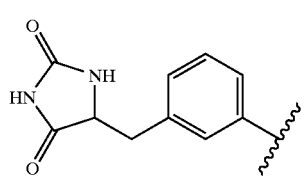 | 407.23 | |

US 6,933,294 B2
TABLE 19-continued
| Ex. # | R | (M + H)+ | Other Data (¹H NMR) |
|---|---|---|---|
| 233 | 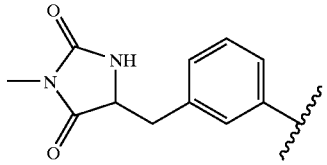 | 421.20 | (TFA salt): 8.29(br s, 1H), 7.74(s, 1H), 7.64(d, J=8.0, 1H), 7.57(br s, 1H), 7.48(m, 1H), 7.38–7.34(m, 2H), 7.15(d, J=7.7, 1H), 4.44(m, 1H), 3.07(dd, J=14.0, 3.1, 1H), 2.99(d, J=4.9, 3H), 2.97(m, 1H), 2.73(s, 3H), 2.70(s, 3H) |
| 234 | 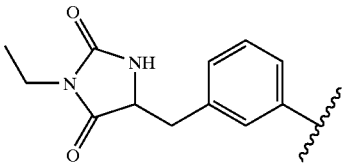 | 435.24 | |
| 235 | 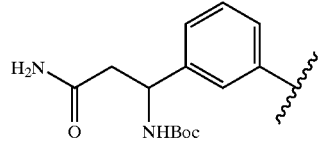 | 481.28 | |
| 236 | 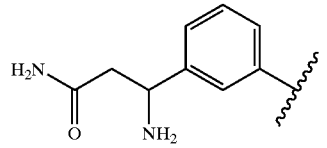 | 381.20 | |
| 237 | 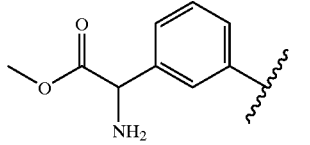 | 382.06 | |
| 238 | 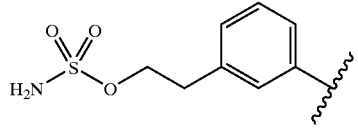 | 418.17 | |
| 239 | 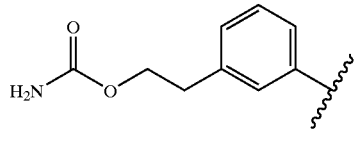 | 382.22 | |
| 240 | 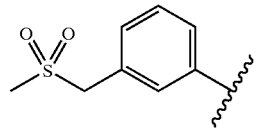 | 387.18 | (Free base): 7.83(m, 1H), 7.78(br s, 1H), 7.77(m, 1H), 7.51–7.48(m, 2H), 7.39(app d, J=7.7, 1H), 7.37 (br s, 1H), 4.56(s, 2H), 2.99(d, J = 4.5, 3H), 2.96(s, 3H), 2.74(s, 3H) |
| 241 | 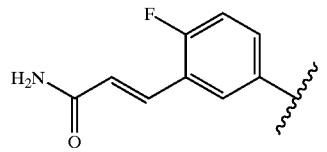 | 382.23 | |

EXAMPLES 242–250

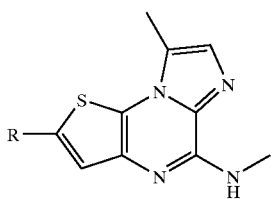

Examples 242–250, having formula shown above, were prepared from the corresponding esters (Example 213 or 214) according to the procedures described for the synthesis of Examples 127, 128 or 131. A number of cases that carry Boc group were deprotected under standard conditions (TFA/CH$_2$Cl$_2$).

TABLE 20

| Ex. # | R | (M + H)$^+$ | Other Data ($^1$H NMR) |
|---|---|---|---|
| 242 | (3-carboxyethyl-phenyl) | 367.19 | |
| 243 | (3-carbamoylethyl-phenyl) | 366.15 | |
| 244 | (5-carboxymethyl-pyridin-3-yl) | 354.06 | |
| 245 | (5-carbamoylmethyl-pyridin-3-yl) | 353.08 | |
| 246 | (5-hydrazinocarbonylmethyl-pyridin-3-yl) | 368.09 | |
| 247 | (3-(carboxymethylamino)-phenyl) | 368.07 | |
| 248 | (3-(2-amino-2-carboxyethyl)-phenyl) | 382.04 | |
| 249 | (3-(amino-carboxy-methyl)-phenyl) | 368.09 | (TFA salt): 8.81(br s, 3H), 7.90–7.88(m, 2H), 7.81(s, 1H), 7.64(m, 1H), 7.56(t, J=7.8, 1H), 7.46(d, J=7.6, 1H), 7.40(s, 1H), 5.23(m, 1H), 3.00(d, J=3.9, 3H), 2.75(s, 3H) |

TABLE 20-continued

| Ex. # | R | (M + H)+ | Other Data (1H NMR) |
|---|---|---|---|
| 250 | (structure shown) | 367.07 | (TFA salt): 8.68–8.63(m, 3H), 7.93 (br s, 1H), 7.90(br s, 1H), 7.88 (d, J=7.9, 1H), 7.81(s, 1H), 7.67 (br s, 2H), 7.55(app t, J=7.8, 1H), 7.48(d, J=7.6, 1H), 7.41(s, 1H), 4.94(m, 1H), 3.00(br d, J=3.9, 3H), 2.75(s, 3H) |

EXAMPLE 251

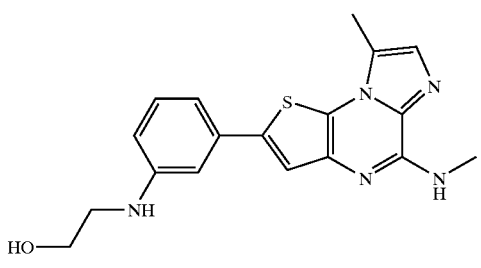

DIBAL-H (0.27 mL of 1M in CH$_2$Cl$_2$, 0.27 mmol) was added to a cooled (0° C.) THF (2.0 mL) suspension of Example 215 (32.1 mg, 0.0842 mmol), the cooling bath was removed, and the reaction mixture was stirred at 25° C. for 22 h. Additional DIBAL-H (50 µL of 1M/CH$_2$Cl$_2$, 0.050 mmol) was added at ambient temperature, and the mixture was stirred for another 3 h. It was then quenched with methanol (2 mL) and all the volatile component was removed in vacuo. The residue was purified by prep-HPLC to afford the TFA salt of Example 251 as a yellow solid (17.4 mg). (ESI) m/z (M+H)$^+$=354.12.

EXAMPLE 252

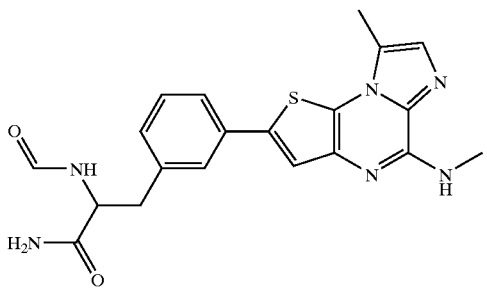

A propylformate (3.0 mL) suspension of Example 224 (46.4 mg, 0.122 mmol) was refluxed for 25 h. The volatile component was removed in vacuo and the residue was triturated from MeOH to afford Example 252 as a tan solid (30 mg). (ESI) m/z (M+H)$^+$=409.18.

EXAMPLE 253

(structure shown)

Trimethylaluminum (0.30 mL of 2M/toluene, 0.60 mmol) was added to a mixture of Example 215 (32.7 mg, 0.0857 mmol) and ammonium chloride (45.0 mg, 0.841 mmol) in 1,4-dioxane (2.0 mL). The reaction mixture was stirred at ambient temperature for 30 min and at 60° C. for 23 h. It was cooled to room temperature and quenched with methanol (2 mL) and stirred for 30 min. The volatile component was removed in vacuo, and the residue was purified by prep-HPLC to afford the TFA salt of Example 253 as a tan solid (12.7 mg). $^1$H NMR: 7.59 (s, 1H), 7.45 (br s, 1H), 7.42 (br s, 1H), 7.18 (app t, J=8.0, 1H), 7.13 (br s, 1H), 6.97 (d, J=8.5, 1H), 6.90 (app t, J=1.9, 1H), 6.58 (dd, J=8.1, 1.7, 1H), 3.68 (s, 2H), 3.03 (br s, 3H), 3.73 (s, 3H). (ESI) n/z (M+H)$^+$= 367.05.

EXAMPLE 254

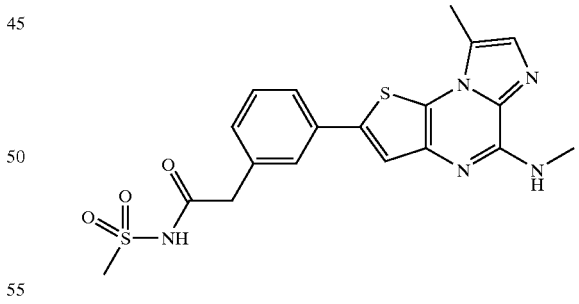

Potassium carbonate (91.8 mg, 0.664 mmol) was added into a 1,4-dioxane (3.0 mL) solution of bromide P75, and the mixture was vigorously stirred for 25 min. Stannane 108A (81.1 mg, 0.213 mmol), LiCl (36.9 mg, 0.870 mmol) and Pd(Ph$_3$P)$_4$ (12.1 mg, 0.0105 mmol) were sequentially added to the above mixture. The heterogeneous mixture was flushed with N$_2$ and heated at 90° C. for 19 h. It was allowed to cool to room temperature, the volatile component was removed in vacuo, and the residue was submitted to Prep-HPLC to afford a mixture of bromide P75 and the TFA salt of Example 254. The mixture was dissolved in MeOH and loaded onto an SCX column (pre-equilibrated with MeOH), and washed with MeOH; the column was then eluted with 2 N NH₃/MeOH to afford Example 254 as a tan solid (3.1 mg). ¹H-NMR: 7.73 (s, 1H), 7.68 (d, J=7.9, 1H), 7.62 (br s, 1H), 7.47 (q, J=4.7, 1H), 7.39 (app t, J=7.8, 1H), 7.36 (s, 1H), 7.23 (d, J=7.6, 1H), 3.60 (s, 2H), 3.12 (s, 3H), 2.99 (d, J=4.6, 3H), 2.73 (s, 3H). (ESI) m/z (M+H)⁺=430.12.

EXAMPLE 255

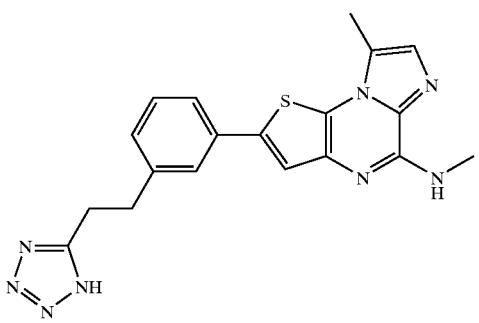

A mixture of NaN₃ (118.2 mg, 1.818 mmol) and NH₄Cl (1.731 mmol) was added to a DMF (3.0 mL) solution of Example 203 (56 mg, 0.161 mmol) and the heterogeneous mixture was heated at 110° C. for 68 h. After it cooled to room temperature, it was treated with 0.5 mL water and stirred for 3.5 h. The volatile component was removed in vacuo and the crude material was purified with a combination of flash chromatography (0–10% MeOH/EtOAc) and Prep-HPLC to afford the TFA salt of Example 255 as an off-white solid (20.8 mg, 33%). ¹H NMR: 7.72 (s, 1H), 7.61–7.60 (m, 2H), 7.43 (s, 1H), 7.37 (m, 1H), 7.21 (app d, J=7.6, 1H), 3.28 (t, J=7.8, 2H), 3.12 (t, J=7.7, 2H), 3.02 (br s, 3H), 2.74 (d, J=0.6, 3H). (ESI) m/z (M+H)⁺=391.10.

EXAMPLE 256–275

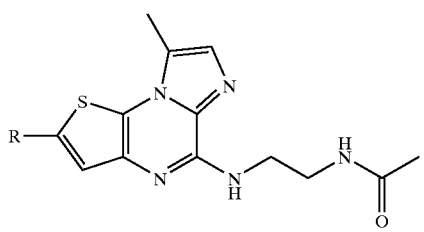

Compounds having the formula shown above, wherein R has the values listed in Table 21, were prepared following Steps A-C below.

Step A:

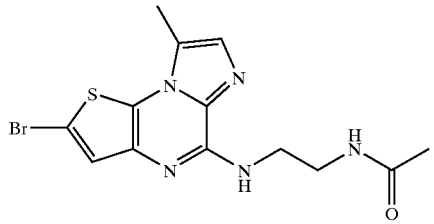

(256A)

Example 59, which is obtained as a bis TFA salt from a Boc deprotection step, was free-based according to the procedure described in the synthesis of Examples 159–173.

Ac₂O (220 uL, 2.332 mmol) was added drop-wise, over 1 min, to a turbid CH₂Cl₂ (20.0 mL) solution of the free-base form of Example 59 (630 mg, 1.93 mmol) and Et₃N (300 uL, 2.152 mmol). The reaction mixture was stirred for about 4 h and the volatile component was removed in vacuo. A silica gel mesh was prepared and submitted to flash chromatography (5–10% MeOH/EtOAc) to afford bromide 256A as an off-white solid (690 mg, >95%). ¹H NMR: 7.99 (br t, J=5.4, 1H), 7.52 (br t, J=5.7, 1H), 7.46 (s, 1H), 7.36 (d, J=0.9, 1H), 3.52 (app q, J=6.1, 2H), 3.31 (app q, J=6.1, 2H), 2.64 (s, 3H), 1.8 (s, 3H). (ESI) m/z (M+H)⁺=367.95/369.95.

Step B:

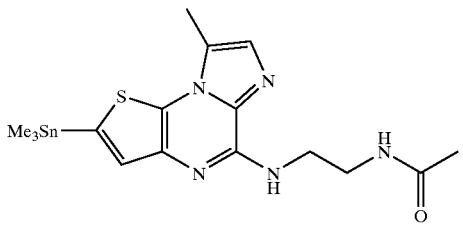

(256B)

Bromide 256A (485 mg, 1.317 mmol) and Pd(Ph₃P)₄ (41.1 mg, 0.0356 mmol) were added to a 1,4-dioxane (19.5 mL) solution of hexamethylditin (1.627 g, 4.966 mmol) and Et₃N (360 uL, 2.583 mmol). The reaction mixture was heated at 100° C. for 1 h, and was allowed to cool to room temperature. A brown residue was filtered and the filterate was rotovaped. The residue was triturated with ether (10 mL), and the ash colored suspension was filtered and washed with ether to afford stannane 256B (279 mg, 46.8%). ¹H NMR: 8.00 (br m, 1H), 7.34 (s, 1H), 7.32 (m, 1H), 7.30 (s, 1H), 3.54 (m, 2H), 3.33 (m, 2H), 2.69 (s, 3H), 1.81 (s, 3H), 0.40 (s; staellite peaks with a J=58.9; 9H). (ESI) m/z (M+H)⁺=453.98.

Step C:

Examples 256–275 were prepared from stannane 256B following the coupling procedure described above for Example 177, using the desire coupling partner ((R7)pA-Br or (R7)pA-I) (see, e.g., Preparations 1–75 or commercially available sources). The resultant product was purified with flash chromatography, Prep-HPLC and/or recrystallization and was obtained as a free-base or TFA salt.

For Example 272, the Boc group present on the coupling product was deprotected under standard condition (20% TFA/CH₂Cl₂). Example 274 was saponified to afford Example 275 according to the procedure described for the synthesis of Example 127.

TABLE 21

| Ex. # | R | (M + H)+ | Other Data (1H NMR) |
|---|---|---|---|
| 256 | 3-fluorophenyl | 384.24 | |
| 257 | 4-fluorophenyl | 384.19 | |
| 258 | pyridin-3-yl | 367.24 | |
| 259 | pyrazin-2-yl | 368.20 | |
| 260 | 3-cyanophenyl | 391.21 | |
| 261 | 5-cyanopyridin-3-yl | 392.18 | (Free base): 9.27(d, J=2.5, 1H), 8.95(d, J=1.8, 1H), 8.72 (app t, J=2.2, 1H), 8.04(s, 1H), 8.01(br t, J=5.3, 1H), 7.56(br t, J=5.7, 1H), 7.41(s, 1H), 3.57(m, 2H), 3.35(m, 2H), 2.74(s, 3H), 1.82(s, 3H). |
| 262 | 3-(2-cyanoethyl)phenyl | 419.21 | |
| 263 | 3-(aminomethyl)-4-fluorophenyl | 413.21 | |
| 264 | 3-(ureidomethyl)-4-fluorophenyl | 456.19 | |

TABLE 21-continued

| Ex. # | R | (M + H)⁺ | Other Data (¹H NMR) |
|---|---|---|---|
| 265 | | 492.16 | |
| 266 | | 438.22 | |
| 267 | | 474.16 | |
| 268 | | 451.09 | (TFA salt): 8.02 (br t, J=5.5, 1H), 7.94 (br t, J=5.5, 1H), 7.73 (s, 1H), 7.62 (d, J=7.9, 1H), 7.59 (br, s 1H), 7.42 (d, J=0.6, 1H), 7.38 (app t, J=7.7, 1H), 7.20 (d, J=7.4, 1H), 3.58 (br m, 2H), 3.37–3.30 (m, 4H), 2.77 (m, 2H), 2.75 (s, 3H), 1.82 (s, 3H), 1.80 (s, 3H). |
| 269 | | 487.03 | |
| 270 | | 452.25 | |
| 271 | | 466.28 | |

TABLE 21-continued

| Ex. # | R | (M + H)+ | Other Data (¹H NMR) |
|---|---|---|---|
| 272 | H₂N-C(=O)-CH(NH₂)-CH₂-[3-phenyl]- | 452.23 | |
| 273 | H₂N-C(=O)-CH₂-[3-phenyl]- | 422.97 | |
| 274 | MeO-C(=O)-CH₂-[3-phenyl]- | 438.01 | (Free base): 8.00 (br t, J=5.5, 1H), 7.72 (s, 1H), 7.70 (app d, J=8.3, 1H), 7.65 (br s, 1H), 7.46 (br t, J=5.8, 1H), 7.41 (app t, J=7.8, 1H), 7.38 (d, J=0.9, 1H), 7.25 (d, J=7.7, 1H), 3.77 (s, 2H), 3.64 (s, 3H), 3.57 (m, 2H), 3.35 (m, 2H), 2.74 (s, 3H), 1.82 (s, 3H). |
| 275 | HO-C(=O)-CH₂-[3-phenyl]- | 424.07 | |

EXAMPLE 276–287

Step A:

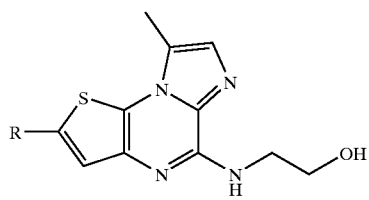

Ammonium hydroxide (10 mL, 29% wt/H₂O) was added into a THF (25.0 mL) solution of Example 1D (5.026 g, 20.390 mmol) in a Parr-bomb, the apparatus was capped and heated at 100° C. until the chloride is completely consumed (>24 h). It was allowed to cool to room temperature, and the precipitate (which was a mixture of white solid and yellow crystals) was filtered and washed with copious water to afford bromide 276 (3.985 g). The filterate was rotovaped, and the residual solid was treated with water, filtered and washed with copious water to retrieve a second batch which has the same purity as the first one (465 mg; a combined yield of 96.1%). ¹H NMR: 7.80 (s, 1H), 7.33 (br s, 2H), 7.29 (s, 1H), 2.38 (s, 3H). (ESI) m/z (M+H)⁺=226.97/228.96.

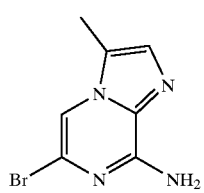
(276A)

Step B:

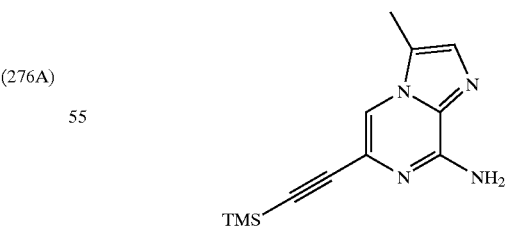
(276B)

Bromide 276A (1.016 g) was converted to alkyne 276B following the procedure of Example 1, Step F, except: (a) 30% less catalyst and co-catalyst were employed; and (b) the column was eluted with 80% EtOAc/hexanes. Alkyne 276B was retrieved as a light brown solid (1.03 g, 94.2%). ¹H NMR: 7.88 (s, 1H), 7.31 (s, 1H), 7.01 (s, 2H), 2.40 (s, 3H), 0.23 (s, 9H). (ESI) m/z (M+H)⁺=245.07.

Step C:

(276C)

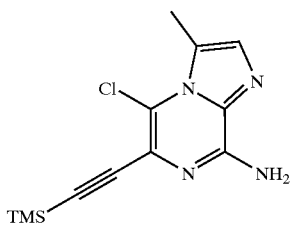

Alkyne 276B (1.016 g) was converted to chloride 276C following the procedure of Example 5, Step C, except: (a) during the aqueous work-up only a single wash was conducted; (b) the column was eluted with 50% EtOAc/hexanes. Alkyne 276C was retrieved as a fluffy yellow solid (980 mg, 83.4%). $^1$H NMR (CDCl$_3$, δ=7.26): 7.27 (s, 1H), 5.51 (br s, 2H), 2.78 (d, J=1.0, 3H), 0.28 (s, 9H). (ESI) m/z (M+H)$^+$=279.06.

Step D:

(276D)

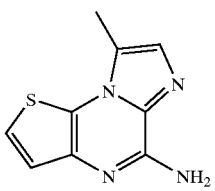

The cyclization of chloroalkyne 276C (6.36 g) to amine 276D was set-up according to the procedure of Example 5, Step D. After all the volatile component was removed in vacuo, the residue was treated with 20% MeOH/CHCl$_3$ (150 mL) and stirred for 15 min. Silica gel was added and the volatile component was removed in vacuo; the resultant mesh was submitted to flash chromatography (0–3% MeOH/EtOAc) to afford the cyclized product (276D) as an orangish-brown solid (1.934 g, 41.5%). $^1$H NMR: 7.52 (d, J=5.5, 1H), 7.37 (d, J=0.7, 1H), 7.19 (d, J=5.5, 1H), 6.80 (br s, 2H), 2.70 (d, J=0.6, 3H). (ESI) m/z (M+H)$^+$=205.07.

Step E:

(276Ea)

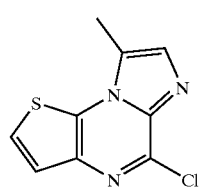

(276Eb)

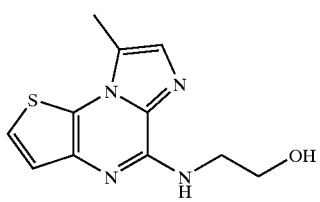

An aqueous (11.5 mL) solution of NaNO$_2$ (4.291 g, 62.19 mmol) was added drop wise over 50 min to a cooled (0° C.) mixture of concentrated HCl (70.0 mL, ~37%) and amine 276D (4.658 g, 22.81 mmol). The reaction mixture was stirred for 5.5 h while allowing the bath to thaw. The bath was then cooled back to 0° C. and the mixture was neutralized with saturated aqueous K$_2$CO$_3$ solution. It was diluted with water (160 mL) and extracted with 20% MeOH/CHCl$_3$, until no more material is extracted. [Note: in the event that a precipitate is formed during extraction, it is filtered and mixed with the final collection of organic extracts]. The combined organic phase was rotovaped, and a silica gel mesh was prepared from the residue and submitted to flash chromatography (1.5–10% MeOH/CHCl$_3$) to afford chloride 276Ea (2.545 g, 49.9%) and the hydrolysis byproduct 276Eb (1.84, 39.5%), both as a light yellow solid. 276Ea: $^1$H NMR: 7.83 (d, J=5.5, 1H), 7.72 (d, J=0.9, 1H), 7.58 (d, J=5.8, 1H), 2.81 (d, J=0.6, 3H). (ESI) m/z (M+H)$^+$=224.01; 276Eb: $^1$H NMR: 11.95 (br s, 1H), 7.56 (d, J=5.5, 1H), 7.32 (d, J=0.9, 1H), 7.00 (d, J=5.8, 1H), 2.63 (d, J=0.6, 3H). (ESI) m/z (M+H)$^+$=206.05.

The byproduct 276Eb could be converted to chloride 276Ea as follow. PhNEt$_2$ (2.9 mL, 18.22 mmol) and POCl$_3$ (29.0 mL)were added to tricycle 276Eb (2.08 g, 10.13 mmol), and the reaction mixture was refluxed for 26.5 h. The volatile component was removed in vacuo, and the residue was partitioned between water and EtOAc. The aqueous phase was neutralized with K$_2$CO$_3$ and extracted with EtOAc, until no more compound was coming. The combined organic phase was rotovaped, and a silica gel mesh was prepared from the residue and submitted to flash chromatography (CHCl$_3$) to afford chloride 276Ea (2.104 g, 92.8%).

Step F:

(276F)

Ethanolamine (6.0 mL) was added into a THF (20 mL) solution of chloride 276Ea (979.2 mg, 4.378 mmol) and the reaction mixture was refluxed for 18 h. It was allowed to cool to room temperature and the volatile component was removed in vacuo. A silica gel mesh was prepared and submitted to flash chromatography (0–5% MeOH/EtOAc) to retrieve a yellow solid along with oily residue believed to be ethanolamine. The solid was washed with copious ether and EtOAc (6 mL). Alcohol 276F was obtained as a yellow solid (1.005 g, 92.5%). $^1$H NMR: 7.52 (d, J=5.5, 1H), 7.36 (d, J=0.9, 1H), 7.26 (d, J=5.5, 1H), 7.13 (br t, J=5.5, 1H), 4.82 (t, J=5.3, 1H), 3.63 (m, 2H), 3.56 (m, 2H), 2.69 (d, J=0.6, 3H). (ESI) m/z (M+H)$^+$=249.08.

Step G:

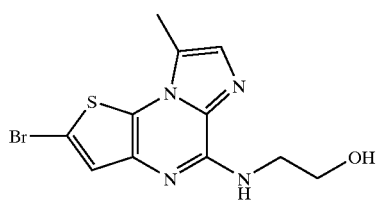
(276G)

N-Bromosucinimide (761.7 mg, 4.279 mmol) was added to a cooled (0° C.) THF (50 mL) semi-suspension of alcohol 276F (1.005 g, 4.047 mmol), and the reaction mixture was stirred for 14 h, while allowing the bath to thaw to ~11° C. Silica gel was added to it, and the solvent was removed in vacuo. The resultant silica gel mesh was submitted to flash chromatography (0–5% MeOH/EtOAc) to afford bromide 276G as a yellow solid (1.101 g); the sample contained alcohol 276F as an impurity in a 10:1 mole ratio ($^1$H NMR). $^1$H NMR: 7.47 (s, 1H), 7.36 (d, J 1.0, 1H), 7.27 (br m, 1H), 4.79 (t, J=5.5, 1H), 3.61 (m, 2H), 3.55 (m, 2H), 2.64 (s, 3H). (ESI) m/z (M+H)$^+$=326.90/328.90.

Step H:

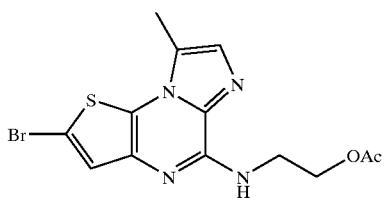
(276H)

Et$_3$N (780 uL, 5.596 mmol), Ac$_2$O (440 uL, 4.663 mmol) and DMAP (39.7 mg, 0.325 mmol) were added into a THF (30.0 mL) suspension of alcohol 276G prepared above (<1.100 g, 3.362 mmol). The heterogeneous mixture was stirred for 70 min, and the volatile component was removed in vacuo. A silica gel mesh was prepared and submitted to flash chromatography (80% EtOAc/hexanes) to afford bromide 276H as an off-white solid (1.170 g, a 2 steps combined yield of 78.3%). $^1$H NMR: 7.62 (br t, J=5.8, 1H), 7.48 (s, 1H), 7.37 (d, J=0.9, 1H), 4.23 (t, J=5.8, 2H), 3.70 (m, 2H), 2.64 (s, 3H), 1.99 (S, 3H). (ESI) m/z (M+H)$^+$=368.94/370.94.

Step I:

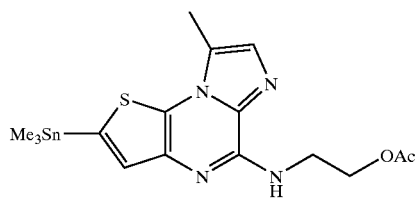
(276I)

The stannylation of bromide 276H (972.6 mg, 2.634 mmol) was set-up according to the procedure described for compound 69A. After the reaction is over, it was cooled to room temperature, filtered and the filterate was rotovaped. The oily residue was treated with warm hexanes (50 mL), and swirled briefly and the hexanes was decanted into a flask and allowed to stand at room temperature. The resulting precipitate was filtered and washed with hexanes to afford stannane 276I as a mixture of light brown solid and crystals (770 mg). $^1$H NMR analysis indicates the sample contains minor impurities. $^1$H NMR: 7.43 (br t, J=6.0, 1H), 7.35 (d, J=0.9, 1H), 7.31 (s, 1H), 4.24 (t, J=6.0, 2H), 3.71 (m, 2H), 2.69 (s, 3H), 2.00 (s, 3H), 0.40 (s; satellite peaks with J=60.2, 57.6; 9H). (ESI) m/z (M+H)$^+$=454.88.

Step J:

Examples 276–287, having formula shown above and where R is shown in Table 22, were prepared from stannane 276I and the appropriate arylbromides or iodides (see, e.g. Preparations 1–75 or commercially available compounds) according to the coupling procedure described for Example 177, followed by deprotection of the alcohol under standard protocol (K$_2$CO$_3$, THF/MeOH). The resultant product was purified with flash chromatography, Prep-HPLC and/or recrystalization and was obtained as a free-base or TFA salt.

Example 286 was saponified to afford Example 287 according to the procedure described for the synthesis of Example 127.

TABLE 22

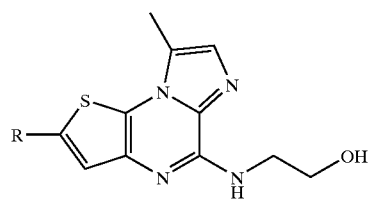

| Ex. # | R | (M + H)$^+$ | Other Data ($^1$H NMR) |
|---|---|---|---|
| 276 | 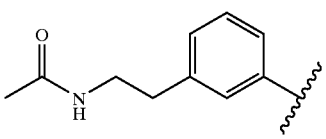 | 410.04 | |

TABLE 22-continued

| Ex. # | R | (M + H)+ | Other Data (¹H NMR) |
|---|---|---|---|
| 277 | (methylsulfonylaminoethyl-phenyl) | 445.98 | |
| 278 | (sulfamoylaminomethyl-phenyl) | 432.98 | |
| 279 | (ureidomethyl-phenyl) | 397.05 | |
| 280 | (oxazolidinon-5-yl-phenyl) | 410.04 | |
| 281 | (imidazolidinon-1-yl-ethyl-phenyl) | 437.08 | |
| 282 | (cyanoethyl-phenyl) | 378.10 | |
| 283 | (carbamoylmethylaminomethyl-phenyl) | 411.07 | |
| 284 | (carbamoylmethylaminoethyl-phenyl) | 425.22 | |

TABLE 22-continued

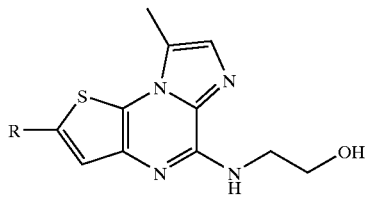

| Ex. # | R | (M + H)+ | Other Data (1H NMR) |
|---|---|---|---|
| 285 | ![H2N-C(=O)-CH2-phenyl] | 382.04 | |
| 286 | ![MeO-C(=O)-CH2-phenyl] | 397.05 | (Free base): 7.74 (s, 1H), 7.70 (br d, J=8.0, 1H), 7.65 (br s, 1H), 7.41 (app t, J=7.7, 1H), 7.38 (d, J=0.9, 1H), 7.26–7.24 (m, 2H), 4.84 (t, J= 5.4, 1H), 3.77 (s, 2H), 3.64 (s, 3H), 3.63 (m, 2H), 3.58 (m, 2H), 2.74 (s, 3H). |
| 287 | ![HO-C(=O)-CH2-phenyl] | 383.01 | |

EXAMPLES 288–297

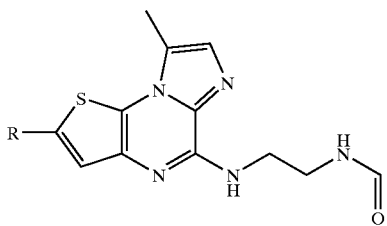

Step A:

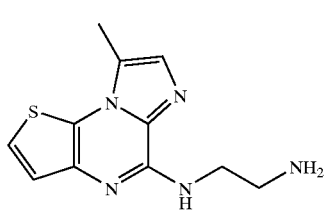
(288A)

A mixture of chloride 276Ea (1.077 g, 4.815 mmol) and ethylenediamine (70 mL) was stirred at room temperature for about 7 hours. The volatile component was removed in vacuo and the resulting semi-solid crude material was submitted to the formylation step below with out purification. (ESI) m/z (M+H)+=248.23

Step B:

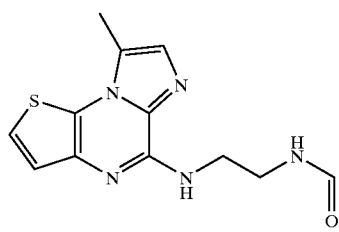
(288B)

Propylformate (22 mL) and Et$_3$N (800 uL, 5.740 mmol) were added into amine 288A, and the reaction mixture was heated at 80° C. for 19.5 h. It was allowed to cool to room temperature, silica gel was added and the volatile component was removed in vacuo. The resultant mesh was submitted to flash chromatography (5% MeOH/CHCl$_3$) to afford formamide 288B as a dense dark solid containing noticeable amount of impurity (1.296 g). The material was submitted to the bromination step without further purification. $^1$H NMR: 8.14 (br m, 1H), 8.04 (d, J=1.2, 1H), 7.53 (d, J=5.5, 1H), 7.39 (br t, J=5.6, 1H), 7.36 (d, J=1.0, 1H), 7.26 (d, J=5.5, 1H), 3.57 (m, 2H), 3.40 (m, 2H), 2.69 (s, 3H). (ESI) m/z (M+H)+=276.23.

Step C:

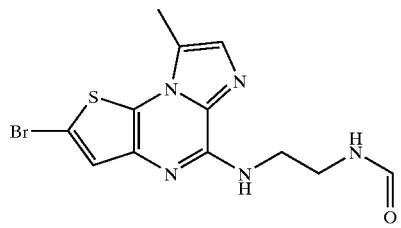

(288C)

NBS (864.7 mg, 4.858 mmol) was added in batches over a few min to a cooled (0° C.) THF (100 mL) suspension of impure formamide 288B, and the reaction mixture was stirred for 23 h by allowing the bath to thaw to 13° C. It was cooled back to 0° C. and two batches of NBS (157.0 mg & 291.3 mg; 2.51 mmol) were added 9 h apart, and the reaction mixture was stirred overnight while allowing the bath to thaw to 15° C. The volatile component was removed in vacuo, and a silica gel mesh was prepared and submitted to flash chromatography (0–3% MeOH/CHCl$_3$) to afford bromide 288C as a light yellow solid (1.149 g, 67.4% combined yield for 3 steps). $^1$H NMR: 8.12 (br m, 1H), 8.04 (d, J=1.5, 1H), 7.54 (br t, J=5.6, 1H), 7.47 (s, 1H), 7.36 (d, J=0.9, 1H), 3.54 (m, 2H), 3.38 (m, 2H), 2.63 (s, 3H). (ESI) m/z (M+H)$^+$=354.10/356.10.

Step D:

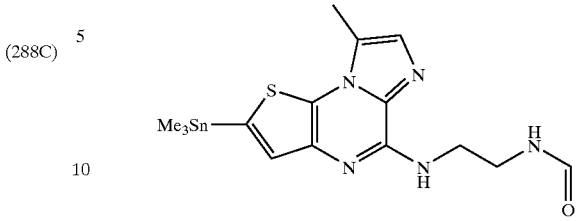

(288D)

The stannylation of 288C (1.145 g, 3.232 mmol) was set-up according to the procedure described for compound 69A with the exception that the solvent was increased by 220%. After the reaction is over, heating was stopped and a few minutes later the mixture was filtered through a filter-paper, and the filterate was evaporated in vacuo. The resultant bi-phasic oil was treated with diethyl ether (25 mL), shaken briefly, and the ether layer was decanted and allowed to stand at room temperature. The precipitate was filtered and washed with ether; stannane 288D was obtained as and ash colored solid containing substantial impurity. The impurity is Me$_3$SnX origin as is apparent from $^1$H NMR analysis. The impure sample was used for the coupling step without further purification. (ESI) m/z (M+H)$^+$=440.15.

Step E:

Examples 288–297, having formula shown above where R is described in Table 23, were prepared from stannane 288D and the appropriate arylbromides or iodides (see, e.g. Preparations 1–75 or commercially available compounds) according to the coupling procedure described for Example 177. The resultant product was purified with flash chromatography, Prep-HPLC and/or recrystalization and was obtained as a free-base or TFA salt.

TABLE 23

| Ex. # | R | (M + H)$^+$ | Other Data ($^1$H NMR) |
|---|---|---|---|
| 288 | 3,5-difluorophenyl | 388.10 | |
| 289 | 3-cyanophenyl | 377.16 | |

TABLE 23-continued
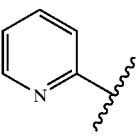
| Ex. # | R | (M + H)+ | Other Data (¹H NMR) |
|---|---|---|---|
| 290 | 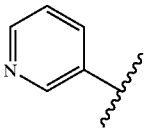 | 353.14 | |
| 291 | 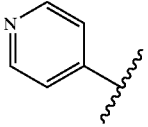 | 353.15 | |
| 292 | 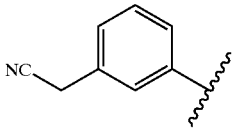 | 353.15 | |
| 293 | 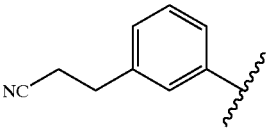 | 391.21 | |
| 294 | 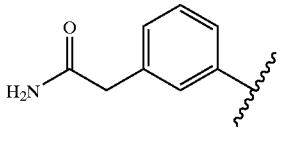 | 405.24 | |
| 295 | 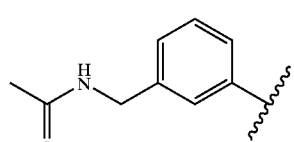 | 409.25 | (Free base; 400 MHZ): 8.14 (br m, 1H), 8.06 (d, J=1.8, 1H), 7.72 (s, 1H), 7.67 (app d, J=7.1, 1H), 7.63 (br s, 1H), 7.53 (br s, 1H), 7.48 (app t, J=5.9, 1H), 7.40–7.36 (m, 2H), 7.24 (d, J=7.6, 1H), 6.93 (br s, 1H), 3.59 (m, 2H), 3.44 (s, 2H), 3.42 (m, 2H), 2.74 (d, J=0.7, 3H). |
| 296 | 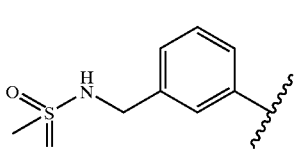 | 423.22 | |
| 297 |  | 459.23 | |

EXAMPLE 298

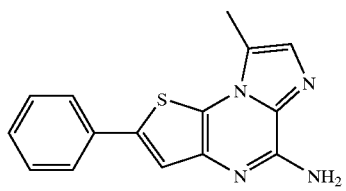

Step A:

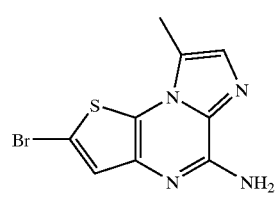

(298A)

NBS (284 mg, 1.596 mmol) was added in one batch to a cooled (0° C.) CHCl₃ (13.0 mL) suspension of amine 276D (285 mg, 1.396 mmol), and the reaction mixture was stirred for 19 h while allowing the bath to thaw to room temperature. Two batches of NBS (54.5 mg, 57.4 mg; 0.629 mmol) were added 6 h apart, and the reaction mixture was stirred for an additional 1 h. The volatile component was removed in vacuo, and water (10 mL) was added to the residue and vigorously stirred for 30 min. The solid was filtered and washed with copious water. After it was briefly dried, a silica gel mesh was prepared and submitted to flash chromatography (EtOAc) to afford bromide 298A as a light yellow solid (159.9 mg, 40.5%). ¹H NMR: 7.40 (s, 1H), 7.37 (d, J=0.9, 1H), 6.96 (br s, 2H), 3.32 (s, 3H). (ESI) m/z (M+H)⁺= 283.02/285.02.

Step B:

LiCl (39.8 mg, 0.918 mmol) and Pd(Ph₃P)₄ (10.6 mg, 0.009 mmol) were sequentially added into a mixture of bromide 298A (74 mg, 0.261 mmol), trimethyl(phenyl)tin (201.7 mg, 0.837 mmol) and 1,4-dioxane (3.0 mL). The reaction mixture was flushed with N₂ and heated at 90° C. for 77 h. After it was allowed to cool to room temperature, the volatile component was removed in vacuo. A silica gel mesh was prepared from the residue and submitted to flash chromtagraphy (0–5% MeOH/EtOAc) to afford a solid, which was carefully washed with a few ml of McOH to remove colored residues. Example 298 was retrieved as a dull-yellow solid (46.9 mg, 64%). ¹H NMR: 7.76 (d, J=7.3, 2H), 7.65 (s, 1H), 7.46 (app t, J=7.8, 2H), 7.39 (d, J=0.6, 1H), 7.36 (app t, J=7.3, 1H), 6.90 (br s, 2H), 2.74 (s, 3H). (ESI) m/z (M+H)⁺=281.11.

EXAMPLE 299–302

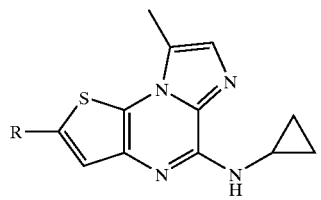

Step A:

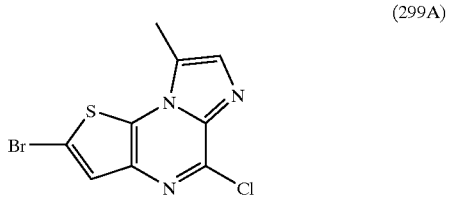

(299A)

NBS (82.1 mg, 0.461 mmol) was added in one batch to a THF (3.0 mL) solution of chloride 276Ea (52.7 mg, 0.2356 mmol) and the reaction mixture was stirred in a diffused light for about 21 h. Silica gel was added and the volatile component was removed in vacuo, and the resulting silica gel mesh was submitted to flash chromatography (40% EtOAc/hexanes) to isolate bromochloride 299, contaminated with chloride 276Ea, as an orange solid (52.5 mg, ~73%). ¹H NMR (400 MHZ): 7.86 (s, 1H), 7.73 (s, 1H), 2.76 (S, 3H). (ESI) m/z (M+H)⁺=303.89.

Step B:

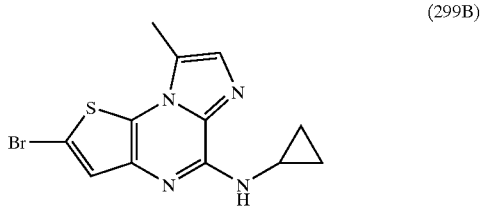

(299B)

A cyclopropyl amine (5.0 mL) suspension of bromochloride 299A (120 mg, 0.397 mmol) was refluxed for 16 hours. The reaction mixture was cooled to room temperature and the volatile component was removed in vacuo. A silica gel mesh was prepared and submitted to flash chromatography to afford bromide 299B as a light yellow solid (102 mg, 79.6%). ¹H NMR: 7.63 (d, J=3.7, 1H), 7.52 (s, 1H), 7.34 (d, J=0.9, 1H), 2.93 (m, 1H), 2.64 (s, 3H), 0.74–0.64 (m, 4H). (ESI) m/z (M+H)⁺=323.06/325.06.

Step C:

Examples 299–302, having formula shown above where R is described in Table 24, were prepared from stannane 299B and the appropriate arylhalide (see, e.g. Preparations 1–75) according to the coupling procedure described for the synthesis of Example 177.

TABLE 24

| Ex. # | R | (M + H)+ | Other Data (¹H NMR) |
|---|---|---|---|
| 299 | *m-acetamidomethyl-phenyl* | 392.17 | (TFA salt; 400 MHZ): 8.42 (br t, J= 5.9, 1H), 7.79 (s, 1H), 7.69 (d, J= 7.9, 1H), 7.64 (s, 1H), 7.43 (app t, J= 7.7, 1H), 7.27 (d, J=7.2, 1H), 4.33 (d, J=6.1, 2H), 2.94 (m, 1H), 2.76 (s, 3H), 1.91 (s, 3H), 0.86 (m, 2H), 0.77 (m, 2H). |
| 300 | *2-fluoro-5-acetamidomethyl-phenyl* | 410.14 | |
| 301 | *m-methanesulfonamidomethyl-phenyl* | 428.19 | |
| 302 | *2-fluoro-5-methanesulfonamidomethyl-phenyl* | 446.16 | |

EXAMPLE 303

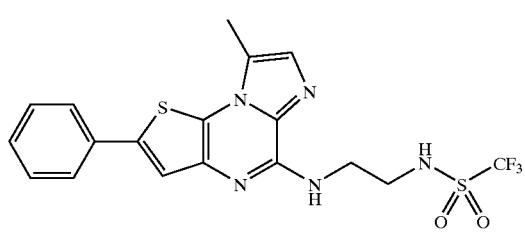

Trifluoromethanesulfonyl chloride (1 mL of 0.093 M in THF, 0.093 mmol) was added drop-wise to a cooled, −40° C., mixture of Example 5 (30.2 mg, 0.0934 mmol, free-base form) and triethylamine (13 μL, 0.093 mmol) in THF (1 mL). The reaction mixture was allowed to warm up to room temeprature over 16 h. The volatile component was removed in vacuo and the residue was purified by prep-HPLC to afford the TFA salt of Example 303 as an off-white solid (28.5 mg).

EXAMPLE 304

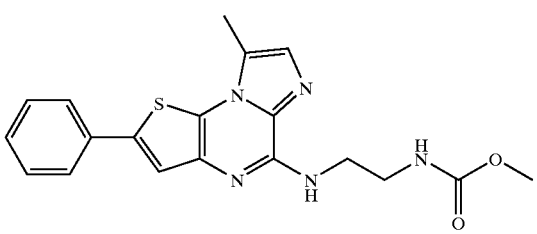

Methyl chloroformate (1.0 mL of 0.124 M in THF, 0.124 mmol) was added to a cooled (0° C.) mixture of Example 5 (39.6 mg, 0.122 mmol; free-base form) and triethylamine (17 μL, 0.122 mmol) in THF (1 mL). The reaction mixture was allowed to warm up to room temperature over 8 h. All the volatile component was removed in vacuo and the residue was purified by prep-HPLC to afford the TFA salt of Example 304 as an off-white solid (25.8 mg).

EXAMPLE 305

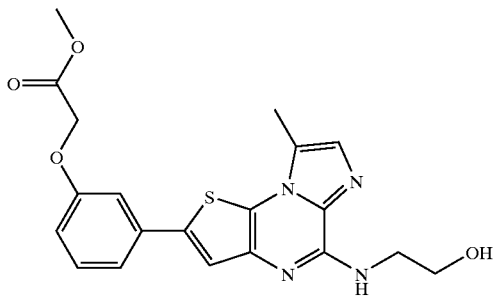

Step A:

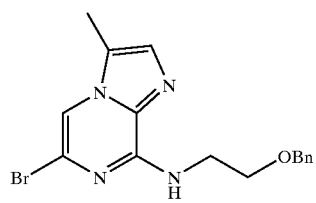

(305A)

Preparation 79 (460 mg, 3.04 mmol) was added into a THF (5 ml) solution of chloride from Example 1, Step 1D (500 mg, 2.03 mmol) and triethyl amine (1.35 ml, 9.69 mmol) in a pressure tube. The reaction mixture was stirred at 65° C. for 21 h. The reaction mixture was cooled to rt and solvent was removed in vacuo. The residue was dissolved in ethyl acetate and washed with water. The organic layer was washed with brine, dried (MgSO$_4$), filtered and evaporated in vacuo. The crude material was submitted to flash chromatography (ethyl acetate/hexane=50/50) to afford pale yellow solid (500 mg, 68%). $^1$H NMR (DMSO, 400MHZ): 7.80 (s, 1H), 7.76 (s, 1H), 7.28 (m, 6H), 4.52 (s, 2H), 3.65 (s, 4H), 2.39 (d, J=0.6, 3H). (ESI) m/z (M+H)$^+$=363.18.

Step B:

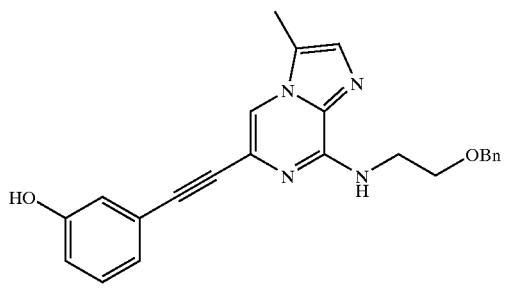

(305B)

A mixture of Pd(PPh$_3$)$_4$ (65 mg, 0.056 mmol) and CuI (10.7mg, 0.056 mmol) was added to a pressure tube containing a DMF (5 ml) solution of bromide 305A (100 mg, 0.28 mmol), 3-ethynyl-phenol (82 mg, 0.69 mmol), and TEA (0.16 ml, 1.12 mmol). The reaction flask was flushed with nitrogen, capped, and heated at 66° C. for 19 h. The reaction mixture was then allowed to cool to rt and the precipitate was filtered. The filtrate was exposed to vacuum to remove the DMF and the other volatile components. A silica gel mesh was prepared from the residue and submitted to flash chromatography (50–90%EtOAc/hexanes) to afford alkyne 305B as a yellow foam (97 mg, 87%). $^1$H NMR (MeOH, 400 MHZ): 7.17 (b, 8H), 6.96 (d, J=7.0, 2H), 6.79 (t, J=4.5, 1H), 4.89 (s, 2H), 3.71 (d, J=3.6, 2H), 3.68 (d, J=3.6, 2H), 2.31 (s, 3H). (ESI) m/z (M+H)$^+$=399.12.

Step C:

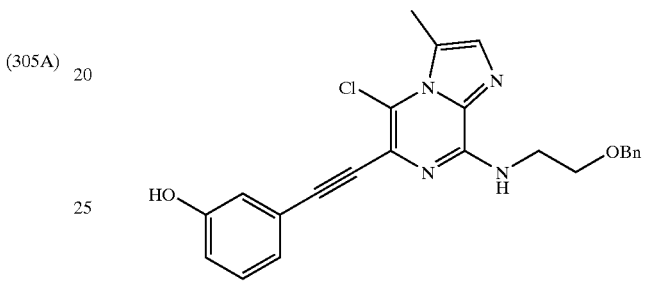

(305C)

N-Chlorosuccinimide (32 mg, 0.24 mmol) was added to a THF (2.5 ml) solution of alkyne 305B (96 mg, 0.24 mmol), and the resulting reaction mixture was heated with an oil bath (50° C.) for 21 h. The solvent was removed in vacuo, and the residue was dissolved in EtOAc and washed with water (2×) and brine. The organic layer was dried (MgSO$_4$), filtered, and evaporated in vacuo. The crude material was submitted to flash chromatography (the sample was loaded onto column with the chloroform solvent; 30% EtOAc/hexanes) to afford a clean chloride 305C (66 mg, 63%). $^1$H NMR (MeOH, 400 MHZ): 7.22 (m, 7H), 6.98 (m, 2H), 6.80 (m, 1H), 4.53 (s, 2H), 3.70 (s, 4H), 2.69 (d, J=0.64, 3H). (ESI) m/z (M+H)$^+$=433.02.

Step D:

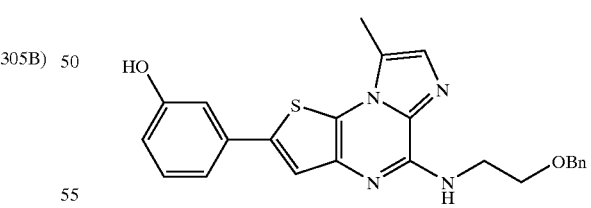

(305D)

DMF (1.5 ml) was added to a mixture of chloroalkyne 305C (66 mg, 0.15 mmol) and Na$_2$S.9H$_2$O (110 mg, 0.46 mmol; the solid was crushed with mortar and pestle; 99.99% pure). The resulting heterogeneous reaction mixture was heated for 1 hr with an oil bath pre-equilibrated at 100° C. The reaction mixture was allowed to cool to rt and the volatile component removed in vacuo. A silica gel mesh of the residue was prepared and submitted to flash chromatography (50% EtOAc/hexanes) to afford amine 305D as a light yellow solid (40 mg, 62%). $^1$H NMR (MeOH, 400 MHZ): 7.19 (m, 8H), 6.95 (m, 2H), 6.68 (d, J=9.32, 1H), 4.54 (s, 2H), 3.71 (m, 2H), 3.65 (m, 2H), 2.51 (d, J=0.72, 3H). (ESI) m/z (M+H)$^+$= 431.08.

Step E:

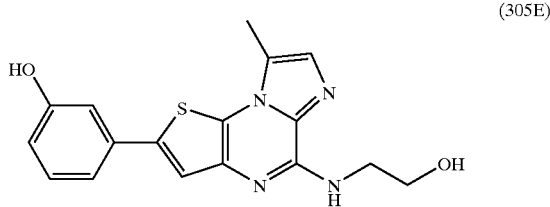

(305E)

Boron trifluoride-methyl sulfide complex (4.3 ml, 40.5 mmol) was added drop wise to a CH$_2$Cl$_2$ (100 ml) solution of amine 171D (2.18 g, 5.06 mmol) at −78° C. The reaction mixture was allowed to rise to rt and stirred for 4 h. The solvent was removed in vacuo. The residue was dissolved in ethyl acetate and washed with PH=7 buffer solution. Sodium bicarbonate was used to neutralize the solution. The organic layer was washed with brine, dried (MgSO$_4$), filtered and evaporated in vacuo. A silica gel mesh of the residue was prepared and submitted to flash chromatography (90% EtOAc/hexanes) to afford ester 305E as a white solid (910 mg, 53%). $^1$H NMR (MeOH, 400 MHZ): 7.50 (d, J=4.1, 2H), 7.27 (t, J=7.8, 1H), 6.68 (m, 1H), 7.11 (t, J=2.0, 1H), 6.82 (m, 1H), 3.89 (t, J=5.2, 2H), 3.77 (t, J=5.2, 2H), 2.80(d, J=0.68, 3H). (ESI) m/z (M+H)$^+$=341.10.

Step F:

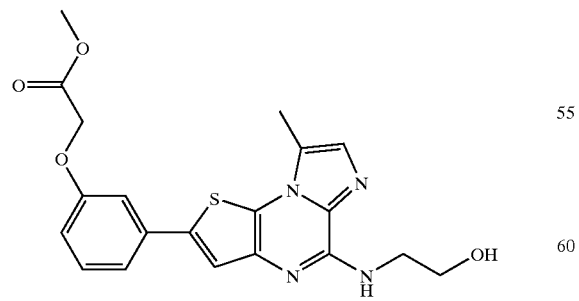

(305F)

DMF (12 ml) was added to a mixture of bromo-acetic acid methyl ester (83 ul, 0.882 mmol), potassium carbonate (325 mg, 2.35 mmol) and phenol 171E (200 mg, 0.588 mmol). The resulting heterogeneous reaction mixture was stirred for 20 h at rt. The solvent was removed in vacuo. The residue was dissolved in ethyl acetate and washed with PH=7 buffer solution. The organic layer was washed with brine, dried (MgSO$_4$), filtered and evaporated in vacuo. A silica gel mesh of the residue was prepared and submitted to flash chromatography (30–80% EtOAc/hexanes) to afford ester 305F as a white solid (188 mg, 77%). $^1$H NMR (MeOH, 500 MHZ): 7.46 (d, J=5.8, 2H), 7.33 (t, J=8.0, 1H), 7.26 (m, 1H), 7.19 (t, J=2.1, 1H), 6.91 (m, 1H), 4.86 (s, 2H), 3.89 (t, J=5.3, 2H), 3.81 (s, 3H), 3.76 (t, J=5.3,2H), 2.74 (d, J=0.6, 3H). (ESI) m/z (M+H)$^+$=413.04.

EXAMPLE 306

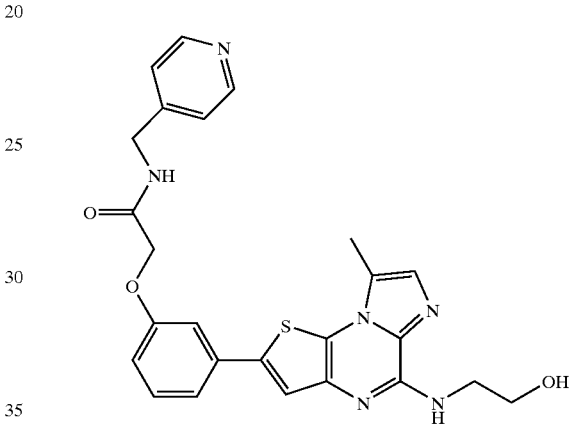

THF (1 ml) was added to a mixture of ester 305F (18.9 mg, 0.0458 mmol) and C-Pyridin-4-yl-methylamine (13 mg, 0.137 mmol). After replaced with nitrogen, AlMe$_3$ (69 ul, 0.137 mmol) was added slowly. Large amount of gas was produced. The reaction mixture was stirred for 20 h at rt. 1N HCl was added to neutralize the solution. Small amount of 1N HaOH was used to adjust to PH=8. Solvent was removed in vacuo. Prep HPLC was used to purify the residue to obtain white solid (9.3 mg, 43%). $^1$H NMR (MeOH, 400 MHZ): 8.66 (d, J=7.4, 2H), 8.31 (d, J=7.4, 2H), 7.58 (s, 1H), 7.52 (d, J=0.88, 1H), 7.37 (m, 3H), 7.07 (m, 1H), 4.91 (s, 2H), 3.90 (t, J=5.3, 2H), 3.79 (t, J=5.3, 2H), 2.79 (t, J=3.4, 3H). (ESI) m/z (M+H)$^+$=489.11.

EXAMPLES 307–347

The compounds shown below in Table 25 were synthesized using the methods described in Example 306 and commercially available amines.

TABLE 25
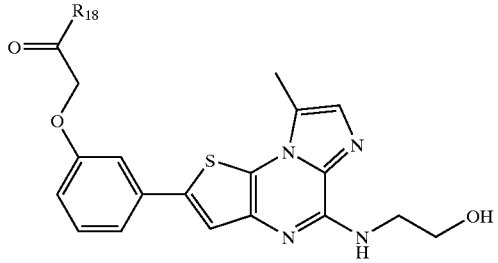
| Ex. # | R$_{18}$ | (M + H)$^+$ | $^1$H NMR (MeOH, 400 MHZ) |
|---|---|---|---|
| 307 | 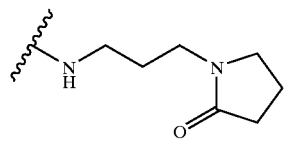 | 523.19 | |
| 308 | 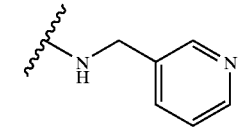 | 489.17 | |
| 309 | 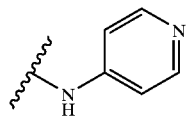 | 475.16 | |
| 310 | 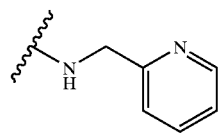 | 489.17 | (TFA salt): 8.62 (d, J=5.0, 1H), 8.16 (t, J=3.9, 1H), 7.65 (m, 2H), 7.58 (s, 1H), 7.52 (d, J=0.84, 1H), 7.39 (m, 3H), 7.06 (m, 1H), 4.73 (s, 4H), 3.90 (t, J=5.3, 2H), 3.79 (t, J=5.3, 2H), 2.81 (s, 3H) |
| 311 | 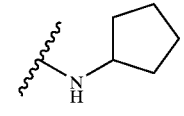 | 466.07 | |
| 312 | 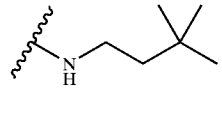 | 482.11 | (TFA salt): 8.18 (b, 1H), 7.48 (t, J=3.8, 2H), 7.36 (m, 3H), 6.98 (m, 1H), 4.54 (s, 2H), 3.89 (t, J=5.4, 2H), 3.77 (t, J=5.4, 2H), 2.76 (d, J=0.68, 3H), 1.47 (t, J=8.3, 4H), 0.93 (d, J=8.5, 9H) |
| 313 | 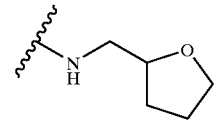 | 482.19 | |
| 314 | 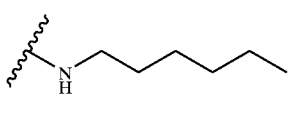 | 482.12 | |
| 315 | 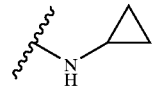 | 438.06 | |

TABLE 25-continued
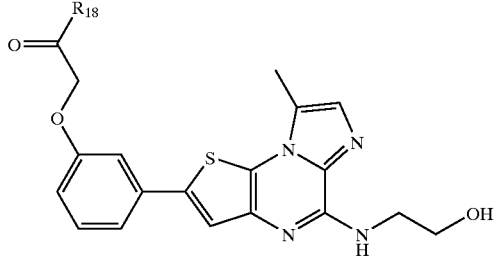
| Ex. # | R<sub>18</sub> | (M + H)⁺ ¹H NMR (MeOH, 400 MHZ) |
|---|---|---|
| 316 | 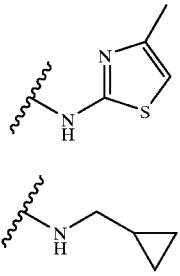 | 495.04 |
| 317 | 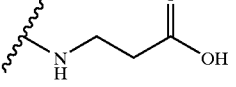 | 452.07 |
| 318 | 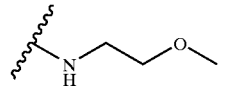 | 470.05 |
| 319 | 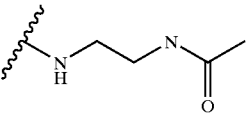 | 456.06 |
| 320 | 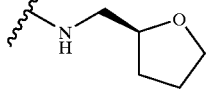 | 483.25 |
| 321 | 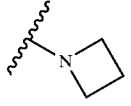 | 482.19 |
| 322 | 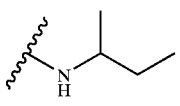 | 438.19 |
| 323 | 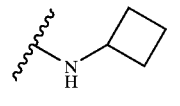 | 454.06 |
| 324 | 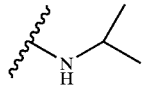 | 452.06 |
| 325 | | 440.08 |

US 6,933,294 B2
167 168
TABLE 25-continued
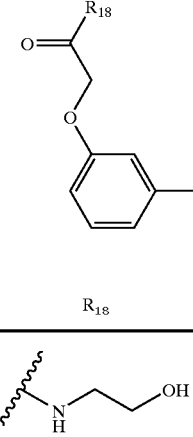
| Ex. # | R$_{18}$ | (M + H)$^+$ | $^1$H NMR (MeOH, 400 MHZ) |
|---|---|---|---|
| 326 | 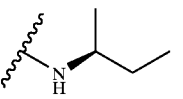 | 442.04 | |
| 327 | 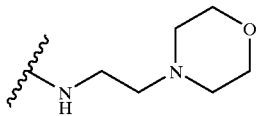 | 454.06 | |
| 328 | 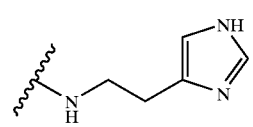 | 511.09 | (TFA salt): 7.58 (s, 1H), 7.53 (d, J=0.8, 1H), 7.34 (m, 3H), 7.04 (m, 1H), 4.64 (s, 2H), 4.04 (b, 2H), 3.98 (m, 2H), 3.92 (t, J=5.3, 2H), 3.80 (t, J=5.3, 3H), 3.72 (b, 6H), 3.10 (m, 2H), 3.79 (d, J=0.68, 3H) |
| 329 | 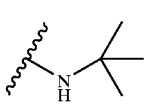 | 492.08 | |
| 330 | 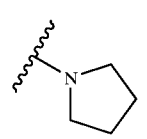 | 454.06 | |
| 331 | 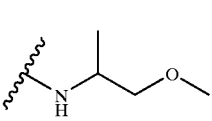 | 452.06 | |
| 332 | 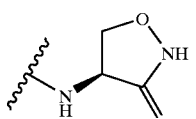 | 470.08 | |
| 333 | 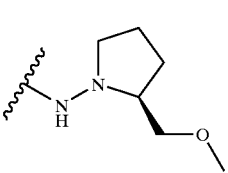 | 483.02 | |
| 334 | | 511.29 | |

TABLE 25-continued
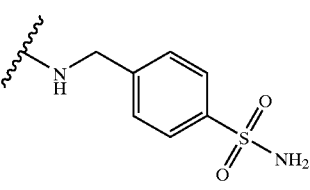
| Ex. # | R18 | (M + H)+ | 1H NMR (MeOH, 400 MHZ) |
|---|---|---|---|
| 335 | 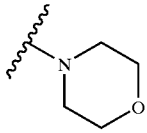 | 567.15 | |
| 336 | 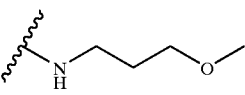 | 468.06 | |
| 337 |  | 470.05 | |
| 338 | 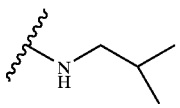 | 470.07 | |
| 339 | 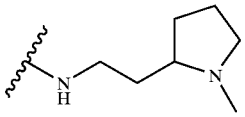 | 454.07 | |
| 340 | 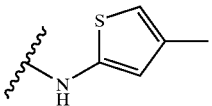 | 509.10 | |
| 341 | 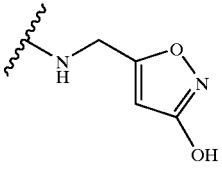 | 494.98 | |
| 342 | 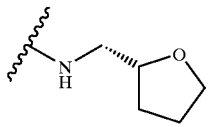 | 494.98 | |
| 343 | | 482.02 | |

TABLE 25-continued

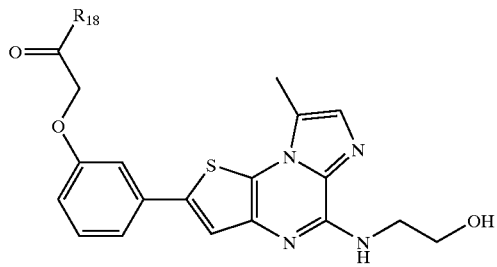

| Ex. # | R$_{18}$ | (M + H)$^+$ | $^1$H NMR (MeOH, 400 MHZ) |
|---|---|---|---|
| 344 | | 510.06 | |
| 345 | | 469.18 | |
| 346 | | 466.99 | |
| 347 | | 483.03 | |

EXAMPLE 348

Step A:

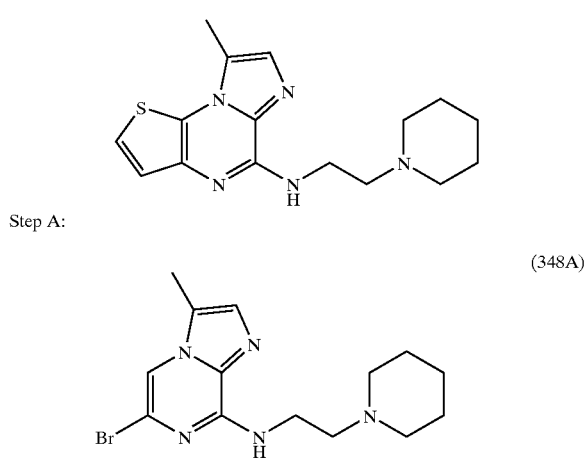
(348A)

Example 1D (5.00 g, 20.28 mmol) was added to a THF (37.0 ml) solution of 1-(2-aminoethyl) piperidine (3.01 g, 23.50 mmol) and triethylamine (6.0 ml, 39.22 mmol). The reaction mixture was heated with an oil bath (~65° C.) for 17 h, cooled to room temperature and the precipitate was filtered. Silica gel was added to the filtrate and evaporated in vacuo. The resulting silica gel mesh was submitted to flash chromatography (50–70% EtOAc/hexane) to afford bromide compound 348A as an off-white solid (6.17 g, 90% yield). m/z (M+H)$^+$=339.

Step B:

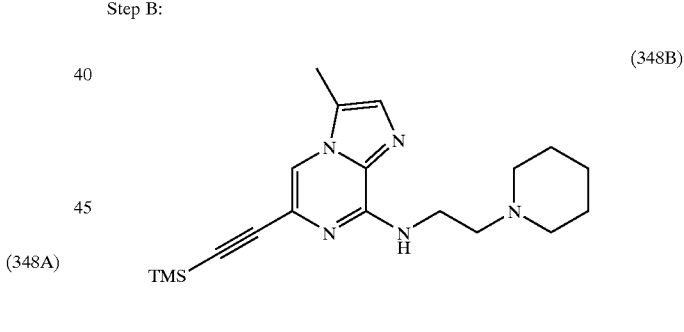
(348B)

A mixture of Pd(Ph$_3$P)$_4$ (0.94 g, 0.8112 mmol) and CuI (0.31g, 1.622 mmol) was added to a pressure tube containing a DMF (50 ml) solution of bromide 348A (6.86 g, 20.28 mmol), (trimethylsilyl)acetylene (6.49 ml, 45.63 mmol) and triethylamine (11.31 ml, 81.12 mmol). The reaction flask was flushed with nitrogen, capped and heated at 64° C. for ~3 h. The reaction mixture was then allowed cooling to room temperature and the precipitate was filtered. The filtrate was exposed to vacuum to remove the DMF and other volatile components. The residue was washed with ether. A silica gel mesh was prepared from the residue and submitted to flash chromatography (50–80% EtOAc/hexane) to afford alkyne 348B as a yellow foam (5.90 g, 82% yield). m/z (M+H)$^+$= 356

Step C:

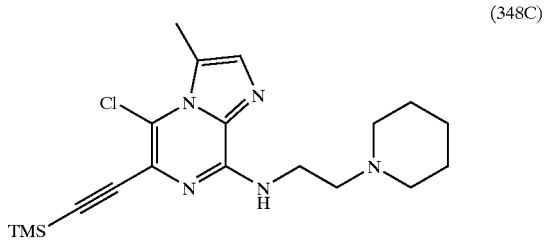
(348C)

N-Chlorosuccinimide (2.45 g, 18.39 mmol) was added to a THF (80 ml) solution of alkyne 348B (5.44 g, 15.32), and the resulting reaction mixture was heated with an oil bath (~60° C.) for 8 h. The solvent was removed in vacuo, and the residue was dissolved in $CH_2Cl_2$ and washed with water (2×) and brine. The organic layer was dried ($MgSO_4$), filtered and evaporated in vacuo. The crude material was submitted to flash chromatography (90% $CHCl_3$/MeOH) to afford a clean chloride 348C (4.78 g, 80% yield) m/z $(M+H)^+=391$.

Step D:

DMF (18.0 ml) was added to a mixture of chloroalkyne 348C (1.00 g, 2.56 mmol) and $Na_2S.9H_2O$ (1.93 g, 8.03 mmol); the solid was crushed with mortar and pestle; 99.99% pure), and the resulting heterogeneous reaction mixture was heated for 1 hour with an oil bath pre-equilibrated at 100° C. The reaction mixture was allowed to cool to room temperature and all the volatile component was removed in vacuo. A silica gel mesh of the residue was prepared and submitted to flash chromatography (50~100% EtOAc/hexane) to afford the title compound as a light yellow solid (0.36 g, ~45%). m/z $(M+H)^+=316$.

EXAMPLE 349

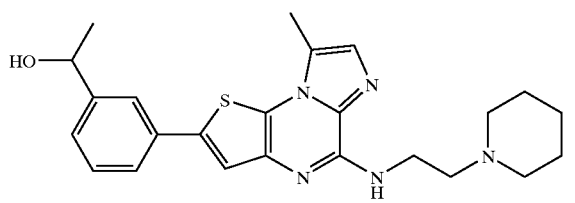

Step A:

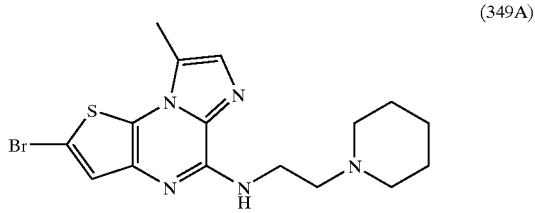
(349A)

N-Bromosuccinimide (373 mg, 2.10 mmol) was added in batches over 3 min to a cooled (ice-water) THF (12.0 ml) semi-solution of amine 348D (617 mg, 1.96 mmol). The reaction mixture was stirred for 17 h while allowing the bath to thaw. After removing the solvent in vacuo, the resultant solid residue was dissolved in $CHCl_3$ (pre-washed with $NaHCO_3$ solution) and washed with water (3×) and brine. It was dried ($MgSO_4$), filtered and evaporated in vacuo. A silica gel mesh of the crude material was prepared and submitted to flash chromatography (50–100% EtOAc/hexane) to afford bromide 349A as an off-white fluffy solid (618 mg, ~80% yield). m/z $(M+H)^+=394/396$.

Step B:

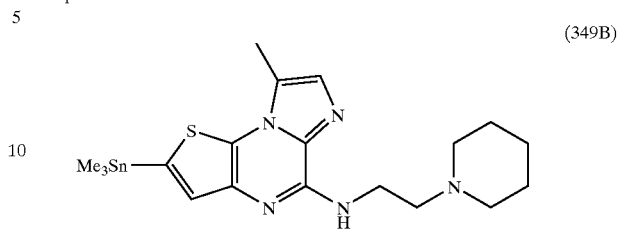
(349B)

A toluene (10 ml) solution of hexamethylditin (1.149 g, 3.51 mmol) was treated with bromide 349A (378 mg, 0.959 mmol) and triethylamine (0.27 mL, 1.919 mmol). After nitrogen was bubbled through the mixture for 5 min, $Pd(Ph_3P)_4$ (38.0 mg, 0.033 mmol) was added. The reaction mixture was heated with a 100° C. oil bath for 35 min. The dark reaction mixture was cooled to room temperature, filtered through a pad of Celite, washed with EtOAc, and the filtrate was evaporated in vacuo. The residue was triturated with ether, and the light brown solid was filtered and washed with copious ether and dried in vacuo (344 mg of stannane 349B was retrieved). LC/MS analysis of the sample indicated that it contains minor impurities including amine 348D. m/z $(M+H)^+=479$.

Step C:

Stannane 349B (54.4 mg, ~0.1138 mmol), 3-bromo-alpha-methylbenzyl alcohol (45.7 mg, 0.2276 mmol), $PdCl_2(Ph_3P)_2$ (7.99 mg, 0.0114 mmol), KF (15.1 mg, 0.2603 mmol) and DMF (2.0 ml) were sequentially added into a vial. Nitrogen was bubbled through the heterogeneous reaction mixture for about a minute, and it was lowered into a 90° C. oil bath and heated for at least 6 h. When the stannane is completely consumed, the DMF was removed in vacuo, and the crude material was purified with a PREP HPLC to afford the title compound (125 mg, 60%). m/z $(M+H)^+=436$.

EXAMPLE 350

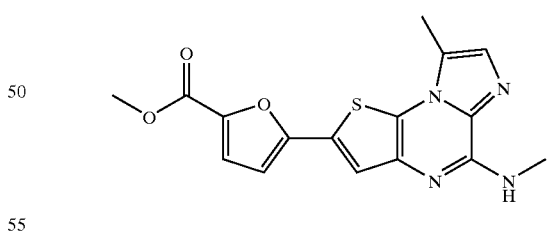

Stannane 108A (160 mg, ~0.4199 mmol), methyl 5-bromo-2-furoate (258.3 mg, 1.2598 mmol), $PdCl_2(Ph_3P)_2$ (28.9 mg, 0.0412 mmol), KF (50.6 mg, 0.8704 mmol) and DMF (5.2 mL) were sequentially added into a vial. Nitrogen was bubbled through the heterogeneous reaction mixture for about a minute, and it was lowered into a 90° C. oil bath and heated for at least 6 h. When the stannane is completely consumed, the mixture was filtered, washed with DMF and the resultant title product was purified with PREP-HPLC (86 mg, 60%). m/z $(M+H)^+=343.1$.

EXAMPLE 351

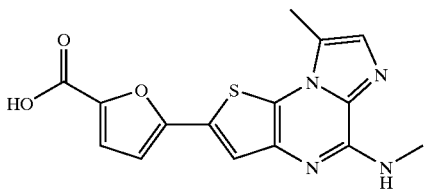

Example 350 (25 mg, 0.0731 mmol) was treated with 1N NaOH (0.73 ml, 0.731 mmol). The reaction mixture was put in a sonicator for 1 hr and the resultant title product was purified with PREP-HPLC (25 mg, 78%). m/z (M+H)$^+$=329.

EXAMPLE 352

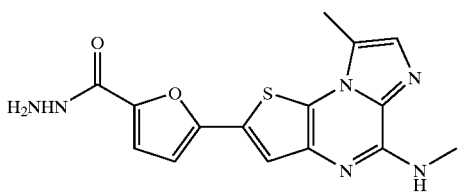

The mixture of Example 350 (20 mg, 0.058 mmol) and hydrazine (18.6 mg, 0.58 mmol) in EtOH (1.0 ml)/DMSO (1.0 ml) was heated in an oil bath at 90° C. for 2 h. The resultant title product was purified with PREP-HPLC. Yield is 15 mg, 76%. m/z (M+H)$^+$=343.

EXAMPLE 353

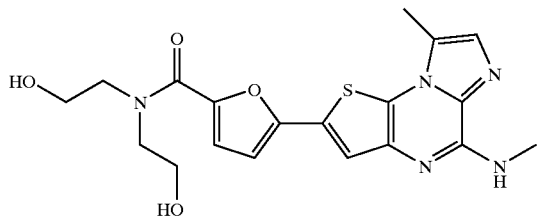

The mixture of Example 350 (20 mg, 0.058 mmol) and diethanolamine (60.9 mg, 0.58 mmol) in EtOH (1.0 ml)/DMSO (1.0 ml) was heated in an oil bath at 90° C. overnight. The resultant title product was purified with PREP-HPLC. Yield is 17 mg, 70%. m/z (M+H)$^+$=416.

EXAMPLE 354

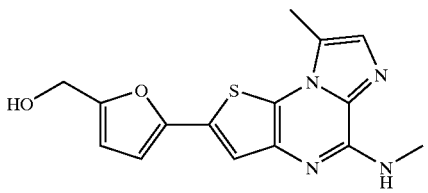

Stannane 108A (80 mg, ~0.210 mmol), 5-bromo-2-furylmethylalcohol (111 mg, 0.630 mmol), PdCl$_2$(Ph$_3$P)$_2$ (14.4 mg, 0.021 mmol), KF (25.3 mg, 0.435 mmol) and DMF (3.0 ml) were sequentially added into a vial. Nitrogen was bubbled through the heterogeneous reaction mixture for about a minute, and it was lowered into a 90° C. oil bath and heated for 16 h. When the stannane is completely consumed, the mixture was filtered, washed with DMF and the resultant title product was purified with PREP-HPLC. Yield is 42.8 mg, 65%. m/z (M+H)$^+$=315.

EXAMPLE 355

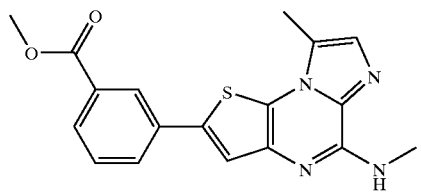

Stannane 108A (160 mg, ~0.4199 mmol), methyl 3-bromobenzoate (270.9 mg, 1.2598 mmol), PdCl$_2$(Ph$_3$P)$_2$ (28.9 mg, 0.0412 mmol), KF (50.6 mg, 0.8704 mmol) and DMF (5.2 ml) were sequentially added into a vial. Nitrogen was bubbled through the heterogeneous reaction mixture for about a minute, and it was lowered into a 90° C. oil bath and heated for 16 h. When the stannane is completely consumed, the mixture was filtered, washed with DMF and the filtered solid contained desired title product (purity: 90%). Yield is 118 mg, 80%. $^1$H NMR (DMSO, δ=2.50 ppm; 500 MHZ) 8.19 (m, 1H), 8.10 (app d, J=7.5, 1H), 7.92 (app d, J=7.5, 1H), 7.85 (s,1H), 7.62 (app t, J=7.5, 1H), 7.40 (m, 1H), 7.39(m, 1H), 3.91 (s, 3H), 3.00 (d, J=4, 3H), 2.74 (s, 3H). m/z (M+H)$^+$=353.1.

EXAMPLE 356

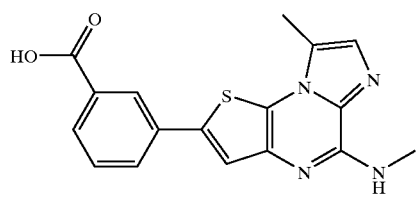

Example 355 (20 mg, 0.057 mmol) was treated with 1N NaOH (0.57 ml, 0.57 mmol). The reaction mixture was put in a sonicator for 1 hr and the resultant title product was purified with PREP-HPLC. Yield is 15.4 mg, 80%. m/z (M+H)$^+$=339.

EXAMPLE 357

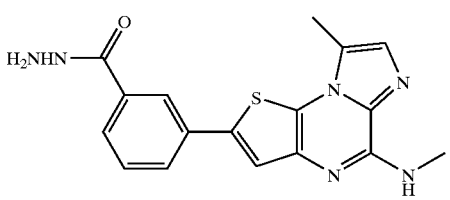

A mixture of Example 355 (20 mg, 0.057 mmol) and hydrazine (18.2 mg, 0.57 mmol) in EtOH (1.0 ml)/DMSO (1.0 ml) was heated in an oil bath at 90° C. for 2 h. The resultant title product was purified with PREP-HPLC. Yield is 15.6 mg, 78%. m/z (M+H)$^+$=353.

EXAMPLE 358

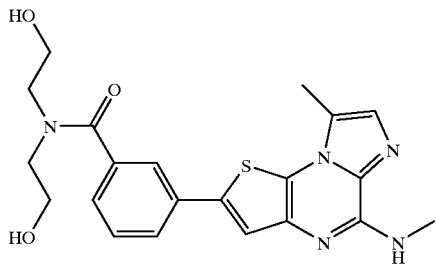

A mixture of Example 355 (20 mg, 0.057 mmol) and diethanolamine (59.9 mg, 0.57 mmol) in DMSO (2.0 ml) was heated in an oil bath at 90° C. overnight. The resultant title product was purified with PREP-HPLC. Yield is 18 mg, 75%. m/z (M+H)$^+$=426.

EXAMPLE 359

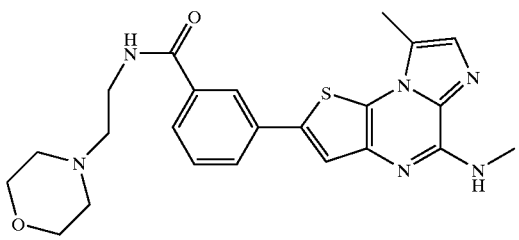

A mixture of Example 355 (20 mg, 0.057 mmol) and N-(2-aminoethyl)-morpholine (74.1 mg, 0.57 mmol) in DMSO (2.0 ml) was heated in an oil bath at 90° C. for 2 days. The resultant title product was purified with PREP-HPLC. Yield is 19 mg, 74%. $^1$H NMR (DMSO, δ=2.50 ppm; 500 MHZ): 9.00 (app t, J=5.0, 1H), 8.34 (m, 1H), 8.12 (app d, J=7.5, 1H), 7.99 (s, 1H), 7.98 (app d, J=7.5, 1H), 7.74 (app t, J=7.5, 1H), 7.71 (m, 1H), 7.53 (m, 1H), 3.33–3.90 (m, 8H), 3.22 (m, 2H), 3.04 (m, 2H), 3.14 (d, J=2.5, 3H), 2.89 (s, 3H). m/z (M+H)$^+$=451.1.

EXAMPLE 360

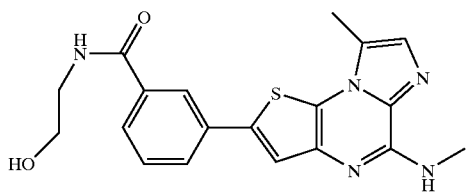

A mixture of Example 355 (20 mg, 0.057 mmol) and 2-aminoethanol (34.8 mg, 0.57 mmol) in DMSO (2.0 ml) was heated in an oil bath at 90° C. for 1 h. The resultant title product was purified with PREP-HPLC. Yield is 16.5 mg, 76%. m/z (M+H)$^+$=25 382.

EXAMPLE 361

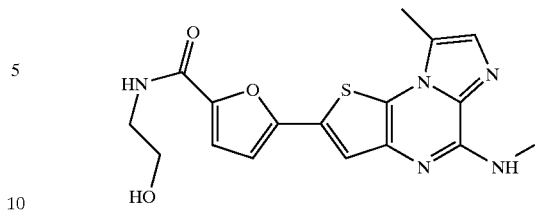

A mixture of Example 350 (20 mg, 0.058 mmol) and 2-aminoethanol (36.4 mg, 0.58 mmol) in DMSO (2.0 ml) was heated in an oil bath at 90° C. for 1 h. The resultant title product was purified with PREP-HPLC. Yield is 16.6 mg, 77%. m/z (M+H)$^+$=372.

EXAMPLE 362

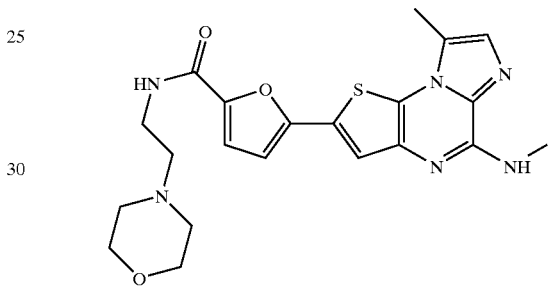

A mixture of Example 350 (20 mg, 0.058 mmol) and N-(2-aminoethyl)-morpholine (75.4 mg, 0.58 mmol) in DMSO (2.0 ml) was heated in an oil bath at 90° C. for 2 days. The resultant title product was purified with PREP-HPLC. Yield is 18.9 mg, 74%. $^1$H NMR (DMSO, δ=2.50 ppm; 500 MHZ): 8.67 (app t, J=5.5, 1H), 7.84 (s, 1H), 7.39 (s, 1H), 7.25 (d, J=4.0, 1H), 7.07 (d, J=3.5, 1H), 3.80–3.33 (m, 8H), 3.20 (m, 2H), 3.00 (m, 2H), 2.99 (m, 3H), 2.73 (s, 3H). m/z (M+H)$^+$=441.1.

EXAMPLE 363

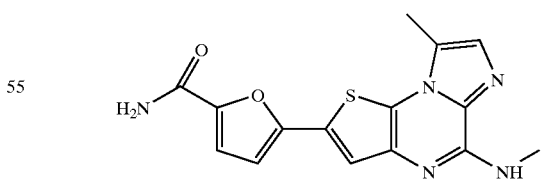

A mixture of Example 350 (20 mg, 0.058 mmol) and NH$_4$OH (~30% in H$_2$O, 4.0 ml) in DMSO (1.0 ml) was heated at 90° C. in a pressure tube for 4 h. The resultant title product was purified with PREP-HPLC. Yield is 14.6 mg, 77%. m/z (M+H)$^+$=328.

EXAMPLE 364

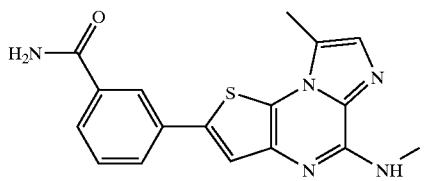

A mixture of Example 355 (20 mg, 0.057 mmol) and NH$_4$OH (~30% in H$_2$O, 4.0 ml) in DMSO (1.0 ml) was heated at 90° C. in a pressure tube for 4 h. The resultant title product was purified with PREP-HPLC. Yield is 15 mg, 78%. m/z (M+H)$^+$=338.

EXAMPLE 365

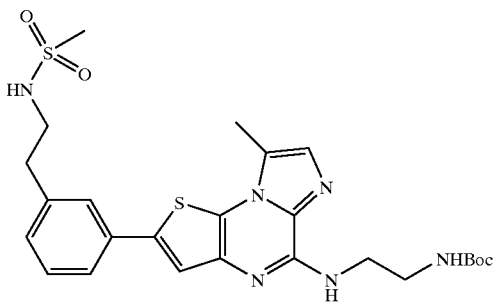

A dioxane (6.0 ml) solution of Example 69A (200 mg, 0.392 mmol) and Preparation 29 (227 mg, 0.816 mmol.) was degassed with nitrogen and treated with Pd(Ph$_3$P)$_4$ (16.9 mg, 0.0146 mmol) and LiCl (57.1 mg, 1.347 mmol). The reaction mixture was stirred at 90° C. for 4 h, cooled to room temperature, diluted with EtOAc, and evaporated onto silica gel. The resulting silica gel mesh was submitted to standard flash chromatography (60–75% EtOAc/Hexane) to isolate the title compound as a white solid (149 mg, 70%). m/z (M+H)$^+$=545.

EXAMPLE 366

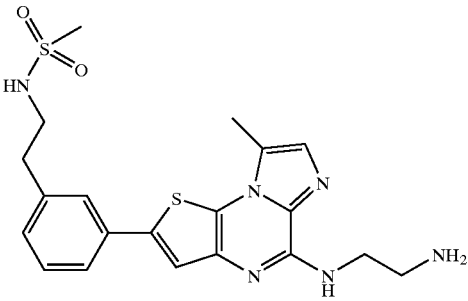

Example 365 (200 mg, 0.376 mmol) was treated with 20% TFA/CH$_2$Cl$_2$ (12 ml) in an ice bath, and then the reaction mixture was stirred at room temperature for 4 h. The volatile component was removed in vacuo, and the residue was triturated with Ether and the resulting crude solid was purified on a PREP-HPLC to afford the TFA salt of the title compound (146 mg, 90%). m/z (M+H)$^+$=445.

EXAMPLE 367

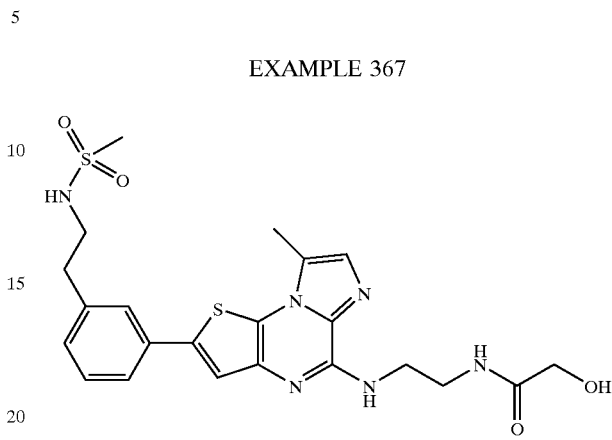

A solution of ethyl chloroformate (10.7 mg, 0.0986 mmol) in THF (1 ml) was added dropwise at −5° C. to a solution glycolic acid (6.8 mg, 0.0896 mmol) and N,N-diisopropylethylamine (12.7 mg, 0.0986 mmol) in THF (1 ml). The reaction mixture was stirred. At −5° C. for 40 min and then a solution of Example 366 (TFA salt, 50 mg, 0.0896 mmol) in THF (1 ml) was added. After stirring at 0° C. for 4 h, the reaction mixture was poured into brine. The resulting mixture was extracted with ethyl acetate twice. The combined extracts were washed with water (2×), dried over MgSO$_4$ and the solvent was evaporated. The resulting title compound was purified on a PREP-HPLC (33.7 mg, 75%). m/z (M+H)$^+$=503.

EXAMPLE 368

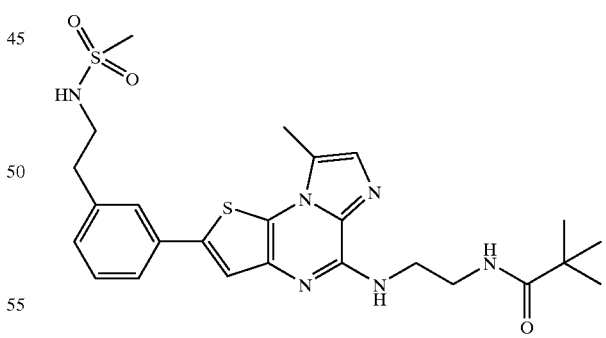

NaHCO$_3$ (15.1 mg, 0.18 mmol) was added to a mixture of Example 366 (TFA salt, 25.1 mg, 0.045 mmol) in EtOH (1 ml)/ H$_2$O (1 ml). The reaction mixture was stirred for 20 mins and then trimethylacetyl chloride (5.43 mg, 0.045 mmol)was added. The reaction mixture was heated at 60° C. overnight. The resulting crude title product was purified on a PREP-HPLC (17.6 mg, 74%). m/z (M+H)$^+$=529.

EXAMPLE 369

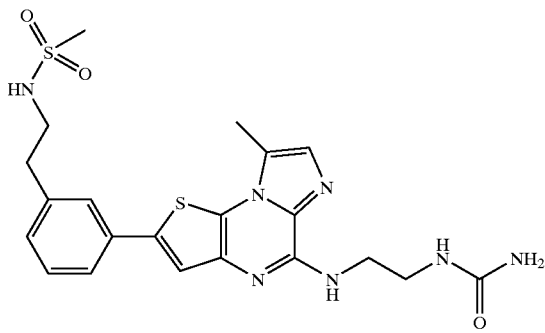

A mixture of Example 366 (TFA salt, 70 mg, 0.125 mmol) and trimethylsilyl isocyanate (85%, 51 mg, 0.0376 mmol) in THF (5.0 ml) was stirred at 65° C. in a sealed tube for 18 h. The resulting title product was purified on a PREP-HPLC (48.1 mg, 79%). m/z (M+H)$^+$=488.

EXAMPLE 370

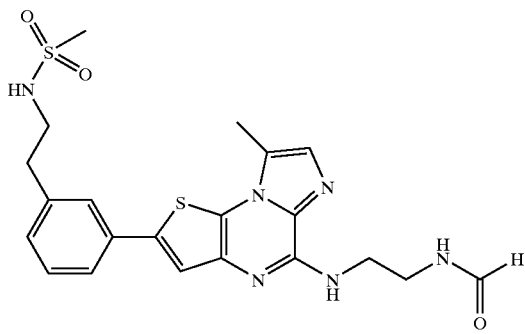

A mixture of Example 366 (100 mg, 0.225 mmol) and ethyl formate (50 mg, 0.676 mmol) in THF (5.0 ml) was stirred at 65° C. in a sealed tube for 12 h. The resulting title product was purified on a PREP-HPLC (82.8 mg, 78%). m/z (M+H)$^+$=473.

EXAMPLE 371

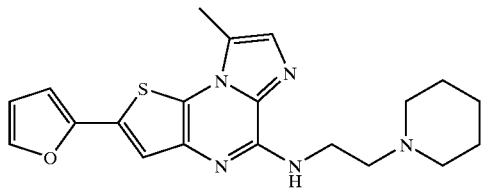

Bromide 349A (100.0 mg, ~0.254 mmol), 2-(tributylstannyl)furan (200.6 mg, 0.562 mmol), PdCl$_2$(Ph$_3$P)$_2$ (37.9 mg, 0.054 mmol), KF (57.2 mg, 0.985 mmol) and DMF (3.2 ml) were sequentially added into a vial. Nitrogen was bubbled through the heterogeneous reaction mixture for about a minute, and it was lowered into a 100° C. oil bath and heated for 16 h. DMF was removed in vacuo. Redissolved in EtOAc and washed with water, brine, dried over MgSO$_4$ and concentrated. The resultant title product (dark brown) was purified with PREP-HPLC (59 mg, 61%). $^1$H NMR (DMSO, δ=2.50 ppm; 500 MHZ) 7.79 (br t, J=5.6, 1H), 7.77 (d, J=1.5, 1H), 7.49 (s, 1H), 7.43 (m, 1H), 6.94 (d, J=3.5, 1H), 6.65 (dd, J 3.5, 1.5, 1H), 3.86 (app q, J=6.0, 2H), 3.63 (m, 2H), 3.40 (m, 2H), 2.95 (m, 2H), 2.73 (s, 3H), 1.83 (m, 2H ), 1.64 (m, 3H), 1.41(m, 1H). m/z (M+H)$^+$=382.1.

EXAMPLE 372

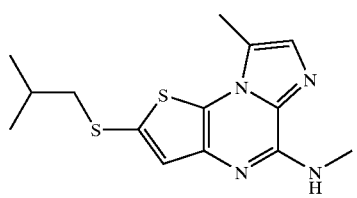

372

A solution of N-(2-bromo-8-methyl-1-thia-4,6,8a-triaza-as-indacen-5-yl)-N-methylamine (0.050 g, 0.168 mmol) in N,N-dimethylformamide (4 mL) was treated with 2-methyl-1-propanethiol (150 μL, 2.0 mmol) and potassium hydroxide (0.038 g, 0.67 mmol). The mixture was heated at 85° C. overnight in a sealed tube, then diluted with ethyl acetate, washed with water and brine. The organic layer was dried over anhydrous magnesium sulfate and the residue was purified on preparative HPLC (acetonitrile/water/ammonium acetate) to yield Compound 372 (0.014 g, 28%). $^1$H NMR (CDCl$_3$, 400 MHz) δ: 7.46 (1H, q, J=4.6 Hz), 7.38 (1H, s), 7.34 (1H, s), 2.96 (3H, d, J=4.6 Hz), 2.81 (2H, d, J=7.1 Hz), 2.66 (3H, s), 1.81 (1H, m), 1.00 (6H, d, J=7.1 Hz). LRMS (ESI, m/z, M+H$^+$) 306.

EXAMPLE 373

373

A solution of N-(2-(2-methylpropylthio)-8-methyl-1-thia-4, 6,8a-triaza-as-indacen-5-yl)-N-methyl-amine (0.005 g, 0.016 mmol) in dichloromethane (3 mL) was treated with peracetic acid (0.1 M in acetic acid, 0.195 mL, 0.019 mmol) at −15° C. The reaction was allowed to slowly reach room temperature for 5 hours and then quenched with dimethylsulfide (IM solution in methanol). The solvents were evaporated to give Compound 373 (0.0045 g, 90%) as a white solid. NMR (DMSO-d$_6$, 400 MHz) δ: 7.81 (1H, s), 7.70 (1H, br s), 7.41 (1H, s), 3.12 (1H, m), 2.99 (3H, d, J=3.4 Hz), 2.95 (1H, m), 2.73 (3H, s), 2.04 (1H, m), 1.07 (3H, d, J=6.5 Hz), 1.06 (3H, d, J=6.6 Hz). LRMS (ESI, m/z, M+H$^+$) 323.

EXAMPLE 374

374

A solution of N-(2-(2-methylpropylthio)-8-methyl-1-thia-4, 6,8a-triaza-as-indacen-5-yl)-N-methyl-amine (0.003 g, 0.010 mmol) in dichloromethane (3 mL) was treated with peracetic acid (0.1 M in acetic acid, 0.190 mL, 0.019 mmol) at room temperature. The mixture was stirred overnight then peracetic acid (0.190 mL, 0.019 mmol) was added and the mixture was refluxed. The reaction was quenched with dimethylsulfide (1M solution in methanol) and the solvents were evaporated to give Compound 374 (0.003 g, quantitative) as an off-white solid. NMR (DMSO-d$_6$, 400 MHz) δ: 7.97 (1H, s), 7.75 (1H, q, J=4.5 Hz), 7.43 (1H, s), 3.44 (2H, d, J=6.1 Hz), 2.99 (3H, d, J=4.5 Hz), 2.72 (3H, s), 2.10 (1H, m), 1.02 (6H, d, J=7.2 Hz). LRMS (ESI, m/z, M+H$^+$) 339.

EXAMPLE 375

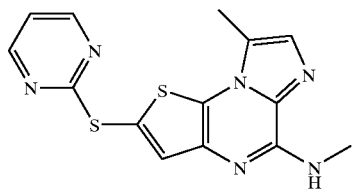

375

A solution of tris(dibenzylideneacetone)-dipalladium(0) (0.010 g) and bis[(2-diphenylphosphino)phenyl]ether (0.010 g) in toluene (6 mL) was bubbled with argon for 3 minutes. N-(2-Bromo-8-methyl-1-thia-4,6,8a-triaza-as-indacen-5-yl)-N-methyl-amine (0.020 g, 0.067 mmol) was added followed by 2-mercaptopyrimidine (0.011 g, 0.1 mmol) and potassium tert-butoxide (1.0 M solution in tetrahydrofuran, 0.1 mL, 0.1 mmol). The mixture was heated under reflux for 2 hours. The mixture was filtered over celite and the solvent was evaporated. The residue was purified by Prep HPLC to give Compound 375 (0.004 g, 18%) as a white solid. $^1$H NMR (DMSO-d$_6$, 400 MHz) δ: 8.68 (2H, d, J=4.6 Hz), 7.62 (1H, s), 7.54 (1H, br q), 7.39 (1H, s), 7.33 (1H, t, J=4.6 Hz), 2.98 (3H, d, J=4.7 Hz), 2.68 (3H, s). LRMS (ESI, m/z, M+H$^+$) 329.

EXAMPLE 376

376

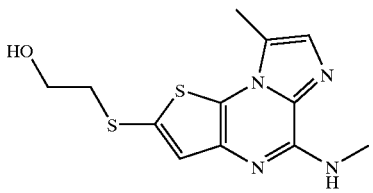

A solution of N-(2-bromo-8-methyl-1-thia-4,6,8a-triaza-as-indacen-5-yl)-N-methyl-amine (0.025 g, 0.0841 mmol) in N,N-dimethylformamide (3 mL) was treated with 2-hydroxyethanethiol (15 μL, 0.168 mmol), potassium hydroxide (0.009 g, 0.168 mmol) and copper(I) oxide (0.012 g, 0.0841 mmol). The mixture was heated at 85° C. for 3 hours in a sealed tube, then diluted with ethyl acetate, washed with water and brine. The organic layer was dried over anhydrous magnesium sulfate and the residue was purified on preparative HPLC (acetonitrile/water/ammonium acetate) to yield Compound 376 (0.005 g, 20%). $^1$H NMR (CDCl$_3$, 400 MHz) δ: 7.45 (1H, s), 7.27 (1H, s), 5.98 (1H, m), 3.83 (2H, t, J=6.2 Hz), 3.80 (1H, t, J=6.1 Hz), 3.19 (3H, d, J=5.1 Hz), 3.04 (2H, t, J=6.1 Hz), 2.72 (3H, s). LRMS (ESI, m/z, M+H$^+$) 295.

EXAMPLE 377

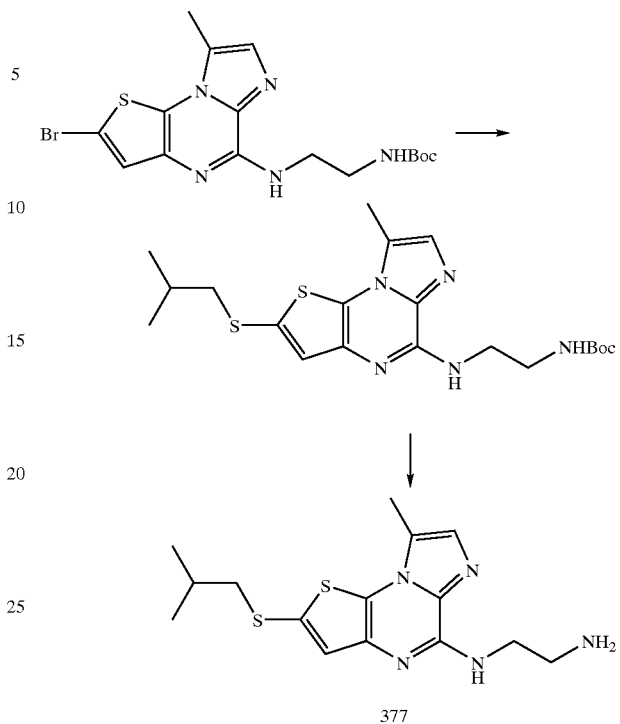

377

N-(2-Bromo-8-methyl-1-thia-4,6,8a-triaza-as-indacen-5-yl)-N-(2-tert-butoxycarbonylaminoethyl)-amine (0.010 g, 0.023 mmol) was reacted as described in Example 1 to afford N-(2-(2-methylpropylthio)-8-methyl-1-thia-4,6,8a-triaza-as-indacen-5-yl)-N-(2-tert-butoxycarbonylaminoethyl)-amine (0.004 g, 40%). This compound was then stirred in a solution of dichloromethane/trifluoroacetic acid (8:2, 3 mL) at room temperature for 3 hours. The solvents were evaporated to give Compound 377 as a brown solid (0.003 g, 61%, 2 TFA salts). NMR (DMSO-d$_6$, 400 MHz) δ: 7.77 (2H, br s), 7.67 (1H, t, J=5.5 Hz), 7.41 (1H, s), 7.37 (1H, s), 3.72 (2H, q, J=5.9 Hz), 3.11 (2H, m), 2.83 (2H, d, J=6.5 Hz), 2.68 (3H, s), 1.81 (1H, m), 1.00 (6H, d, J=6.6 Hz). LRMS (ESI, m/z, M+H$^+$) 336.

The following examples were prepared as described in Example 377.

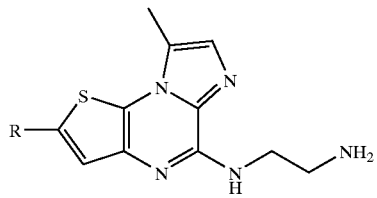

| Ex | R | HPLC Ret. time (min)[a] | Purity % | MS (e/z) (M + H)$^+$ |
|---|---|---|---|---|
| 378 | SCH(CH$_3$)$_2$ | 1.69 | 100 | 322 |
| 379 | SCH$_2$CH(OH)CH$_2$OH | 1.13 | 100 | 354 |

-continued

| Ex | R | HPLC Ret. time (min)[a] | Purity % | MS (e/z) (M + H)+ |
|---|---|---|---|---|
| 380 | furfuryl-S | 1.65 | 100 | 360 |
| 381 | S(CH$_2$)$_4$CH$_3$ | 2.14 | 100 | 350 |
| 382 | S-C$_6$H$_4$-OMe | 1.8 | 96.3 | 386 |
| 383 | SCH$_2$CH(CH$_3$)CH$_2$CH$_3$ | 2.05 | 100 | 350 |
| 384 | SCH$_2$CH$_2$CH(CH$_3$)$_2$ | 2.09 | 100 | 350 |
| 385 | S-2,4-dimethylphenyl | 2.28 | 100 | 384 |
| 386 | S-2,5-dimethylphenyl | 2.27 | 100 | 384 |
| 387 | S-cyclopentyl | 2.07 | 100 | 348 |
| 388 | S-3-methylphenyl | 2.09 | 100 | 370 |
| 389 | S-C$_6$H$_4$-NH$_2$ | 1.51 | 91.3 | 371 |
| 390 | SCH$_2$CH$_2$NH$_2$ | 1.38 | 81.8 | 323 |

[a]HPLC conditions used to determine retention times; 2 mm gradient 0–100% B in A; (A; 5 mM NH$_4$OAc in 90/10 water/acetonitrile; B; 5 mM NH$_4$OAc in 10/90 water/acetonitrile) using a Primesphere C-18 4.6 × 30 mm column at 254 nm

EXAMPLE 391

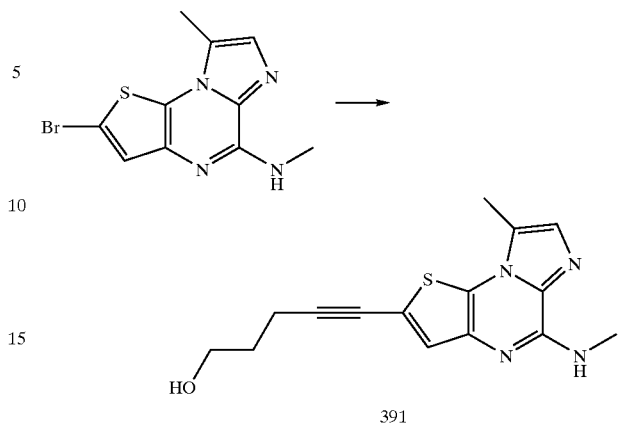

391

A solution of N-(2-bromo-8-methyl-1-thia-4,6,8a-triaza-as-indacen-5-yl)-N-methyl-amine (0.050 g, 0.168 mmol) (0.050 g, 0.168 mmol) in N,N-dimethylformamide (3 mL) was added copper(I) iodide (15 mgs), triethylamine (0.1 mL) and 5-hydroxy-pentyne (0.392 μL, 4.2 mmol). Argon was bubbled in the solution, then palladium(II) triphenylphosphine (15 mgs) was added and the mixture was stirred at 80° C. for 4 hours. The mixture was filtered on celite and the solvent was evaporated. The residue was purified by Prep HPLC to give Compound 391 (0.044 g, 88%). $^1$H NMR (DMSO-d$_6$, 400 MHz) δ: 7.49 (1H, q, J=4.5 Hz), 7.36 (1H, s), 7.35 (1H, s), 4.56 (1H, br t), 3.52 (2H, br q), 2.97 (3H, d, J=4.5 Hz), 2.66 (3H, s), 2.55 (2H, t, J=7.1 Hz), 1.71 (2H, m). LRMS (ESI, m/z, M+H$^+$) 301.

EXAMPLE 392

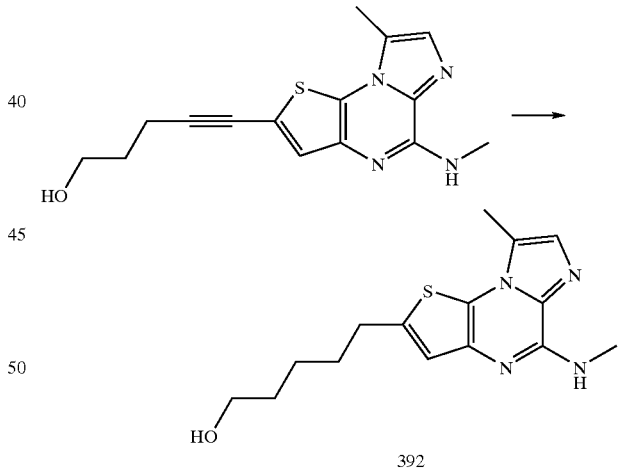

392

A solution of N-(2-(hydroxy-pentyn-5-yl)-8-methyl-1-thia-4,6,8a-triaza-as-indacen-5-yl)-N-methyl-amine (0.015 g, 0.05 mmol) in ethanol (10 mL) was hydrogenated (Parr, 15 psi) in presence of 10% Pd/C. The mixture was stirred for 2.5 hours, then filtered on Celite and washed with ethanol and dichloromethane/methanol (9: 1). The solvents were evaporated and the residue was purified by Prep HPLC to give Compound 392 (5 mgs, 33%). $^1$H NMR (DMSO-d$_6$, 400 MHz) δ: 7.31 (1H, s), 7.29 (1H, m), 7.02 (1H, s), 4.35 (1H, t, J=5.0 Hz), 3.40 (2H, m), 2.96 (3H, d, J=4.5 Hz), 2.86 (2H, t, J=7.4 Hz), 2.66 (3H, s), 1.68 (2H, m), 1.49–1.36 (4H, m). LRMS (ESI, m/z, M+H$^+$) 305.

EXAMPLE 393

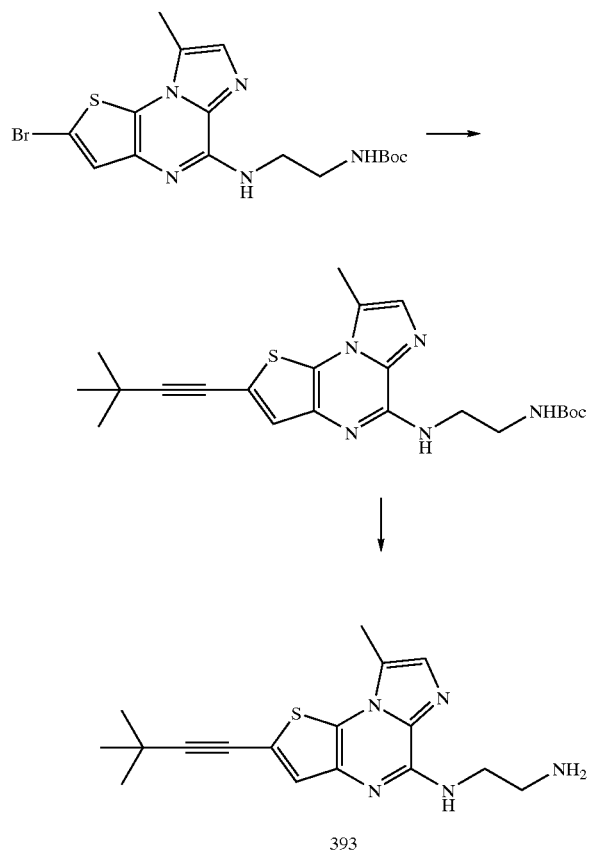

393

A solution of N-(2-bromo-8-methyl-1-thia-4,6,8a-triaza-as-indacen-5-yl)-N-(2-tert-butoxycarbonylaminoethyl)-amine (0.030 g, 0.070 mmol) in N,N-dimethylformamide (1 mL) was added copper(I) iodide (10.5 mgs), triethylamine (0.05 mL) and 2,2-dimethyl-but-3-yne (200 μL, 3.65 mmol). Argon was bubbled in the solution, then palladium(II) triphenylphosphine (13.8 mgs) was added and the mixture was stirred at 80° C. for 2 hours. The mixture was filtered on celite and the solvent was evaporated. The residue was purified by silica gel chromatography (50% ethyl acetate in hexane) to give N-(2-(hydroxy-pentyn-5-yl)-8-methyl-1-thia-4,6,8a-triaza-as-indacen-5-yl)-N-(2-tert-butoxycarbonylaminoethyl)-amine (0.021 g, 70%). This compound was dissolved in dichloromethane (1 mL) and treated with trifluoroacetic acid (0.2 mL) for 45 minutes. The solvents were evaporated and the residue was dissolved in methanol and treated with MP-carbonate resin. This mixture was stirred at room temperature for 2 hours, then filtered. The resin was washed with methanol and the filtrate was evaporated to give Compound 393 (0.014 g, 87%). NMR (DMSO-d$_6$, 400 MHz) δ: 7.36 (2H, s), 7.27 (1H, s), 7.25 (1H, s), 3.51 (2H, q, J=5.6 Hz), 2.87 (2H, m), 2.65 (3H, s), 1.24 (9H, s). LRMS (ESI, m/z, M+H$^+$) 327. HRMS for C$_{17}$H$_{21}$N$_5$S calcd: 327.1518, found: 327.1516.

The following examples were prepared as described in Example 393.

| Ex | R | HPLC Ret. time (min.)$^a$ | Purity % | MS (e/z) (M + H)$^+$ |
|---|---|---|---|---|
| 394 | ⟶≡⟶CH(OH)–Ph | 2.11 | 100 | 378 |
| 395 | ⟶≡⟶(2-pyridyl) | 1.73 | 100 | 349 |
| 396 | ⟶≡⟶C(CH$_3$)=CH$_2$ | 2.18 | 100 | 312 |
| 397 | ⟶≡⟶CH=CH–CH$_2$OH | 1.47 | 100 | 328 |
| 398 | ⟶≡⟶CH$_2$CH$_2$OH | 1.36 | 100 | 316 |
| 399 | ⟶≡⟶CH$_2$–cyclohexyl | 3.01 | 97 | 368 |
| 400 | ⟶≡⟶CH$_2$–cyclopentyl | 2.8 | 100 | 354 |
| 401 | ⟶≡⟶(3-hydroxyphenyl) | 1.84 | 100 | 364 |
| 402 | ⟶≡⟶CH(CH$_3$)$_2$ | 2.2 | 100 | 314 |

-continued

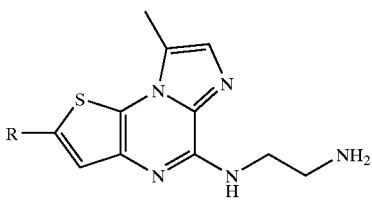

| Ex | R | HPLC Ret. time (min.)[a] | Purity % | MS (e/z) (M + H)+ |
|---|---|---|---|---|
| 403 | ⤳—≡—CH₂CH₂—OH | 1.22 | 100 | 330 |
| 404 | ⤳—≡—CH₂CH₂—Cl | 2.11 | 100 | 348 |
| 405 | ⤳—≡—CH₂—CH(CH₃)₂ | 2.69 | 100 | 342 |
| 406 | ⤳—≡—Ph | 2.43 | 100 | 348 |
| 407 | ⤳—≡—CH₂—O—CH₃ | 1.65 | 100 | 316 |
| 408 | ⤳—≡—CH₂—OH | 1.29 | 100 | 302 |

[a]HPLC conditions used to determine retention times; 2 min gradient 0–100% B in A; (A; 5 mM NH₄OAc in 90/10 water/acetonitrile; B; 5 mM NH₄OAc in 10/90 water/acetonitrile) using a Primesphere C-18 4.6 × 30 mm column at 254 nm

EXAMPLE 409

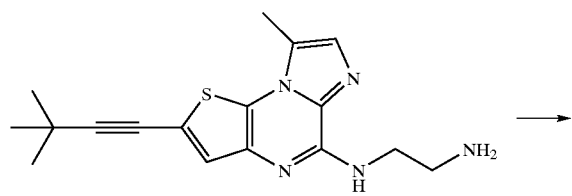

-continued

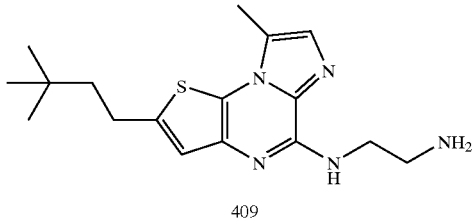

409

A solution of N-(2-(2,2-Dimethyl-butynyl)-8-methyl-1-thia-4,6,8a-triaza-as-indacen-5-yl)-N-(2-aminoethyl)-amine (0.017 g, 0.0519 mmol) in methanol (1 mL) was treated with 10% Pd/C (0.002 g), and stirred under hydrogen for 5 hours. The mixture was filtered on celite and the solvent was evaporated to give Compound 409 (0.004 g, 29%) as a gummy solid. NMR (DMSO-$d_6$, 400 MHz) δ: 0.96 (9H, s), 1.62 (2H, m), 2.69 (3H, s), 2.85 (2H, m), 3.23 (2H, t, J=5.6 Hz), 3.81 (2H, t, J=5.6 Hz), 6.97 (1H, s), 7.30 (1H, s). LRMS (ESI, m/z, M+H+) 332. HRMS for $C_{17}H_{26}N_5S$ calcd: 332.1909, found: 332.1912.

EXAMPLE 410

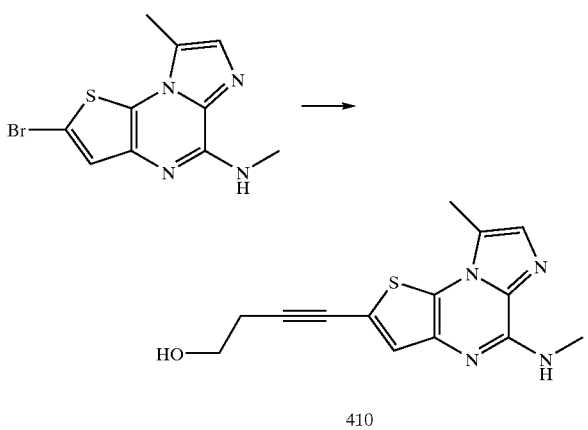

410

A solution of N-(2-bromo-8-methyl-1-thia-4,6,8a-triaza-as-indacen-5-yl)-N-methyl-amine (0.040 g, 0.135 mmol) in N,N-dimethylformamide (3 mL) was treated with 3-butyn-1-ol (0.4 mL,), triethylamine (0.1 mL), cupper(I) iodide (0.01 g), and tetrakis(triphenylphosphine) palladium(0) (0.01 g). The mixture was stirred at 100° C. for 3 hours. The reaction was filtered on celite and the filtrate was evaporated. The residue was purifed by prep HPLC to give Compound 410 (0.029 g, 74%). NMR (DMSO-$d_6$, 400 MHz) δ: 7.49 (1H, q, J=4.7 Hz), 7.35 (2H, s), 4.95 (1H, br t), 3.60 (2H, br qa), 2.97 (3H, d, J=4.7 Hz), 2.66 (3H, s), 2.64 (2H, t, J=6.9 Hz). LRMS (ESI, m/z, M+H+) 287.

EXAMPLE 411

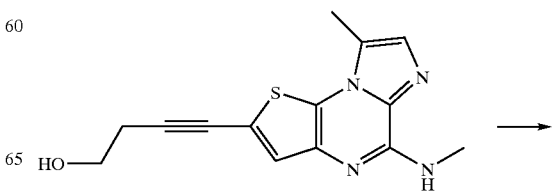

-continued

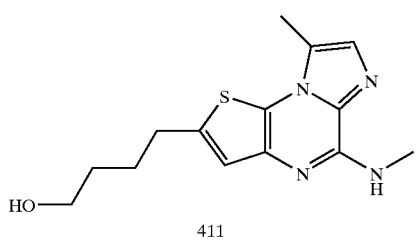

411

A solution of N-(2-(4-hydroxy-butynyl)-8-methyl-1-thia-4,6,8a-triaza-as-indacen-5-yl)-N-methyl-amine (0.008 g, 0.028 mmol) in ethanol (5 mL) was treated with 10% Pd/C (0.005 g) and hydrogenated (15 psi) in a Parr hydrogenator. The mixture was filtered on Celite which was then washed with dichloromethane/methanol (1:1). The solvents were evaporated to give Compound 411 (0.004 g, 50%). NMR (DMSO-$d_6$, 400 MHz) δ: 7.32 (1H, s), 7.31 (1H, qa, J=5.1 Hz), 7.02 (1H, s), 4.41 (1H, t, J=5.2 Hz), 3.45 (2H, q, J=6.3 Hz), 2.95 (3H, d, J=5.1 Hz), 2.87 (2H, t, J=7.4 Hz), 2.66 (3H, s), 1.71 (2H, m), 1.03 (2H, m). LRMS (ESI, m/z, M+H$^+$) 291.

The following examples that have been prepared as described in Example 410.

| Ex | R | HPLC Ret. time (min.)[a] | Purity % | MS (e/z) (M + H)$^+$ |
|---|---|---|---|---|
| 412 | —C≡C—C(OH)(cyclopentyl) | 1.65 | 100 | 327 |
| 413 | —C≡C—(CH$_2$)$_4$—OH | 1.51 | 100 | 315 |
| 414 | —C≡C—C(OH)(cyclohexyl) | 1.74 | 100 | 341 |
| 415 | —C≡C—C(CH$_3$)$_2$OH | 1.47 | 83 | 301 |
| 416 | —C≡C—CH(OH)CH$_3$ | 1.38 | 100 | 287 |
| 417 | —C≡C—CH$_2$—CH(OH)CH$_3$ | 1.43 | 91 | 301 |
| 418 | —C≡C—CH(OH)CH$_2$CH$_3$ | 1.52 | 100 | 301 |

-continued
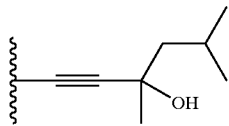
| Ex | R | HPLC Ret. time (min.)[a] | Purity % | MS (e/z) (M + H)+ |
|---|---|---|---|---|
| 419 | 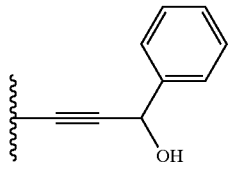 | 1.87 | 100 | 343 |
| 420 | 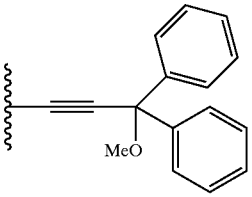 | 1.68 | 100 | 349. |
| 421 | 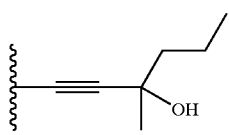 | 2.45 | 100 | 439 |
| 422 | 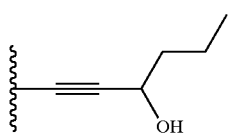 | 1.74 | 100 | 329 |
| 423 | 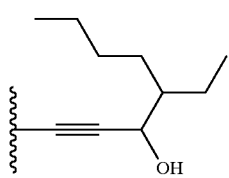 | 1.66 | 92 | 315 |
| 424 | 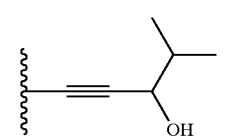 | 2.18 | 100 | 371 |
| 425 | 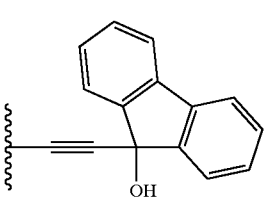 | 1.65 | 100 | 315 |
| 426 |  | 1.92 | 95 | 423 |

-continued
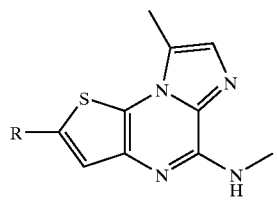
| Ex | R | HPLC Ret. time (min.)[a] | Purity % | MS (e/z) (M + H)+ |
|---|---|---|---|---|
| 427 | HO-CH(Et)-CH2-C≡C- | 1.56 | 100 | 315 |
| 428 | (iBu)2C(OH)-C≡C- | 2.31 | 100 | 385 |
| 429 | iBu-CH(OH)-C≡C- | 1.77 | 100 | 329 |
| 430 | CH3-CH(Pr)-CH(OH)-C≡C- | 1.92 | 100 | 343 |
| 431 | Et(Bu)C(OH)-C≡C- | 2.02 | 100 | 357 |
| 432 | 3-HO-C6H4-C≡C- | 1.78 | 91 | 335 |
| 433 | HOCH2-C≡C- | 1.30 | 96 | 273 |
[a]HPLC conditions used to determine retention times; 2 min gradient 0–100% B in A; (A; 5 mM NH4OAc in 90/10 water/acetonitrile; B; 5 mM NH4OAc in 10/90 water/acetonitrile) using a Primesphere C-18 4.6 × 30 mm column at 254 nm The following examples were prepared as described in Example 411.
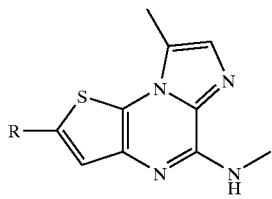
| Ex | R | HPLC Ret. time (min.)[a] | Purity % | MS (e/z) (M + H)+ |
|---|---|---|---|---|
| 434 | | 1.61 | 100 | 331 |
| 435 | | 1.55 | 100 | 319 |
| 436 | | 1.74 | 98 | 345 |
| 437 | | 1.41 | 100 | 305 |
| 438 | | 1.34 | 100 | 291 |
| 439 | | 1.43 | 94 | 305 |
| 440 | | 1.82 | 89 | 347 |
| 441 | | 1.65 | 96 | 353 |

-continued
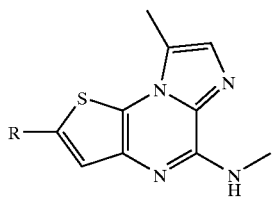
| Ex | R | HPLC Ret. time (min.)[a] | Purity % | MS (e/z) (M + H)+ |
|---|---|---|---|---|
| 442 | | 1.66 | 95 | 333 |
| 443 | | 1.6 | 97 | 319 |
| 444 | | 2.12 | 86 | 375 |
| 445 | | 1.59 | 100 | 319 |
| 446 | | 1.55 | 100 | 319 |
| 447 | | 1.72 | 99 | 333 |
| 448 | | 1.87 | 94 | 347 |
| 449 | | 1.95 | 88 | 361 |

-continued

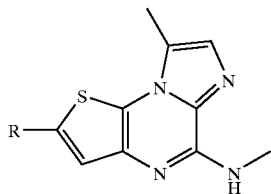

| Ex | R | HPLC Ret. time (min.)[a] | Purity % | MS (e/z) (M + H)+ |
|---|---|---|---|---|
| 450 | 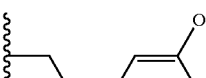 | 1.65 | 81 | 339 |
| 451 | 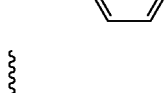 | 1.26 | 95 | 277 |

[a]HPLC conditions used to determine retention times; 2 min gradient 0-100% B in A; (A; 5 mM NH₄OAc in 90/10 water/acetonitrile; B; 5 mM NH₄OAc in 10/90 water/acetonitrile) using a Primesphere C-18 4.6 × 30 mm column at 254 nm

EXAMPLE 452

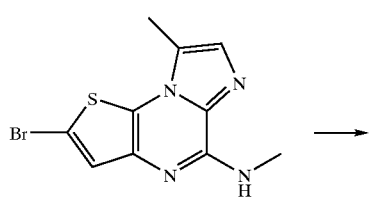

452

A stirred solution of N-(2-bromo-8-methyl-1-thia-4,6,8a-triaza-as-indacen-5-yl)-N-methyl-amine (0.050 g, 0.168 mmoles) in N-methylpyrrolidinone (4 mL) was treated with N-Boc-1,2,3,6-tetrahydro-4-tributylstannylpyridine (0.119 g, 0.252 mmol), tris-dibenzylideneacetone dipalladium (10 mgs) and triphenylarsine (15 mgs). The reaction was heated at 90° C. overnight and was then diluted with ethyl acetate, washed with water and dried over anhydrous magnesium sulfate. After filtration, the organic phase was evaporated to give a residue which was purified by preparative thin layer chromatography followed by Prep Hplc to give Compound 452 (0.035 g, 52%). NMR (DMSO-d₆, 400 MHz) δ: 1.44 (9H, s), 2.69 (3H, s), 2.55 (2H, br s), 2.96 (3H, d, J=4.7 Hz), 3.57 (2H, t, J=5.6 Hz), 4.02 (2H, br s), 6.19 (1H, br s), 7.29 (1H, s), 7.34 (1H, s), 7.40 (1H, q). LRMS (ESI, m/z, M+H⁺) 399.

EXAMPLE 453

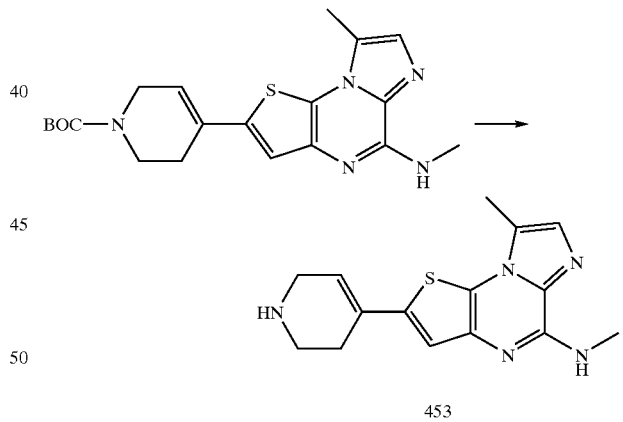

453

N-(2-(N-Tert-butyloxycarbonyl-1,2,3,6-tetrahydropyridin-4-yl)-8-methyl-1-thia-4,6,8a-triaza-as-indacen-5-yl)-N-methyl-amine (0.028 g, 0.0701 mmol) was dissolved in a solution of trifluoroacetic acid (20%) in dichloromethane (3 mL). The reaction was stirred for 3 hours, then the solvent was evaporated to give the trifluoroacetic acid salt of Compound 453 (0.033 g, 89%). NMR (DMSO-d₆, 400 MHz) δ: 2.65 (3H, s), 2.74 (2H, br s), 2.97 (3H, s), 3.33 (2H, t, J=6.1 Hz), 3.74 (2H, br s), 6.19 (1H, br t), 7.29 (1H, s), 7.36 (1H, s).

EXAMPLE 454

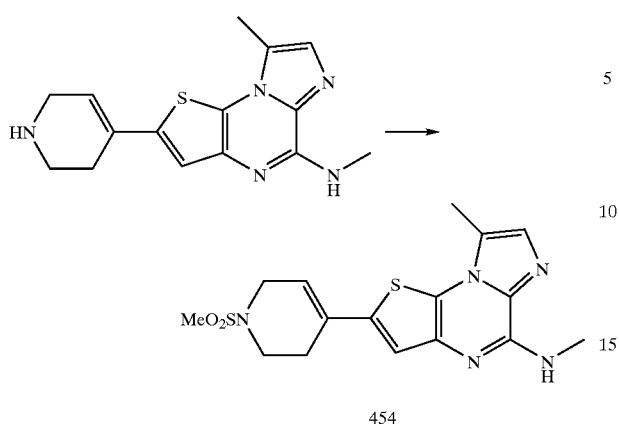

454

A solution of N-(2-(1,2,3,6-tetrahydropyridin-4-yl)-8-methyl-1-thia-4,6,8a-triaza-as-indacen-5-yl)-N-methyl-amine (0.011 g, 0.0367 mmol) in dichloromethane (3 mL) was treated with triethylamine (0.15 mL, 0.11 mmol) and methanesulfonyl chloride (4 μL, 0.044 mmol) at 0° C. The reaction was stirred at room temperature for 3 hours, then quenched with water and diluted with dichloromethane. The organic layer was washed with water and brine then dried over anhydrous sodium sulfate, filtered and concentrated. The residue was purified by Prep TLC to give Compound 454 (0.005 g, 36%). NMR (DMSO-$d_6$, 400 MHz) δ:2.69 (5H, m), 2.96 (3H, s), 2.97 (3H, s), 3.41 (2H, d, J=5.9 Hz), 3.89 (2H, d, J=3.1 Hz), 6.23 (1H, t, J=3.5 Hz), 7.32 (1H, s), 7.35 (1H, s), 7.41 (1H, d, J=5.1 Hz). LRMS (ESI, m/z, M+H$^+$) 378.

EXAMPLE 455

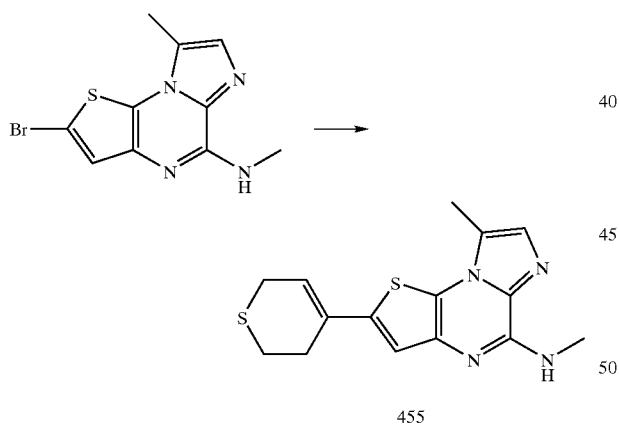

455

A stirred solution of N-(2-bromo-8-methyl-1-thia-4,6,8a-triaza-as-indacen-5-yl)-N-methyl-amine (0.100 g, 0.336 mmoles) in N-methylpyrrolidinone (10 mL) was treated with (3,6-dihydro-2H-thiopyran-4-yl)-trimethyl-stannane (0.196 g, 0.504 mimol), tris-dibenzylideneacetone dipalladium (20 mgs) and triphenylarsine (30 mgs). The reaction was heated at 100° C. overnight and was then diluted with ethyl acetate, washed with water (2x) and dried over anhydrous magnesium sulfate. After filtration, the organic phase was evaporated to give a residue which was purified by column chromatography (hexane/ethylacetate 50%) to give Compound 455 (0.014 g, 52%).NMR (DMSO-$d_6$, 400 MHz) δ: 2.67 (3H, s), 2.50–2.72 (2H, m), 2.86 (2H, t, J=5.8 Hz), 2.94 (3H, d, J=4.8 Hz), 3.30 (2H, m overlapped by HDO), 6.40 (1H, t, H=5.8 Hz), 7.28–7.35. (3H, m).

EXAMPLE 456

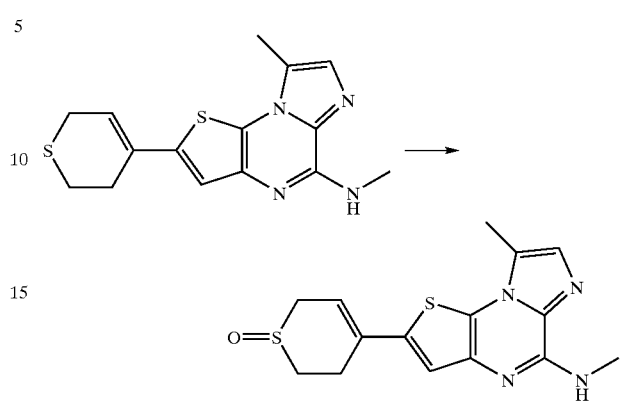

456

To a stirred solution of [2-(3,6-dihydro-2H-thiopyran-4-yl)-8-methyl-1-thia-4,5,8a-triaza-as-indacen-5-yl]-methyl-amine (0.009 g, 0.0284 mmol) in dichloromethane (3 mL) at −78° C. was added peracetic acid (0.1N in acetic acid, 0.3 mL). The reaction was slowly warmed up to room temperature over a period of 5 hours. The reaction was then quenched with dimethylsulfide (1N in methanol, 10 eq), diluted with dichloromethane, washed with water and brine. The organic layer was dried over anhydrous magnesium sulfate, filtered and concentrated. The residue was purified by Prep HPLC (ammonium acetate/water/acetonitrile) to give Compound 456 (0.007 g, 78%) as a solid. NMR (DMSO-$d_6$, 400 MHz) δ: 2.51–2.56 (1H, m overlapped by DMSO-$d_6$), 2.68–2.69 (1H, m), 2.69 (3H, s), 2.81–3.18 (2H, m), 2.97 (3H, d, J=4.6 Hz), 3.44 (1H, dd, J=16.6 and 5.0 Hz), 3.67 (1H, dd, J=16.6 and 5.0 Hz), 6.11 (1H, t, J=5.0 Hz), 7.35 (1H, s), 7.40 (1H, s), 7.42 (1H, q, J=4.6 Hz). LRMS (ESI, m/z, M+H$^+$) 333.

EXAMPLE 457

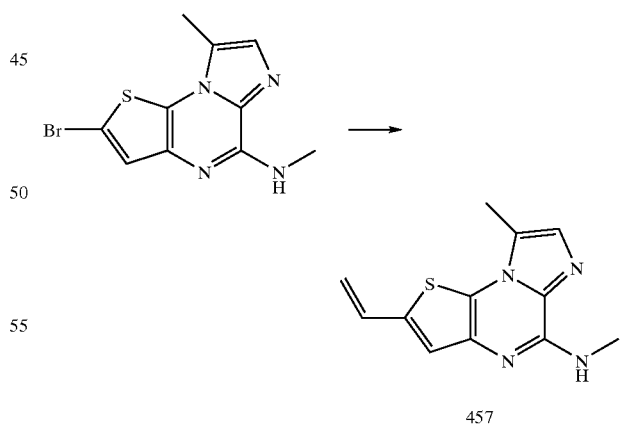

457

A stirred solution of N-(2-bromo-8-methyl-1-thia-4,6,8a-triaza-as-indacen-5-yl)-N-methyl-amine (0.120 g, 0.403 mmoles) in N-methylpyrrolidinone (8 mL) was treated with a solution of vinyltributylstannane (0.170 g, 0.53 mmol) in N-methylpyrrolidinone (1 mL) and tetrakistriphenylphosphinepalladium(O) (20 mgs). The reaction was heated at 115° C. for 4 hours. The reaction was diluted with ethyl acetate and washed with water. The organic layer was dried over anhydrous magnesium sulfate, filtered and concentrated. The residue was purified by silica gel chromatography (50 to 100% ethyl acetate/hexane) and by Prep HPLC (acetonitrile/water/trifluoroacetic acid) to give Compound 457 as a trifluoroacetic acid salt (0.080 g, 81%). NMR (DMSO-$d_6$, 400 MHz) δ: 2.68 (3H, s), 2.96 (3H, s), 5.23 (1H, d, J=11.0), 5.62 (1H, d, J=17.4 Hz), 6.94 (1H, dd, J=17.4 and 11.0 Hz), 7.29 (1H, s), 7.34 (1H, s), 7.50 (1H, m). IR (v, $cm^{-1}$): 3298, 1684, 1594, 1575. LRMS (ESI, m/z, M+H$^+$) 245. HRMS for $C_{12}H_{12}N_4S$ calcd: 244.0783; found: 244.0777.

The Following Conditions Apply to Examples 458–510

Thin-layer chromatography was done on E. Merck silica gel 60 $F_{254}$ plates (0.5 mm). Hplc purity determinations were done using either a Shimadzu LC-10AS with a SPD-10AV UV-Vis detector and one of the folowing columns; YMC Combiscreen ODS-A (4.6×50 mm), or HP Zorbax SB-C18 (4.6×750 mm); or, an HP 1090 DR5 with a diode array detector and a Waters Nova-Pak C18 column (3.9×150 mm). Infrared spectra were recorded on a Nicolet Protégé 460 FTIR as thin films or KBr pellets. $^1$HNMR spectra were recorded on either a Bruker AMX-400 or a Bruker ARX-500 NMR spectrometer.

EXAMPLE 458

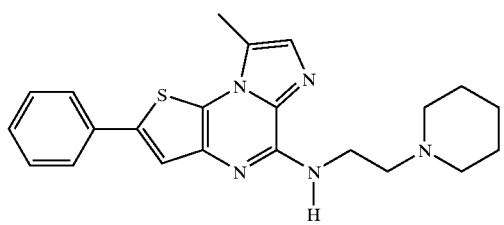

458

Step A:

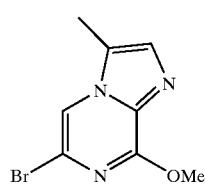

(458A)

To a mixture of methanol (2 mL) and MeONa in methanol (25% wt, 88 μL 0.397 mmmol) was added the compound of Example 1D (0.1 g, 0.406 mmol). The reaction mixture was heated under reflux for 3 h and the solvent was evaporated to dryness. Water was added to the residue and the target compound was extracted with ethyl acetate (3×25 mL). The organic solution was dried (MgSO$_4$) and concentrared in vacuo to give compound 458A as a beige solid. (91 mg, 93%); mp 127–130° C.; IR (KBr, $cm^{-1}$) 3062, 2996, 2947, 1743,1521,1109; $^1$H NMR (DMSO) δ 8.41 (s, 1H), 7.53 (s, 1H), 4.10 (s, 3H), 2.56 (s, 3H); LC/MS 100% (220 nm), m/z (M+H$^+$) 242.

Step B:

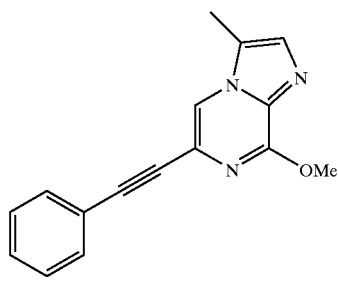

(458B)

To a solution of Compound 458A (2.0 g, 8.26 mmol) in DMF (10 mL) in a sealed tube was added tetrakis(triphenylphosphine)pallidium(0) (477 mg, 0.413 mmol) copper iodide (126 mg, 0.661 mmol) phenylacetylene (1.36 mL, 12.4 mmol) and triethylamine (4.60 mL, 33 mmol). The reaction mixture was heated at 70° C. for 2.5 h. Then the solvent was evaporated in vacuo and the crude material was purified on silicagel dried column using AcOEt:Hexane (2:1) to (4:1) to afford compound 458B as a beige solid. (2.10 g, 96%); mp 112° C.; IR (KBr, $cm^{-1}$) 3420,1700,1652, 1499,1209; $^1$H NMR (DMSO) δ 8.43 (s, 1H), 7.60–7.58 (m, 2H), 747–7.44 (m, 2H), 4.05 (s, 3H), 3.29 (s, 3H). LC/MS 100% (220 nm), m/z (M+H$^+$) 264.

Step C:

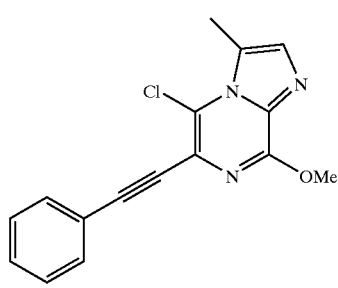

(458C)

To compound 458B (8.4 g 31.9 mmol) in THF was added N-chlorosuccinimide (4.69 g, 35.01 mmol). The reaction mixture was stirred at 55° C. for 18 h. Then, the solvent was evaporated in vacuo and the crude material was purified on silicagel dry column using AcOEt:Hexane (2:1) to (4:1) as solvents to afford compound 458C as a yellow solid (1.71 g, 18%); mp 105° C.; IR (KBr, $cm^{-1}$) 3446, 1700, 1532, 1219; $^1$H NMR (DMSO) δ 7.62–7.60 (m, 2H), 7.50–7.46 (m, 4H), 4.04 (s, 3H), 2.77(s, 3H); LC/MS 95.1% (220 nm), m/z (M+H$^+$) 298.

Step D:

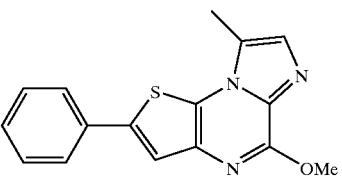

(458D)

To compound 458C (200 mg, 0.672 mmol) in DMF was added sodium sulfide nonahydrate (403 mg, 1.68 mmol). The reaction mixture was stirred in a sealed tube at 90° C.

for 18 h. Then, DMF was evaporated in vacuo and the crude material was purified on silicagel dry column using AcO-Et:Hexane (1:2) to (2:1) as solvents to afford compound 458D as a beige solid (0.160 mg, 81%); mp 127–130° C.; IR (KBr, cm$^{-1}$) 3159, 3082, 1695, 1192; $^1$H NMR (DMSO) δ 7.91 (s, 1H), 7.82–7.79 (m, 2H), 7.51–7.46 (m, 3H), 7.41–7.37 (m, 1H), 4.10 (s, 3H), 2.79 (s, 3H); LC/MS 96% (220 nm), m/z (M+H$^+$) 296.

Step E:

(458E)

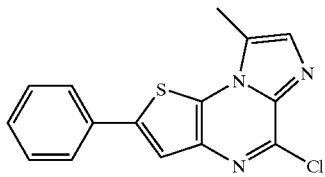

A solution of compound 458D (300 mg, 1.07 mmol) in phosphorus oxychloride (12 mL) was heated in a sealed tube at 90° C. for 18 h. Then, phosphorus oxychloride was evaporated in vacuo and ice (50 mL) was added to the solid. The aqueous solution was neutralized with a saturated solution of sodium bicarbonate (pH=8) and the organic material was extracted with AcOEt:THF (4:1) (4×25 mL). Combined organic solutions were dried (MgSO$_4$) and concentrated in vacuo to afford compound 458E as a white solid. (279 mg, 87%); mp 197° C., IR (KBr, cm$^{-1}$) 3421, 3077, 1408, 1313; $^1$H NMR (DMSO) δ 7.81 (s, 1H), 7.62–7.60 (m, 2H), 7.50 (s, 1H), 7.32–7.24 (m, 2H), 7.19–7.16 (m, 1H), 2.62 (s, 3H); LC/MS 100% (220 nm), m/z (M+H$^+$) 300.

Step F (Method 1):

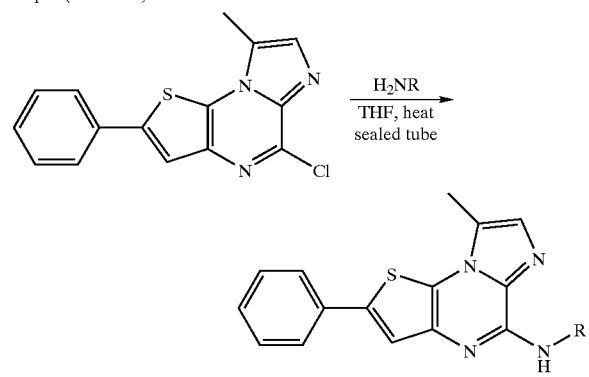

To a solution of compound 458E (55 mg, 0.183 mmol) in THF (3 mL) was added the amine (1.83 mmol) and the reaction mixture was stirred in a sealed tube at 85° C. until completion (1 to 10 days). Then, THF was evaporated in vacuo and crude material was purified by silicagel dry column using CH$_2$Cl$_2$:MeOH as solvents, by crystallization in hot isopropanol or by preparative HPLC to afford the desired product.

Step F (Method 2):

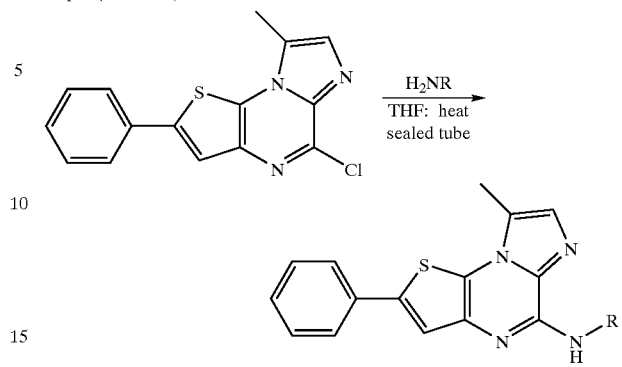

To a solution of compound 458E (55 mg, 0.183 mmol) in THF:DMSO (2 mL:2 mL) was added the amine (1.83 mmol) and N,N-diisopropylethylamine (368 μL, 4.03 mmol). The reaction mixture was stirred in a sealed tube at 120° C. until completion (2 to 8 days). Then, solvents were evaporated in vacuo and crude material was purified. by silicagel dry column using CH$_2$Cl$_2$:MeOH as solvents, by crystallization in hot ispropanol or by preparative HPLC to afford the desired product.

Step G (Compound 458):

Compound 458 was prepared from compound 458E and 1-(2-aminoethyl)piperidine using Step F (method 1), and was retrieved as an off-white solid. (61%); mp 137–139° C.; IR (KBr, cm$^{-1}$) 3326, 2929, 1559, 1404; $^1$H NMR (DMSO) 7.78–7.75 (m, 3H), 7.48–7.44 (m, 2H), 7.38–7.36 (m, 2H), 7.12 (br s, 1H), 3.62–3.57 (m, 2H), 2.74 (s, 3H), 2.58 (br s, 2H), 2.42 (br s, 4H), 1.54–1.51 (m, 4H), 1.42–1.40 (m, 2H); MS ($^+$ESI, M+H$^+$) m/z 392; HPLC: 96.13% (220 nm); HRMS calcd for C$_{22}$H$_{25}$N$_5$S: 392.1908; found 392.1907

EXAMPLE 459

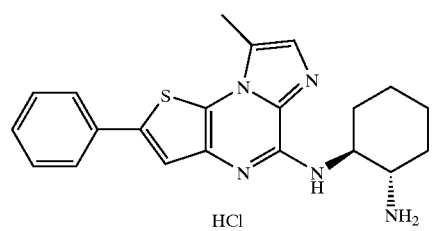

Compound 459 was prepared from intermediate 458E and trans-1,2-diaminocyclohexane using Step F (method 1), described in the synthesis of Example 458. Compound 459 was retrieved as a yellow solid. (12%); mp 162–164° C.; IR (KBr, cm$^{-1}$) 3360, 2920, 2858; $^1$H NMR (DMSO) 7.72–7.71 (d, J=7.4, 2H), 7.64 (s, 1H), 7.45–7.43 (m, 2H), 7.38–7.33 (m, 2H), 4.07–4.01 (m, 1H), 3.06–2.99 (m, 1H), 2.71 (s, 3H), 2.43 (br s, 2H), 2.01–1.15 (br m, 6H); MS ($^+$ESI, M+H$^+$) m/z 378; HPLC: 99.0% (220 nm); HRMS calcd for C$_{21}$H$_{23}$N$_5$S: 377.1674; found 377.1693

EXAMPLE 460

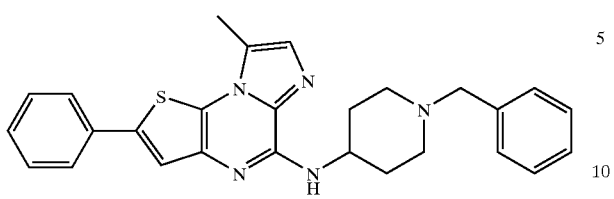

Compound 460 was prepared from intermediate 458E and 4-amino-1-benzylpiperidine using Step F (method 1), described in the synthesis of Example 458. Compound 460 was retrieved as a beige solid. (10%); mp 91–94° C.; IR (KBr, cm$^{-1}$) 3415, 2922, 2799, 1540, 1074; $^1$H NMR (DMSO) 7.78–7.76 (m, 3H), 7.47–7.43 (m, 2H), 7.37–7.26 (m, 7H), 7.12–7.10 (d, J=8.2, 2H), 4.12–4.07 (m, 1H), 3.5. (br s, 2H), 2.85 (br d, 2H), 2.73 (s, 3H), 2.10 (br t, 2H), 1.91 (br d, 2H), 1.72 (m, 2H); MS ($^+$ESI, M+H$^+$) m/z 454; HPLC: 99.0% (220 nm); HRMS calcd for C$_{27}$H$_{27}$N$_5$S: 454.2065; found 454.2074

EXAMPLE 461

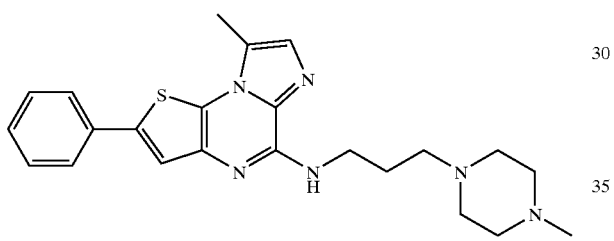

Compound 461 was prepared from intermediate 458E and 1-(3-aminopropyl)-4-methylpiperidine using Step F (method 1), described in the synthesis of Example 458. The compound was retrieved as a beige solid. (11%); mp 129–131° C.; IR (KBr, cm$^{-1}$) 3424, 2933, 2833, 2788, 1550, 1166; $^1$H NMR (DMSO) 7.77 (d, J=7.5, 2H), 7.74 (s, 1H), 7.61 (t, J=5.5, 1H), 7.48–7.44 (m, 2H), 7.37–7.34 (m, 2H), 3.53 (m, 2H), 2.74 (s, 3H), 2.51–2.28 (m, 10H), 2.17 (s, 3H), 1.85–1.77 (m, 2H); MS ($^+$ESI, M+H$^+$) m/z 421; HPLC: 92.5% (220 nm); HRMS calcd for C$_{23}$H$_{28}$N$_6$S: 421.2174; found 421.2164

EXAMPLE 462

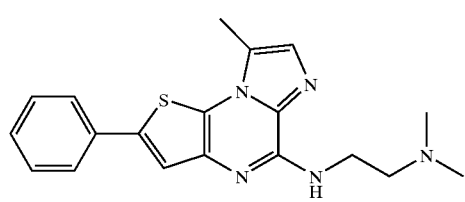

Compound 462 was prepared from intermediate 458E and N,N-dimethylethylenediamine using Step F (method 1), described in the synthesis of Example 458. The desired compound was retrieved as a beige solid. (18%); mp 133–135° C.; IR (KBr, cm$^{-1}$) 3743, 3266, 2939, 2812, 2770, 1559, 1038; $^1$H NMR (DMSO) 7.77–7.74(m, 3H), 7.47–7.43 (m, 2H), 7.08 (br t, 1H), 3.57. (m, 2H), 2.73 (s, 3H), 2.57–2.53 (m, 2H), 2.23 (s, 6H), 1.85–1.77 (m, 2H); MS ($^+$ESI, M+H$^+$) m/z 351; HPLC: 98.7% (220 nm); HRMS calcd for C$_{19}$H$_{21}$N$_5$S: 351.1518; found 351.1518

EXAMPLE 463

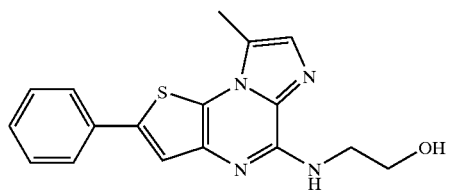

Compound 463 was prepared from intermediate 458E and ethanolamine using Step F (method 1), described in the synthesis of Example 458. The desired compound was retrieved as a beige solid. (58%); mp 104–106° C.; IR (KBr, cm$^{-1}$) 3370, 3148, 2911, 2848, 1554, 1071; $^1$H NMR (DMSO) 7.78–7.74 (m, 3H), 7.51–7.44 (m, 2H), 7.41–7.34 (m, 2H), 7.21 (br t, 1H), 4.83 (t, J=5.3 1H), 3.67–3.56 (m, 4H), 2.74 (s, 3H); m/z 324; HPLC: 94.8% (220 nm); HRMS calcd for C$_{17}$H$_{16}$N$_4$OS: 324.1045; found 324.1038

EXAMPLE 464

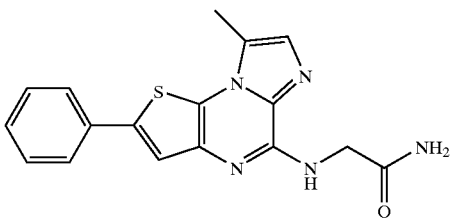

Compound 464 was prepared from intermediate 458E and glycinamide hydrochloride using Step F (method 1), described in the synthesis of Example 458. The desired compound was retrieved as a beige solid. (36%); mp 268° C.; IR (KBr, cm$^{-1}$) 3375, 3277, 1652, 1558, 1541, 1331; $^1$H NMR (DMSO) 7.78–7.76 (m, 3H), 7.47–7.33 (m, 6H), 7.13 (br s, 1H), 4.03 (d, J=5.7 1H), 2.74 (s, 3H); m/z 338; HPLC: 99.0% (220 nm); HRMS calcd for C$_{17}$H$_{15}$N$_5$OS: 337.0998; found 337.1006

EXAMPLE 465

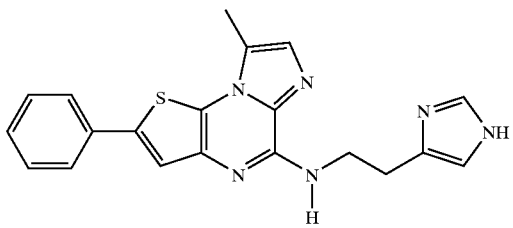

Compound 465 was prepared from intermediate 458E and histamine dihydrochloride using Step F (method 2), described in the synthesis of Example 458. The desired compound was retrieved as an off-white solid; (12%); mp 205° C.; IR (KBr, cm$^{-1}$) 3278, 3095, 1567, 1422; $^1$H NMR (DMSO) 7.78–7.77 (m, 3H), 7.58–7.44 (m, 4H), 7.37–7.34 (m, 2H), 6.94 (br s, 1H), 3.75 (td, J=6.4, 7.1, 2H), 2.74 (s, 3H), 2.93–2.87 (br s, 2H), 2.74 (s, 3H); MS ($^+$ESI, M+H$^+$) m/z 375; HPLC: 100% (220 nm); HRMS calcd for C$_{20}$H$_{18}$N$_6$S: 374.1314; found 374.1305

EXAMPLE 466

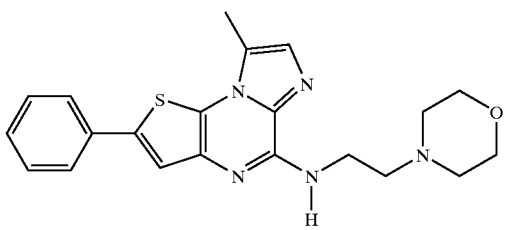

Compound 466 was prepared from intermediate 458E and 4-(2-aminoethyl)morpholine using Step F (method 1), described in the synthesis of Example 458. The desired compound was retrieved as an off-white solid (35%); mp 153° C.; IR (KBr, cm$^{-1}$) 3326, 2929, 1559, 1404; $^1$H NMR (DMSO) 7.78–7.75 (m, 3H), 7.48–7.44 (m, 2H), 7.38–7.36 (m, 2H), 7.12 (br s, 1H), 3.62–3.57 (m, 2H), 2.74 (s, 3H), 2.58 (br s, 2H), 2.42 (br s, 4H), 1.54–1.51 (m, 4H), 1.42–1.40 (m, 2H); MS ($^+$ESI, M+H$^+$) m/z 392; HPLC: 96.13% (220 nm); HRMS calcd for C$_{22}$H$_{25}$N$_5$S: 392.1908; found 392.1907

EXAMPLE 467

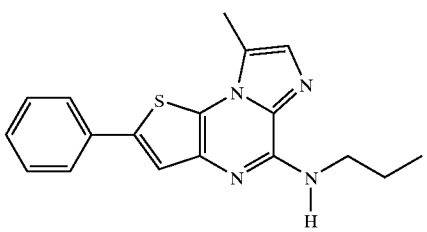

Compound 467 was prepared from intermediate 458E and propylamine using Step F (method 1), described in the synthesis of Example 458. The desired compound was retrieved as an off-white solid (48%); mp 166° C.; IR (KBr, cm$^{-1}$) 3359, 2963, 2923, 1558, 1421; $^1$H NMR (DMSO) 7.78–7.75 (m, 3H), 7.48–7.44 (m, 2H), 7.41–7.33 (m, 3H), 3.46 (br quad, 2H), 2.74 (s, 3H), 1.67 (m, 2H), 0.94 (br t, 3H); MS ($^+$ESI, M+H$^+$) m/z 323; HPLC: 97.5% (220 nm); HRMS calcd for C$_{18}$H$_{18}$N$_4$S: 322.1252; found 322.1259

EXAMPLE 468

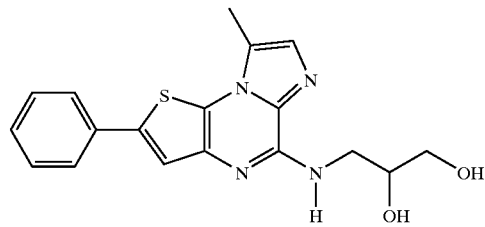

Compound 468 was prepared from intermediate 458E and 3-amino-1,2-propanediol using Step F (method 1), described in the synthesis of Example 458. The desired compound was retrieved as a light yellow solid (34%); mp 187° C.; IR (KBr, cm$^{-1}$) 3403, 3253, 2921, 1540, 1399; $^1$H NMR (DMSO) 7.78–7.77 (m, 2H), 7.74 (s, 1H), 7.48–7.44 (m, 2H), 7.39–7.36 (m, 2H), 7.10 (br t, 1H), 5.02 (d, J=5.1, 1H), 4.70 (br t, 1H), 3.85–3.65 (m, 2H), 3.45–3.40 (m, 4H), 2.74 (s, 3H); MS ($^+$ESI, M+H$^+$) m/z 355; HPLC: 97.7% (220 nm); HRMS calcd for C$_{18}$H$_{18}$O$_2$N$_4$S: 354.1150; found 354.1129

EXAMPLE 469

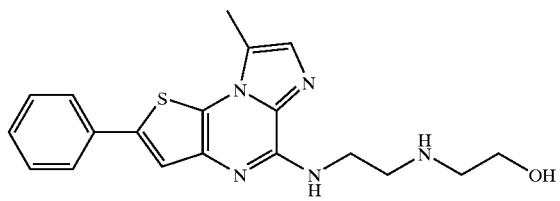

Compound 469 was prepared from intermediate 458E and 2-(2-aminoethylamine)ethanol using Step F (method 1), described in the synthesis of Example 458. The desired compound was retrieved as a light yellow solid (30%); mp>220° C.; IR (KBr, cm$^{-1}$) 3420, 3324, 2920, 2732, 1558, 1361; $^1$H NMR (DMSO) 7.78–7.74 (m, 4H), 7.48–7.44 (m, 3H), 7.40–7.36 (t, J=7.3, 1H), 5.3 (br s, 1H), 3.80 (br q, 2H), 3.68 (br t, 2H), 3.50 (m, 2H), 3.39 (br t, 2H), 2.76 (s, 3H); MS ($^+$ESI, M+H$^+$) m/z 368; HPLC: 94.7% (220 nm); HRMS calcd for C$_{19}$H$_{21}$ON$_5$S: 367.1467; found 367.1475

EXAMPLE 470

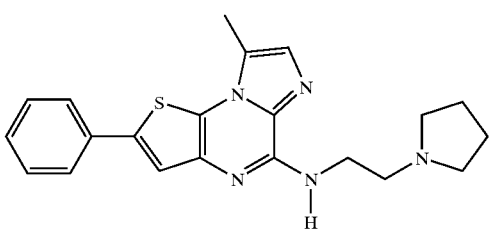

Compound 470 was prepared from intermediate 458E and 1-(2-aminoethyl)pyrrolidine using Step F (method 1), described in the synthesis of Example 458. The desired compound was retrieved as a light yellow solid (13%); mp 115° C.; IR (KBr, cm$^{-1}$) 3395, 2959, 2788, 1558, 1540; $^1$H NMR (DMSO) 7.79–7.76 (m, 3H), 7.48–7.44 (m, 2H), 7.38–7.34 (m, 2H), 7.18 (br t, 1H), 3.62 (br q, 2H), 2.74 (br s, 5H), 2.56–2.44 (br m, 3H), 1.72–1.66 (br m, 5H), 2.76 (s, 3H); MS (+ESI, M+H+) m/z 378; HPLC: 97.1% (220 nm); HRMS calcd for $C_{21}H_{23}N_5S$: 377.1674; found 377.1665

EXAMPLE 471

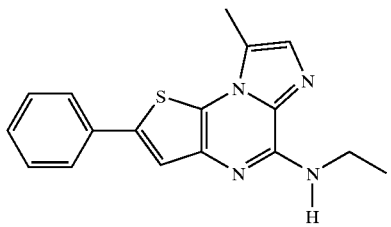

471

Compound 471 was prepared from intermediate 458E and ethylamine using Step F (method 1), described in the synthesis of Example 458. The desired compound was retrieved as a white solid (48%); mp 205° C.; IR (KBr, cm$^{-1}$) 3352, 2964, 2927, 1554, 1422; $^1$H NMR (DMSO) 7.78–7.76 (m, 3H), 7.48–7.44 (m, 2H), 7.42–7.34 (m, 3H), 3.53 (q d, J=5.6, 7.1 2H), 2.74 (s, 3H), 1.23 (t, J=7.06 3H); MS (+ESI, M+H+) m/z 309; HPLC: 99.2% (220 nm); HRMS calcd for $C_{17}H_{16}N_4S$: 308.1096; found 308.1088

EXAMPLE 472

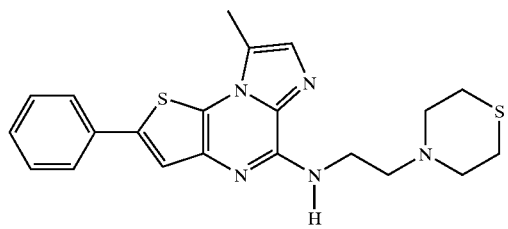

472

Compound 472 was prepared from intermediate 458E and 1-(2-aminoethyl)thiomorpholine using Step F (method 1), described in the synthesis of Example 458. The desired compound was retrieved as a light yellow solid (64%); mp 169–72° C.; IR (KBr, cm$^{-1}$) 3399, 2911, 2809, 1541, 1398; $^1$H NMR (DMSO) 7.78–7.75 (m, 3H), 7.48–7.44 (m, 2H), 7.38–7.34 (m, 2H), 7.18 (t, J=5.6, 1H) 3.60 (br q, 2H), 2.77–2.74 (m, 7H), 2.67–2.61 (m, 6H); MS (+ESI, M+H+) m/z 410; HPLC: 93.0% (220 nm); HRMS calcd for $C_{17}H_{16}N_4S$: 410.1473; found 410.1466

EXAMPLE 473

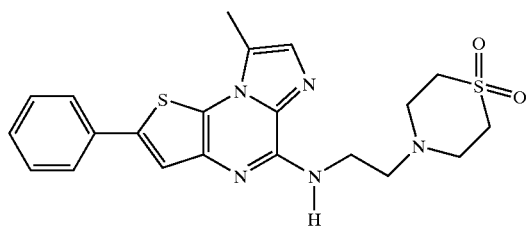

473

To the compound of example 472 (26 mg, 0.0634 mmol) in CH$_2$Cl$_2$ (2 mL) at −15° C. was added dropwise a peracetic acid solution in acetic acid (0.1M, 1.90 mL, 0.190 mmol). After 10 min. the reaction mixture was warmed up to 0° C. and strired 30 min. Then, a solution of dimethylsulfure in CH$_2$Cl$_2$ (1M, 0.064 mmol) was added and solvents were evaporated in vacuo. The crude material in DMF (2 mL) was treated with a basic resin (MP-Carbonate, 2.0 g) for two h. The resin was removed by filtration and DMF evaporated in vacuo. The crude material was crystallized in hot isopropanol to afford the desired product as a light beige solid (20%); mp 203–205° C.; IR (KBr, cm$^{-1}$) 3420, 2931, 1566, 1539, 1007; $^1$H NMR (MeOD) 7.70 (d, J=7.2, 2H), 7.56 (s, 1H), 7.43 (dd,J=7.7, 7.2, 2H), 7.33 (m, 2H), 4.21–4.15 (m, 3H), 3.79 (t, 6.5, 2H), 3.63–3.55(m, 2H), 3.25(m, 2H), 3.03 (m, 2H), 2.76 (s, 3H); MS (+ESI, M+H+) m/z 442; HPLC: 95.2% (220 nm); HRMS calcd for $C_{21}H_{23}N_5O_2S_2$: 442.1371; found 442.1378.

EXAMPLE 474

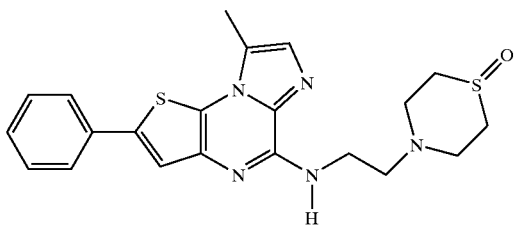

474

To the compound of example 472 (26 mg, 0.0634 mmol) in CH$_2$Cl$_2$ (2 mL) at −15° C. was added dropwise a peracetic acid solution in acetic acid (0.1M, 0.64 mL, 0.064 mmol). After 10 min. the reaction mixture was warmed up to 0° C. and strired 30 min. Then, a solution of dimethylsulfide in CH$_2$Cl$_2$(1M, 0.064 mmol) was added and solvents were evaporated in vacuo. The crude material in DMF (2 mL) was treated with a basic resin (MP-Carbonate, 2.0 g) for two h. The resin was removed by filtration and DMF evaporated in vacuo. The crude material was crystallized from hot isopropanol to afford the desired product as a light beige solid. (46%); mp 171–174° C.; IR (KBr, cm$^{-1}$) 3421, 2921, 1558, 1540, 1029; $^1$H NMR (DMSO) 7.79–7.75 (m, 3H), 7.47–7.44 (m, 2H), 7.38–7.34 (m, 2H), 7.24 (t, J=6.0, 1H), 3.63 (td, J=6.4, 6.0. 2H), 3.01–2.86 (m, 4H), 2.79–2.68 (m, 9H); MS (+ESI, M+H+) m/z 426; HPLC: 94.7% (220 nm); HRMS calcd for $C_{21}H_{23}N_5OS_2$: 426.1422; found 426.1426.

EXAMPLE 475

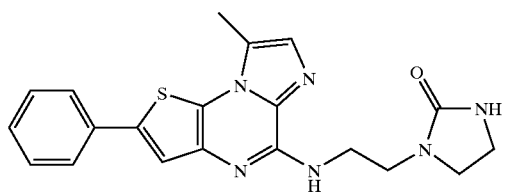

475

Compound 475 was prepared from intermediate 458E and 1-(2-aminoethyl)imidazolidin-2-one using Step F (method 1), described in the synthesis of Example 458. The desired compound was retrieved as a light-yellow solid (39%); mp 193–195° C.; IR (KBr, cm$^{-1}$) 3271, 1684, 1559, 1275; $^1$H NMR (DMSO) 7.79–7.76 (m, 3H), 7.48–7.42 (m, 3H), 7.37–7.34 (m, 2H), 6.25 (s, 1H), 3.60 (br q, 2H), 3.49–3.45 (br t, 2H), 3.38–3.34 (m, 2H), 3.28–3.19 (m, 2H), 2.74 (s, 3H); MS (+ESI, M+H+) m/z 493; HPLC: 95.0% (220 nm); HRMS calcd for $C_{20}H_{20}N_6OS$: 392.1419; found 392.1434

EXAMPLE 476

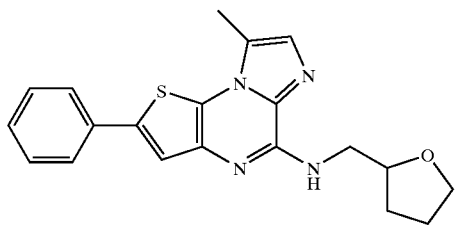

Compound 476 was prepared from intermediate 458E and tetrahydrofurfurylamine using Step F (method 1), described in the synthesis of Example 458. The desired compound was retrieved as a light-yellow solid (56%); mp 169° C.; IR (KBr, cm$^{-1}$) 3264, 2965, 1556, 1078; $^1$H NMR (DMSO) 7.79–7.77 (m, 3H), 7.48–7.44 (m, 2H), 7.39–7.34 (m, 2H), 7.17 (t, J=6.2, 1H), 4.17(m, 1H), 3.82 (br q, 1H), 3.69–3.52 (m, 3H), 2.74 (s, 3H), 1.96–1.66 (m, 4H); MS ($^+$ESI, M+H$^+$) m/z 365; HPLC: 93.1% (220 nm); HRMS calcd for C$_{20}$H$_{20}$N$_4$OS: 364.1358; found 364.1358

EXAMPLE 477

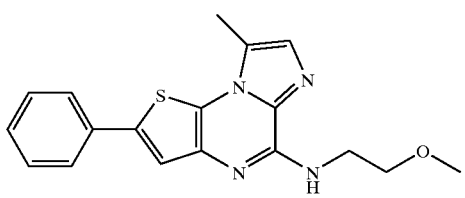

Compound 477 was prepared from intermediate 458E and 2-methoxyethylamine using Step F (method 1), described in the synthesis of Example 458. The desired compound was retrieved as a light-yellow solid (49%); mp 185° C.; IR (KBr, cm$^{-1}$) 3264, 2923, 1559, 1119; $^1$H NMR (DMSO) 7.78–7.77 (m, 3H), 7.48–7.44 (m, 2H), 7.38–7.34 (m, 2H), 7.17 (t, J=5.6, 1H) 3.68 (br q, 2H), 3.59 (br t, 2H), 3.31(s, 3H), 2.74 (s, 3H); MS ($^+$ESI, M+H$^+$) m/z 339; HPLC: 94.9% (220 nm); HRMS calcd for C$_{18}$H$_{18}$N$_4$OS: 338.1201; found 338.1208

EXAMPLE 478

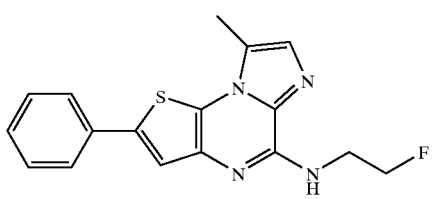

Compound 478 was prepared from intermediate 458E and 2-fluoroethylamine using Step F (method 2), described in the synthesis of Example 458. The desired compound was retrieved as a beige solid (22%); mp 189° C.; IR (KBr, cm$^{-1}$) 3384, 2923, 1547, 1404, 1034; $^1$H NMR (DMSO) 7.79–7.77 (m, 3H), 7.56 (t, J=5.8, 1H), 7.48–7.44 (m, 2H), 7.41–7.36 (m, 2H), 4.66 (dt, J=47.6, 5.6, 2H), 3.82(d q, J=24.2, 5.4, 2H), 2.74 (s, 3H); MS ($^+$ESI, M+H$^+$) m/z 327; HPLC: 95.4% (220 nm); HRMS calcd for C$_{17}$H$_{15}$FN$_4$S: 327.1079; found 327.1082

EXAMPLE 479

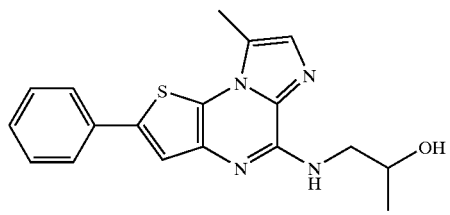

Compound 479 was prepared from intermediate 458E and DL-1-amino-2-propanol using Step F (method 1), described in the synthesis of Example 458. The desired compound was retrieved as a beige solid (59%); mp 225° C.; IR (KBr, cm$^{-1}$) 3377, 2961, 2916, 1540, 1420, 1144; $^1$H NMR (DMSO) 7.78–7.77 (d, J=7.14, 2H), 7.74 (s, 1H), 7.48–7.45 (m, 2H), 7.39–7.34 (m, 2H), 7.11 (t, J=5.6, 1H), 4.92 (d, J=3.55 1H), 3.53 (m, 1H), 3.40 (m, 1H), 3.37 (m, 1H), 2.75 (s, 3H); MS ($^+$ESI, M+H$^+$) m/z 339; HPLC: 97.5% (220 nm); HRMS calcd for C$_{18}$H$_{18}$N$_4$OS: 339.1279; found 339.1286

EXAMPLE 480

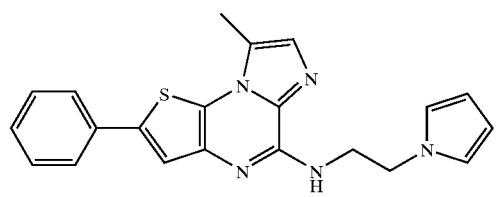

Compound 480 was prepared from intermediate 458E and 2(1H-pyrrol-1-yl)-1-ethanamine using Step F (method 1), described in the synthesis of Example 458. The desired compound was retrieved as a ligth brown solid (48%); IR (KBr, cm$^{-1}$) 3314, 2941, 1558, 1540, 1088; $^1$H NMR (DMSO) 7.79–7.77 (m, 3H), 7.48–7.45 (m, 3H), 7.38–7.34 (m, 2H), 6.80 (d, J=2,2, 2H), 5.99(d, J=2.2 2H), 4.22 (t, J=6.3, 2H), 3.82 (td, J=6.1, 5.9, 2H), 2.75 (s, 3H); MS ($^+$ESI, M+H$^+$) m/z 374; HPLC: 95.5% (220 nm); HRMS calcd for C$_{21}$H$_{19}$N$_5$S: 374.1437; found 374.1439

EXAMPLE 481

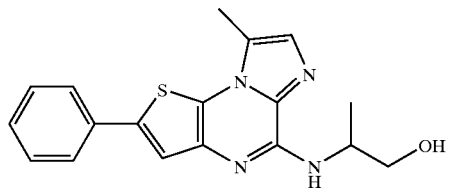

Compound 481 was prepared from intermediate 458E and DL-2-amino-1-propanol using Step F (method 1), described in the synthesis of Example 458. The desired compound was retrieved as a beige solid (38%); mp 175° C.; IR (KBr, cm$^{-1}$) 3395, 2973, 1546, 1424, 1095; $^1$H NMR (DMSO) 7.78–7.76 (m, 3H), 7.48–7.45 (m, 2H), 7.38–7.34 (m, 2H), 6.87 (d, J=7.9, 1H), 4.85 (t, J=5.5 1H), 4.31(m, 1H), 3.57 (m, 1H), 3.52 (m, 1H), 2.74 (s, 3H); LC/MS 90% (220 nm), m/z (M+H$^+$) 339

EXAMPLE 482

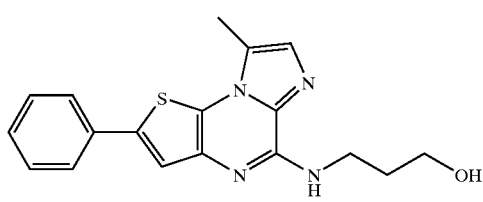

Compound 482 was prepared from intermediate 458E and 3-amino-1-propanol using Step F (method 1), described in the synthesis of Example 458. The desired compound was retrieved as a beige solid (46%); IR (KBr, cm$^{-1}$) 3304, 2935, 2909, 1589, 1570, 1421; $^1$H NMR (DMSO) 7.78–7.76 (d, J=7.0, 2H), 7.75 (s, 1H), 7.48–7.44 (m, 2H), 7.42–7.33 (m, 3H), 4.60(t, J=5.3, 1H), 3.59–3.51 (m, 4H), 2.74 (s, 3H), 1.84–1.78 (m, 2H); MS ($^+$ESI, M+H$^+$) m/z 339; HPLC: 95.7% (220 nm); HRMS calcd for $C_{18}H_{18}N_4OS$: 339.1280; found 339.1278

EXAMPLE 483

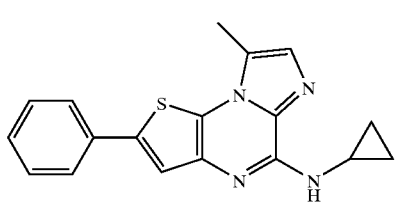

Compound 483 was prepared from intermediate 458E and cyclopropylamine using Step F (method 1), described in the synthesis of Example 458. The desired compound was retrieved as a beige solid (50%); IR (KBr, cm$^{-1}$) 3292, 3003, 1539, 1422; $^1$H NMR (DMSO) 7.73 (s, 1H), 7.70 (d, J=6.9, 2H), 7.46 (d, J=3.3, 1H), 7.40–7.36 (m, 2H), 7.29–7.25 (m, 2H), 2.90–2.86 (m, 1H), 2.66 (s, 3H), 0.70–0.58 (m, 4H); MS ($^+$ESI, M+H$^+$) m/z 321; HPLC: 98.0% (220 nm); HRMS calcd for $C_{18}H_{16}N_4S$: 321.1174; found 321.1177

EXAMPLE 484

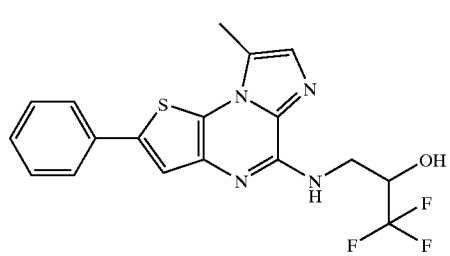

Compound 484 was prepared from intermediate 458E and 3-amino-1,1,1-trifluoro-2-propanol using Step F (method 1), described in the synthesis of Example 458. The desired compound was retrieved as a beige solid (33%); IR (KBr, cm$^{-1}$) 3391, 3078, 2851, 1541, 1423, 1166, 1130; $^1$H NMR (DMSO) 7.78 (d, J=7.0, 1H), 7.77 (s, H), 7.48–7.34 (m, 5H), 6.52 (d, J=5.8, 1H), 4.49–4.42(m, 1H), 3.88–3.83 (m, 1H), 3.66–3.60(m, 1H), 2.75 (s, 1H); LC/MS 98.2% (220 nm), m/z (M+H$^+$) 393

EXAMPLE 485

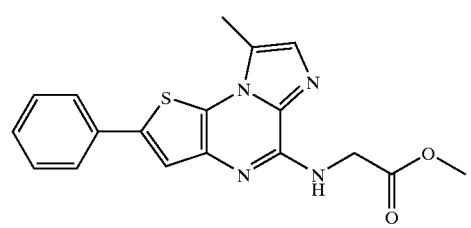

Compound 485 was prepared from intermediate 458E and glycine methy ester hydrochloride using Step F (method 2), described in the synthesis of Example 458. The desired compound was retrieved as a light yellow solid (24%); IR (KBr, cm$^{-1}$) 3421, 3268, 2923, 1747, 1559, 1540, 1208; $^1$H NMR (DMSO) 7.79–7.76 (m, 4H), 7.48–7.43 (m, 3H), 7.38 (br t, 1H), 4.25 (d, J=6.1, 2H), 3.64 (s, 3H), 2.76 (s, 3H); MS ($^+$ESI, M+H$^+$) m/z 353; HPLC: 90.5% (220 nm); HRMS calcd for $C_{18}H_{16}N_4O_2S$: 353.1082; found 353.1072.

EXAMPLE 486

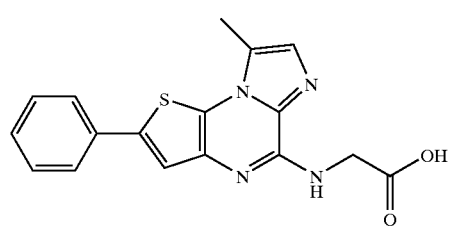

Compound 486 was prepared from the compound of Example 485 (12 mg, 0.034 mmol), which was treated with a solution of KOH (19 mg, 0.34 mmol) in MeOH:H$_2$O (0.5 mL:0.5 mL) for 2 h at 23 C. Then, the reaction mixture was purified by preparative HPLC using C18 column to afford the desired product as a beige solid (45%); IR (KBr, cm$^{-1}$) 3407, 1558, 1437; $^1$H NMR (DMSO) 7.78–7.76 (m, 3H), 7.47–7.43 (m, 2H), 7.39–7.33 (m, 2H), 3.91–3.89 (br d, 2H), 2.75 (s, 3H); LC/MS 93.3% (220 nm), m/z (M+H$^+$) 339.

EXAMPLE 487

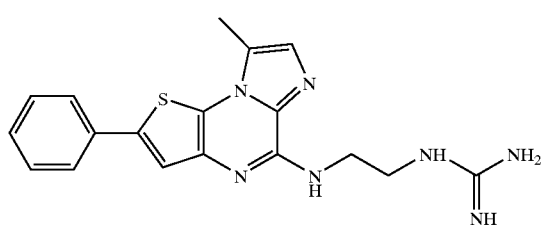

2 TFA

To a solution of the compound of Example 9 (55 mg, 0.170 mmol) in THF:H$_2$O (15 mL:1 mL) at 23° C. was added 1,3-Bis(t-butoxycarbonyl)-2-methyl-2-thiopseudourea (54 mg, 0.187 mmol). The reaction rmixture was stirred at 23° C. for 96 h and at 60° C. for 4 h. Then, H$_2$O was added and the organic material was extracted with AcOEt:THF (4:1) (3×15 mL). The combined organic solutions was dried (MgSO4) concentrated and purified preparative HPLC using C18 column. Elution solvents were evaporated and the organic solid was dissolved in CH$_2$Cl$_2$ (2 mL). The solution was cooled to 0° C. and TFA (1 mL) was added. The reaction mixture was stirred at 23° C. for 18 h and solvents were evaporated in vacuo to afford the TFA salt of the desired product as a light yellow solid (51%); IR (KBr, cm$^{-1}$) 3377, 1677, 1437, 1203, 1135; $^1$H NMR (DMSO) 7.77 (d, J=7.1, 2H), 7.74 (s, 1H), 7.69 (br t,1H), 7.56 (br t, 1H),7.49 (br t, 2H),7.43 (s, 1H), 7.38 (m,1H), 3.64 (td, J=6.0,6.2, 2H), 3.42 (td, J=6.0, 6.1, 2H), 2.76 (s, 3H); MS ($^+$ESI, M+H$^+$) m/z 366; HPLC: 94.7% (220 nm); HRMS calcd for C$_{18}$H$_{19}$N$_7$S: 365,1423; found 365.1455.

EXAMPLE 488

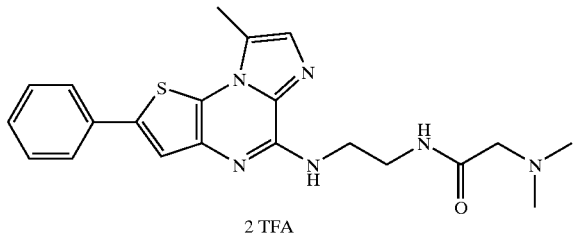

488

2 TFA

To a solution of N,N-dimethylamine glycine hydrochloride in DMF was added 1,3-diisopropylcarbodiimide (73 μL, 0.464 mmol), hydroxybenzotriazole (63 mg, 0.464 mmol), 4-dimethylaminopyridine (4 mg, 0.0309 mmol), N,N-diisopropylethylamine (28 μL, 0.309 mmol) and the compound of Example 9 (100 mg, 0.309 mmol). The reaction mixture was stirred at 23° C. for 18 h. The reaction mixture was poured into a SPE-SCX column and was eluted with a solution of ammonia in methanol (2N, 40 mL). Solvent was evaporated in vacuo and crude material was purified on preparative HPLC with a C18 column using acidic conditions to afford the TFA salt of the desired product as a light yellow glassy compound (15%); IR (KBr, cm$^{-1}$) 3431, 1653, 1559, 1203, 1129; $^1$H NMR (DMSO+D$_2$O) 8.62 (t, J=5.5, 1H), 7.75 (d, J=7.5, 2H), 7.68 (s, 1H), 7.47 (dd, J=7.7, 7.6, 2H), 7.40–7.35 (m, 2H), 3.84 (s, 2H), 3.60 (m, 2H), 3.48–3.46 (m, 2H), 2.77 (s, 6H), 2.73 (s, 3H); MS ($^+$ESI, M+H$^+$) m/z 409; HPLC: 96% (220 nm); HRMS calcd for C$_{21}$H$_{24}$N$_6$OS: 409.1811; found 409.1804.

EXAMPLE 489

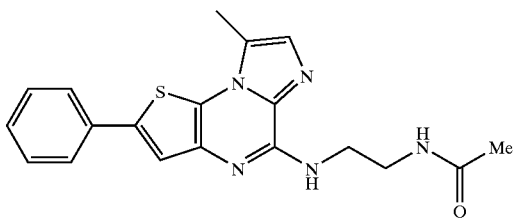

489

To a solution of the compound of Example 9 (60 mg, 0.186 mmol) in THF (3 mL) at 23° C. was added triethylamine (78 μL, 0.223 mmol) and acetylchloride (16 μL, 23 mmol ). The reaction mixture was stirred at 23° C. for 18 h. Then, solvent was evaporated in vacuo and a sodium bicarbonate saturated solution was added (10 mL). Organic material was extracted with AcOEt:THF (4:1) (3×10 mL). Organic solution were combined dried (MgSO$_4$) and concentrated in vacuo.The crude material was purified by crystallization in hot isopropanol (3 mL). to afford the desired product as awhite solid (23%); IR (KBr, cm$^{-1}$) 3297, 3078, 2928, 1635, 1559, 1363; $^1$H NMR (DMSO+D$_2$O) 8.01 (t, J=5.3, 1H), 7.77 (d, J=7.2, 2H), 7.74 (s, 1H), 7.47 (m, 2H), 7.38–7.34 (m, 2H), 3.57 (br td, 2H), 3.35 (br td, 2H), 2.74 (s, 3H), 1.83 (s, 3H) LC/MS 95.4% (220 nm), m/z (M+H$^+$) 366.

EXAMPLE 490

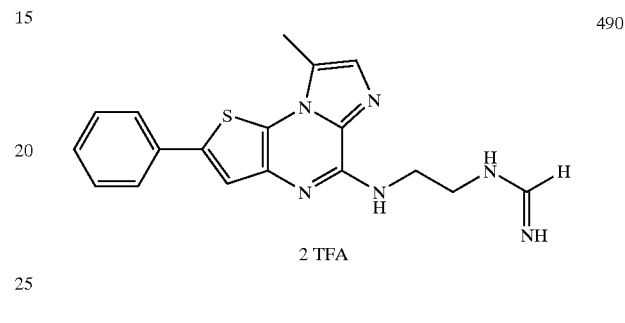

490

2 TFA

To a solution of the compound of Example 9 (75 mg, 0.232 mmol) in ethanol (3 mL) at 23° C. was added N,N-diisopropylethylamine (38 μL, 0.417 mmol) and formamidine acetate (43 mg, 0.417 mmol). The reaction mixture was stirred at 23° C. for 18 h. Then, solvent was evaporated in vacuo and the crude material was purified by preparative HPLC using C18 column in acidic conditions to afford the TFA salt of the desired product as a light yellow solid (13%); IR (KBr, cm$^{-1}$) 3420, 3058, 1683, 1652, 1559, 1436, 1203, 1131; $^1$H NMR (DMSO+D$_2$O) 7.72–7.61 (m, 4H), 7.44–7.30 (m, 4H), 3.70–3.48 (br m, 4H), 2.69 (s, 3H); LC/MS 90% (220 nm), m/z (M+H$^+$) 351.

EXAMPLE 491

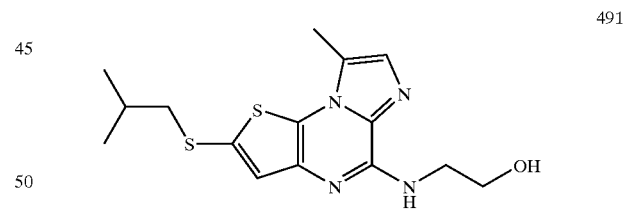

491

To 2-methyl-1-propanethiol (138 μL, 1.27 mmol) and KOH (89 mg, 1.59 mmol) in DMF (3 mL) was added compound 276G (95 mg, 0.318 mmol). The reaction mixture was stirred at 75° C. in a sealed tube for six h. Then solvent was evaporated in vacuo and the crude material was purified on silicagel dry column using CH$_2$Cl$_2$:MeOH (99:1) to (90:10) to afford compound 491 as an orange oil (10%); IR (KBr, cm$^{-1}$) 3377, 2956, 1559, 1540, 1404; $^1$H NMR (MeOD) 7.34 (s, 1H), 7.31 (s, 1H), 3.84 (t, J=5.5 2H), 3.72 (t, J=5.5, 2H), 2.81 (d, J=7.1, 2H), 2.74 (s, 3H), 1.89 (m, 1H), 1.06 (d, J=7.1, 6H); MS ($^+$ESI, M+H$^+$) m/z 337; HPLC: 90% (220 nm); HRMS calcd for C$_{15}$H$_{20}$N$_4$OS$_2$:337.1157; found 337.1155.

EXAMPLE 492

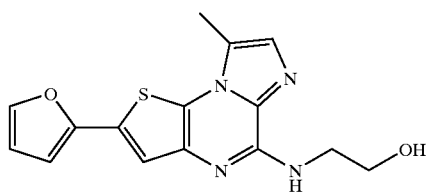

To compound 276G (85 mg, 0.26 mmol) in NMP (1.5 mL) was added 2-(tributylstannyl)furan (139 mg, 0.39 mmol), tris(dibenzylideneacetone)dipalladium (0) (24 mg, 0.026 mmol) and triphenylarsine (11.9 mg, 0.039 mmol) The reaction mixture was stirred at 90° C. in a sealed tube for four h.Then solvent was evaporated in vacuo and the crude material was purified on silicagel dry column using $CH_2Cl_2$:MeOH (99:1) to (90:10) to afford compound 492 as a beige solid (24%); IR (KBr, $cm^{-1}$) 3361, 2977, 2919, 2853, 1558, 1540, 11360; $^1$H NMR (DMSO) 7.76 (br m, 1H), 7.53 (s, 1H), 7.38 (s, 1H), 7.25 (t, J=5.5, 1H), 6.92 (d, J=4.1, 1H), 6.65 (m, 1H), 4.82 (br s, 1H), 3.64–3.55 (m, 4H), 2.72 (s, 3H); MS ($^+$ESI, M+H$^+$) m/z 337; HPLC: 93% (220 nm); HRMS calcd for $C_{15}H_{14}N_4O_2S$: 315.0916; found 315.091 1.

EXAMPLE 493

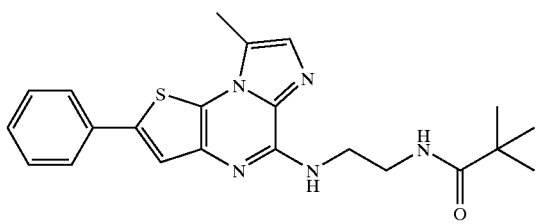

A solution of the compound of Example 9 (0.102 g, 0.315 mmol) in tetrahydrofuran (3 mL) was treated with triethylamine (0.16 mL, 1.11 mmol) and trimethylacetyl chloride (47 μL, 0.38 mmol) at 0° C. The reaction was stirred at room temperature for 1 h, then quenched with water and diluted with dichloromethane. The organic layer was washed with water and brine then dried over anhydrous magnesium sulfate, filtered and concentrated. The residue was purified by flash chromatography to give compound 493 (0.059 g, 46%); IR (KBr, $cm^{-1}$) 1636, 1560, 1540; $^1$H NMR (DMSO-d6) 7.77–7.75 (m, 2H), 7.72 (s, 1H), 7.63 (m, 1H), 7.47–7.43 (m, 3H), 7.37–7.33 (m, 2H), 3.58–3.55 and 3.37–3.35 (m, 2H), 2.73 (s, 3H), 1.06 (s, 9H); MS ($^+$ESI, M+H$^+$) m/z 408; HPLC: 98% (220 nm); HRMS calcd for $C_{22}H_{26}N_5O_1S_1$: 408.1858; found 408.1862.

EXAMPLE 494–505

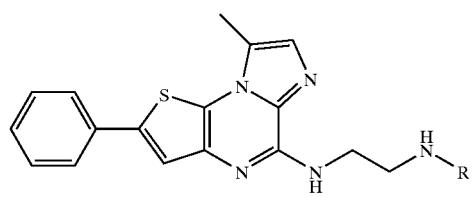

These compounds, where R is described in the table below, were prepared from the compound of Example 9 according to the procedure described for Example 493.

| Ex | R | HPLC Ret. time (min)[a] | Purity % | MS (e/z) (M + H)$^+$ |
|---|---|---|---|---|
| 494 | -S(O$_2$)-phenyl | 5.14 | 96 | 464 |
| 495 | -S(O$_2$)-C$_6$H$_4$-F (para) | 5.36 | 93 | 482 |
| 496 | -S(O$_2$)-C$_6$H$_4$-CF$_3$ (meta) | 5.97 | 92 | 532 |
| 497 | -S(O$_2$)-C$_6$H$_4$-OMe (para) | 5.17 | 98 | 494 |
| 498 | -S(O$_2$)-Me | 4.27 | 98 | 402 |
| 499 | -S(O$_2$)-NMe$_2$ | 4.70 | 99 | 431 |
| 500 | -C(O)-phenyl | 5.15 | 95 | 428 |
| 501 | -C(O)-C$_6$H$_4$-CF$_3$ | 5.94 | 95 | 496 |
| 502 | -C(O)-C$_6$H$_4$-OMe | 5.26 | 95 | 458. |
| 503 | -C(O)-CF$_3$ | 5.22 | 98 | 420 |
| 504 | -C(O)-NMe$_2$ | 4.44 | 99 | 395 |
| 505 | 2-pyrimidinyl | 4.10 | 90 | 402 |

EXAMPLE 506

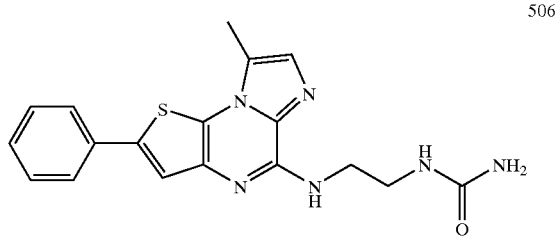

A solution of the compound of Example 9 (35 mg, 0.108 mmol) was dissolved in dry THF (1 ml) and trimethylsilyl isocyanate (44 µL, 0.325 mmol) was added. The reaction mixture was stirred in a sealed tube at 65° C. for 48 h. Then THF was evaporated in vacuo and the crude material was purified by preparative HPLC with a C18 column using NH$_4$OAc conditions to afford compound 506 as a light yellow glass.(22%); IR (KBr, cm$^{-1}$) 3412, 1683, 1653,1559, 1429, 1202; $^1$H NMR (MeOD) 7.74 (m, 2H), 7.67 (s, 1H), 7.52 (m, 1H), 7.44 (m, 3H), 3.76 (t,J=6.6, 2H), 3.51 (t,J=6.6, 2H), 2.85 (s, 3H), MS ($^+$ESI, M+H$^+$) m/z 367; HPLC: 91% (220 nm); HRMS calcd for C$_{18}$H$_{18}$N$_6$OS: 367.13411; found 367.13431.

EXAMPLE 507

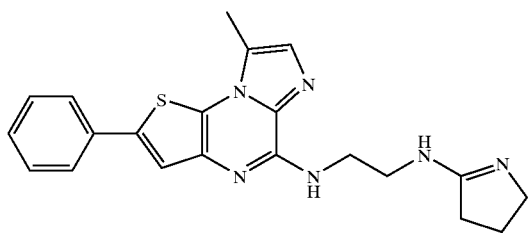

A solution of the compound of Example 9 (35 mg, 0.108 mmol) was dissolved in DMSO (1 ml) and 5-ethoxy-3,4-dihydro-2H-pyrrole (122 mg, 1.08 mmol) (Synthetic Comm. 18(14), pp 2625–1636 (1988)) was added. The reaction mixture was stirred in a sealed tube at 95° C. for 48 h. Then, DMSO was evaporated in vacuo and the crude material was purified by preparative HPLC with a C18 column using TFA conditions to afford compound 507 as a light brown glass (50%); IR (KBr, cm$^{-1}$) 3202, 3064, 1683, 1430, 1200; $^1$H NMR (MeOD) 7.78 (d,J=7.1, 2H), 7.59 (s, 1H), 7.49 (m, 3H), 7.41 (m, 1H), 3.93 (t,J=6.1, 2H), 3.80 (t,J=7, 2H), 3.68 (t,J=6.1, 2H), 2.89 (t,J=8.1, 2H), 2.85 (s, 3H), 2.25 (m, 2H); MS ($^+$ESI, M+H$^+$) m/z 391; HPLC: 92% (220 nm); HRMS calcd for C$_{21}$H$_{22}$N$_6$S: 391.17049; found 391.17128.

EXAMPLE 508

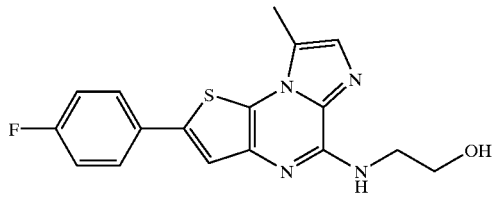

A stirred solution of compound 276G (0.090 g, 0.28 mmoles) in N-methylpyrrolidinone (2 mL) was treated with tributyl-(4-fluoro-phenyl)-stannane (0.162 g, 0.42 mmol), tris-dibenzylideneacetone dipalladium (26 mg) and triphenylarsine (13 mg). The reaction was heated at 90° C. for 18 h. The cold mixture was placed on a SCX colunm, washed with MeOH and then with a 2M solution of NH$_3$ in MeOH to recover the crude product. This crude material was purified by preparative HPLC with a C18 column to afford compound 508 as a yellow solid.(0.018 g, 19%); IR (KBr, cm$^{-1}$) 3358, 3182, 1552; $^1$H NMR (DMSO-d6) 7.82–7.78 (m, 2H), 7.71 (s, 1H), 7.36 (s, 1H), 7.28 (t, J=8.8, 2H), 7.21 (t, 1H), 4.81 (t,J=5.3, 1H), 3.64–3.61 and 3.58–3.56 (m, 2H), 3.68 (t,J=6.1, 2H), 2.72 (s, 3H); MS ($^+$ESI, M+H$^+$) m/z 343; HPLC: 100% (220 nm); HRMS calcd for C$_{17}$H$_{16}$N$_4$O$_1$F$_1$S$_1$: 343.1029; found 343.1040.

EXAMPLE 509

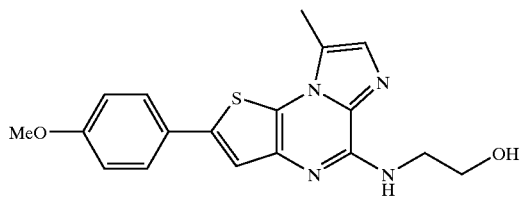

A stirred solution of compound 276 G (0.087 g, 0.27 mmoles) in N-methylpyrrolidinone (2 mL) was treated with tributyl-(4-methoxy-phenyl)-stannane (0.163 g, 0.41 mmol), tris-dibenzylideneacetone dipalladium (25 mg) and triphenylarsine (13 mg). The reaction was heated at 90° C. for 18 h. The cold mixture was placed on a SCX colunm, washed with MeOH and then with a 2M solution of NH$_3$ in MeOH to recover the crude product. This crude material was purified by preparative HPLC with a C18 column to afford compound 509 as a white solid.(0.055 g, 57%); IR (KBr, cm$^{-1}$) 3355, 1554, 1506, 1255; $^1$H NMR (DMSO-d6) 7.68 (d, J=8.8, 2H), 7.58 (s, 1H), 7.35 (s, 1H), 7.17 (t, J=5.4, 1H), 7.01 (d, J=8.8, 2H), 4.81 (t, J=5.3, 1H), 3.79 (s, 3H), 3.65–3.61 and 3.58–3.54 (m, 2H), 3.68 (s, 3H), 2.71 (s, 3H); MS ($^+$ESI, M+H$^+$) m/z 355; HPLC: 100% (220 nm); HRMS calcd for C$_{18}$H$_{19}$N$_4$O$_2$S$_1$: 355.1229; found 355.1233.

EXAMPLE 510

510

A stirred solution of the compound of Example 509 (0.044 g, 0.124 mmoles) in dichloromethane (10 mL) at −78° C. was treated with a 1M solution of BBr$_3$ in dichloromethane (0.75 mL, 0.74 mmol) and the mixture was warmed to room temperature. After stirring for 4 hrs at room temperature, the reaction mixture was then cooled to −78° C. MeOH (3 mL) was added and the mixture was warmed to room temperature and concentrated. This crude material was purified by preparative HPLC with a C18 column to afford compound 510 as a yellow solid.(0.022 g, 52%); IR (KBr, cm$^{-1}$) 3358, 3117, 1554, 1280; $^1$H NMR (DMSO-d6) 9.72 (s, 1H), 7.56 (d, J=8.6, 2H), 7.49 (s, 1H), 7.35 (s, 1H), 7.17 (s, 1H), 6.83 (d, J=8.6, 2H), 4.80 (br s, 1H), 3.64–3.61 and 3.58–3.55 (m, 2H), 2.70 (s, 3H); MS ($^+$ESI, M+H$^+$) m/z 341; HPLC: 97% (220 nm); HRMS calcd for C$_{17}$H$_{17}$N$_4$O$_2$S$_1$: 341.1072; found 341.1067.

We claim:

1. A compound of formula (I)

(I)

enantiomers, diastereomers, and pharmaceutically-acceptable salts thereof, wherein R$_1$, R$_2$, and R$_3$ are independently selected from hydrogen, halogen, alkyl, and perfluoroalkyl;

R$_4$ is —(CR$_5$R$_6$)$_m$-Z or -(cycloalkyl)-Z;

R$_5$, R$_{5a}$, R$_6$ and R$_{6a}$ at each occurrence are independently selected from hydrogen, alkyl, substituted alkyl, amino, alkylamino, substituted alkylamino, hydroxy, alkoxy, substituted alkoxy, cycloalkyl, heterocycle, aryl, and heteroaryl;

R$_7$ at each occurrence is selected independently of each other R$_7$ from alkyl, substituted alkyl, alkenyl, substituted alkenyl, halogen, cyano, —(CR$_{5a}$R$_{6a}$)$_q$—OR$_{8a}$, —(CR$_{5a}$R$_{6a}$)$_q$—SR$_{8a}$, —(CR$_{5a}$R$_{6a}$)$_q$—SO$_2$R$_{10}$, —(CR$_{5a}$R$_{6a}$)$_q$—NR$_8$R$_9$, —(CR$_{5a}$R$_{6a}$)$_q$—NR$_8$SO$_2$, —(CR$_{5a}$R$_{6a}$)$_q$—NR$_8$SO$_2$R$_{10}$, —(CR$_{5a}$R$_{6a}$)$_q$—SO$_2$NR$_8$R$_9$, —(CR$_{5a}$R$_{6a}$)$_q$—NR$_{8a}$C(=O)R$_{9a}$, —(CR$_{5a}$R$_{6a}$)$_q$—NR$_{8a}$CO$_2$R$_{9a}$, —(CR$_{5a}$R$_{6a}$)$_q$—C(=O)R$_{8a}$, —(CR$_{5a}$R$_{6a}$)$_q$—CO$_2$R$_{8a}$, —(CR$_{5a}$R$_{6a}$)$_q$—OC(=O)R$_{8a}$, —(CR$_{5a}$R$_{6a}$)$_q$—C(=O)NR$_8$R$_9$, —(CR$_{5a}$R$_{6a}$)$_q$—CO$_2$NR$_8$R$_9$, —(CR$_{5a}$R$_{6a}$)$_q$—OC(=O)NR$_8$R$_9$, —(CR$_{5a}$R$_{6a}$)$_q$—C(=O)NR$_{8a}$—NR$_8$R$_9$, —(CR$_{5a}$R$_{6a}$)$_q$—C(=O)NR$_{8a}$SO$_2$R$_{10}$, —(CR$_{5a}$R$_{6a}$)$_q$—NR$_{8a}$C(=O)NR$_8$R$_9$, —(CR$_{5a}$R$_{6a}$)$_q$—NR$_{8a}$SO$_2$NR$_8$R$_9$, —(CR$_{5a}$R$_{6a}$)$_q$—NR$_{8a}$C(=O)—C(=O)—NR$_8$R$_9$, —(CR$_{5a}$R$_{6a}$)$_q$—NR$_{8a}$C(=O)—CO$_2$R$_{9a}$, —(CR$_{5a}$R$_{6a}$)$_q$—N(SO$_2$R$_{10}$)(SO$_2$R$_{10a}$), —(CR$_{5a}$R$_{6a}$)$_q$—OSO$_2$NR$_8$R$_9$, cycloalkyl, (cycloalkyl)alkyl, heterocycle, (heterocyclo)alkyl, aryl, (aryl)alkyl, heteroaryl, and (heteroaryl)alkyl, or when A is heterocyclene or cycloalkylene, one of R$_7$ may be keto (=O), and when A is a bond, then R$_7$ may be hydrogen;

X is a bond, O, S, —NR$_{11}$—, —(CH$_2$)$_n$—, —CH=CH—, or —C≡C—;

A is a bond, arylene, heteroarylene, heterocyclene, or cycloalkylene;

Z is selected from hydrogen, methyl, OR$_{14}$, —C(=O)OR$_{14}$, —NR$_{12}$C(=O)R$_{13}$, —NHC(=NR$_{14a}$)R$_{15a}$, —NR$_{12}$CO$_2$R$_{13}$, —NR$_{12}$SO$_2$R$_{13}$, —C(=O)NR$_{14}$R$_{15}$, —NR$_{14}$R$_{15}$ and —NR$_{12}$—C(=O)NR$_{14}$R$_{15}$;

R$_8$ R$_{8a}$, R$_9$ and R$_{9a}$ are independently selected from hydrogen, alkyl, substituted alkyl, alkenyl, substituted alkenyl, cycloalkyl, (cycloalkyl)alkyl, heterocycle, (heterocylco)alkyl, aryl, (aryl)alkyl, heteroaryl, and (heteroaryl)alkyl;

or R$_8$ and R$_9$ together with the nitrogen atom to which they are bonded may combine to form a heterocyclo ring;

R$_{10}$ and R$_{10a}$ are independently alkyl, substituted alkyl, cycloalkyl, heterocycle, aryl, or heteroaryl;

R$_{11}$ is hydrogen, alkyl, aminoalkyl, or hydroxyalkyl;

R$_{12}$ is hydrogen or lower alkyl;

R$_{13}$ is hydrogen, alkyl, substituted alkyl, cycloalkyl, heterocyclo, aryl or heteroaryl;

R$_{14}$ R$_{14a}$, R$_{15}$ and R$_{15a}$ are independently selected from hydrogen, alkyl, substituted alkyl, cycloalkyl, (cycloalkyl)alkyl, heterocycle, (heterocylo)alkyl, aryl, (aryl)alkyl, heteroaryl, and (heteroaryl)alkyl;

or R$_{14}$ and R$_{15}$ together with the nitrogen atom to which they are bonded may combine to form a heterocyclo ring;

m and q are independently 0, 1, 2, 3, 4, 5 or 6;

n is 1 or 2; and p is 0, 1, 2, 3 or 4, except when A is a bond, then p is 1.

2. A compound according to claim 1 wherein

R$_1$ is selected from hydrogen, halogen, and C$_{1-4}$alkyl;

R$_2$ is hydrogen;

R$_3$ is hydrogen or lower alkyl;

R$_4$ is —(CH$_2$)$_m$-Z;

R$_7$ at each occurrence is selected independently of each other R$_7$ from hydrogen, cyano, trifluoromethyl, halogen, —(CR$_{5a}$R$_{6a}$)$_q$—OR$_{8a}$, —(CR$_{5a}$R$_{6a}$)$_q$—NR$_8$R$_9$, —(CR$_{5a}$R$_{6a}$)$_q$—C(=O)NR$_8$R$_9$, —(CR$_{5a}$R$_{6a}$)$_q$—C(=O)R$_{8a}$, —(CR$_{5a}$R$_{6a}$)$_q$—CO$_2$R$_{8a}$, —(CR$_{5a}$R$_{6a}$)$_q$—CO$_2$NR$_8$R$_9$, five to six-membered heterocycle or heteroaryl in turn optionally substituted with one to two R$_{19}$, and C$_{1-4}$alkyl optionally substituted with one to three of hydroxy, cyano, halogen, amino, —NH(C$_{1-4}$alkyl), —NH(C$_{1-4}$hydroxyalkyl), —NH(C$_{1-4}$aminoalkyl), —N(C$_{1-4}$alkyl)$_2$, —NH(C=O)H, —NH(C=O)(C$_{1-4}$alkyl), —NHSO$_2$(C$_{1-4}$alkyl), —C(=O)H, —C(=O)C$_{1-4}$alkyl, —C(=O)NH$_2$, —C(=O)NH(C$_{1-4}$alkyl), —C(=O)N(C$_{1-4}$alkyl)$_2$, —C(=O)(heterocycle), —CO$_2$H, —CO$_2$(C$_{1-4}$alkyl), and/or five to six membered heterocycle or heteroaryl in turn optionally substituted with one to two R$_{19}$; or when A is an heterocycle or cycloalkyl, one of R$_7$ may be keto (=O);

X is a bond;

Z is selected from hydrogen, methyl, hydroxy, —NH$_2$, —NH(C$_{1-4}$alkyl), —NHCO$_2$(C$_{1-4}$alkyl), and —N(C$_{1-4}$alkyl)$_2$;

R$_8$ and R$_9$ are independently selected from hydrogen, C$_{1-4}$alkyl, and C$_{1-4}$alkyl substituted with one to two of hydroxy, —NH$_2$, —NH(C$_{1-4}$alkyl), —N(C$_{1-4}$alkyl)$_2$, —CO$_2$(C$_{1-4}$alkyl), and/or five to six membered heterocycle or heteroaryl in turn optionally substituted with one to two R$_{20}$;

R$_{19}$ and R$_{20}$ at each occurrence are selected independently of each other R$_{19}$ and R$_{20}$ from the group consisting of C$_{1-4}$alkyl, halogen, cyano, nitro, trifluoromethyl, hydroxy, keto (=O), C$_{1-4}$alkoxy, C$_{1-4}$hydroxyalkyl, amino, —NH(C$_{1-4}$alkyl), and —N(C$_{1-4}$alkyl)$_2$;

m is 1, 2, 3, or 4; and p is 0, 1, 2, or 3.

3. A compound according to claim 1 in which R$_1$ is CH$_3$.

4. A compound according to claim 1 in which R$_2$ is hydrogen.

5. A compound according to claim 1 in which R$_3$ is hydrogen or C$_{1-4}$alkyl.

6. A compound according to claim 1 in which R$_4$ is —(CH$_2$)$_m$-Z and m is 1, 2, 3 or 4.

7. A compound according to claim 1 in which Z is hydrogen, methyl, hydroxy, —NH$_2$, —NH(C$_{1-4}$alkyl), —NHCO$_2$(C$_{1-4}$alkyl), or —N(C$_{1-4}$alkyl)$_2$.

8. A compound according to claim 1, or a pharmaceutically-acceptable salt, hydrate or prodrug thereof, in which A is selected from phenyl, pyridyl, pyrimidinyl, pyrazinyl, pyridazinyl, imidazolyl, pyrazolyl, thienyl, thiazolyl, furyl, pyrrolyl, pyranyl, triazolyl, tetrazolyl, quinolyl, isoquinolyl, dihydropyridyl, and

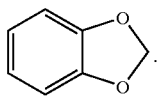

9. A compound according to claim 1, having the formula:

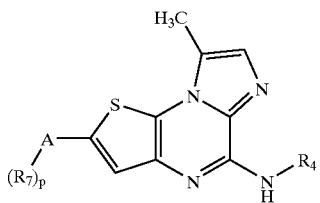

or a pharmaceutically-acceptable salt thereof.

10. A compound according to claim 9, or a pharmaceutically-acceptable salt thereof, in which:

R$_4$ is —(CH$_2$)$_m$-Z;

Z is hydrogen, methyl, hydroxy, —NH$_2$, —NH(C$_{1-4}$alkyl), —NHCO$_2$(C$_{1-4}$alkyl) or —N(C$_{1-4}$alkyl)$_2$;

A is phenyl;

R$_7$ is —(C R$_{5a}$R$_{6a}$)$_q$—NR$_8$R$_9$, —(CR$_{5a}$R$_{6a}$)$_q$—CO$_2$R$_{8a}$, —(CR$_{5a}$R$_{6a}$)$_q$—C(=O)NR$_8$R$_9$, (heterocyclo)alkyl, C$_{1-4}$alkyl, C$_{1-4}$hydroxyalkyl, C$_{1-4}$alkoxy, halogen, cyano, hydroxy, amino, alkylamino, trifluoromethyl, or OCF$_3$; and m is 1, 2, 3 or 4.

11. A compound having the formula,

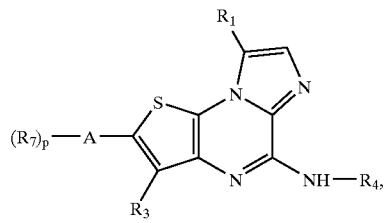

enantiomers, diastereomers, and salts thereof wherein

R$_1$ and R$_3$ are independently selected from hydrogen, halogen, C$_{1-4}$alkyl, and trifluoromethyl;

R$_4$ is —(CR$_5$R$_6$)$_m$-Z;

R$_5$ and R$_6$ at each occurrence are independently selected from hydrogen, C$_{1-4}$alkyl, amino, C$_{1-4}$alkylamino, hydroxy, and C$_{1-4}$alkoxy, wherein when R$_5$ and R$_6$ are selected from C$_{1-4}$alkyl, C$_{1-4}$alkylamino, and C$_{1-4}$alkoxy, each of said R$_5$ and R$_6$ in turn is optionally substituted with one to two groups selected from hydroxy, methoxy, halogen, and amino;

R$_7$ at each occurrence is selected independently of each other R$_7$ from:

a) cyano, trifluoromethyl, halogen, —(C R$_{5a}$R$_{6a}$)$_q$—OR$_8$, —(C R$_{5a}$R$_{6a}$)$_q$—NR$_8$R$_9$, —(C R$_{5a}$R$_{6a}$)$_q$—C(=O)NR$_8$R$_9$, —(C R$_{5a}$R$_{6a}$)$_q$—C(=O)R$_8$, —(C R$_{5a}$R$_{6a}$)$_q$—CO$_2$R$_8$, and/or —(C R$_{5a}$R$_{6a}$)$_q$—CO$_2$NR$_8$R$_9$;

b) phenyl, C$_{3-7}$cycloalkyl, heterocyclo, (heterocyclo)alkyl, heteroaryl or (heteroaryl)alkyl optionally substituted with one to three R$_{20}$;

c) C$_{1-6}$alkyl optionally substituted with one to three of hydroxy, cyano, halogen, —NR$_{17}$R$_{18}$, —NR$_{17}$(C=O)R$_{18}$, —NR$_{17}$SO$_2$(C$_{1-4}$alkyl), —C(=O)NR$_{17}$R$_{18}$, —C(=O)R$_{17}$, —CO$_2$R$_{17}$, phenyl, C$_{3-7}$cycloalkyl, and/or five to six membered heterocycle or heteroaryl in turn optionally substituted with one to three R$_{20}$;

d) two R$_7$ taken together form a fused cycloalkyl, heterocycle, heteroaryl, or benzo ring; and e) when A is an unsaturated heteroaryl, one of R$_7$ may be keto (=O); and f) when A is absent, R$_7$ may be hydrogen;

A is phenyl, five-to-six membered heteroaryl, five to six membered heterocycle, C$_{3-7}$cycloalkyl, or is a bond;

Z is selected from hydrogen, methyl, hydroxy, O(C$_{1-6}$alkyl), —NH$_2$, —NH(C$_{1-6}$alkyl), —NH(heteroaryl or heterocycle), —N(C$_{1-6}$alkyl)$_2$, —NHC(=O)(C$_{1-6}$alkyl), —NHC(=O)(phenyl), —NHCO$_2$(C$_{1-4}$alkyl), —NHCO$_2$(phenyl), —NHSO$_2$(C$_{1-6}$alkyl), —NHSO$_2$(phenyl), —C(=O)NH$_2$, —C(=O)NH(C$_{1-6}$alkyl), and —C(=O)N(C$_{1-6}$alkyl)$_2$, wherein each group Z is in turn optionally substituted with one to two of hydroxy, halogen, alkoxy, amino, trifluoromethyl, cyano, nitro, C$_{1-4}$alkyl, —NH(C$_{1-4}$alkyl), —N(C$_{1-4}$alkyl)$_2$ alkoxy substituted with hydroxy, and/or alkylamino or aminoalkyl substituted with hydroxy;

R$_8$ and R$_9$ are independently selected from hydrogen, C$_{1-6}$alkyl, C$_{2-6}$alkenyl, C$_{3-7}$cycloalkyl, phenyl, and five to six membered heteroaryl or heterocycle, wherein each R$_8$ and R$_9$ in turn is optionally substituted with one to two R$_{20}$;

R$_{17}$ and R$_{18}$ are independently selected from hydrogen, C$_{1-4}$alkyl, C$_{1-4}$hydroxyalkyl, aminoalkyl, $C_{3-7}$cycloalkyl, phenyl, and five to six membered heteroaryl or heterocycle, wherein each $R_{17}$ and $R_{18}$ in turn is optionally substituted with one to two $R_{20}$;

$R_{20}$ at each occurrence is selected independently of each other $R_{20}$ from the group consisting of $C_{1-4}$alkyl, $C_{2-4}$alkenyl, halogen, cyano, nitro, trifluoromethyl, $OCF_3$, hydroxy, $C_{1-4}$alkoxy, $C_{1-4}$hydroxyalkyl, amino, —NH($C_{1-4}$alkyl), —N($C_{1-4}$alkyl)$_2$, —NH(C=O)H, —NH(C=O)($C_{1-4}$alkyl), —NHSO$_2$($C_{1-4}$alkyl), —C(=O)H, —C(=O)$C_{1-4}$alkyl, —C(=O)NH$_2$, —C(=O)NH($C_{1-4}$alkyl), —C(=O)N($C_{1-4}$alkyl)$_2$, —CO$_2$H, and/or —CO$_2$($C_{1-4}$alkyl), or in the case of a substituent on an alkyl group or non-aromatic ring, $R_{20}$ may also be selected from keto (=O);

m and q are independently 0, 1, 2, 3, or 4; and p is 0, 1, 2, or 3, except when A is a bond, then p is 1.

12. A compound according to claim 11 having the formula

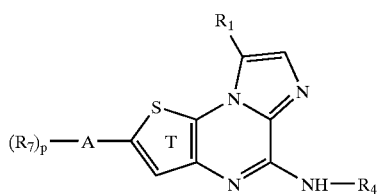

in which A is a bond, or A is selected from

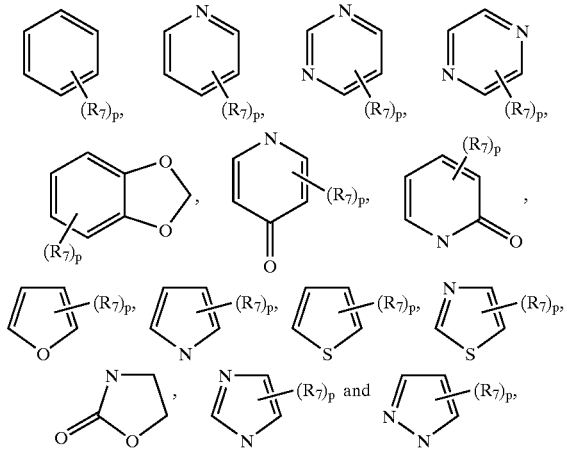

and p is 0, 1, or 2.

13. A compound according to claim 12 wherein $R_1$ is $CH_3$;

$R_4$ is —(CH$_2$)$_m$-Z; and

Z is hydrogen, methyl, hydroxy, —NH$_2$, —NH($C_{1-4}$alkyl), or —N($C_{1-4}$alkyl)$_2$.

14. A compound having the formula

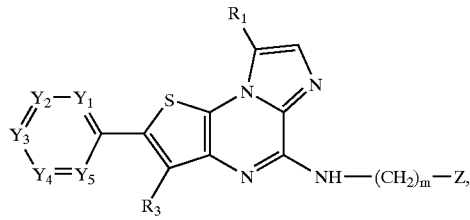

or a pharmaceutically-acceptable salt thereof, in which:

$R_1$ and $R_3$ are independently selected from hydrogen, halogen, $C_{1-4}$alkyl, and trifluoromethyl;

$Y_1$, $Y_2$, $Y_3$, $Y_4$, and $Y_5$ are selected from —CR$_7$ and nitrogen, provided that no more than four of $Y_1$, $Y_2$, $Y_3$, $Y_4$, and $Y_5$ are nitrogen;

$R_7$ at each occurrence is selected independently of each other $R_7$ from:

a) hydrogen, cyano, trifluoromethyl, halogen, hydroxy, —(CR$_{5a}$R$_{6a}$)$_q$—O(C$_{1-4}$alkyl), —(CR$_{5a}$R$_{6a}$)$_q$—NH$_2$, —(CR$_{5a}$R$_{6a}$)$_q$—NH(C$_{1-4}$alkyl), —(CR$_{5a}$R$_{6a}$)$_q$—NH(C$_{1-4}$aminoalkyl), —(CR$_{5a}$R$_{6a}$)$_q$—NH(C$_{1-4}$hydroxyalkyl), —(CR$_{5a}$R$_{6a}$)$_q$—N(C$_{1-4}$alkyl)$_2$, , —(CR$_{5a}$R$_{6a}$)$_q$—NH(CH$_2$)$_r$(alkylamino), —(CR$_{5a}$R$_{6a}$)$_q$—NH(CH$_2$)$_r$(pyrrolidinyl), —(CR$_{5a}$R$_{6a}$)$_q$—NHC(=O)H, —(CR$_{5a}$R$_{6a}$)$_q$—NHC(=O)C$_{1-4}$alkyl, —(CR$_{5a}$R$_{6a}$)$_q$—C(=O)C$_{1-4}$alkyl, —(CR$_{5a}$R$_{6a}$)$_q$—C(=O)(CH$_2$)$_r$(morpholinyl), —(CR$_{5a}$R$_{6a}$)$_q$—C(=O)(CH$_2$)$_r$(imidazolyl), —(CR$_{5a}$R$_{6a}$)$_q$—C(=O)(CH$_2$)$_r$(alkylamino), —(CR$_{5a}$R$_{6a}$)$_q$—C(=O)(CH$_2$)$_r$NH$_2$, —(CR$_{5a}$R$_{6a}$)$_q$—CO$_2$H, —(CR$_{5a}$R$_{6a}$)$_q$—CO$_2$(C$_{1-4}$alkyl), —(CR$_{5a}$R$_{6a}$)$_q$—CO$_2$(CH$_2$)$_r$NH$_2$, —(CR$_{5a}$R$_{6a}$)$_q$—CO$_2$(CH$_2$)$_r$NH(C$_{1-4}$alkyl), and —(CR$_{5a}$R$_{6a}$)$_q$—CO$_2$(CH$_2$)$_r$N(C$_{1-4}$alkyl)$_2$, wherein each (CH$_2$)$_r$, pyrrolidinyl, morpholinyl, or imidazolyl group in turn is optionally substituted with one to two $R_{22}$;

b) morpholinyl, piperazinyl, pyrrolidinyl,

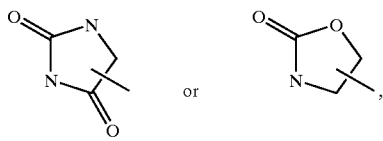

in turn optionally substituted with one to three $R_{22}$, and c) $C_{1-6}$alkyl optionally substituted with one to two of hydroxy, cyano, halogen, —NH$_2$, —NH(C$_{1-4}$alkyl), —NH(C$_{1-4}$aminoalkyl), —NH(C$_{1-4}$hydroxyalkyl), —N(C$_{1-4}$alkyl)$_{2a}$, —NH(C=O)H, —NH(C=O)C$_{1-4}$alkyl, —NHSO$_2$(C$_{1-4}$alkyl), —C(=O)(CH$_2$)$_r$NH$_2$, —C(=O)(CH$_2$)$_r$NH(alkyl), —C(=O)(CH$_2$)$_r$N(alkyl)$_2$, —C(=O)(CH$_2$)$_r$(morpholinyl), —CO$_2$H, —CO$_2$(C$_{1-4}$alkyl), morpholinyl, pyrazolyl, imidazolyl, piperazinyl, and/or pyrrolidinyl, wherein each —(CH$_2$)$_r$, morpholinyl, pyrazolyl, imidazolyl, piperazinyl, or pyrrolidinyl group in turn is optionally substituted with one to two $R_{22}$; or d) two $R_7$ groups join to form a fused five or six membered heterocyclo ring;

Z is selected from hydrogen, methyl, hydroxy, O(C$_{1-6}$alkyl), —NH$_2$, —NH(C$_{1-6}$alkyl), —NH (heteroaryl or heterocycle), —N(C$_{1-6}$alkyl)$_2$, —NHC (=O)

(C$_{1-6}$alkyl), —NHC(=O)(phenyl), —NHCO$_2$ (C$_{1-4}$alkyl), —NHCO$_2$(phenyl), —NHSO$_2$(C$_{1-6}$alkyl), —NHSO$_2$(phenyl), —C(=O)NH$_2$, —C(=O)NH (C$_{1-6}$alkyl), and —C(=O)N(C$_{1-6}$alkyl)$_2$, wherein each group Z in turn is optionally substituted with one to two $R_{23}$;

$R_{22}$ and $R_{23}$ at each occurrence are independently selected from hydroxy, halogen, trifluoromethyl, cyano, nitro, $C_{1-4}$alkyl, hydroxy$C_{1-4}$alkyl, —NH(C$_{1-4}$alkyl), —N(C$_{1-4}$alkyl)$_2$, —C(=O)H, —C(=O)C$_{1-4}$alkyl, amino, $C_{1-4}$alkoxy optionally substituted with hydroxy, and/or $C_{1-4}$alkylamino or amino$C_{1-4}$alkyl optionally substituted with hydroxy;

m is 0, 1, 2, 3, or 4;

q is 0, 1, 2, 3, 4, 5 or 6; and r is 0, 1, 2 or 3.

15. A compound according to claim 14, having the formula

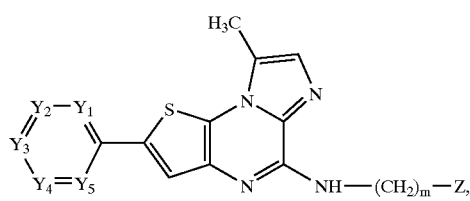

or a pharmaceutically acceptable salt thereof, in which $Y_1$, $Y_2$, $Y_3$, $Y_4$, and $Y_5$ are —$CR_7$.

16. A pharmaceutical composition comprising (a) at least one compound according to claim 1, or a pharmaceutically acceptable salt, hydrate or prodrug thereof, and (b) a pharmaceutically-acceptable carrier or diluent.

17. A pharmaceutical composition comprising (a) at least one compound according to claim 11, or a pharmaceutically-acceptable salt, hydrate or prodrug thereof, and (b) a pharmaceutically-acceptable carrier or diluent.

18. A method of treating disorders comprising administering to a mammal in need thereof a therapeutically effective amount of at least one compound according to claim 1, where in the disorder is selected from rheumatoid arthritis, asthma, ulcerative colitus, Crohn's disease, chronic obstructive pulmonary disease, and psoriasis.

19. A compound of claim 1 having the formula

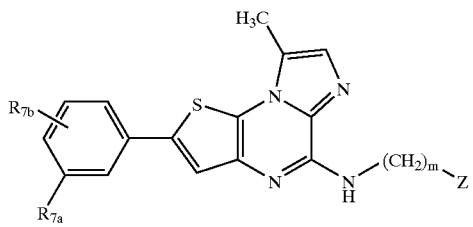

wherein
$R_{7a}$ is
  a) —$(CR_{5a}R_{6a})_q$—$NR_8R_9$, and
    $R_{5a}$ and $R_{6a}$ at each occurrence are selected from hydrogen, methyl, hydroxy, amino or alkylamino;
    $R_8$ is hydrogen or alkyl;
    $R_9$ is alkyl substituted with —C(=O)$NH_2$ or —C(=O)NH(alkyl);
    q is 0, 1 or 2;
  b) —$(CR_{5a}R_{6a})_q$—$CO_2R_{8a}$
    $R_{5a}$ and $R_{6a}$ at each occurrence are selected from hydrogen, methyl, hydroxy, amino or alkylamino;
    $R_{8a}$ is alkyl;
    q is 0, 1 or 2;
  c) —$(CR_{5a}R_{6a})_q$—C(=O)$NR_8R_9$
    $R_{5a}$ and $R_{6a}$ at each occurrence are selected from hydrogen, methyl, hydroxy, amino or alkylamino;
    $R_8$ is hydrogen;
    $R_9$ is alkyl;
    q is 0, 1 or 2;
  d) heterocyclo or (heterocyclo)alkyl; and
$R_{7b}$ is absent or halo.

* * * * *

UNITED STATES PATENT AND TRADEMARK OFFICE
CERTIFICATE OF CORRECTION

PATENT NO. : 6,933,294 B2 Page 1 of 1
APPLICATION NO. : 10/400387
DATED : August 23, 2005
INVENTOR(S) : Makonen Belema et al.

It is certified that error appears in the above-identified patent and that said Letters Patent is hereby corrected as shown below:

Title page,
Item [56], References Cited, OTHER PUBLICATIONS, insert
-- C. Daveu et al., "Definition of a Pharmacophore for Partial Agonists of Serotonin 5-$HT_3$ Receptors", *J. Chem. Inf. Comput. Sci.*, Vol 39, pp. 362-369, 1999. --.

Column 225,
Line 47, delete "$(CR_5R6)_m$" and insert -- $(CR_5R_6)_m$ --.

Column 226,
Line 42, delete "thenp" and insert -- then p --.
Line 66, delete "heterocycle or cycloalkyl" and insert -- heterocyclene or cycloalkylene --.

Column 228,
Line 43, delete "heteroaryl" and insert -- heteroarylene --.

Column 231,
Lines 22 and 27, delete "hydrate or prodrug".

Signed and Sealed this

Twenty-seventh Day of June, 2006

JON W. DUDAS
*Director of the United States Patent and Trademark Office*